(12) United States Patent
Stuart et al.

(10) Patent No.: US 11,298,478 B2
(45) Date of Patent: Apr. 12, 2022

(54) RESET MECHANISM FOR AN INHALER

(71) Applicant: KINDEVA DRUG DELIVERY L.P., Woodbury, MN (US)

(72) Inventors: Adam J. Stuart, Loughborough (GB); Hannah J. S. Allan, Huntingdon (GB)

(73) Assignee: Kindeva Drug Delivery L.P., Woodbury, MN (US)

( * ) Notice: Subject to any disclaimer, the term of this patent is extended or adjusted under 35 U.S.C. 154(b) by 393 days.

(21) Appl. No.: 16/331,278

(22) PCT Filed: Sep. 5, 2017

(86) PCT No.: PCT/US2017/050064
§ 371 (c)(1),
(2) Date: Mar. 7, 2019

(87) PCT Pub. No.: WO2018/048795
PCT Pub. Date: Mar. 15, 2018

(65) Prior Publication Data
US 2019/0351160 A1 Nov. 21, 2019

(30) Foreign Application Priority Data
Sep. 7, 2016 (GB) ...................................... 1615185

(51) Int. Cl.
*A61M 15/00* (2006.01)
(52) U.S. Cl.
CPC ...... *A61M 15/0096* (2014.02); *A61M 15/009* (2013.01); *A61M 15/0026* (2014.02); *A61M 15/0095* (2014.02)

(58) Field of Classification Search
CPC .......... A61M 15/0026; A61M 15/0095; A61M 15/0096; A61M 15/009
See application file for complete search history.

(56) References Cited

U.S. PATENT DOCUMENTS

| | | | |
|---|---|---|---|
| 5,217,004 A * | 6/1993 | Blasnik | A61M 15/0091 128/200.23 |
| 5,450,336 A * | 9/1995 | Rubsamen | A61M 15/0091 341/120 |
| 5,497,764 A | 3/1996 | Riston | |
| 6,405,727 B1 | 6/2002 | MacMichael et al. | |

(Continued)

FOREIGN PATENT DOCUMENTS

| CN | 1062091 A | 6/1992 |
|---|---|---|
| CN | 101528358 A | 9/2009 |

(Continued)

OTHER PUBLICATIONS

International Search report for PCT International Application No. PCT/US17/50064 dated Nov. 9, 2017, 3 pages.

(Continued)

*Primary Examiner* — Kathryn E Ditmer
(74) *Attorney, Agent, or Firm* — Mueting Raasch Group

(57) ABSTRACT

A valved-container inhaler (150) has a mechanical return assembly with a spring (214) and a transfer (212) configured to transfer stored potential energy from the spring to a canister (51) and a clutch (208, 210) in a load path of the force between the spring and the transfer, the clutch being rotatable between a first condition in which load is transferred from the spring to the transfer, and a second condition in which the spring and the transfer can move relative to one another to interrupt the load path and thereby allow the canister to resile after actuation.

20 Claims, 89 Drawing Sheets

(56) References Cited

U.S. PATENT DOCUMENTS

| | | | |
|---|---|---|---|
| 2004/0020486 A1* | 2/2004 | Huxham | A61M 15/0091 128/200.23 |
| 2004/0149772 A1 | 8/2004 | Ouyang | |
| 2004/0237961 A1* | 12/2004 | Snow | A61M 15/0076 128/200.23 |
| 2005/0016528 A1* | 1/2005 | Aslin | A61M 15/0096 128/200.23 |
| 2008/0178872 A1* | 7/2008 | Genova | A61M 15/0026 128/200.23 |
| 2009/0308385 A1 | 12/2009 | Brewer | |
| 2014/0053838 A1 | 2/2014 | Berenshteyn | |
| 2019/0022339 A1* | 1/2019 | Richardson | B65D 83/386 |

FOREIGN PATENT DOCUMENTS

| | | |
|---|---|---|
| GB | 2398251 | 8/2004 |
| WO | WO 92/09323 A1 | 6/1992 |
| WO | WO 2000-016838 | 3/2000 |
| WO | WO 2000-078378 | 12/2000 |
| WO | WO 2003-055548 | 7/2003 |
| WO | WO 2004-028608 | 4/2004 |
| WO | WO 2005-094400 | 10/2005 |
| WO | WO 2008/023019 A2 | 2/2008 |
| WO | WO 2009/024578 A2 | 2/2009 |
| WO | WO 2018-048786 | 3/2018 |

OTHER PUBLICATIONS

Extended European Search Report from the European Patent Office for EP 17849391.2, dated Mar. 30, 2020; 4 pgs.

Chinese Office Action issued by the Chinese Patent Office for CN 201780055046.5, dated Nov. 16, 2020; 12 pgs. including English translation.

* cited by examiner

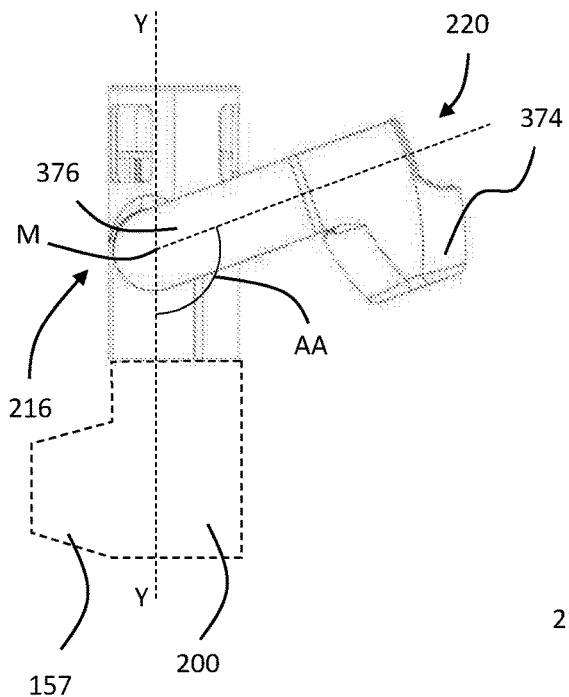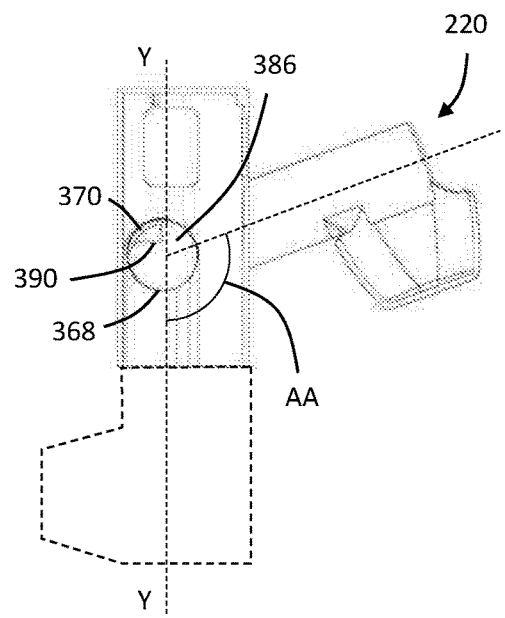
Fig. 13d Fig. 13e
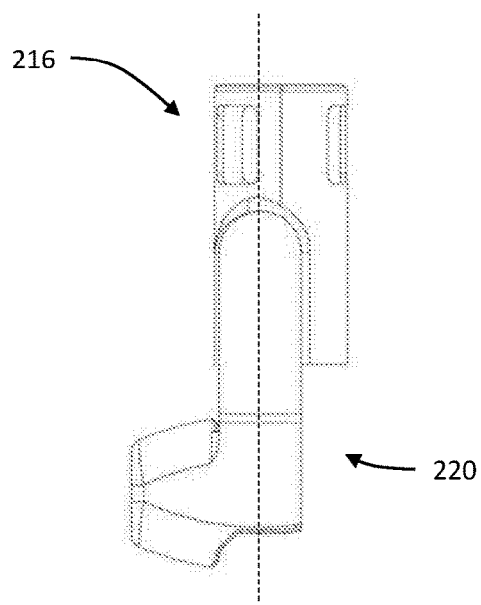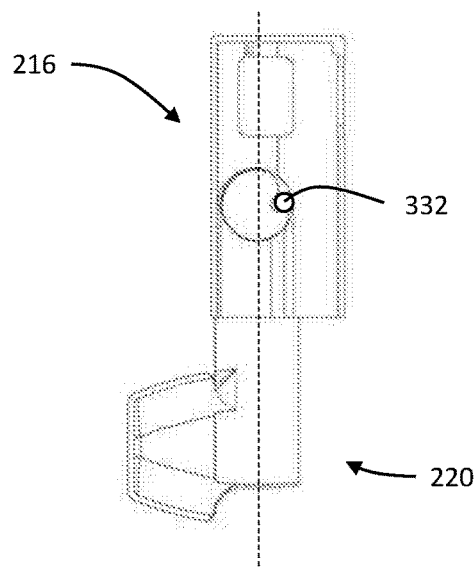
Fig. 13f Fig. 13g

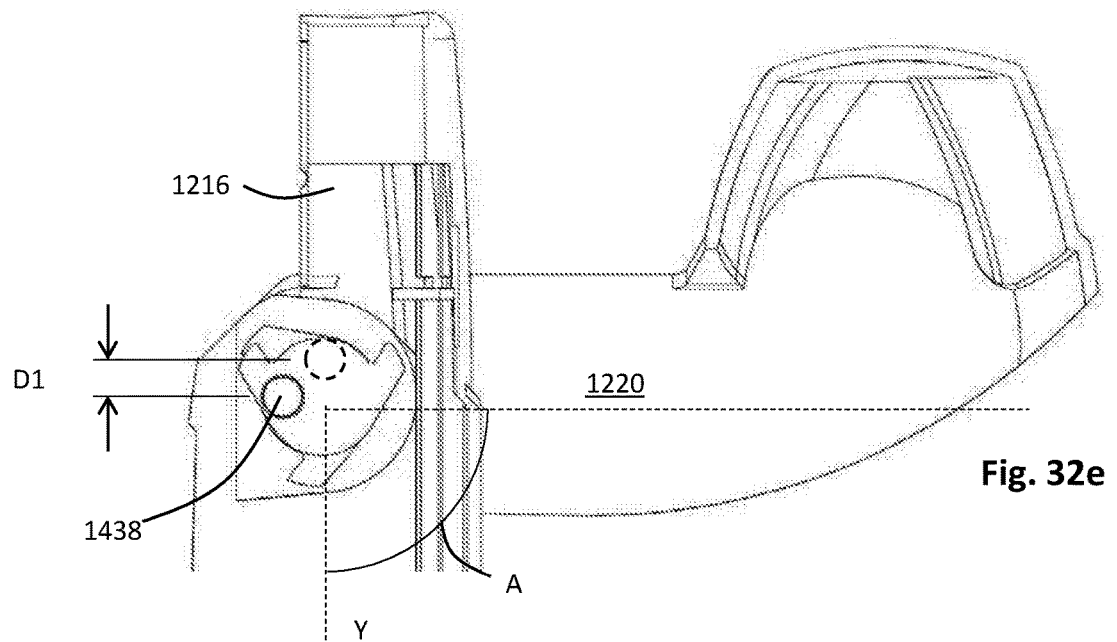
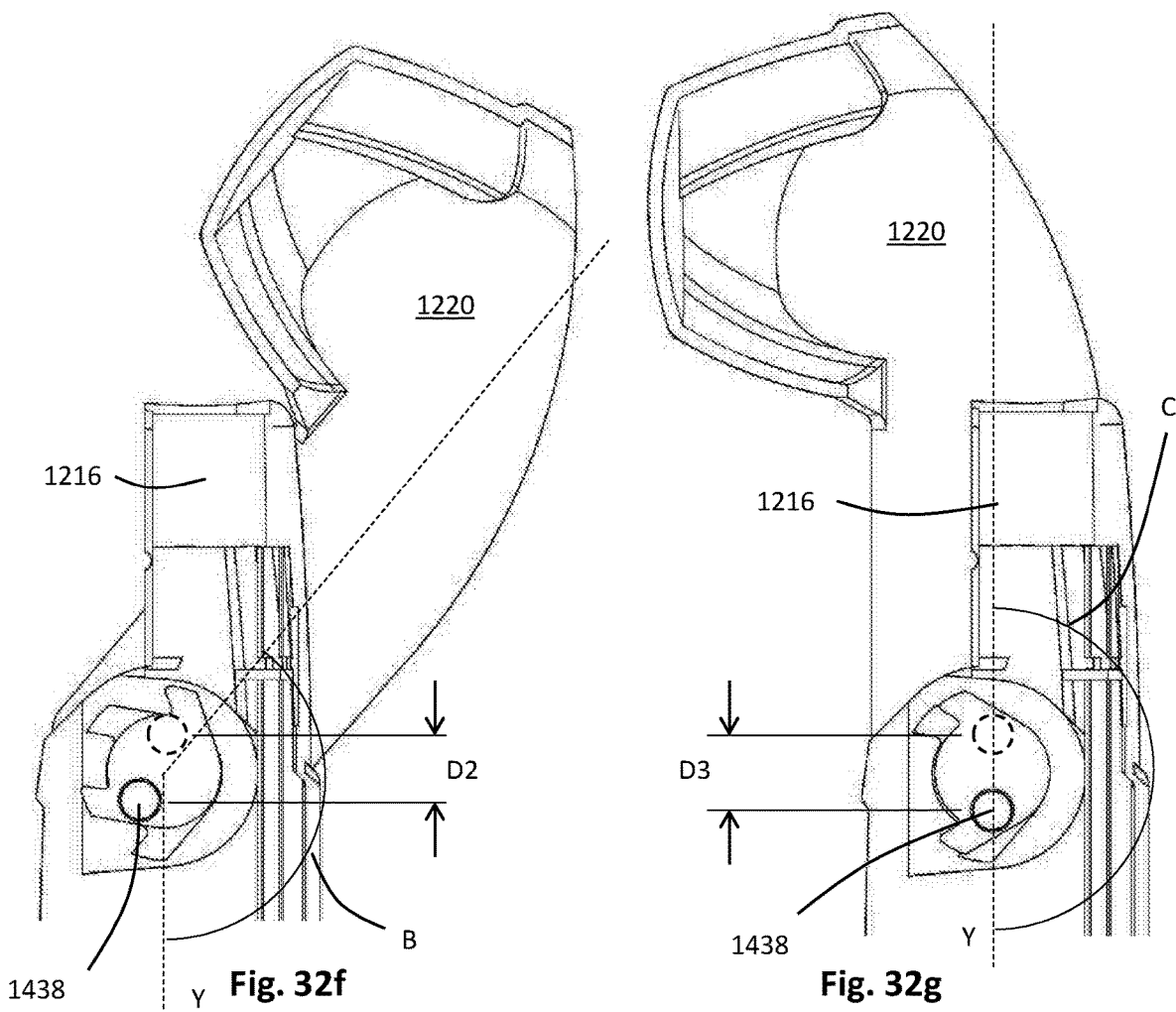

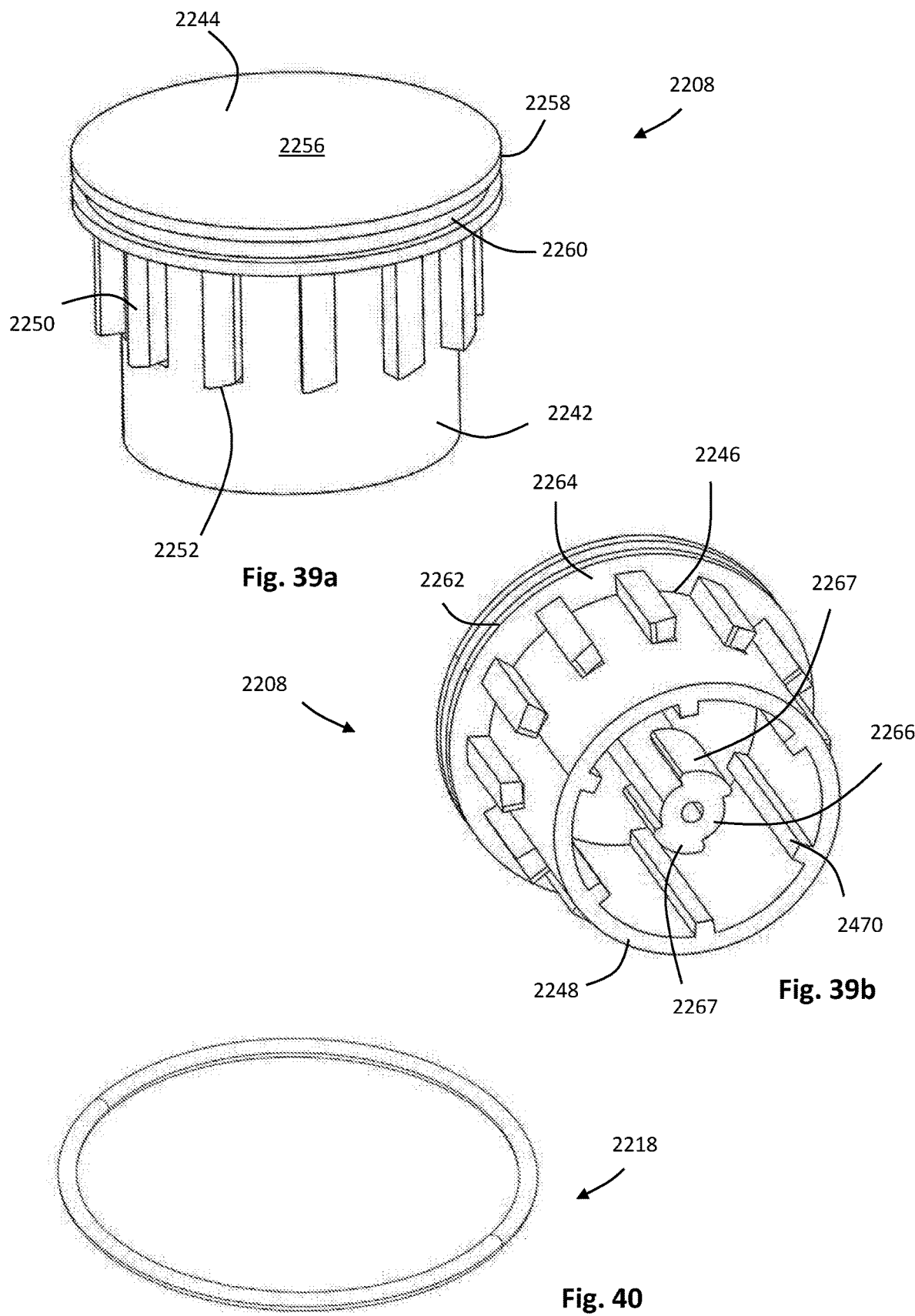

RESET MECHANISM FOR AN INHALER

CROSS REFERENCE TO RELATED APPLICATIONS

This application is a national stage filing under 35 U.S.C. 371 of PCT/US2017/050064, filed Sep. 5, 2017, which claims the benefit of GB Application No. 1615185.4, filed Sep. 7, 2016, the disclosure of which is incorporated by reference in its entirety herein.

FIELD

The present application relates to reset mechanisms for dose release firing mechanisms in valved-container inhalers and, in particular, breath-actuated medicinal inhalers. The application also relates to inhalers and, in particular, medicinal inhalers comprising reset mechanisms.

BACKGROUND

Delivery of aerosolized medicament to the respiratory tract for the treatment of respiratory and other diseases has been done using pressurised metered dose inhalers (pMDI), dry powder inhalers (DPI), and nebulizers. pMDI inhalers are familiar to many patients who suffer from either asthma or chronic obstructive pulmonary disease (COPD). pMDI devices often comprise a canister comprising an aluminium canister that is sealed with a metering valve and contains a medicament formulation. Generally, the medicament formulation is pressurized and contains either fine particles of one or more medicinal compounds suspended in a liquefied hydrofluoroalkane (HFA) propellant, or a solution of one or more medicinal compounds dissolved in a propellant/co-solvent system. Formulations incorporating dugs in both in solution and suspension forms are also known.

In a pulmonary pMDI, the sealed canister is provided to the patient in an actuator. The actuator is a generally L-shaped plastic moulding comprising a generally cylindrical vertical tube that surrounds the canister plus a generally horizontal tube that forms a patient portion (e.g., a mouthpiece or nosepiece) that defines an inspiration (or inhalation) orifice. To use such an inhaler, the patient exhales, places the patient port into a body cavity (e.g., a mouth or nose) and then may inhale to draw air through the inspiration orifice. Many such inhalers are of the pulmonary "press-and-breathe" type, where the patient presses down on the protruding end of the canister to operate the metering valve to release a metered dose of medicament from the canister into the inhaled air stream and thence through the mouthpiece into their lungs. This can require coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

Spacer devices have previously been devised which fit onto the mouthpiece of a pMDI to reduce the velocity of the emergent plume of medicament aerosol and provide a volume in which it can expand and its propellant can evaporate more completely. This serves to avoid some of the problems of coordination and the tendency for high throat deposition caused by excessively fast drug particle inhalation. However, spacer devices can be bulky and retain an excessive proportion of the drug on their walls, thereby reducing the dose that reaches the patient. Spacer devices can also be highly sensitive to electrostatic charge, which can often be strongly affected by the way in which they are washed or dried.

To overcome what can be quite a challenge for some patients, pMDI device designs have been created that employ automatic breath-actuated triggering mechanisms, releasing a dose only in response to the patient's inhaled breath. Typically, an energy storage means is provided which is primed by the user (for example by compressing a spring) and released by the triggering mechanism to provide an actuation load upon the canister and thereby release the medicament. Once triggered, the inhaler needs to be reset for the next operation by a reset mechanism.

The AUTOHALER™ metered dose inhaler, available from 3M Company, St. Paul, Minn., USA and the EASI-BREATHE™ inhaler, available from Teva Pharmaceutical Industries Ltd., Israel, are two such pMDI devices that use breath-actuation to attempt to better coordinate dose release with inhalation. Many other inhaler breath-actuated mechanisms and reset mechanisms have been proposed, but tend to have one or more weaknesses or disadvantages, for example high component counts (and hence high manufacturing costs), complexity (typically giving rise to difficulties of assembly and/or complex dimensional tolerance stack-ups, etc.), performance issues (it is difficult to balance sensitivity (a light triggering force) against stability at rest and/or prior to inhalation) and/or excessive size and/or a less familiar or more awkward overall inhaler shape. Some of the existing devices employ mechanical breath-actuation systems that typically need to be tightly toleranced to be both stable and yet also sensitive. This increases manufacturing cost and can result in higher part rejection.

The issue of cost is a particular concern when considering price-sensitive markets such as those for generic drug products or in Asia. The embodiments of the present disclosure seeks to provide a reset mechanism for breath actuated inhalers at a manufacturing cost low enough to make it highly attractive even in price sensitive markets.

With many breath-actuated inhalers, the events after the dose has been delivered via the pMDI metering valve can also be important. A problem that can exist with some systems is that the pMDI metering valve can remain in its depressed state after firing. This can be due to a mechanical load from the breath-actuated firing system continuing to exert the actuation load onto the pMDI canister. This can give rise to complications, as the metering chamber of the pMDI metering valve can become vulnerable to intrusion of air. Ingress of air can result in vapour lock of the metering chamber, where the presence of the air can prevent complete filling of the metering chamber with the appropriate volume of medicament for the next dose when the valve is eventually returned to the rest position. Subsequently, the next dose that the user receives can contain a lower than intended quantity of drug due to the incomplete filling of the metering chamber.

A further problem associated with patient failure to properly reset the firing mechanism is that formulations of suspended drug particles can start to sediment, cream and/or flocculate during prolonged periods without shaking. As most pMDI metering valves "sample" (i.e., fill with the next dose) at the time of valve stem reset/release, delays in releasing the depressed valve stem can result in inhomogeneous sampling of the next dose from the remaining bulk formulation in the pMDI canister. For example, a creaming formulation may be under-sampled (i.e., an inappropriately low amount of drug may be present in the liquid of the next dose) if too long a delay occurs between shaking of the inhaler (e.g., pMDI) and the time at which the valve stem is allowed to reset. As a result, drug particles may have preferentially creamed (i.e., risen) away from the vicinity of the sampling port(s) of the valve. Conversely, a sedimenting formulation may tend to be over-sampled if its suspended drug loading is given excessive time to settle into the vicinity of the valve. Flocculating formulations may show additional undesirable effects, e.g., the "floccs" of associated suspended particles may become too large to pass readily into the metering valve, effectively being partially filtered out by its sampling port(s), leading to a potentially low next dose.

In addition, the admission into the metering chamber of ambient air containing moisture, e.g., by diffusion, can create problems of medicament formulation stability, etc. Therefore it can be desirable to include a mechanism in an inhaler that allows the valve (e.g., in a pMDI) to automatically return to its rest or reset position.

As well as ensuring that valve reset occurs within a predetermined maximum time, it is also of importance that such a mechanism allows the entire dose to exit the valve, to ensure that the patient receives the intended dose, e.g., that the mechanism does not allow the automatic return of the metering valve to its rest position until full dose release has taken place. For a typical pMDI metering valve, a dose delivery time of 0.5 seconds is generally sufficient for full dose release. Accordingly, it can be desirable to provide a means to ensure a delay time of at least 0.5 seconds between valve actuation (e.g., stem depression in a pMDI canister valve) and valve reset (e.g., stem release in a pMDI canister valve). For a typical pMDI suspension formulation, it can be desirable that only a few seconds pass between the time of shaking and the time of valve reset (i.e., the time of sampling of the next dose).

Accordingly, it is desirable to provide reset mechanism which allows the valve stem to be released within a predetermined time window, typically within 0.5-10 seconds between valve actuation (e.g., stem depression) and valve reset (e.g., stem release).

WO 00/78378 describes a breath actuated inhaler. The described inhaler has two main parts moveable relative to the inhaler body. The first part is actuated by a spring and can drive a second part which is configured to depress a canister. At the end of inhalation, the second part (and canister) is released from the first part. Release of the second part from the first part (to allow the canister to resile) is done by release of a captured pin from a fork-like member.

U.S. Pat. No. 5,497,764 describes an electrically triggered inhaler in which the actuation force for the canister is provided by a compression spring on a cam. After release, rotation of the cam by a torsion spring acts to simultaneously release the canister, recompress the spring and reset the system.

International patent application WO 03/055548 to VALOIS SAS discloses a pMDI inhaler which is primed by the user depressing a button to energise a compression spring. The spring is then released to trigger compression of the canister and release of the medicament. WO 03/055548 is concerned with the aforementioned problem of permitting sufficient "valve open" time for the entire dose of medicament to be released. As such, the subject device describes an inhaler having a brake system to slow actuation of the canister, and a release that allows the canister to return to the rest position without user intervention. The release utilises a deformable element that is constrained until the canister has been actuated, at which point it is released to allow the canister to resile.

WO 00/16838 discloses a breath actuated inhaler in which potential energy is stored in a spring ready to depress a canister. Upon release and actuation, a timer spring acts on a damping element which eventually releases the load on the canister.

WO 2005/094400 discloses a breath actuated inhaler in which a tension spring is used to compress a canister. Breath actuated release causes a rod to release the spring when the canister has been compressed, allowing the canister to resile.

In addition to what are traditionally known in the art as pMDIs, it will be noted that the aforementioned problems may exist in any type of inhaler having a medicament-containing container which has a force actuated valve. This more general class of inhalers (which includes pMDIs) will be referred to as "valved-container inhalers".

SUMMARY

A mechanical return assembly for a valved-container inhaler comprising a resilient structure, a transfer configured to transfer stored potential energy from the resilient structure to a resilient, valved container in the form of a force to thereby release the medicament therefrom, a clutch in a load path of the force between the resilient structure and the transfer, the clutch having a first part and a second part, in which relative rotation of the first and second parts moves the clutch between a first condition in which load is transferred from the resilient structure to the transfer, and a second condition in which the resilient structure and the transfer can move relative to one another to interrupt the load path and thereby allow the valved container to resile after actuation.

Advantageously, the use of a clutch allows the linear force applied to the valved container from the resilient structure to be released by the clutch. This allows the valved container to resile, mitigating the problem of leaving the valve open for too long after actuation. Rotational movement for clutch disengagement provides that release is not instantaneous, and in fact allows the full dose of medicament to be released.

Preferably relative rotation of the first and second parts is effected by a linear force applied to a ramped surface. Preferably the ramped surface is defined on the first and/or second part to effect rotation thereof. This provides a mechanically reliable and easy-to-manufacture mechanism.

Preferably the assembly comprises a housing and a static actuator formation fixed with respect to the housing and configured to engage the ramped surface of the second part. The linear force is applied from the first part to the second part to rotate the second part by engagement of the ramped surface of the second part with the static actuator formation. Again, this provides a simple and easy to manufacture mechanism with minimum complexity and cost and maximum reliability.

Preferably the clutch is configured to move linearly from a first position in which the clutch is in the first condition to a second position in which the clutch is in the first condition to transfer the stored potential energy from the resilient structure to the transfer and the second position to a third position upon engagement of the ramped surface of the second part with the static actuator formation to move the clutch to the second condition. This allows the valved container to be actuated between the first and second positions with the clutch engaged to ensure full medicament release. Once release has occurred, transition to the third condition is made to release the valved container.

Preferably the first and second parts are capable of relative linear movement, and the linear force is applied from the first part to the ramped surface on the second part to effect rotation of the second part. Preferably the first part is rotationally fixed, and rotation of the second part is inhibited for part of the linear movement of the second part. This provides a simple mechanism requiring only sliding axial movement to disengage the clutch.

Preferably the clutch is configured to move linearly through a first stage linear movement in which the clutch is in the first condition to transfer the stored potential energy from the resilient structure to the transfer, during which rotation of the second part is inhibited and a second stage linear movement during which rotation of the second part is permitted to thereby move the clutch to the second condition. This allows the valved container time to release the full medicament and return to a rest (uncompressed) condition within a predetermined time.

Preferably the first part of the clutch and the resilient structure are positioned on opposite sides of the second part of the clutch, in which the first part of the clutch moves into the second part of the clutch when moving from the first to the second condition.

Preferably the first and second parts of the clutch are in sliding engagement.

Preferably the first part of the clutch comprises a first abutment and the second part of the clutch comprises a second abutment, in which in the first condition the first and second abutments are aligned and in contact, and in the second condition the first and second abutments are misaligned. The first and/or second abutments may comprise a plurality of spaced-apart teeth which can abut or slip out of alignment to release the clutch.

Preferably a damper is provided between the transfer and the resilient structure to damp relative movement therebetween upon movement of the clutch to the second condition. This allows controlled return of the valved container to the rest position allowing the metered valve to properly reset.

Preferably the damper comprises a piston engaged in a cylinder. The cylinder may define a fluid leak path to damp relative motion of the piston and cylinder. The fluid leak path may be configured to damp relative motion of the piston and the cylinder in a first direction at a first rate, and to damp relative motion of the piston and the cylinder in a second direction at a second rate, lower than the first. This may be achieved with an opening with a different coefficient of discharge in a first flow direction compared to a second flow direction.

Alternatively, the cylinder may be sealed so as to create a low pressure cavity upon movement of the piston therefrom to provide a resilient return force on the piston.

The resilient structure may comprise a tension spring.

Alternatively, the resilient structure may comprise a compression spring.

In either case, the resilient structure may define a body having an interior space in which to receive the valved container, creating a compact arrangement. If a tension spring, the valved container may fit within the spring. Part of the transfer may be positioned in the interior space to contact the valved container. Preferably the transfer is in sliding engagement with the resilient structure.

Preferably there is provided a priming mechanism configured to transfer energy to the resilient structure. More preferably the priming mechanism is directly user-actuated. For example, it may comprise a mouthpiece cover for the inhaler.

Preferably the priming mechanism comprises a linearly displaceable element engaged with part of the resilient structure to apply a linear force thereto and store energy therein. Preferably the linearly displaceable element is engaged with a body having an interior space in which to receive the valved container.

Preferably there is provided a firing mechanism, in which the return assembly has a rest condition, a stable primed condition in which the resilient structure stores potential energy and a fired condition in which the resilient structure has been released to transfer force to the transfer, and the clutch is in the second condition in which the firing mechanism is configured to release the resilient structure.

Preferably the firing mechanism is configured to inhibit motion of, and release, a valved container and thereby react the force generated by the resilient structure.

There may be an auto-release condition after the fired condition in which the clutch moves from the first to the second condition and a can reset condition in which with the clutch in the second condition, the valved container may resile in a direction opposite to the bias of the resilient structure.

There may also be a return to rest condition in which the resilient member is displaced to its position in the rest condition. Preferably, in the return to rest condition, the clutch is reset by displacement of the resilient member.

Preferably at least one part of the clutch is resiliently biased into the return to rest condition. The at least one part of the clutch may be elastically deformable. Preferably displacement of the resilient member is effected by the priming mechanism.

BRIEF DESCRIPTION OF THE DRAWINGS

FIGS. 13d to 13g are side and side section views of stages of assembly of part of the priming and reset mechanism of FIG. 2;

FIGS. 32e to 32g are section views of stages of motion of part of the priming and reset mechanism of FIG. 19 as it is moved to the primed condition;

FIGS. 39a and 39b are perspective views of a piston of the priming and reset mechanism of FIG. 35;

FIG. 40 is a perspective view of an o-ring of the priming and reset mechanism of FIG. 35.

DETAILED DESCRIPTION

Figure 1:
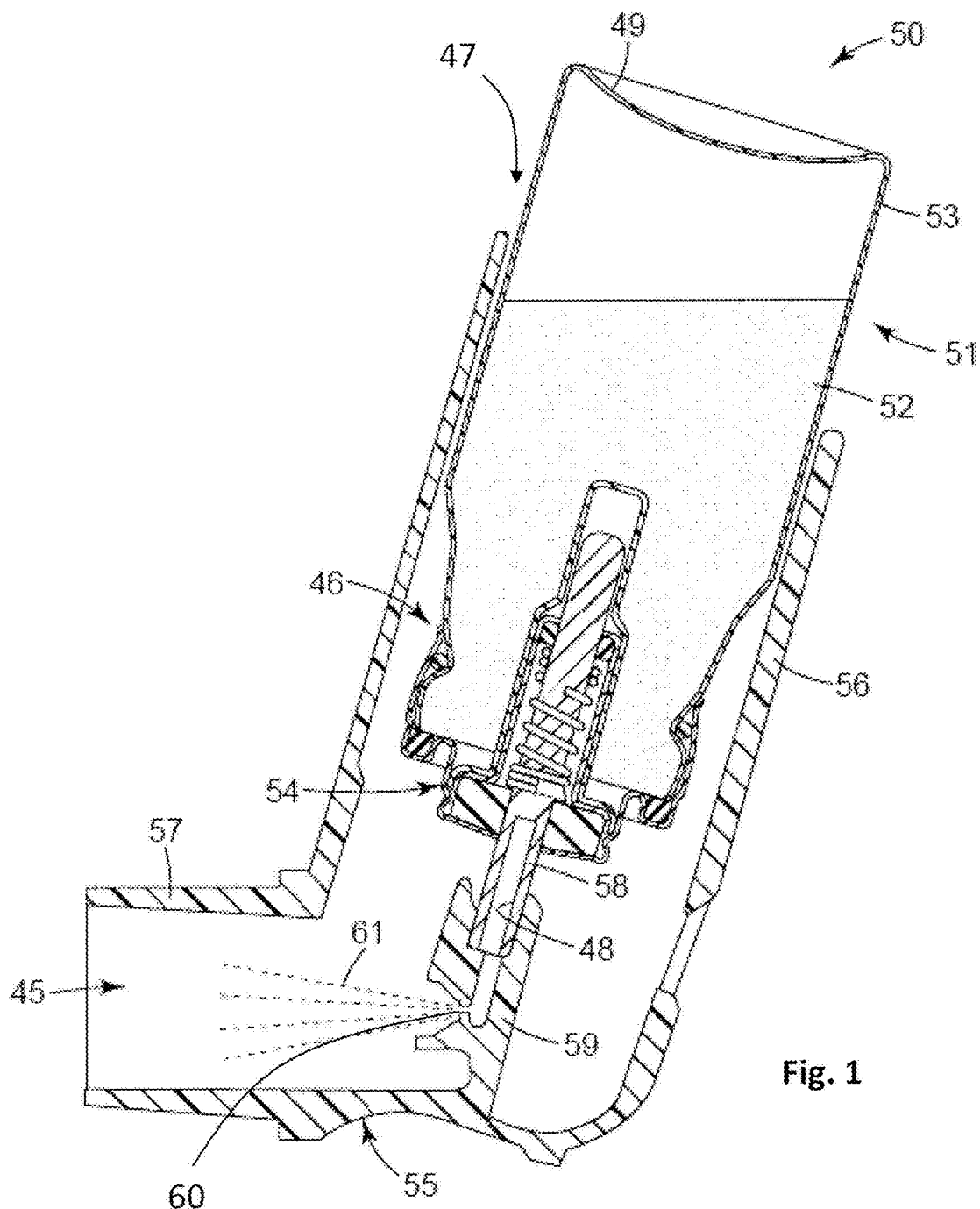
FIG. 1 is a side section view of a prior art pressurized metered dose inhaler (pMDI)
Figure 2:
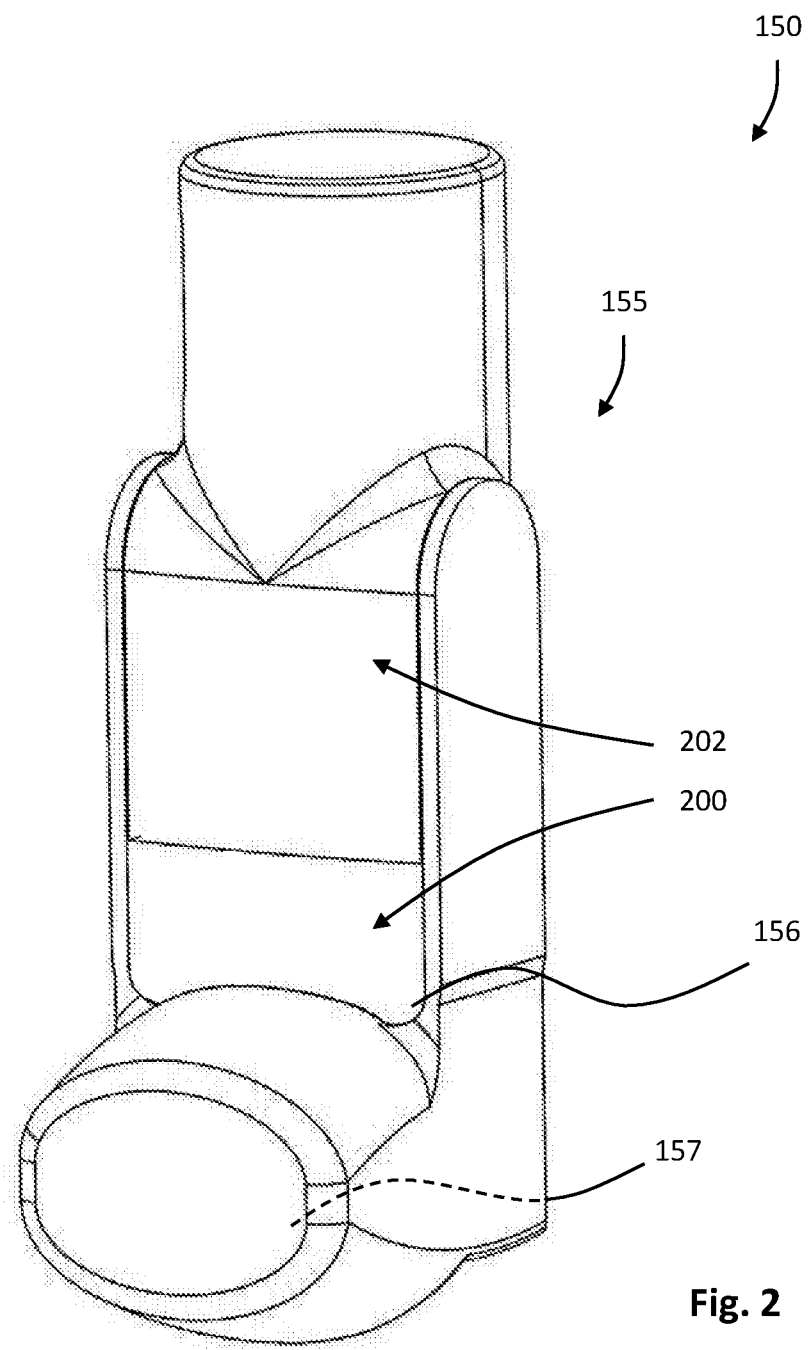
FIG. 2 is a perspective view of a first priming and reset mechanism of a pMDI in accordance with an embodiment of the present invention in a first (rest) condition.

FIG. 1 illustrates a pressurized metered dose inhaler (pMDI) 50 comprising a valved container in the form of a canister 51 containing a medicament formulation 52, the canister comprising a can 53 sealed at a crimp 46 with a metering valve 54. The canister 51 sits within a housing (or "actuator") 55 comprising a tubular sleeve portion 56 having an open end 47 dimensioned to receive the canister 51 and from which its base 49 can protrude, and a portion in the form of a patient port 57 (e.g., in the form of a mouthpiece) that defines an inspiration orifice (or an air outlet) 45. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein. The open upper end 47 of the housing 55 can define an aspiration orifice, or an air inlet, and the air outlet 45 can define an inhalation orifice, or an air outlet.

A stem portion 58 protrudes from the metering valve 54 and is located and retained by friction in a stem socket 59 formed as an integral part of the housing 55. A spray orifice 60 is formed in the stem socket 59, and provides a passage for fluid communication between the valve stem portion 58 and the inspiration orifice 45. In use, a patient places the patient port (e.g., mouthpiece) 57 into a body cavity (e.g., mouth) and then inhales through it while at the same time pressing downwards on the protruding base 49 of the canister 51. The pressing force serves to move the canister 51 downwards relative to the valve's stem portion 58. That relative movement serves to isolate a metered dose of medicament formulation from the bulk formulation in the canister 51 and then to discharge it via a hollow bore 48 formed in the stem portion 58. The discharged dose then passes along the fluid passageway through the stem socket 59 and emerges via a spray orifice in the form of a fine respirable spray 61 that passes through the patient port 57 into the patient's body cavity (e.g., oral cavity and/or nasal cavity) and thence into their respiratory passages, thereby treating their disease.

One important aspect of such a pMDI device 50 that has the potential to limit its efficacy is, in particular, its need for good patient coordination between the timing of the start of inhalation and the moment at which the canister 51 is pressed downwards. This is a challenge for a high proportion of patients, leading to poor and often highly varying efficacy of medicament administration.

The First Embodiment

Turning to FIGS. 2 to 18b, part of a first pMDI 150 according to an embodiment of the present invention is shown. The pMDI 150 comprises a housing or actuator 155 containing a canister (omitted for clarity). The canister contains a medicament formulation. It will be understood that the canister is of the same type as the canister 51 described with reference to FIG. 1 and comprises a can with a metering valve. The canister sits within the housing 155.

The housing 155 comprises a lower section 200 having a tubular sleeve portion 156 dimensioned to receive the can-ister, and a portion in the form of a patient port 157 (e.g., in the form of a mouthpiece) that defines an inspiration orifice (or an air outlet). Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein.

The housing 155 also comprises an upper section 202 which comprises the reset mechanism according to an embodiment of the present invention.

Figure 3:
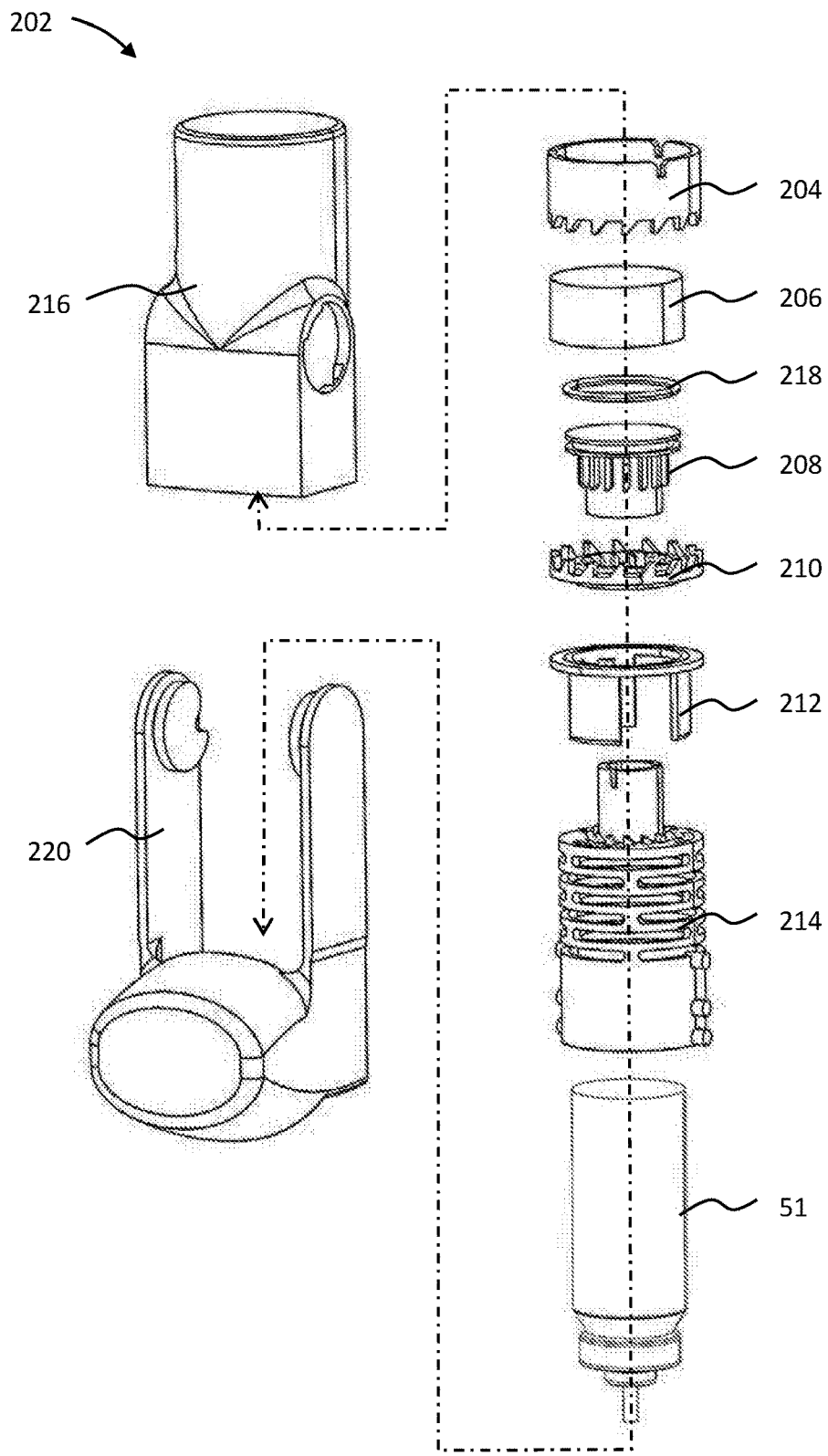
FIG. 3 is an exploded view of the priming and reset mechanism of FIG. 2.

Referring to FIG. 3, an exploded view of the upper section 202 is provided. The upper section comprises an actuator ring 204, a cylinder 206, a piston 208, a collar 210, a transfer 212, a spring 214, an actuator body 216, an o-ring 218 and a mouthpiece cover 220.

Figure 4:
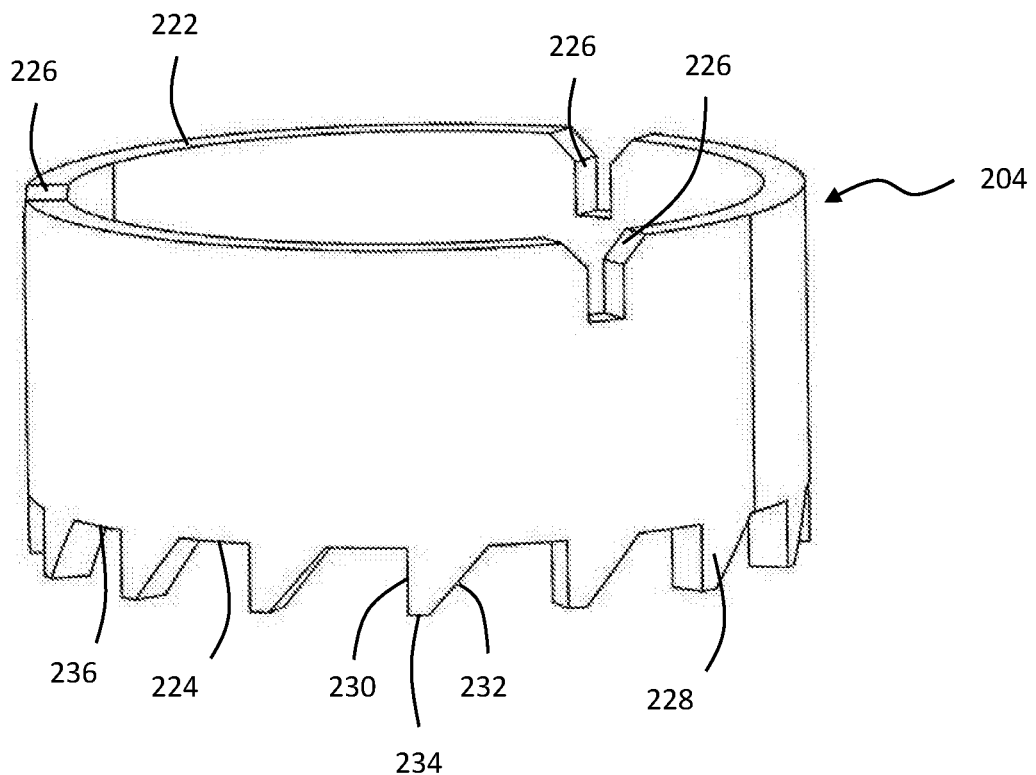
FIG. 4 is a perspective view of an actuator ring of the priming and reset mechanism of FIG. 2.

With reference to FIG. 4, the actuator ring 204 is a unitary cylindrical body constructed from a moulded plastics material having a first, upper, edge 222 and a second, lower, edge 224. The first edge 222 defines three equally spaced alignment grooves 226 in the form of axially extending notches. Each groove has two opposing chamfered regions at the edge 222 forming a tapered mouth. The second edge 224 defines a series of fifteen axially extending teeth 228. Each tooth 228 is generally triangular in shape, having a straight axial edge 230 and a tapered edge 232 (extending both axially and circumferentially) which meet at end flat 234. Each tooth 228 is separated at the edge 224 by an inter-tooth gap 236.

Figure 5:
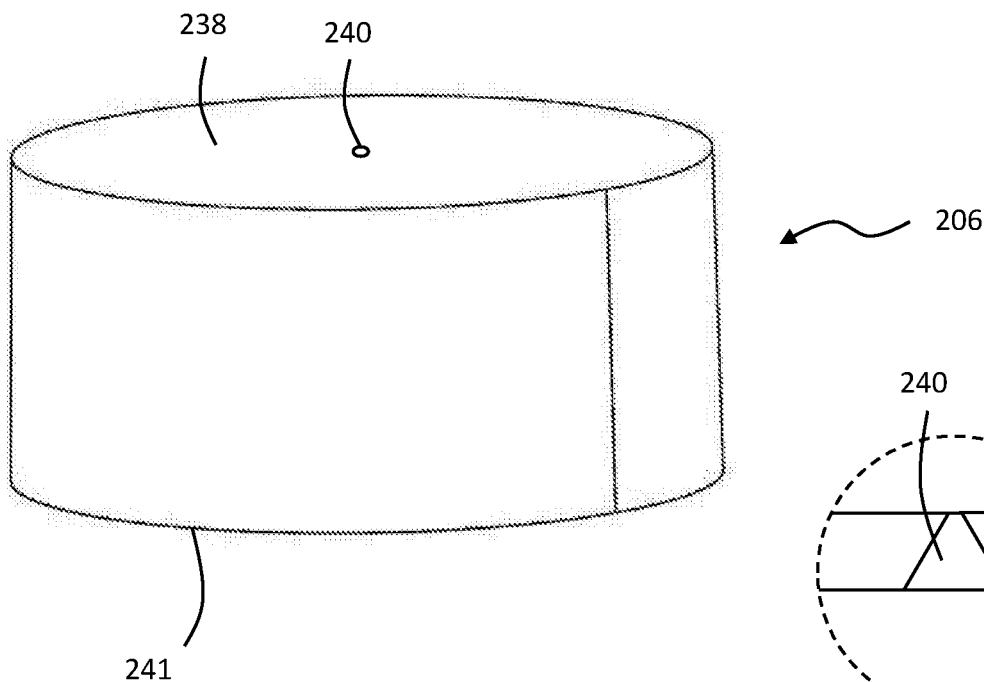
FIG. 5 is a perspective view of a cylinder of the priming and reset mechanism of FIG. 2.
Figure 5A:
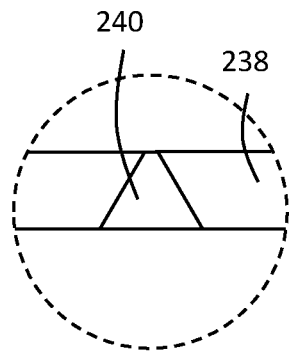
FIG. 5a is a detail section view of a part of the cylinder of FIG. 5.

With reference to FIG. 5, the cylinder 206 is a unitary cylindrical body constructed from a moulded plastics material. The cylinder is closed at a first, upper, end 238 and open at a second, lower, edge 241. In the centre of the upper closed end 238 there is provided a co-axial air leak hole 240. The air leak hole 240 is sized to provide the technical effect described below (damping) and as such the exact size can be determined by the skilled technician. Referring to FIG. 5a, a detail section view of the air leak hole 240 is shown. The hole 240 is tapered to decrease in area from the interior of the cylinder 206 to the exterior of the cylinder 206. This results in a higher coefficient of discharge for fluid exiting the cylinder through the hole 240 than air entering the cylinder through the hole 240. As such, the volumetric flow rate is higher for air exiting the hole 240 than air entering the hole 240 (for the same pressure difference). To put it another way, more resistance is encountered when separating the piston and cylinder than when engaging them.

Figures 6A, 6B, 6C:
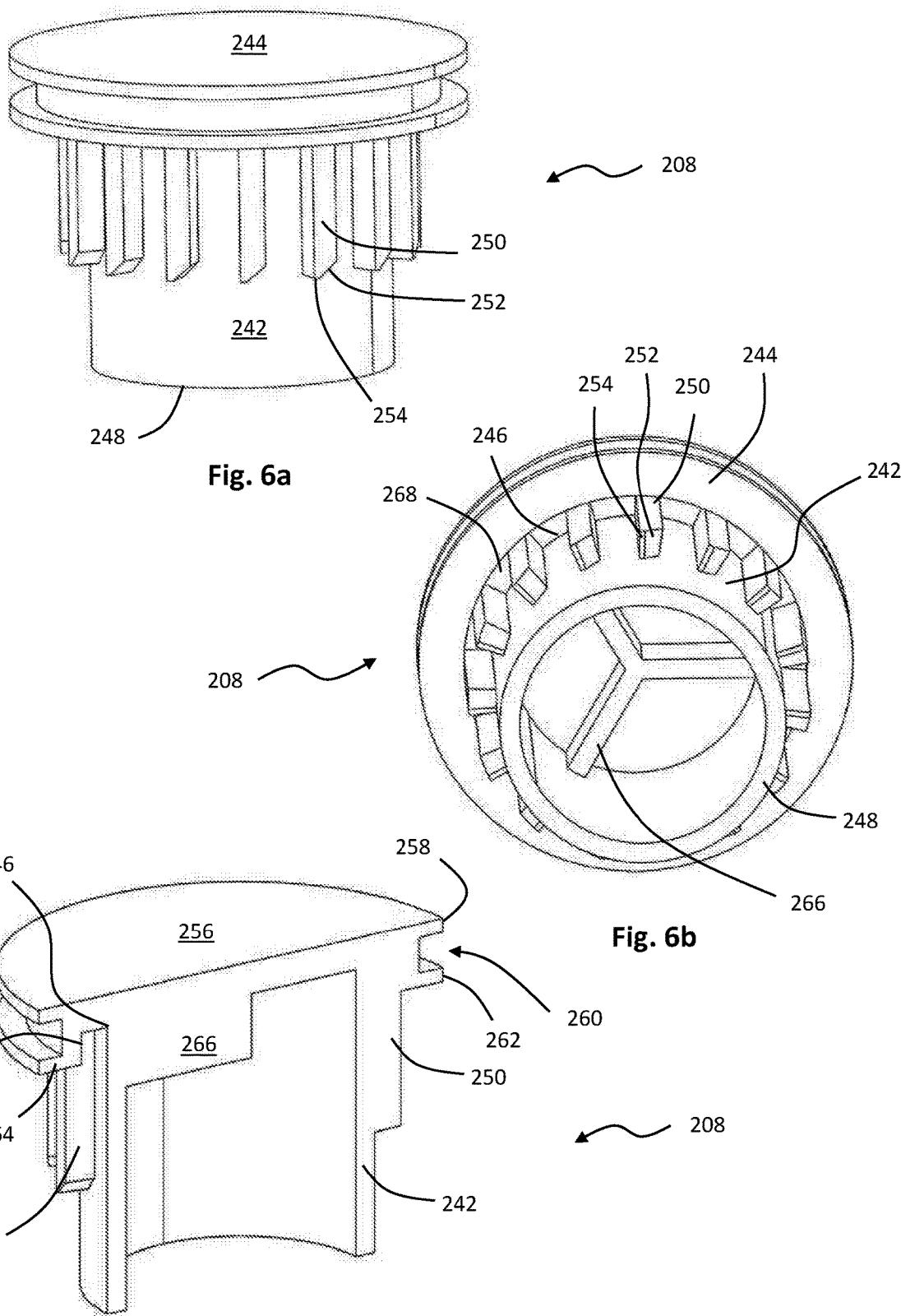
FIGS. 6a to 6c are perspective views of a piston of the priming and reset mechanism of FIG. 2.

With reference to FIGS. 6a to 6c, the piston 208 is shown. The piston 208 is a unitary moulded plastics component. The piston 208 comprises a generally cylindrical piston body 242 and a piston head 244 at one end thereof.

The body 242 is a hollow cylinder having a first, upper, end 246 at which the piston head 244 is located, and a second, lower end 248 which is open. The body 242 defines fifteen identical, equally spaced, axially extending teeth 250 on its outer surface. Each tooth 250 extends from the first end 246 towards the second end 248 (although the teeth only extend partway along the body 242). The teeth 250 each terminate at a free end which defines a tapered surface 252 extending both circumferentially and axially. The free end also defines a small circumferentially extending flat 254 adjacent the tapered surface 252.

The piston head 244 comprises a circular piston end cap 256 having a radial edge 258. The end cap 256 is positioned at the first, upper, end 246 of the body 242. The head 244 comprises an o-ring receiving channel section 260 extending axially towards the second end 248 of the body 242. The o-ring receiving channel section 260 is formed by the radial edge 258 of the cap 256 and a radial edge 262 of an annular ring section 264. On the underside of the end cap 256 (i.e. the surface facing the interior of the body 242) there are provided three equally spaced, radially extending stiffening ribs 266. It will be noted from FIGS. 6b and 6c in particular that the piston head 244 overhangs the body 242 to provide an annular recess 268 into which the teeth 250 extend.

Figure 7:
FIG. 7 is a perspective view of an o-ring of the priming and reset mechanism of FIG. 2.

Turning to FIG. 7, the o-ring 218 is shown. The o-ring 218 is a standard component and is constructed from an elastomeric material designed to form a fluid seal against plastics material.

Figure 8A:
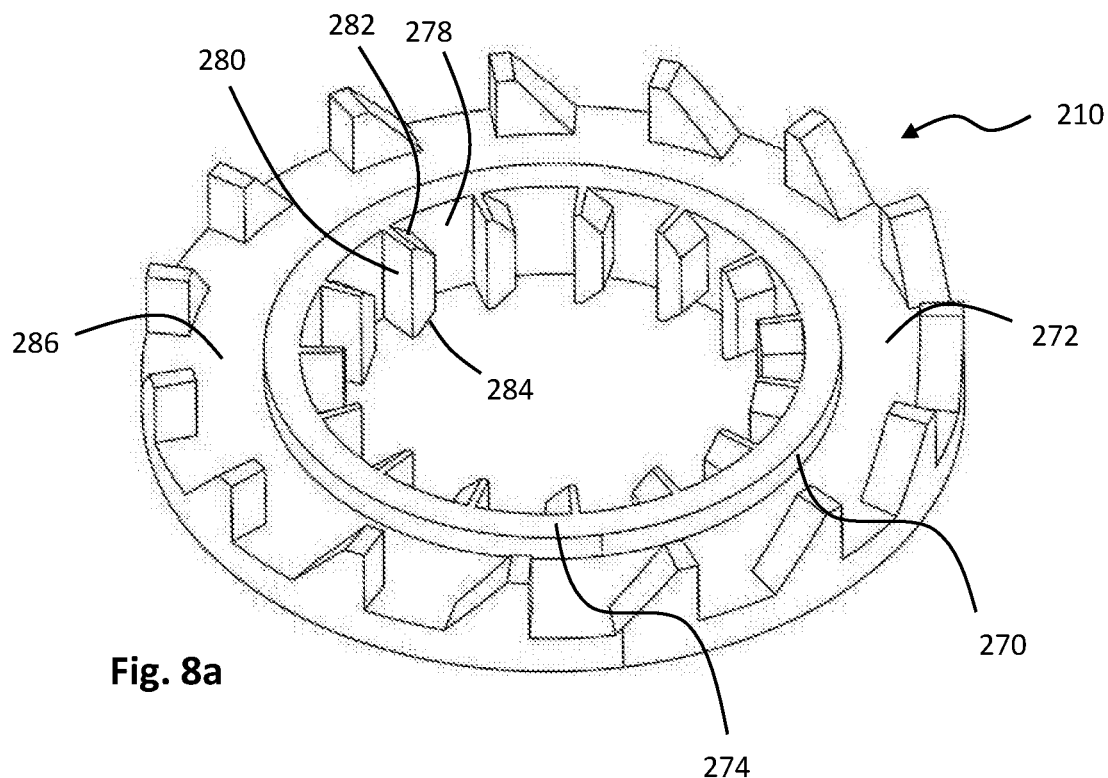
FIGS. 8a and 8b are perspective views of a collar of the priming and reset mechanism of FIG. 2.
Figure 8B:
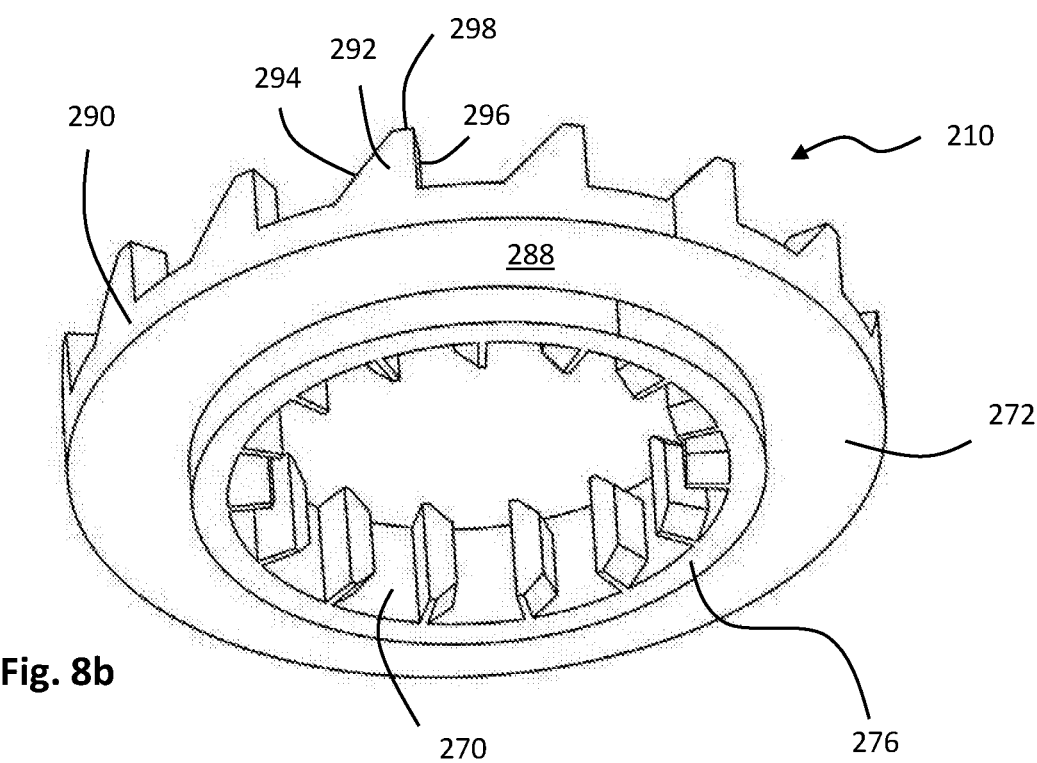

Referring to FIGS. 8a and 8b, the collar 210 is shown. The collar 210 is a unitary moulded plastics component. The collar 218 comprises a central cylindrical shaft 270 and an outer annulus 272.

The shaft 270 has a first, upper, end 274 and a second, lower, end 276. The shaft also defines a radially inwardly facing inner surface 278 on which a series of fifteen equally spaced inner collar teeth 280 are defined. Each inner collar tooth 280 is axially extending and defines (i) a tapered first, upper, end 282 and (ii) a tapered, second, lower end 284. The ends 282, 284 are oppositely tapered giving the teeth 280 an elongate trapezium shape. The sides of the teeth 280 are flat and axially extending. The teeth 280 extend the full axial length of the shaft 270.

The annulus 272 extends outwardly from the shaft 270 midway between the ends 274, 276. The annulus 272 comprises a first, upper surface 286 and a second, lower surface 288. The annulus 272 defines an outer rim 290. At the outer rim 290 there are positioned fifteen outer collar teeth 292. Each collar tooth 292 extends from the first surface 286 of the annulus 272 in an axial sense. Each outer collar tooth 292 is tapered becoming narrower as it extends from the first surface 286. Each tooth 292 defines a tapered or ramped surface 294 and a flat, axial surface 296 which meet at an end flat 298.

Figure 9:
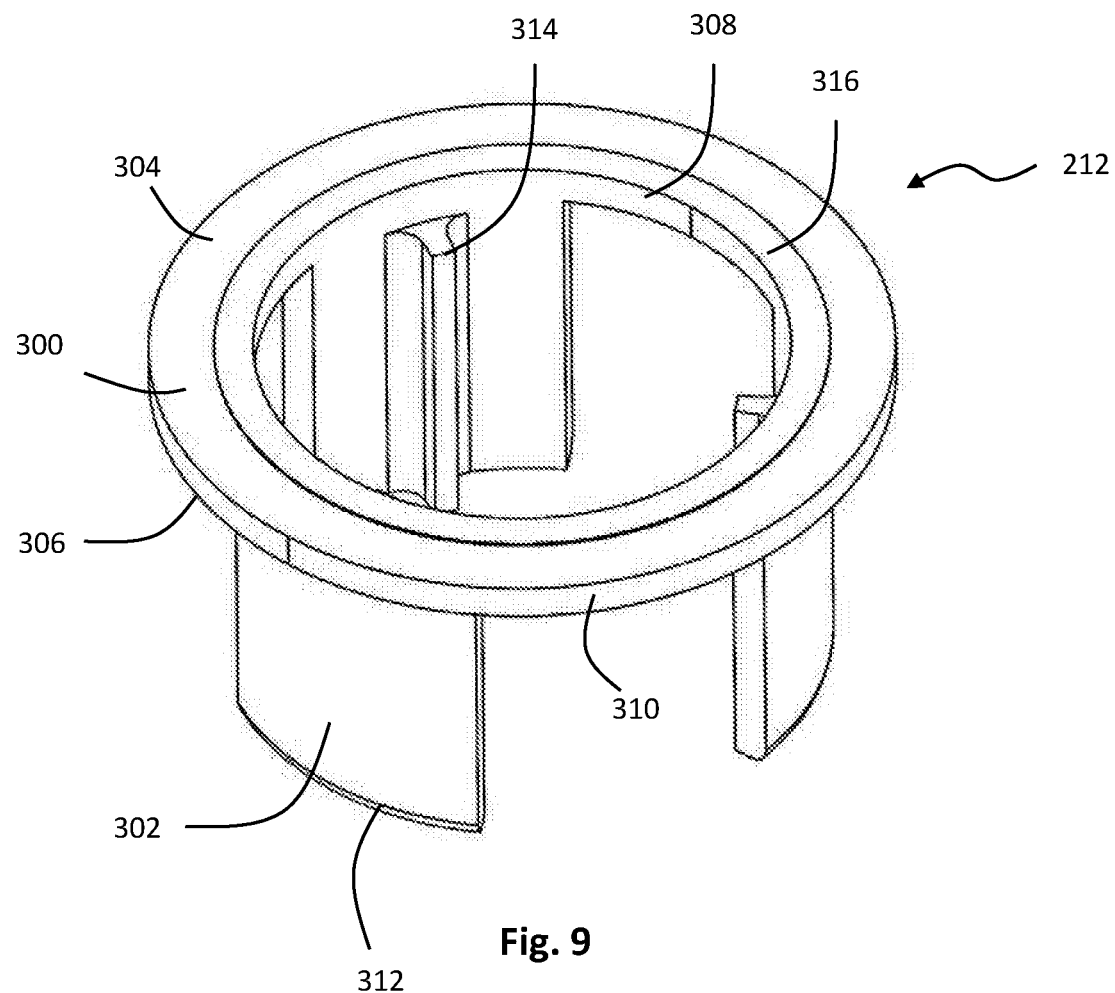
FIG. 9 is a perspective view of a transfer of the priming and reset mechanism of FIG. 2.

Referring to FIG. 9, the transfer 212 is shown in detail. The transfer 212 is a unitary, moulded, plastics component comprising an annular body 300 and three equally spaced, axially extending legs 302 extending therefrom. The annular body 300 comprises a first, upper, surface 304 and a second, lower, surface 306 as well as an inner rim 308 and outer rim 310. The upper surface 304 defines an annular bearing surface 316 proximate the inner rim 308. The annular bearing surface 316 is slightly upstanding from the surface 304. Each leg 302 extends from the second surface 306 and is circle-segment in section, thus forming a part-cylinder. Each leg 302 has a free end 312 and a rib 314 extending in an axial direction along its length from the annular body 300 to the free end 312. Each rib 314 is disposed along the centreline of the inner surface of each leg 302. As such, the ribs 314 face inwardly towards each other.

Figure 10:
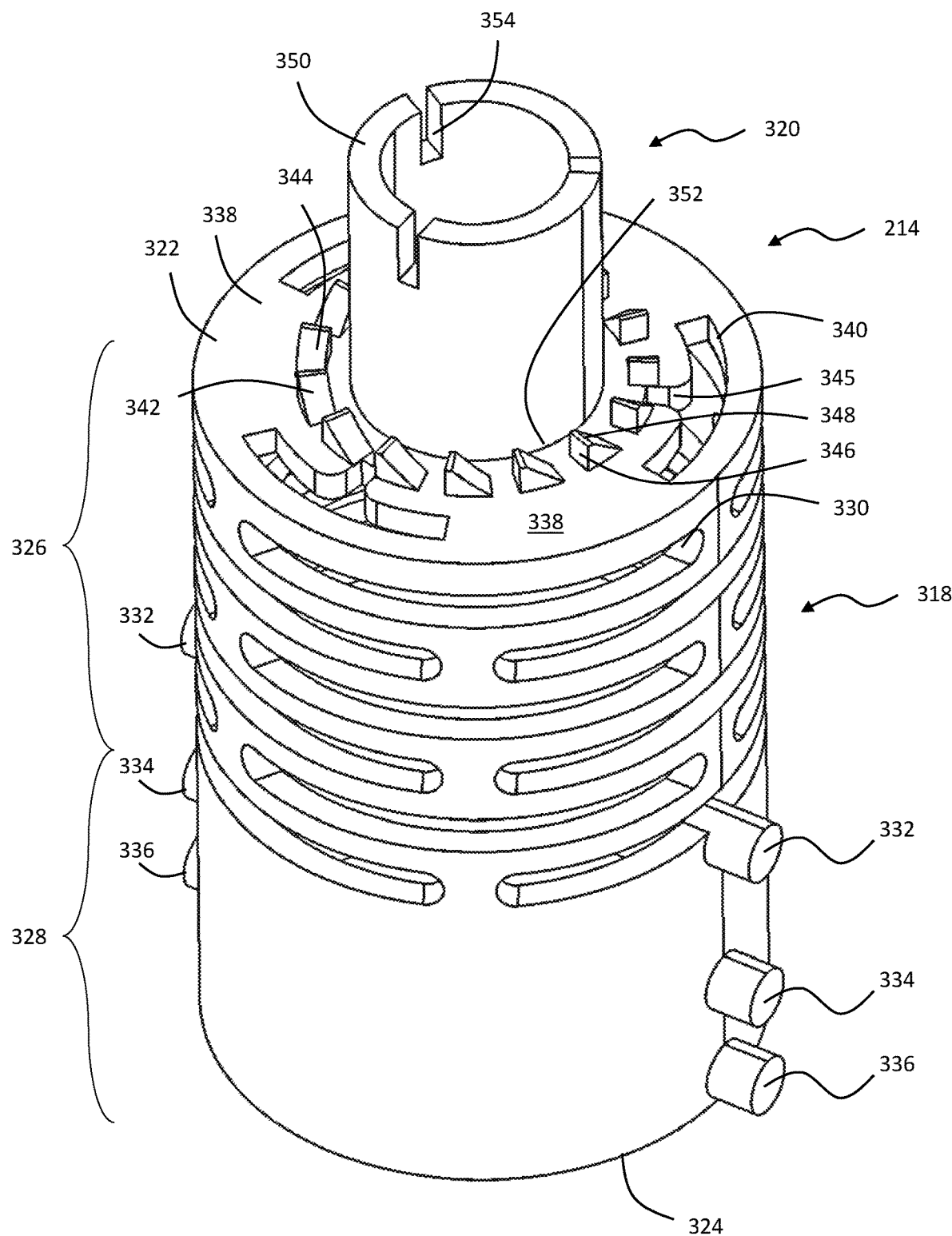
FIG. 10 is a perspective view of a spring of the priming and reset mechanism of FIG. 2.

Referring to FIG. 10 the spring 214 is shown in detail. The spring 214 is a unitary, moulded, plastics component. The spring 214 comprises a cylindrical spring body 318 and a spring shaft 320 projecting therefrom. The spring 214 acts as a unitary energy storage arrangement.

The spring body 318 is generally tubular and cylindrical, acting as a sleeve for the canister 51. The body 318 has a first, upper, end 322 and a second, lower, end 324. The spring body 318 has a first, upper, region 326 and a second, lower region 328.

The first region 326 is axially extensible and resilient. This is achieved by forming a series of six rows of slot-like openings 330 through the wall of the body 318. Each row comprises three openings 330 which are equally spaced around the circumference of the body 318. Each row is rotationally offset from the adjacent row or rows. The openings 330 are formed such that the first region 326 can be elastically extended, and will resile back to a rest condition as shown in FIG. 10. The second region 328 comprises a first, second and third pair of outwardly extending, diametrically opposed pegs 332, 334, 336 respectively. The pegs 332, 334 336 are cylindrical. The first peg is positioned adjacent the first region 326, and the second and third pegs are positioned proximate the second end 324. The second and third pegs 334, 336 are closer together than the first and second pegs 332, 334.

The first end 322 of the body 318 terminates in an annular surface 338 which defines three leg openings 340 and a series of fifteen spring teeth 342. Each leg opening 340 is shaped as a circle-segment. A rib receiving formation 345 extends in a radially inward direction from the centre of each leg opening. Thus each leg opening 340 is approximately "T" shaped. The spring teeth 342 are positioned radially inwardly of the leg openings 340. Each spring tooth 342 is generally tapered and comprises a tapered surface 344 which meets a flat axial surface 346 at a small flat 348.

The spring shaft 320 extends from the centre of the annular surface 338 and is constructed as a hollow cylinder. The spring shaft 320 has a first, upper end 350 and a second, lower, end 352 where it joins the annular surface 338. The spring shaft 320 has three equally spaced spring alignment grooves 354 which extend axially from the first end 350.

Figure 11A:
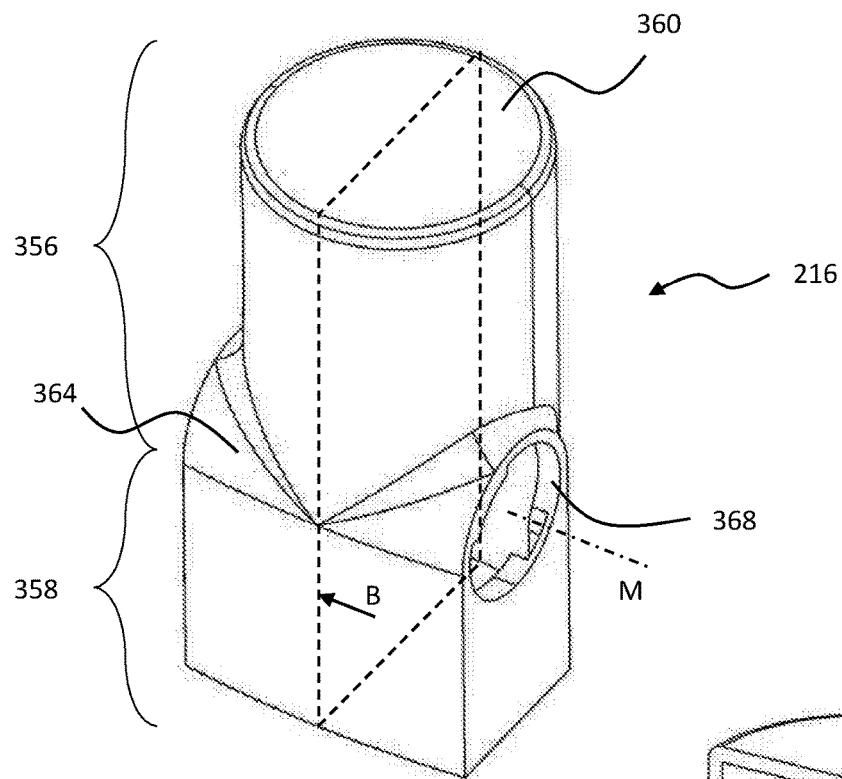
FIGS. 11a and 11b are perspective views of an actuator body of the priming and reset mechanism of FIG. 2.
Figure 11B:
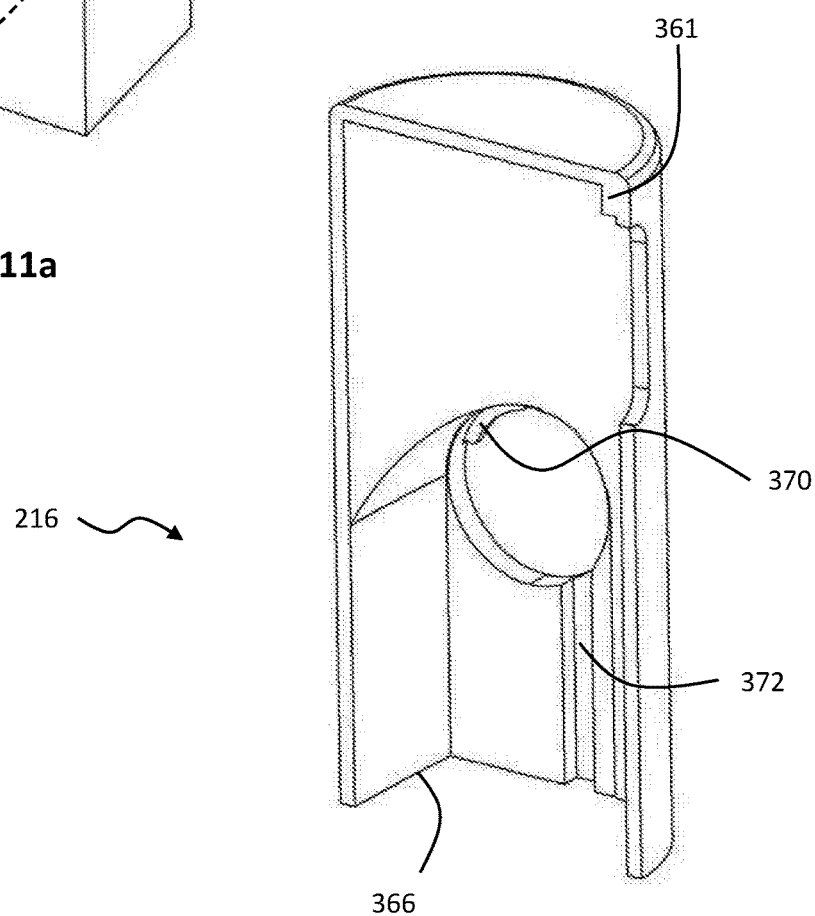

Referring to FIGS. 11a and 11b, the actuator body 216 is shown in detail. FIG. 11b is in cross-section through plane B in FIG. 11a. The actuator body 216 comprises a first, upper, section 356 and a second, lower, section 358. The sections 356, 358 define a generally elongate housing enclosing a cavity which is open at the lower end.

The first section 356 is generally cylindrical having a first, upper end which is closed by an endwall 360. Three equally spaced actuator ring ribs 361 are provided extending axially from the endwall 360 along the sidewalls.

The second section 358 is generally rectangular in cross-section and joins the first section 356 via a pair of shoulders 364. The second section 358 has an open end 366. A pair of diametrically opposed circular apertures 368 are disposed in opposing walls of the second section proximate the shoulders 364. Each aperture 368 defines a retaining flange 370 projecting radially inwardly though a portion of its circumference. Both apertures lie on a mouthpiece cover axis M. Extending from each aperture 368 along the respective interior sidewall of the second section 358 there is provided a spring peg groove 372. The spring peg grooves 372 start from a position substantially opposite the retaining flange 370 and extend axially within the second section 358 to the open end 366.

Figures 12A, 12B:
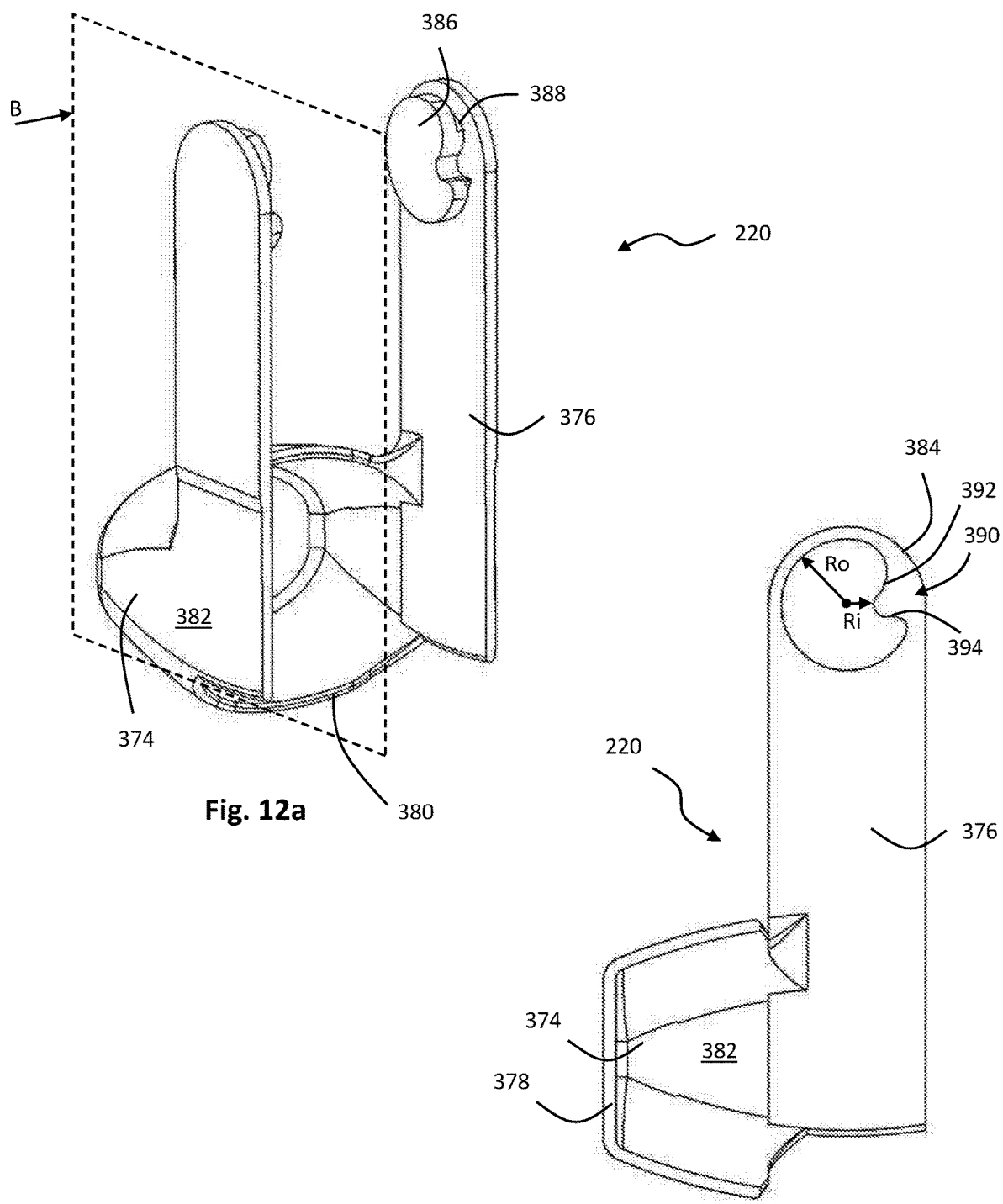
FIGS. 12a and 12b are perspective and section views respectively of a mouthpiece cover of the priming and reset mechanism of FIG. 2.

Referring to FIGS. 12a and 12b, the mouthpiece cover 220 is shown in more detail. The mouthpiece cover 220 is a unitary, moulded plastics component. FIG. 12b is in cross-section through plane B in FIG. 12a. The mouthpiece cover 220 comprises a cap 374 and two arms 376 that are mirror images of each other.

The cap 374 is an internally concave structure suitable for sealing a mouthpiece of the inhaler patient port 157. The cap 374 has a closed end 378 and an open end 380. The cap 374 defines a pair of opposed sidewalls 382 from which the arms 376 extend proximate the open end 380.

Each arm 376 is an elongate, generally planar structure extending to a free end 384. At the free end, and on an inwardly facing surface of each arm 376 there is provided a cam 386. The cam 386 is connected to the arm 376 via an undercut region 388 (it will be understood that the term "undercut" is used in the geometric sense, and does not imply that a cutting operation has taken place).

The cam 386, with reference to FIG. 12b has an outer radius Ro and a peg-receiving notch 390 which extends inwardly of Ro to an inner radius Ri. The notch 390 has a first, shallow surface 392 which curves gently between Ro and Ri and a second surface 394 which extends more steeply between Ro and Ri (almost radially).

Assembly

Figure 13A:
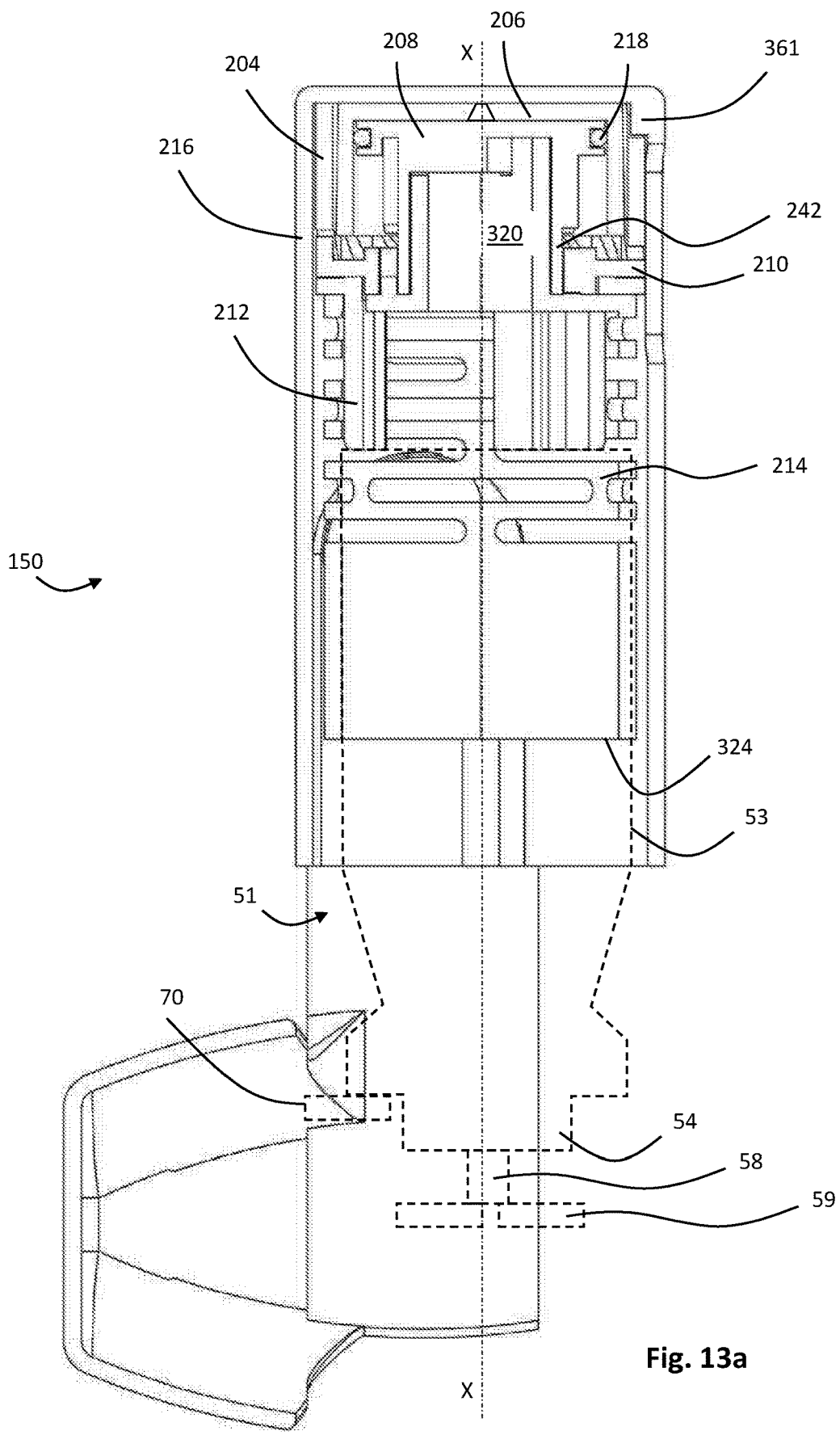
FIGS. 13a to 13c are section views of various parts of the priming and reset mechanism of FIG. 2 in a rest condition.
Figure 13B:
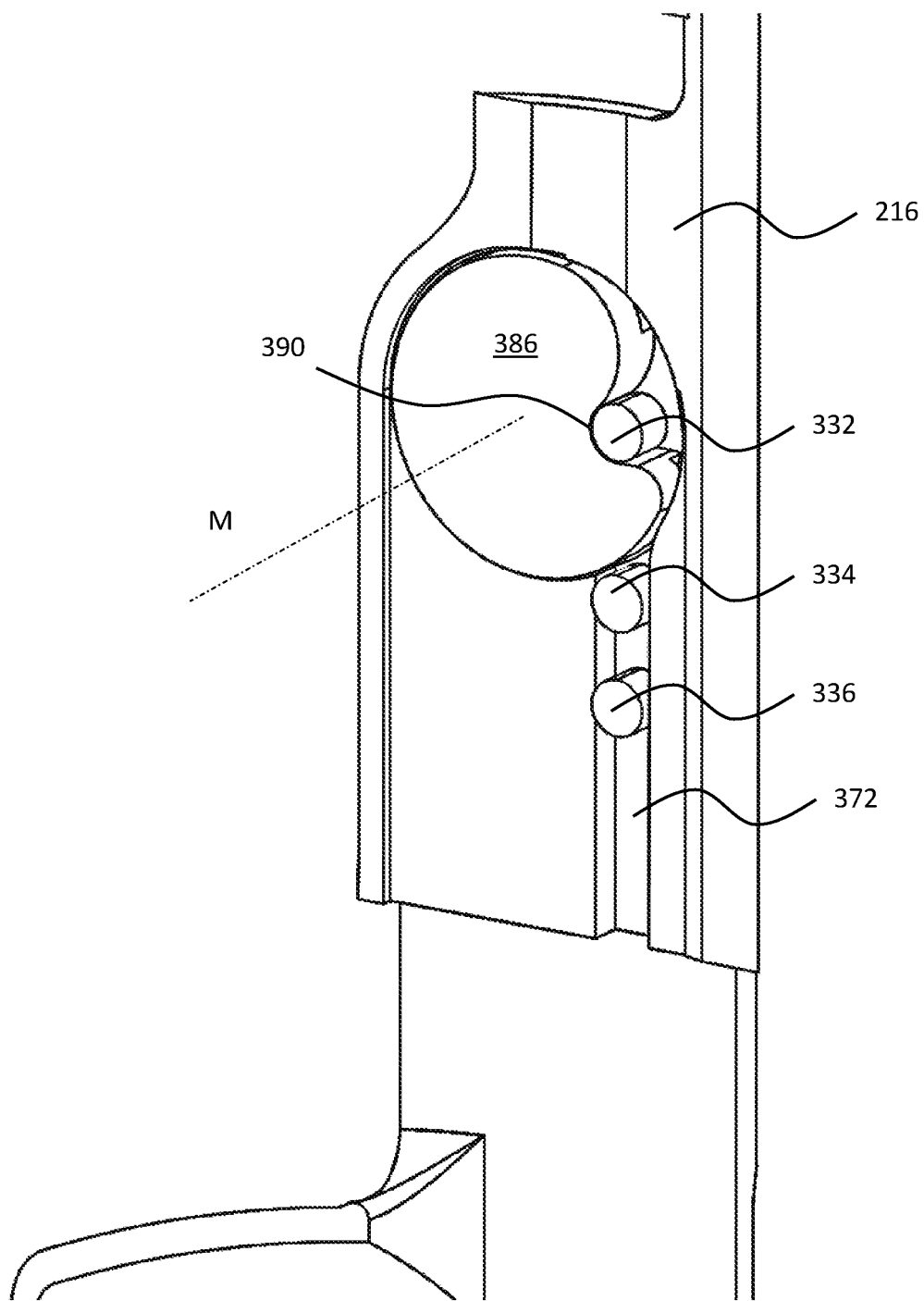
Figure 13C:
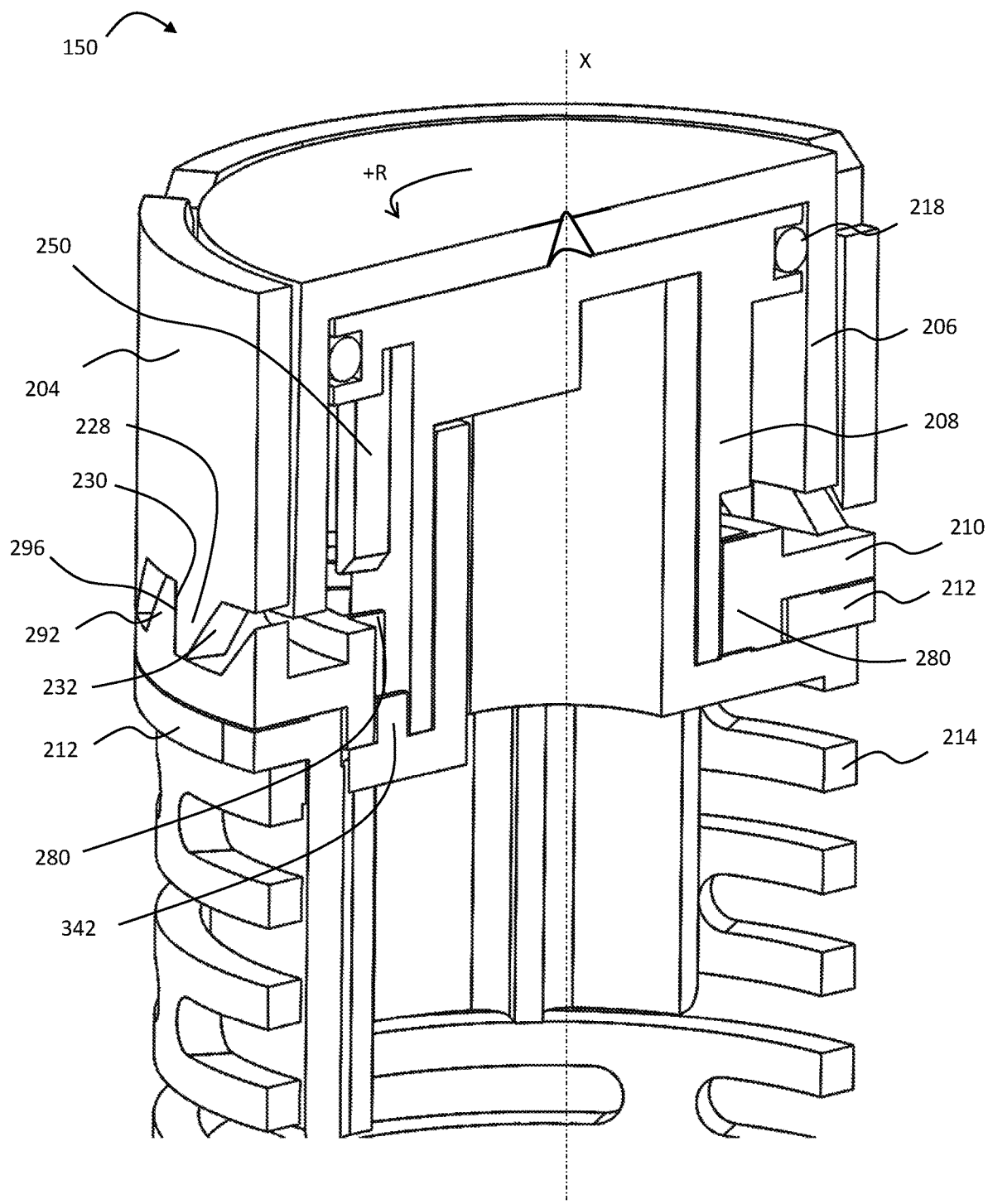

All of the components described above are aligned on a main axis X. Referring to FIGS. 13a to 13c (as well as the exploded view of FIG. 3), the upper section 202 is shown in its assembled state, in a rest condition (used for storage and generally when not in operation).

The actuator ring 204 is secured to the inside of the actuator body 216 by inserting it into the first section 356 such that the actuator ring ribs 361 engage the alignment grooves 226. The tapered mouths of the alignment grooves 226 aid this mating process. Once inserted, the actuator ring 204 is held such that it cannot move relative to the actuator body 216. For example, it may be bonded thereto.

The o-ring 218 is assembled into the groove 260 on the piston 208, and the piston 208 is inserted into the open end of the cylinder 206 to form a seal therewith. The o-ring 218 seals against the inner sidewall of the cylinder 206 such that axial movement of the piston results in airflow through the air leak hole 240. As such, relative motion of the piston 208 and the cylinder 206 is damped. Further, because the hole 240 is tapered, movement of the piston 208 into the cylinder 206 is resisted less than movement of the piston 208 out of the cylinder 206. In other words, separation of the piston 208 and cylinder 206 is damped more than movement of the piston 208 into the cylinder 206.

The piston-cylinder assembly is positioned within the actuator ring 204 and can move axially relative thereto.

Next, the collar 210 is placed into the actuator body 216 such that the outer collar teeth 292 face the actuator ring teeth 228 and are interspersed therebetween. The collar surrounds the piston body 242. The upper surfaces 282 of the inner collar teeth 280 face the downwardly facing surfaces 252 of the piston teeth 250.

Next, the transfer 212 is inserted into the actuator body 216 to engage the underside of the collar 210. The transfer bearing surface 316 bears against the lower surface 288 of the collar annulus 272 and can rotate relative thereto.

Finally, the spring 214 is inserted into the actuator body 216 such that the spring shaft 320 passes into the piston 208. The three alignment grooves 354 are engaged by the ribs 266 and the spring 214 and piston 208 are bonded to prevent relative motion (save for that resulting from deformation of the spring). The legs of the transfer 212 pass through the leg openings 340 in the spring body 318 to allow relative axial movement, but not relative rotational movement between the spring 214 and transfer 212. The spring teeth 342 face the downwardly facing surfaces 284 of the teeth 280 of the collar 210.

As the spring 214 is inserted, the pegs 332, 334, 336 engage the spring peg grooves 372 (FIG. 13b). The first peg 332 is engaged by the notch 390 of the mouthpiece cover 220 which is snap-fitted to the actuator body 216 in the following manner.

Referring to FIGS. 13d to 13g, the installation of the mouthpiece cover 220 on the actuator body 216 is shown in detail. To do this installation, the lower section 200 including the patient port 157 has not yet been assembled onto the actuator body 216. In FIGS. 13d and 13e the intended location of the lower section 200 is shown in dashed outline. The mouthpiece cover 220 has a rest position defining an axis Y which is parallel to the main axis X of the inhaler. In the rest position, the mouthpiece cover 220 covers the inhaler mouthpiece (see FIG. 2).

In FIGS. 13d and 13e, the arms 376 of the mouthpiece cover 220 are resiliently separated such that the cams 386 can be aligned with the openings 368 in the actuator body 216. The cams 386 enter the openings 368 such that the arms 376 of the mouthpiece cover 220 are in sliding contact with the flat walls of the second section 358 of the actuator body 216. It will be noted that in order for full engagement of the cams 386 with the openings 368, the notch 390 needs to be aligned with the retaining flange 370. This only occurs at one specific rotational assembly angle AA of the mouthpiece cover 220, specifically at approximately −110 degrees about the mouthpiece cover axis M.

The mouthpiece cover 220 is rotated to the rest position (in which the cap 374 covers the mouthpiece of the pMDI 150). This is shown in FIGS. 13f and 13g. In this position, the retaining flange 370 is engaged with the undercut region 388 of the cam 386 on the mouthpiece cover 220 to hold the mouthpiece in position (but allow rotation about the axis M). As shown in FIGS. 13b and 13g, the first peg 332 of the spring 214 is captured by the notch 390 in the cam 386 of the mouthpiece cover 220. It will be noted that upon assembly of the lower section 200 including the patient port 157 onto the actuator body 216, the mouthpiece cover is no longer able to rotate towards the assembly position of FIGS. 13d and 13e. This ensures that once the inhaler is fully assembled, it can be difficult to remove the mouthpiece cover.

Operation

The pMDI 150 is used as follows. The operation of the pMDI 150 is best described as passing through a number of operational conditions or stages as will be described below.

1. Rest Condition

The rest condition is shown in FIGS. 13a to 13c. In this condition, a canister 51 having a can 53 and a metering valve 54 with a valve stem 58 is provided within the pMDI. The canister 51 is shown in hidden line for clarity. The stem 58 abuts a stem abutment 59 which is static within the pMDI 150. In the rest condition, downward travel of the canister 51 is inhibited by a trigger abutment 70 which is part of a trigger assembly (not described here, but generally known in the art).

In this position, the canister 51 is positioned partly within the spring 214, and the free ends 312 of the legs 302 of the transfer 212 abut the bottom of the canister 51 (as it is inverted). The transfer 212 supports the collar 210 whose outer collar teeth 292 are interdigitated with the downwardly projecting teeth 228 of the actuator ring 204. The straight edges 230, 296 of each respective tooth 228, 292 abut such that rotation of the collar 210 in a first rotational direction +R about axis X is prevented.

The spring 214 is also in a rest position, and stores no energy. Because it is fixed at its lower end, (with its first peg 332 held in the notch 390 of the mouthpiece cover 220) and is attached to the piston 208 it also supports the cylinder 206. The piston 208 and cylinder 206 are fully engaged with the piston abutting the base of the cylinder as shown in FIG. 13c. The piston teeth 250 are spaced apart along axis X from the inner collar teeth 280.

The annular surface 338 of the spring 214 is abutted by the lower ends of the inner collar teeth 280, such that they are interdigitated with the spring teeth 342.

2. Primed Condition

In this condition, the mouthpiece cover 220 has been rotated about the mouthpiece cover axis M, such that (with reference to FIG. 13b) the first peg 332 has been drawn into the spring peg groove 372. This action tends to apply a tensile force to the first region of the spring 326, drawing it downwards.

Various steps in the motion of the mouthpiece cover moving from the rest to the primed condition are shown in FIGS. 14d to 14i.

Figure 14A:
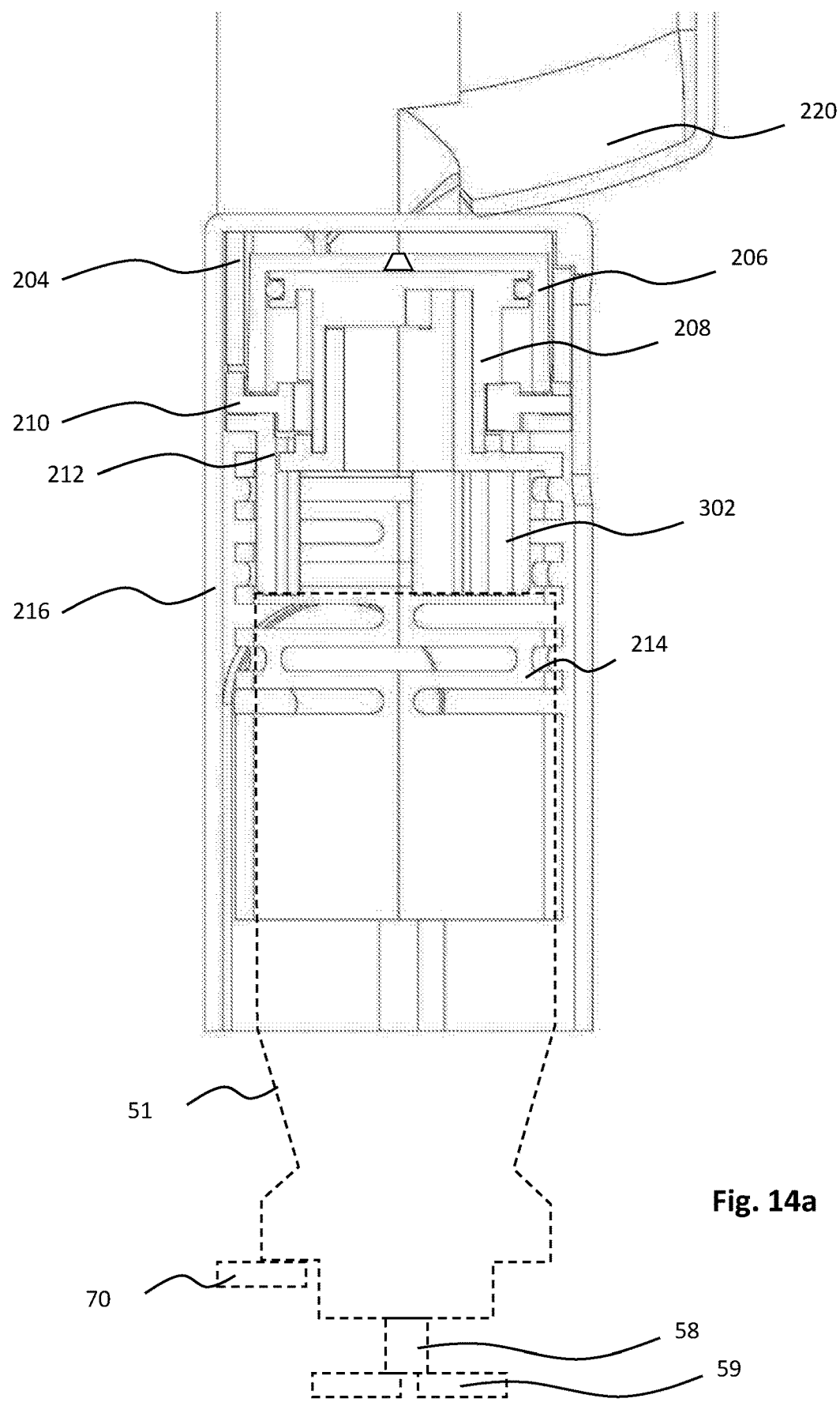
FIGS. 14a to 14c are section views of various parts of the priming and reset mechanism of FIG. 2 in a primed condition.
Figure 14B:
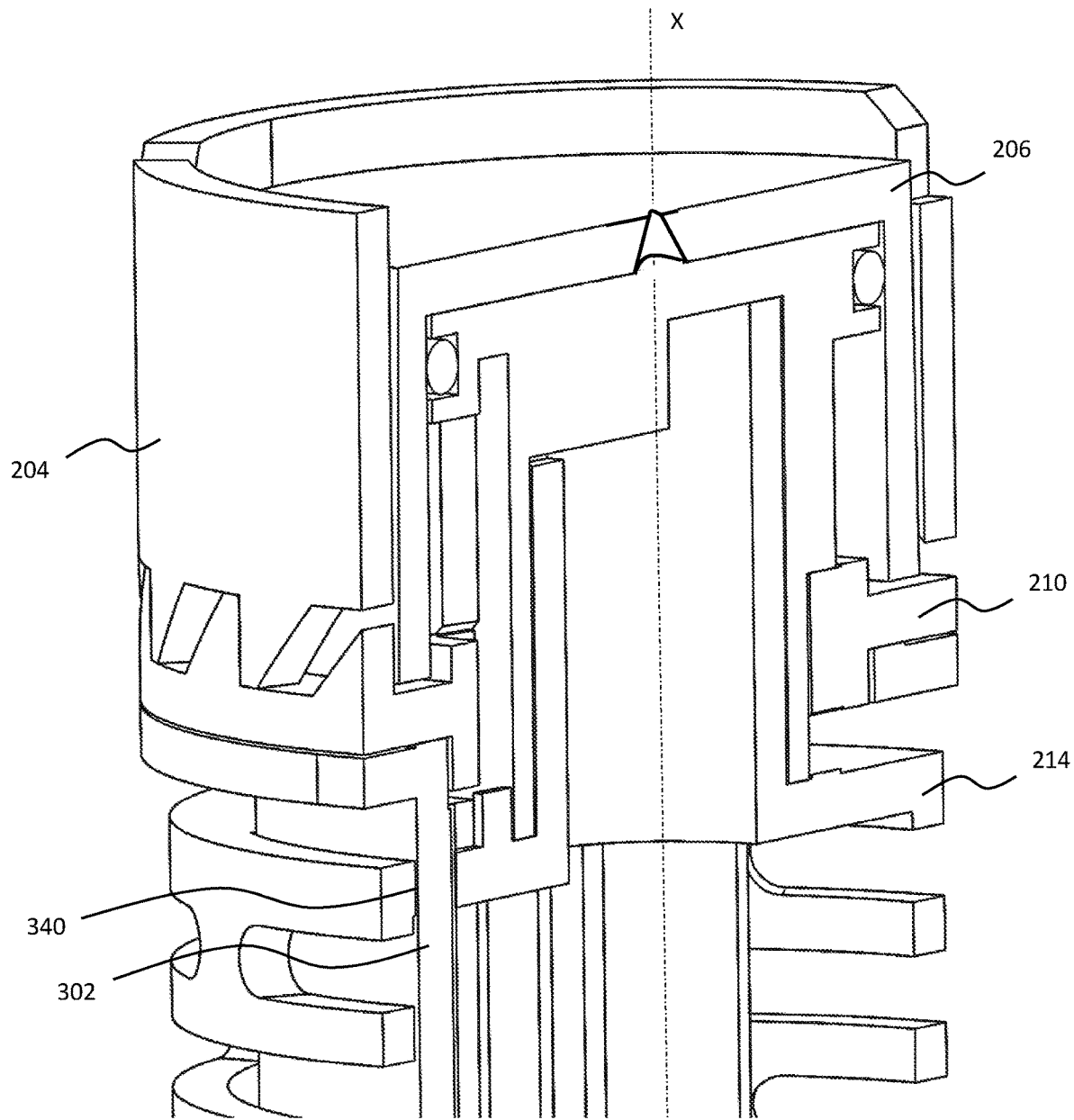
Figure 14C:
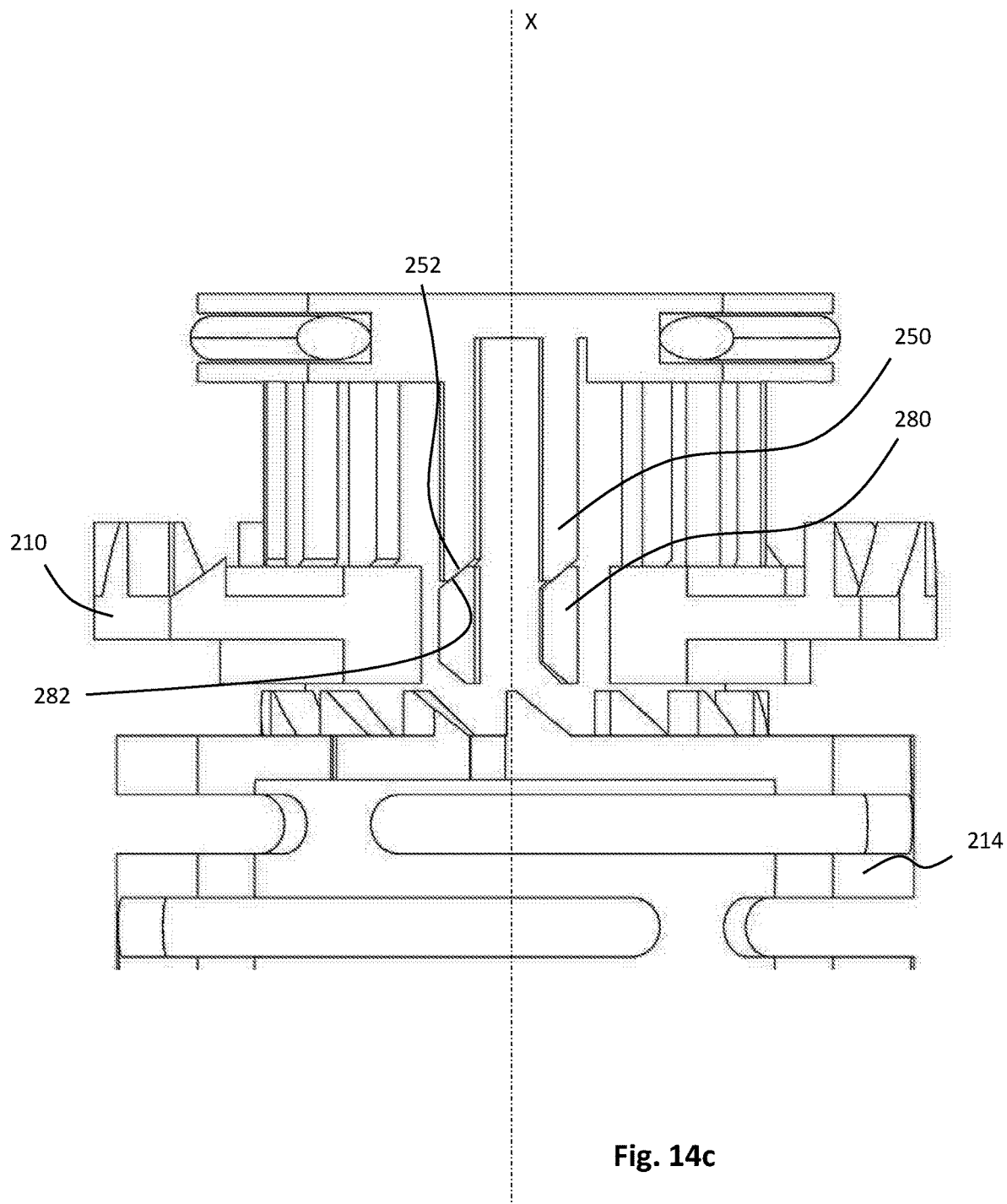
Figures 14D, 14E:
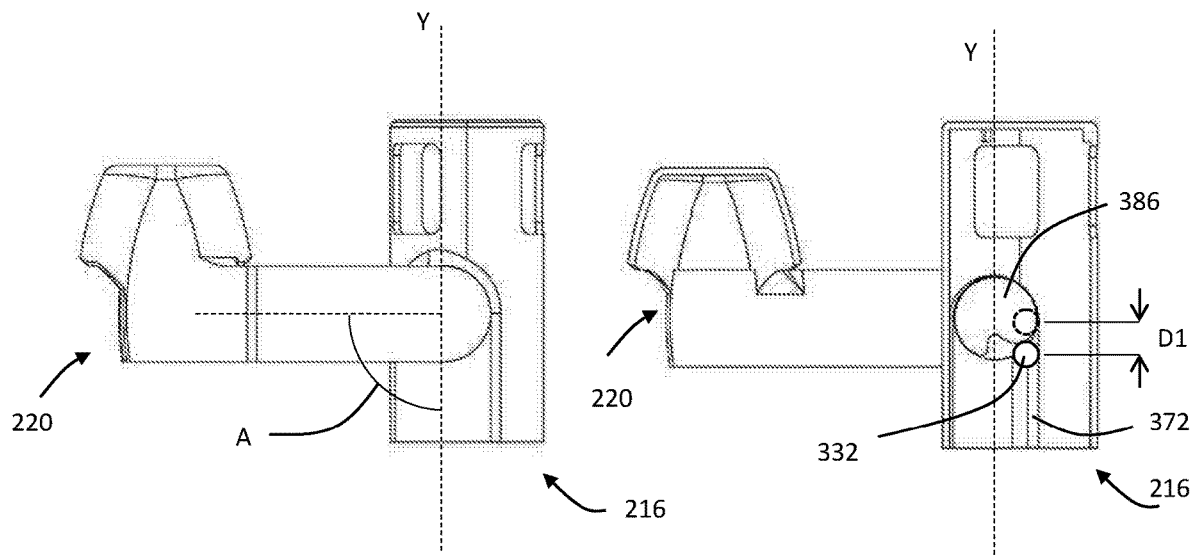
FIGS. 14d to 14i are side and side section views of stages of motion of part of the priming and reset mechanism of FIG. 2 as it is moved to the primed condition.

FIGS. 14d and 14e show the mouthpiece cover 220 at an angle A of 90 degrees to the axis Y. As visible in FIG. 14e, rotation of the cam 386 has urged the peg 332 almost fully into the groove 372. The peg 332 has been displaced from the rest position (shown in hidden line) by D1. At this position, the inhaler is unusable because the mouthpiece cover 220 would clash with the user's face if they tried to place their mouth over the mouthpiece.

Figures 14F, 14G:
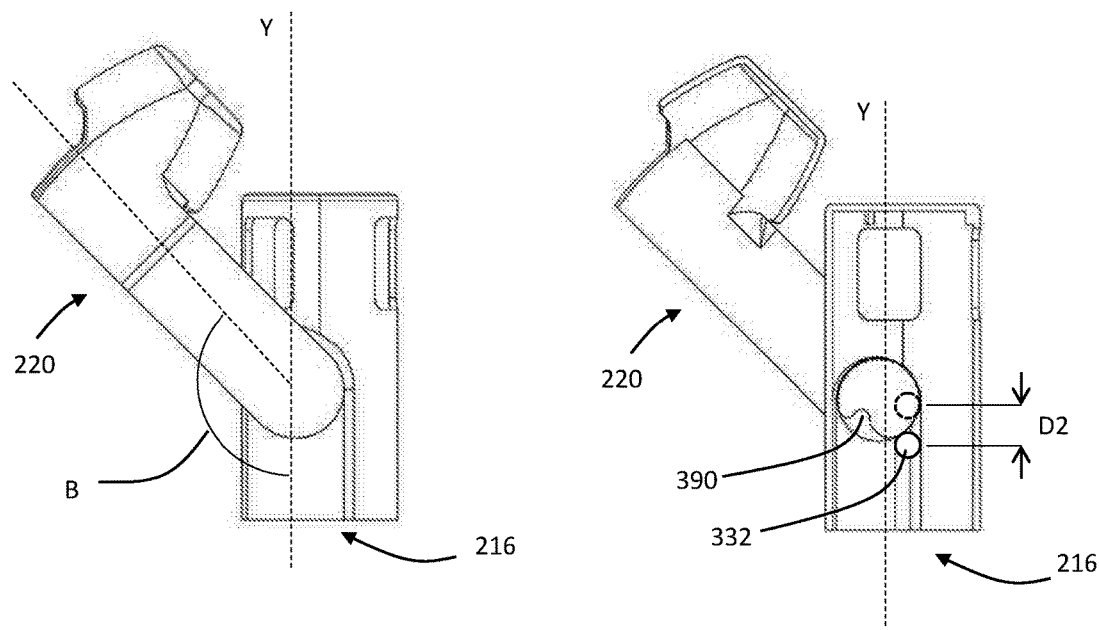

FIGS. 14f and 14g show the position of the mouthpiece cover at an angle B of approximately 135 degrees when the cam 386 has rotated to an extent that the peg 332 is almost fully within the groove 372 and has moved by a total distance of D2. At this point, because the notch 390 has cleared the peg 332, further rotation of the mouthpiece cover 220 has no effect on the linear position of the peg 332 (which remains at D2). At this position it is still not possible to use the inhaler, because the mouthpiece cover is still in a position where it would clash with the user's face.

Figure 14H:
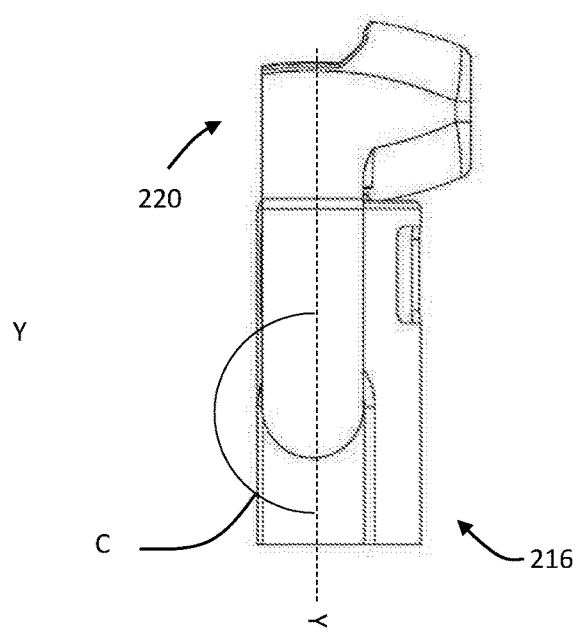
Figure 14I:
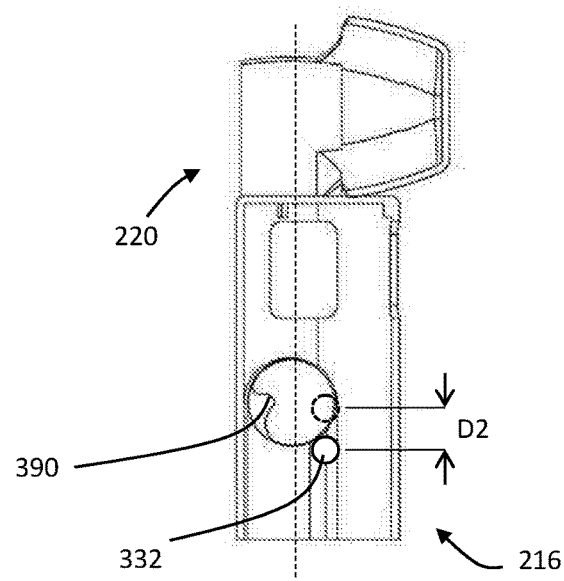

FIGS. 14h and 14i show the final, primed position of the mouthpiece cover at an angle C of 180 degrees. Movement from angle B to C did not cause any further movement of the peg 332 (and therefore no further compression of the spring 214), but served to move the mouthpiece 220 out of the way. This lost motion ensures that should a user attempt to use the inhaler between positions B and C (which may be possible), the inhaler will operate as normal because the spring 214 is fully energised.

Referring back to FIG. 14a, initially this downward force on the spring 214 acts to draw the piston 208 downwards (the piston 208 and spring 214 are attached). Because downward movement of the cylinder 206 is not resisted at this stage, it also moves downwards as shown in FIG. 14a due to gravity and the friction of the o-ring 218, as well as due to air flow resistance through the air hole. The transfer 212 remains stationary at this point, as it abuts the canister 51. As the top of the spring 214 moves downwards along axis X, the spring 214 and the transfer 212 start to move apart due to the fact that the transfer legs 302 can slide in the leg openings 340.

This initial motion occurs until, as shown in FIG. 14c, the tapered surfaces 252 of the piston teeth 250 abut the first tapered ends 282 of the inner collar teeth 280. At this point, a downward force is exerted on the collar 210 which cannot move due to the abutment of the transfer 212 and the canister 51 (held in place by the trigger abutment 70). Therefore the spring shaft 320 can no longer move down a load path established through the piston 208 onto the collar 210, the transfer 212 and the canister 51. As the mouthpiece cover 220 continues to be rotated, the first region of the spring 326 stretches to store potential energy. Once the mouthpiece cover 220 is in the position shown in FIG. 14a, the first peg 332 of the spring 214 has moved down into the peg channel 372 and the spring is "primed".

It will be noted that the abutment of the piston 208 (and more specifically the piston teeth 250) and the collar 210 (and more specifically the inner collar teeth 280) forms a clutch in the load path between the spring 214 and the canister 51.

3. Fired Condition

When the user wishes to dispense the medicament, a trigger mechanism (which is not described here) is fired in which the trigger abutment 70 is moved such that downward motion of the canister 51 is no longer inhibited. Release of the canister 51 releases the transfer 212, collar 210 and piston 208 to move downwards, pulled by the tensile force of the spring 214 on the piston 208. As the stored energy in the spring 214 is released, it serves to push the valve stem 58 onto the valve stem abutment 59. This also acts against the bias of the valve spring within the valve 54 to open the canister 51 and release a dose of medicament. Because the force from the spring 214, Fs, exceeds that from the valve 54, Fv, at this juncture, dose release is ensured.

Figure 15A:
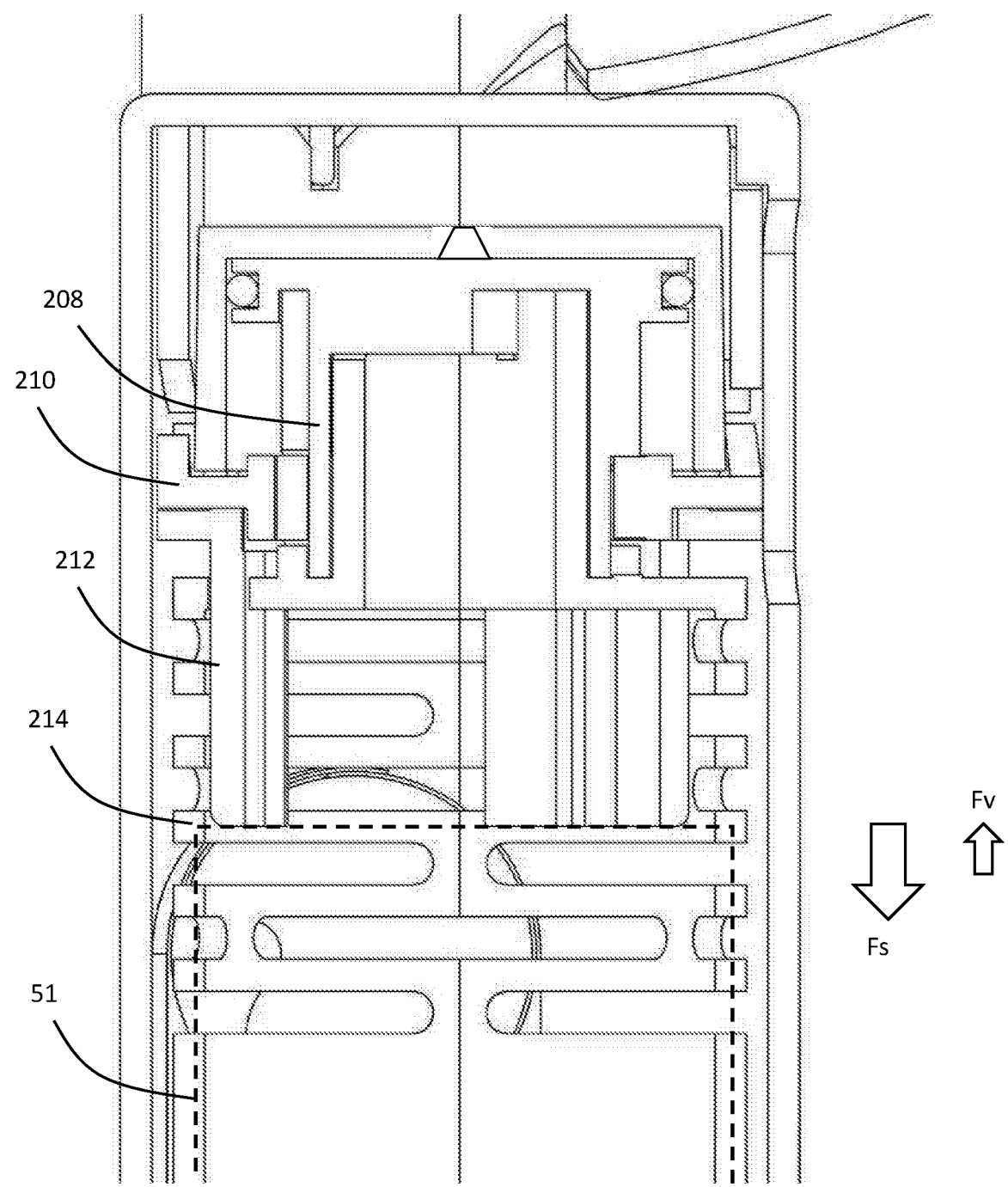
FIGS. 15a and 15b are section views of various parts of the priming and reset mechanism of FIG. 2 in a fired condition.
Figure 15B:
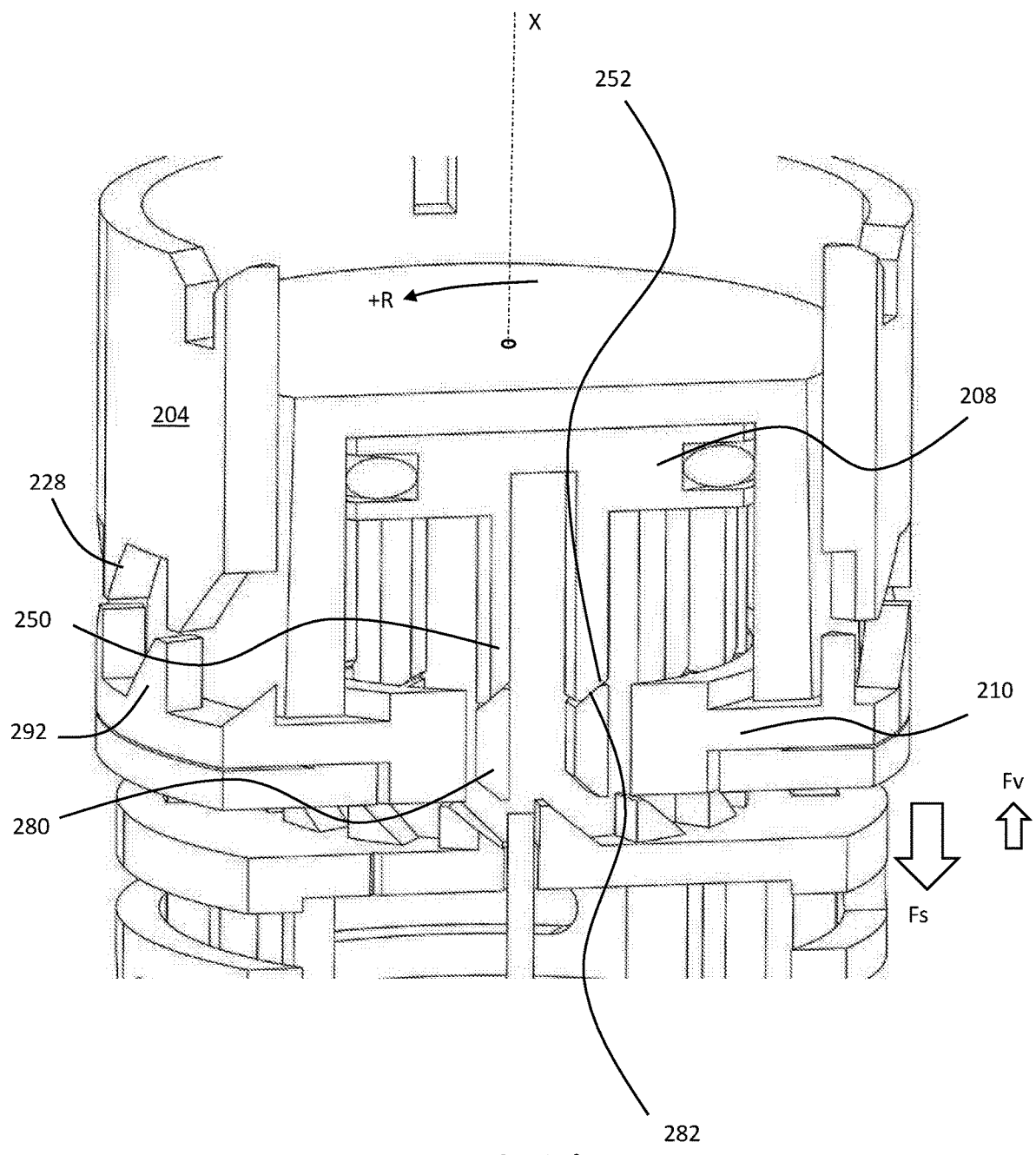

It will also be noted, with reference to FIG. 15b, that force from the piston 208 onto the collar 210 is provided via the tapered surfaces 252 of the piston teeth 250 abutting the first tapered ends 282 of the inner collar teeth 280. In other words, the load path of the spring force Fs is through the clutch formed by the piston 208 (being pulled down by the spring) and the collar 210 (pushing on the transfer 212).

Due to the taper of the piston teeth 250 and the inner collar teeth 280, as well as an axial force, a rotational force on the collar 210 in direction +R about the axis X is produced. This force is reacted by abutment of the axial surfaces 296 of the outer collar teeth 292 and the axial surfaces 230 of the downwardly projecting teeth 228 of the actuator ring 204. It will be understood that FIG. 15b shows that the teeth 292, 228 have just cleared each other due to relative downward motion of the collar 210 relative to the actuator ring 204. Until they have done so, rotation of the collar is prevented.

4. Auto-Release Condition

Figure 16A:
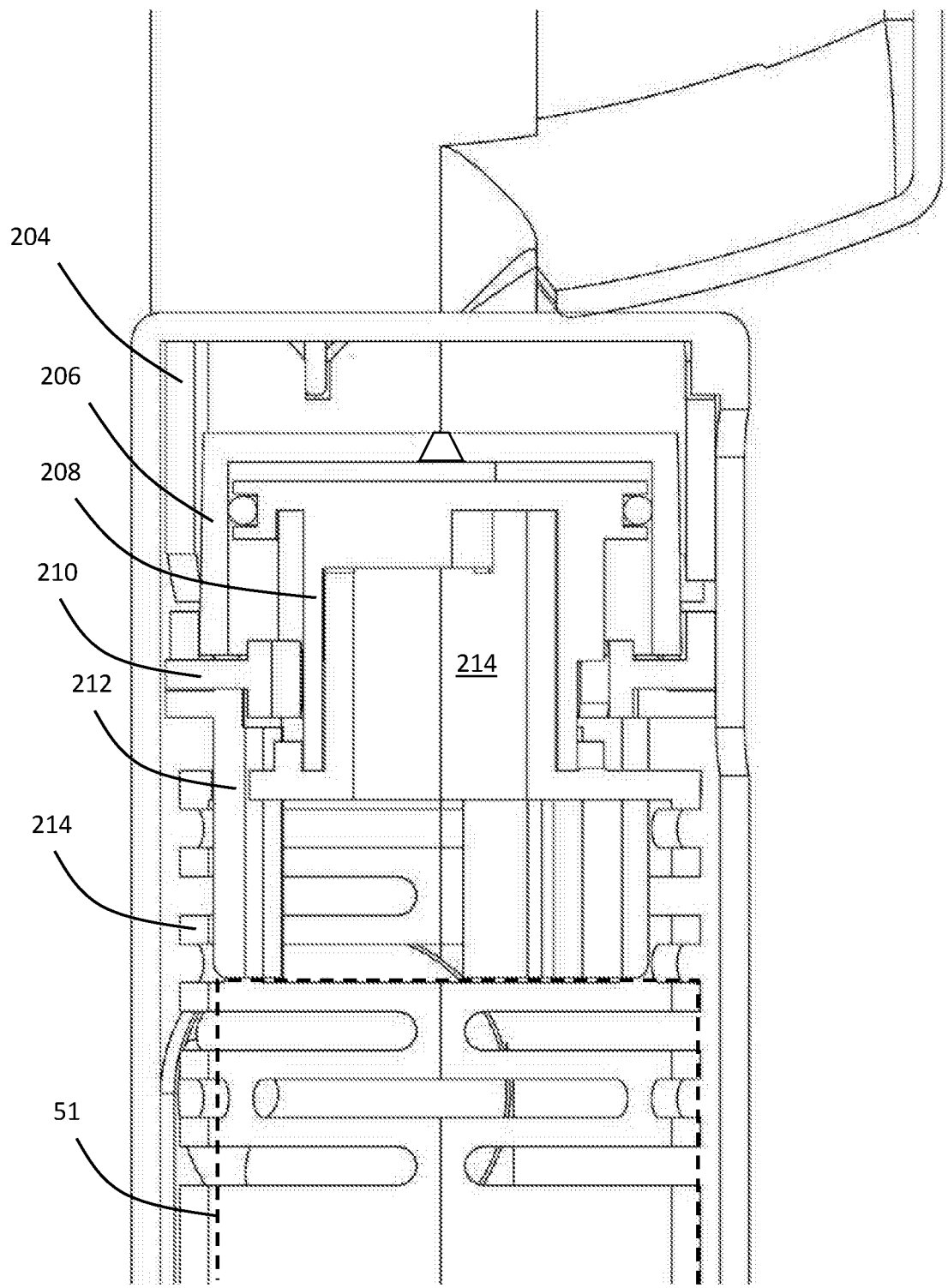
FIGS. 16a to 16c are views of various parts of the priming and reset mechanism of FIG. 2 in an auto-release condition.
Figure 16B:
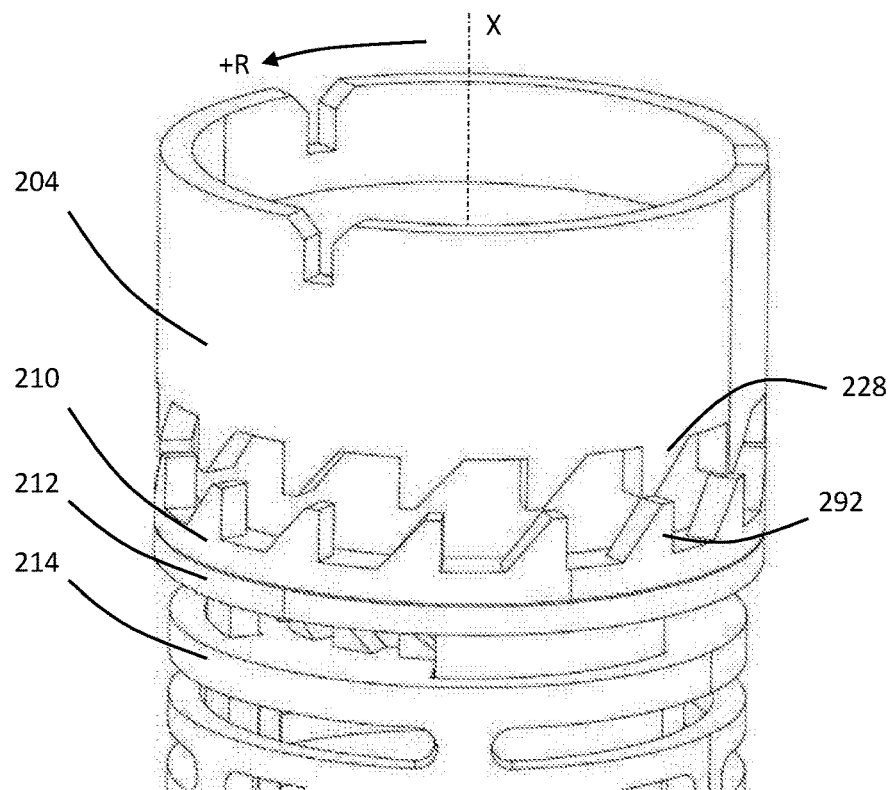
Figure 16C:
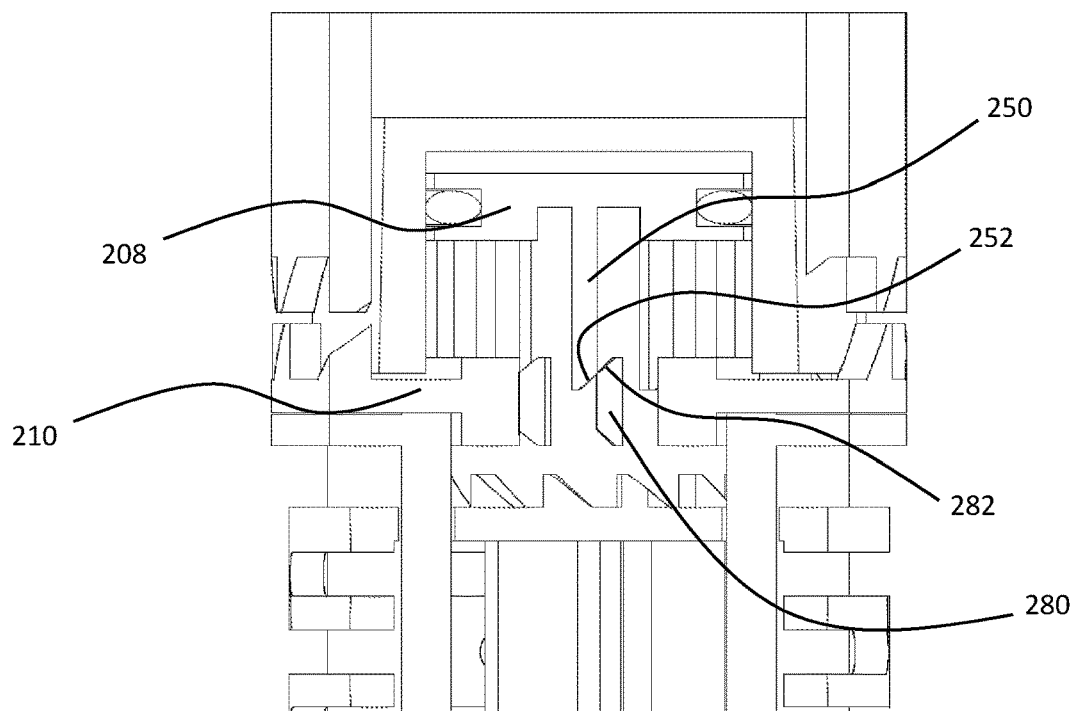

As shown in FIG. 15b, the outer collar teeth 292 eventually clear the actuator ring teeth 228 and allow the collar 210 to rotate about the axis X in direction +R (FIG. 16b). This rotation occurs due to the torque created by the abutment of the tapered surfaces 252 of the piston teeth 250 abutting the first tapered ends 282 of the inner collar teeth 280 (FIG. 16c).

At a predetermined angle of rotation of the collar 210 relative to the piston (which cannot rotate, because it is bonded to the spring, which itself cannot rotate), the collar 210 and piston become detached (or released) in a linear sense. In other words, as the collar 210 rotates, the clutch formed by the collar 210 and piston 208 is released. This is because the inner collar teeth 280 can eventually move through the gaps between the piston teeth 250 allowing relative linear movement between the piston 208 and collar 210.

5. Can Reset Condition

Figure 17A:
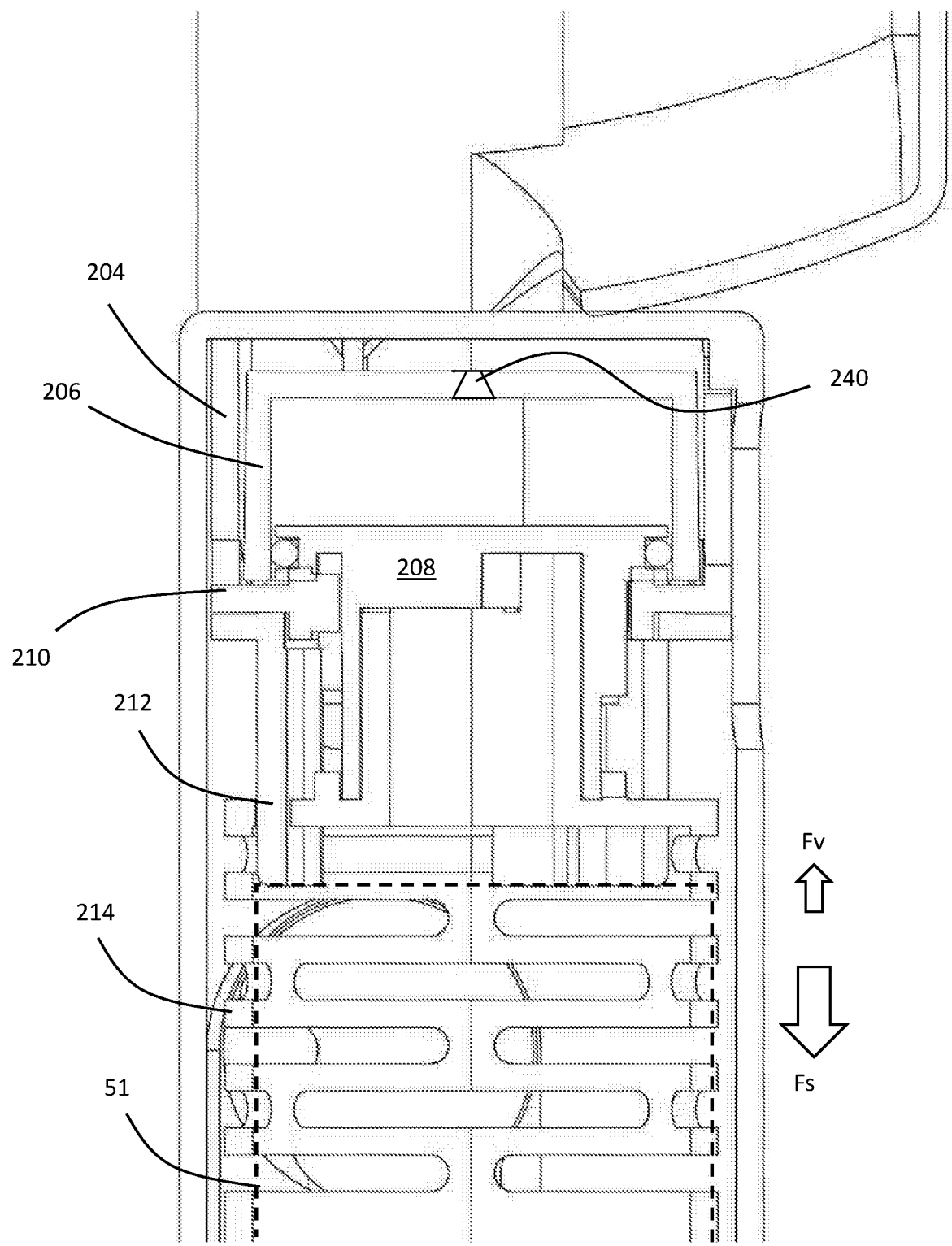
FIGS. 17a to 17b are section views of various parts of the priming and reset mechanism of FIG. 2 in a can reset condition.
Figure 17B:
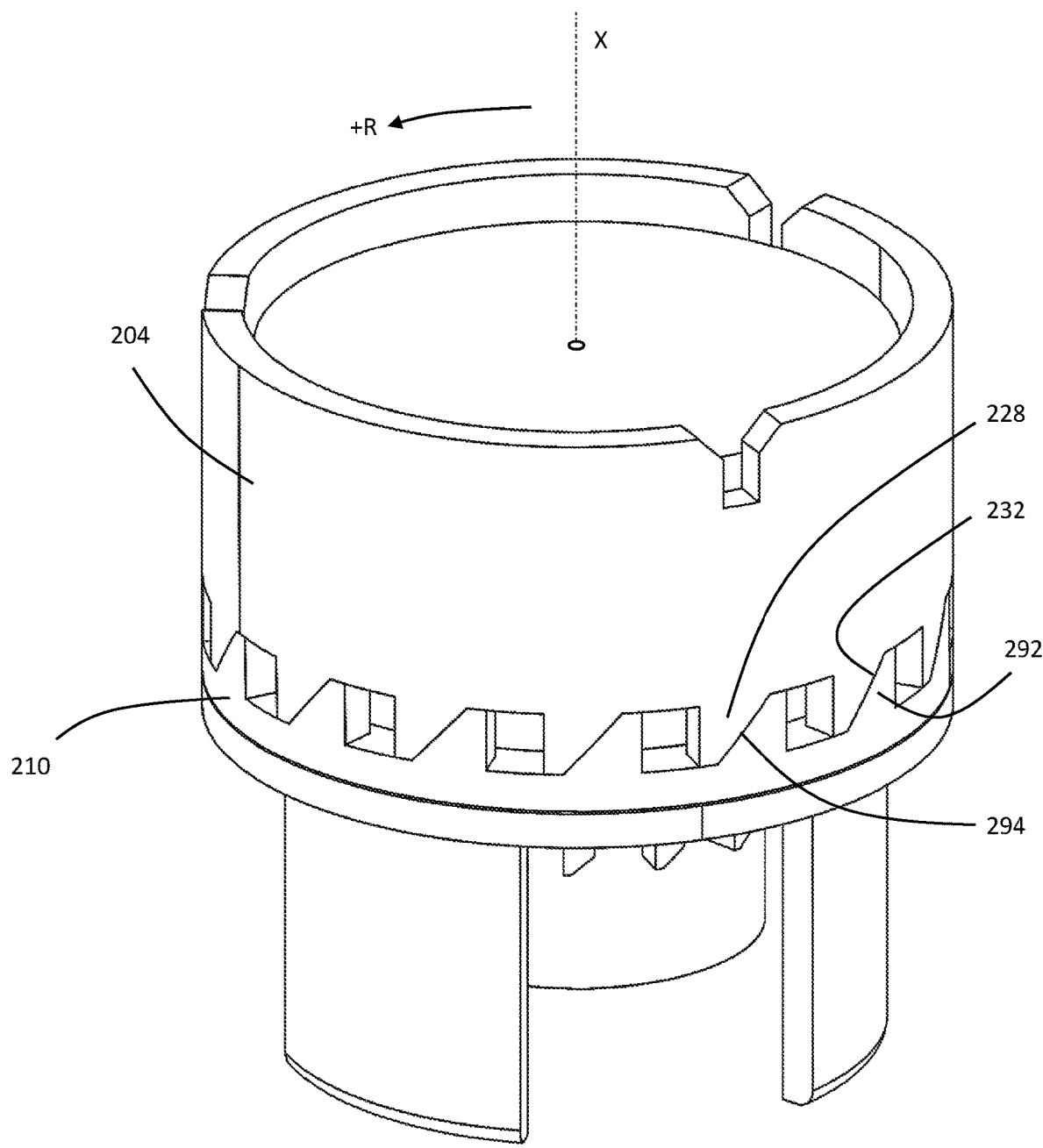

The release of the clutch now separates the system into two sub-assemblies which encounter opposing forces. Reference is made to FIGS. 17a and 17b.

On one hand, the return force of the spring in the canister valve Fv applies an upward force on the transfer (via the canister 51) which in turn lifts the collar 210 towards the actuator ring 204. The collar 210 supports the cylinder 206 which is also raised upwards further into the actuator ring. As the collar 210 approaches the actuator ring 204, the tapered surfaces 294 of the outer collar teeth 292 engage the tapered surfaces 232 of the actuator ring teeth 228 thus rotating the collar further in the direction +R about the axis X to fully engage the collar 210 and actuator ring 204.

On the other hand, the tensile force Fs remaining in the spring 214 acts to draw the piston 208 downwards. Therefore, as the canister 51 resiles to its rest (unactuated) position, its motion is controlled by the separation of the piston 208 and cylinder 206. As mentioned above, relative motion of the piston 208 and cylinder 206 is controlled by ingress of air into the air leak hole 240. As such, the return of the canister 51 (i.e. the timing of return of the canister) is controlled, avoiding the aforementioned problems.

6. Return to Rest Condition

The user rotates the mouthpiece cover 220 back to its original positon, which has the effect of (with reference to FIG. 13b) drawing the first peg 332 upwards, thereby allowing the first region of the spring 326 to return upwards towards its starting (rest) position. This motion re-engages the piston 208 into the cylinder 206, the piston encountering a lower resistance (i.e. is less damped) than when the piston and cylinder were being separated.

Figure 18A:
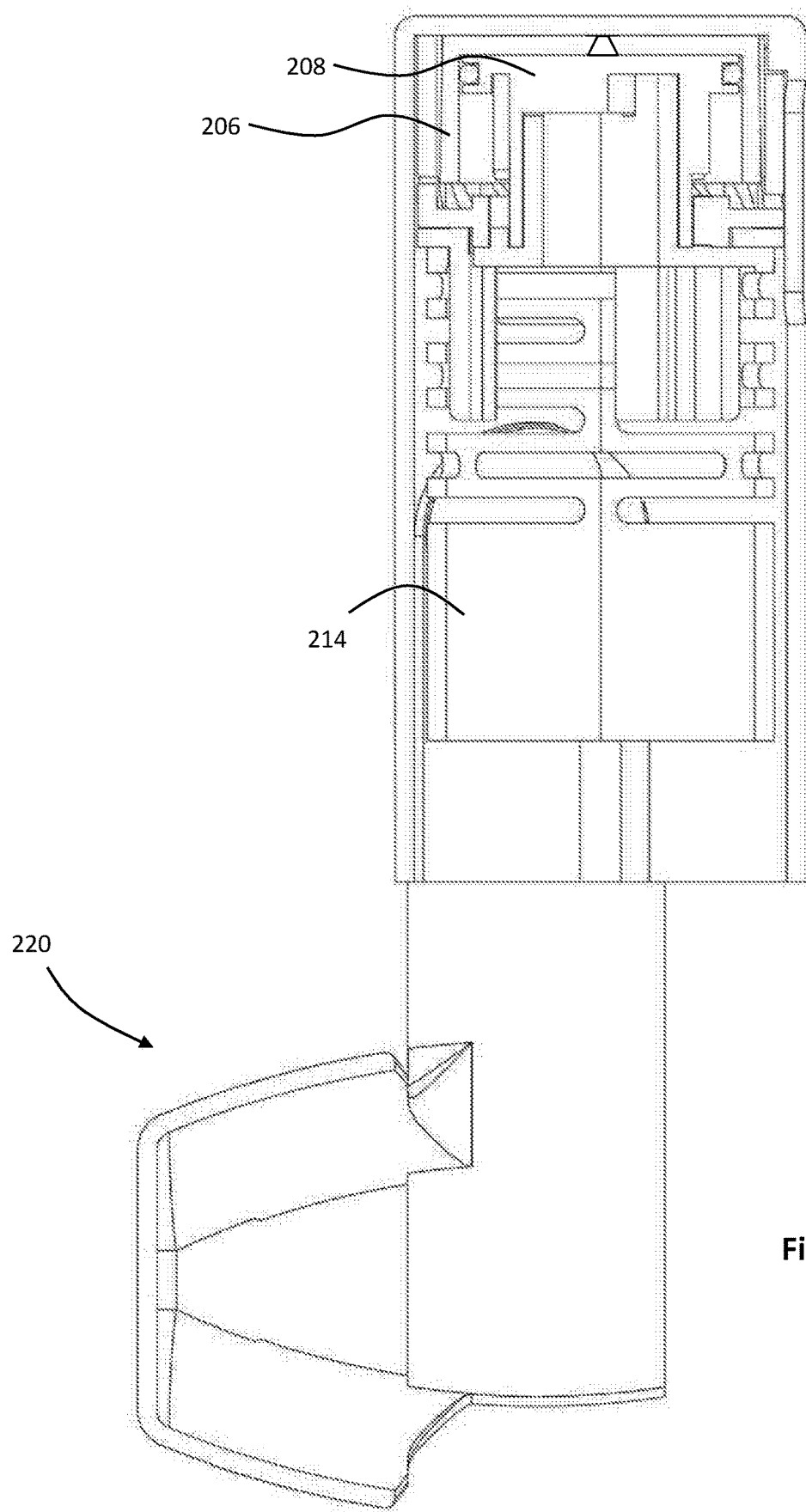
FIGS. 18a to 18b are views of various parts of the priming and reset mechanism of FIG. 2 in a return to its rest condition.
Figure 18B:
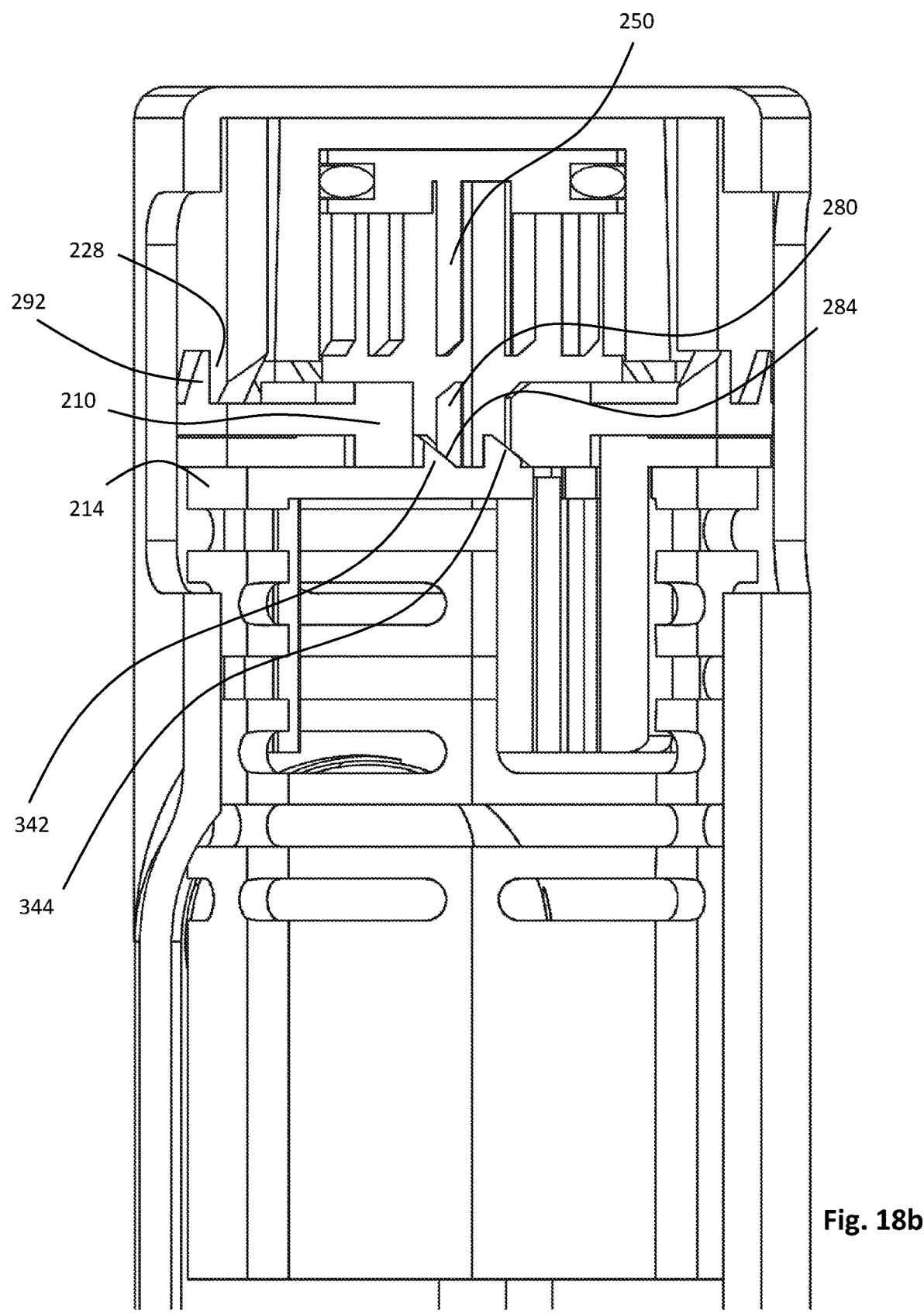
Figure 19:
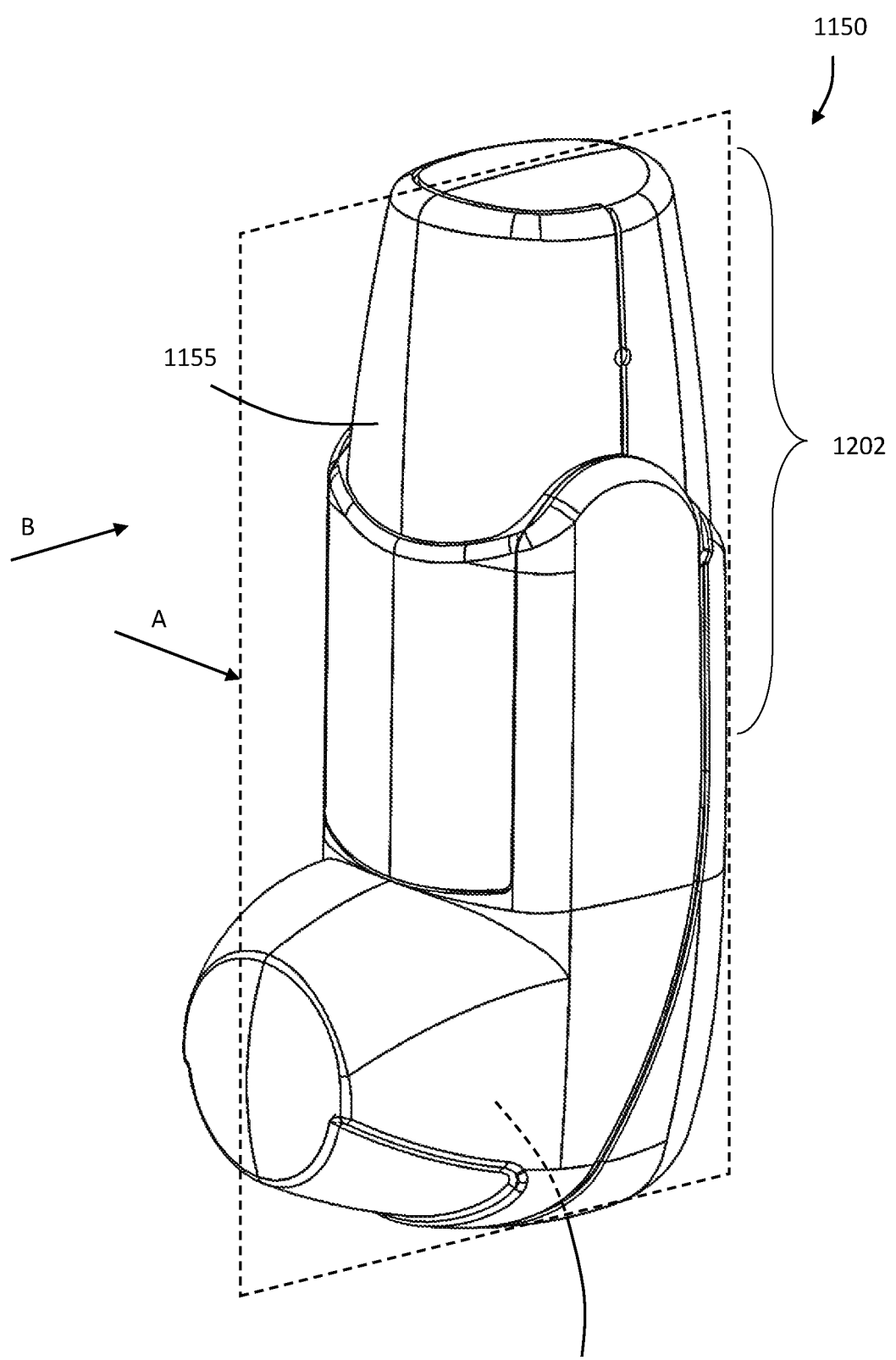
FIG. 19 is a perspective view of a pMDI comprising a second priming and reset mechanism in accordance with an embodiment of the present invention.

Referring to FIGS. 18a and 18b, as the top of the spring 214 moves towards the collar 210, the tapered surface 344 of each spring tooth 342 engages the tapered second end 284 of each inner collar tooth 280 to further rotate the collar 210. The rotation is such that the inner collar teeth 280 are positioned directly below the piston teeth 250, ready for the next operation. In other words, the opposite sides of the clutch are re-aligned. This rotation also brings the straight edges 230 of the actuator ring teeth 228 into abutment with the straight edges 296 of the outer collar teeth 292. As such, further rotation of the collar 210 in a first rotational direction +R about axis X (to release the clutch) is again prevented.

The Second Embodiment

Figure 20:
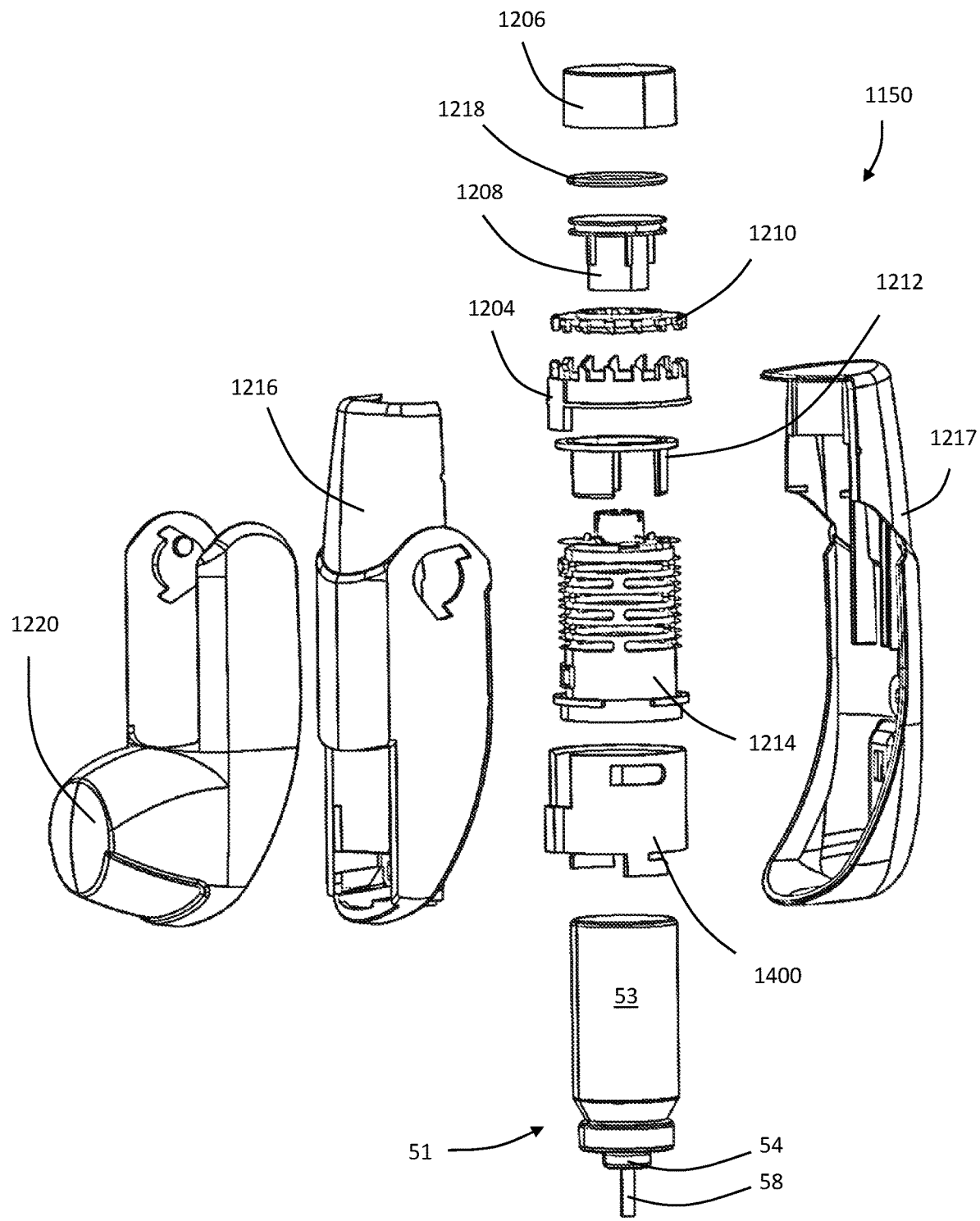
FIG. 20 is an exploded view of the priming and reset mechanism of FIG. 19.

Turning to FIGS. 19 to 29, a second pMDI 1150 according to an embodiment of the present invention is shown. The pMDI 1150 comprises a housing or actuator 1155 containing a canister 51 (FIG. 20). The canister 51 contains a medicament formulation. It will be understood that the canister is of the same type as the canister 51 described with reference to FIG. 1 and comprises a can with a metering valve. The canister sits within the housing 1155. The pMDI 1150 has a stem socket and a trigger assembly that allows downward movement of the canister relative to the valve's stem portion, as described earlier in the detailed description, when the patient inhales through the mouthpiece. The stem socket and trigger assembly have been omitted from FIG. 20 for clarity of the drawing.

The pMDI 1150 comprises a portion in the form of a patient port 1157 (e.g., in the form of a mouthpiece) that defines an inspiration orifice (or an air outlet). Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein.

The housing 1155 also comprises an upper section 1202 that comprises a reset mechanism according to an embodiment of the present invention. Referring to FIG. 20, an exploded view of the reset mechanism is provided. The reset mechanism comprises an actuator ring 1204, a cylinder 1206, a piston 1208, a collar 1210, a transfer 1212, a spring 1214, a spring sleeve 1400, a first actuator body part 1216, a second actuator body part 1217, an o-ring 1218 and a mouthpiece cover 1220.

Figure 21A:
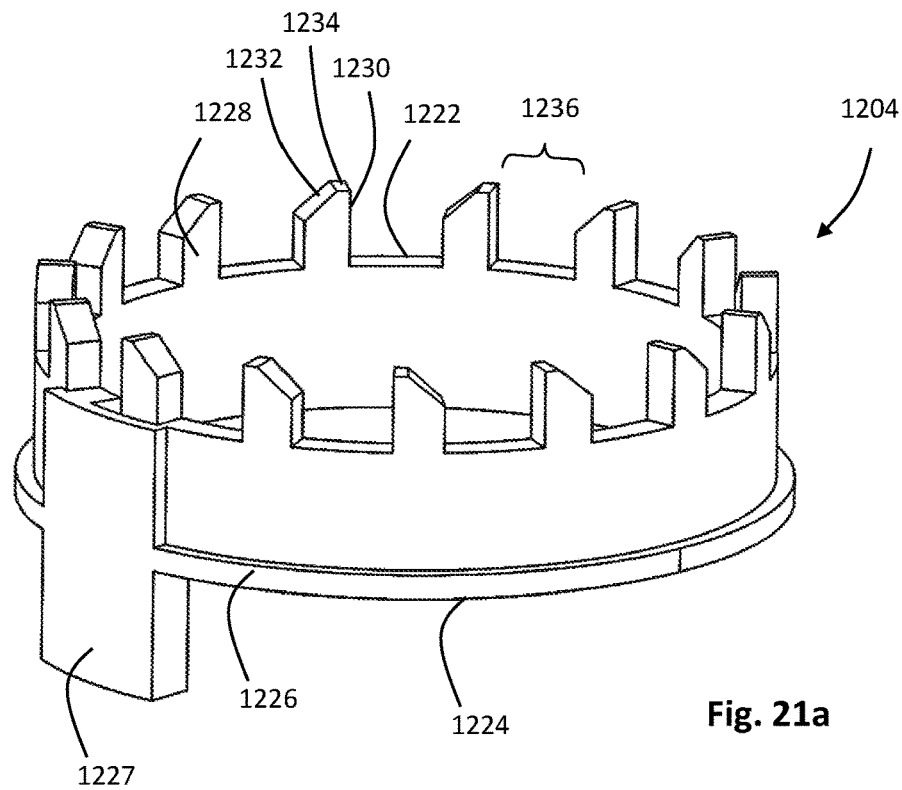
FIGS. 21a and b are perspective views of an actuator ring of the priming and reset mechanism of FIG. 19.
Figure 21B:
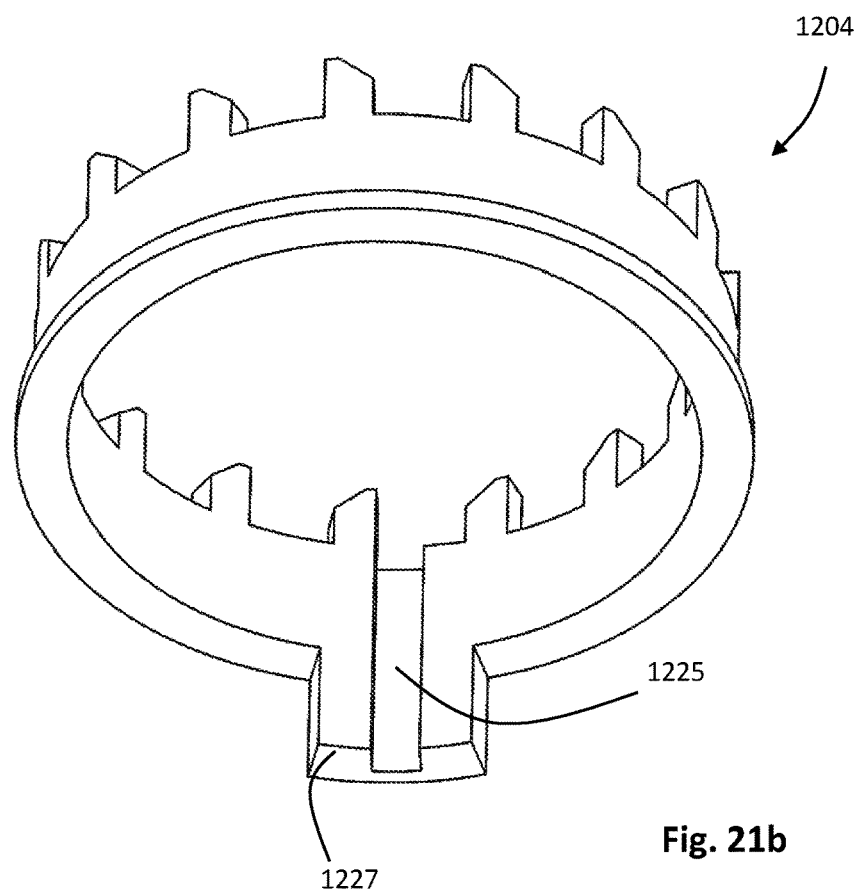

With reference to FIGS. 21a and 21b, the actuator ring 1204 is a unitary cylindrical body constructed from a moulded plastics material having a first, upper, edge 1222 and a second, lower, edge 1224. The first edge 1222 defines a series of fifteen axially extending teeth 1228. Each tooth 1228 is generally triangular in shape, having a straight axial edge 1230 and a tapered surface 1232 (extending both axially and circumferentially) which meet at end flat 1234. Each tooth 1228 is separated at the edge 1222 by an inter-tooth gap 1236. The second edge 1224 defines an outwardly extending rim 1226. At a first circumferential position there is provided an axially extending retention member 1227. On the inner surface of the actuator ring 1204 at the retention member 1227 there is provided an axially extending slot 1225.

Figure 22:
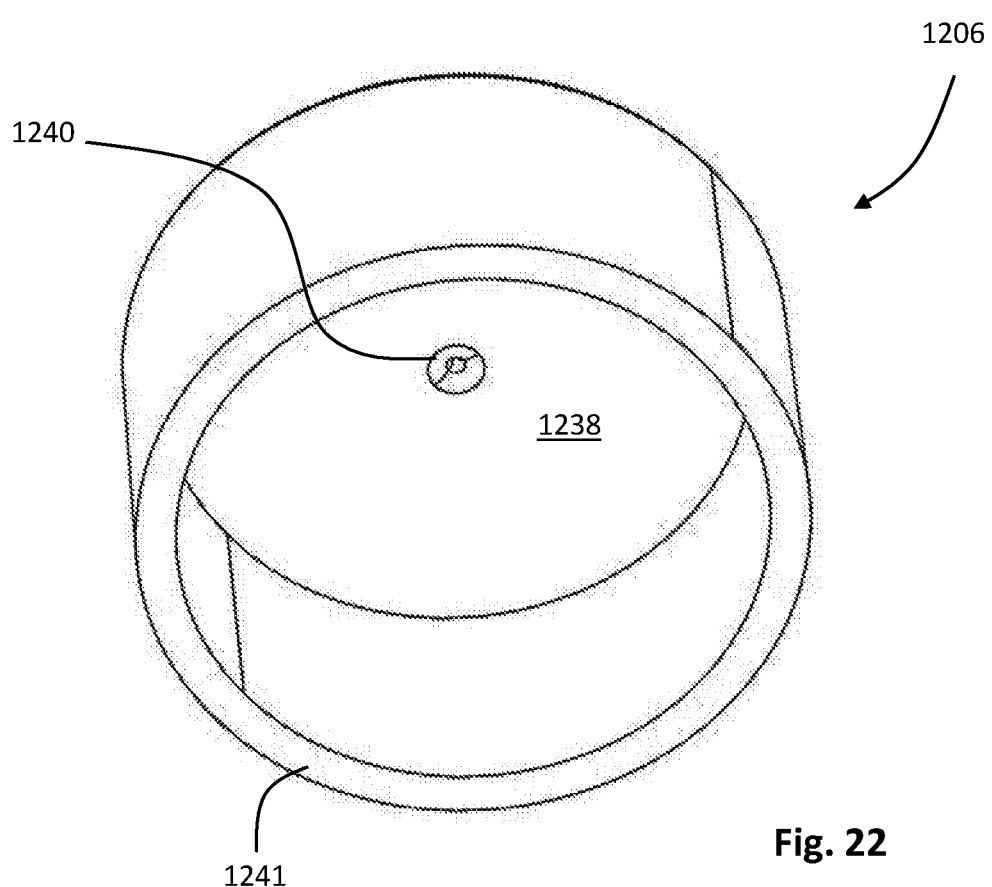
FIG. 22 is a perspective view of a cylinder of the priming and reset mechanism of FIG. 19.

With reference to FIG. 22, the cylinder 1206 is a unitary cylindrical body constructed from a moulded plastics material. The cylinder is closed at a first, upper, end 1238 and open at a second, lower, edge 1241. In the centre of the upper closed end 1238 there is provided a co-axial air leak hole 1240. The air leak hole 1240 is sized to provide the technical effect described below (damping) and as such the exact size can be determined by the skilled technician. As with the air leak hole 240, the air leak hole 1240 is tapered to decrease in area from the interior of the cylinder 1206 to the exterior of the cylinder 1206. This results in a higher coefficient of discharge for fluid exiting the cylinder through the hole 1240 than air entering the cylinder through the hole 1240.

Figure 23A:
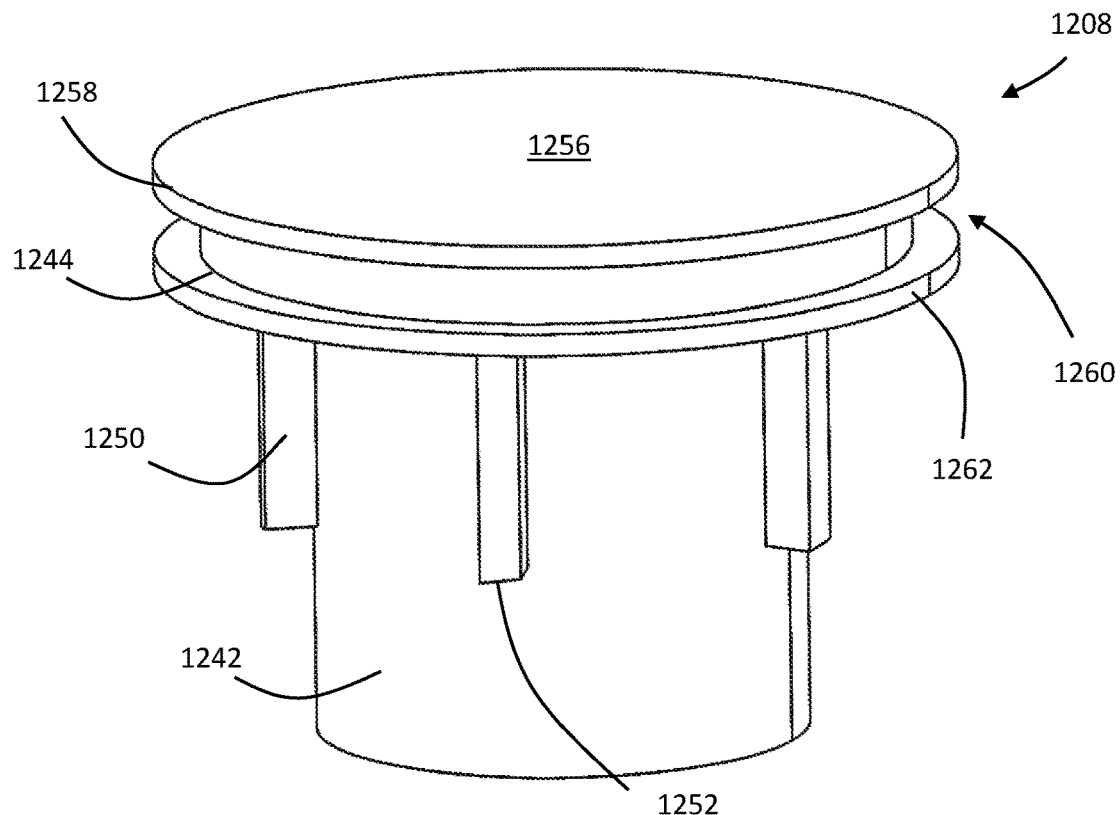
FIGS. 23a and 23b are perspective views of a piston of the priming and reset mechanism of FIG. 19.
Figure 23B:
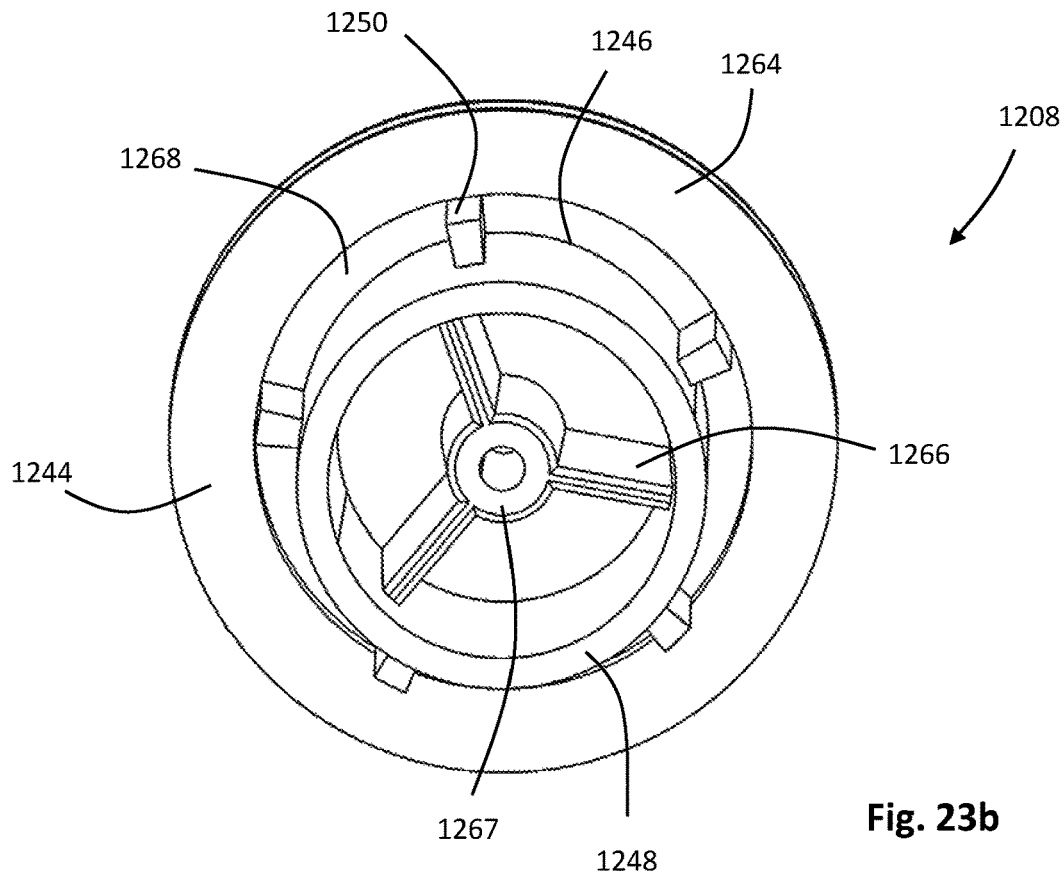

With reference to FIGS. 23a and 23b, the piston 1208 is shown. The piston 1208 is a unitary moulded plastics component. The piston 1208 comprises a generally cylindrical piston body 1242 and a piston head 1244 at one end thereof.

The body 1242 is a hollow cylinder having a first, upper, end 1246 at which the piston head 1244 is located, and a second, lower end 1248 which is open. The body 1242 defines five identical, equally spaced, axially extending teeth 1250 on its outer surface. Each tooth 1250 extends from the first end 1246 towards the second end 1248 (although the teeth only extend part-way along the body 1242). The teeth 1250 each terminate at a free end which defines a tapered surface 1252 extending both circumferentially and axially.

The piston head 1244 comprises a circular piston end cap 1256 having a radial edge 1258. The end cap 1256 is positioned at the first, upper, end 1246 of the body 1242. The head 1244 comprises an o-ring receiving channel section 1260 extending axially towards the second end 1248 of the body 1242. The o-ring receiving channel section 1260 is formed by the radial edge 1258 of the cap 1256 and a radial edge 1262 of an annular ring section 1264. On the underside of the end cap 1256 (i.e. the surface facing the interior of the body 1242) there are provided three equally spaced, radially extending ribs 1266 which meet at a central boss 1267. It will be noted from FIG. 23b in particular that the piston head 1244 overhangs the body 1242 to provide an annular recess 1268 into which the teeth 1250 extend.

Figure 24:
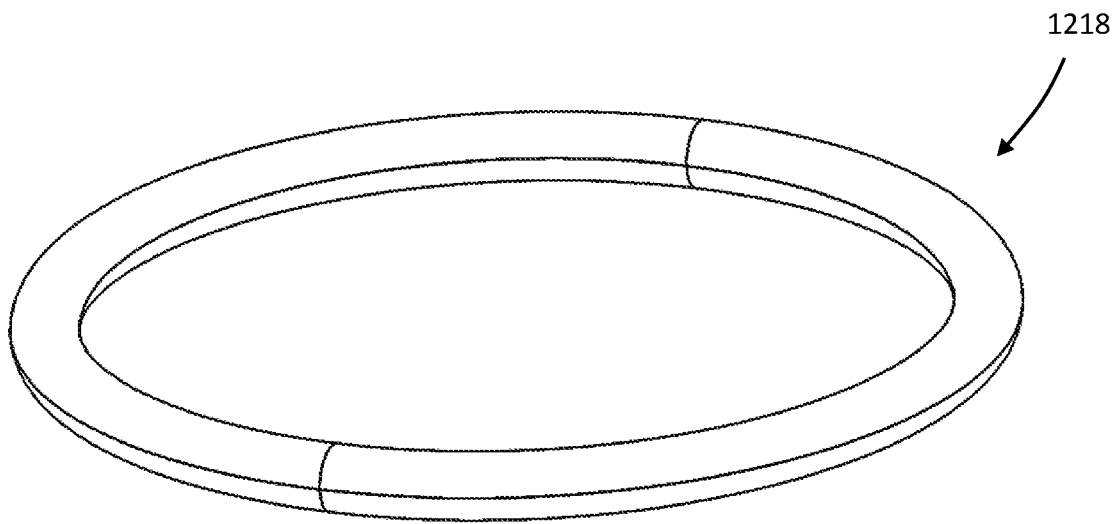
FIG. 24 is a perspective view of an o-ring of the priming and reset mechanism of FIG. 19.

Turning to FIG. 24, the o-ring 1218 is shown. The o-ring 1218 is a standard component and is constructed from an elastomeric material designed to form a fluid seal against plastics material.

Figure 25:
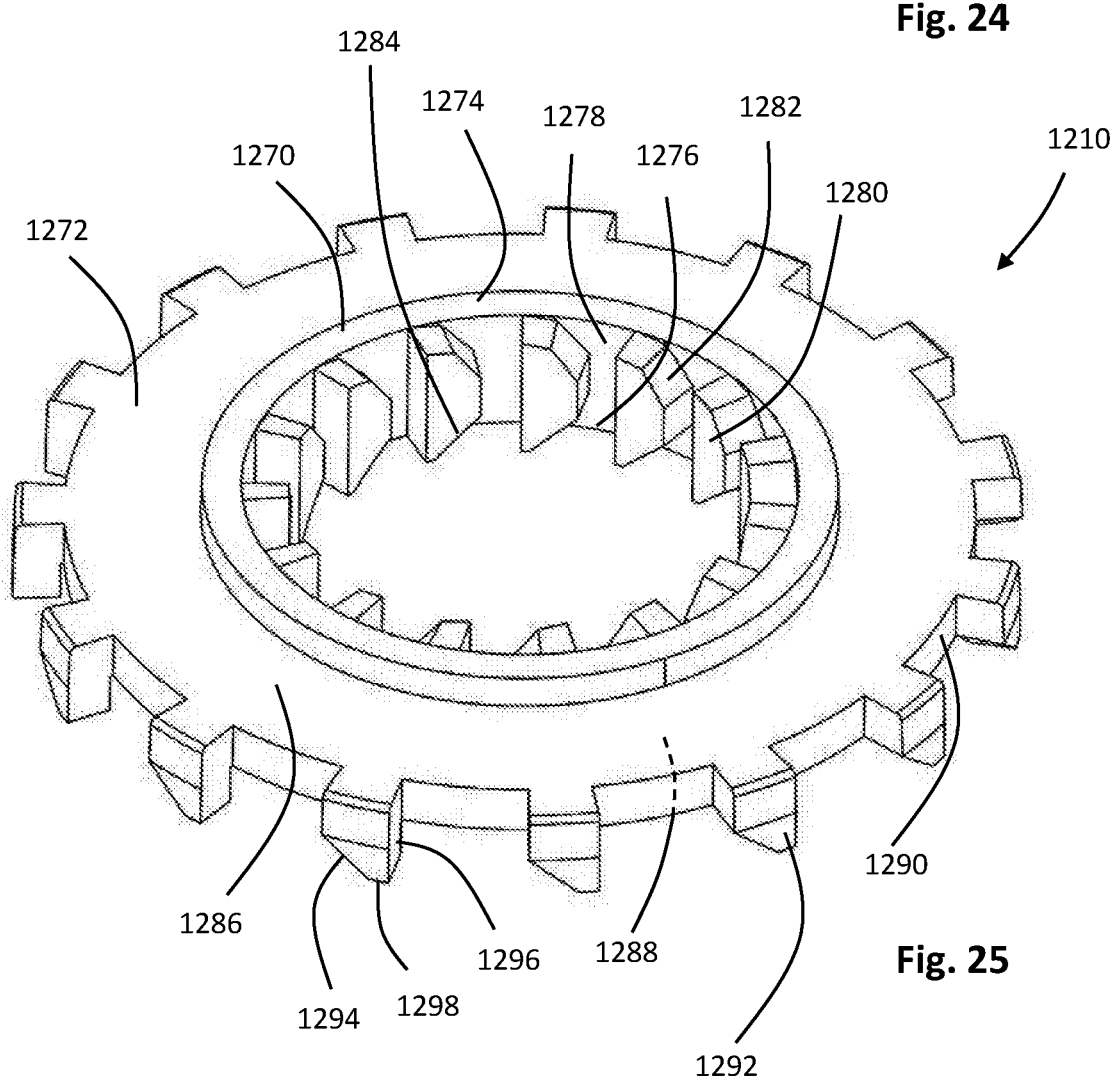
FIG. 25 is a perspective view of a collar of the priming and reset mechanism of FIG. 19.

Referring to FIG. 25, the collar 1210 is shown. The collar 1210 is a unitary moulded plastics component. The collar 1210 comprises a central cylindrical shaft 1270 and an outer annulus 1272.

The shaft 1270 has a first, upper, end 1274 and a second, lower, end 1276. The shaft also defines a radially inwardly facing inner surface 1278 on which a series of fifteen equally spaced inner collar teeth 1280 are defined. Each inner collar tooth 1280 is axially extending and defines (i) a tapered first, upper, end 1282 and (ii) a tapered, second, lower end 1284. The ends 1282, 1284 are oppositely tapered giving the teeth 1280 an elongate trapezium shape. The sides of the teeth 1280 are flat and axially extending. The teeth 1280 extend the full axial length of the shaft 1270.

The annulus 1272 extends outwardly from the shaft 1270 midway between the ends 1274, 1276. The annulus 1272 comprises a first, upper surface 1286 and a second, lower surface 1288. The annulus 1272 defines an outer rim 1290. At the outer rim 1290 there are positioned fifteen outer collar teeth 1292. Each collar tooth 1292 extends radially outwardly and axially downwards away from the second surface 1288. Each outer collar tooth 1292 is tapered becoming narrower as it extends from the second surface 1288. Each tooth 1292 defines a tapered or ramped surface 1294 and a flat, axial surface 1296 which meet at an end flat 1298.

Figure 26:
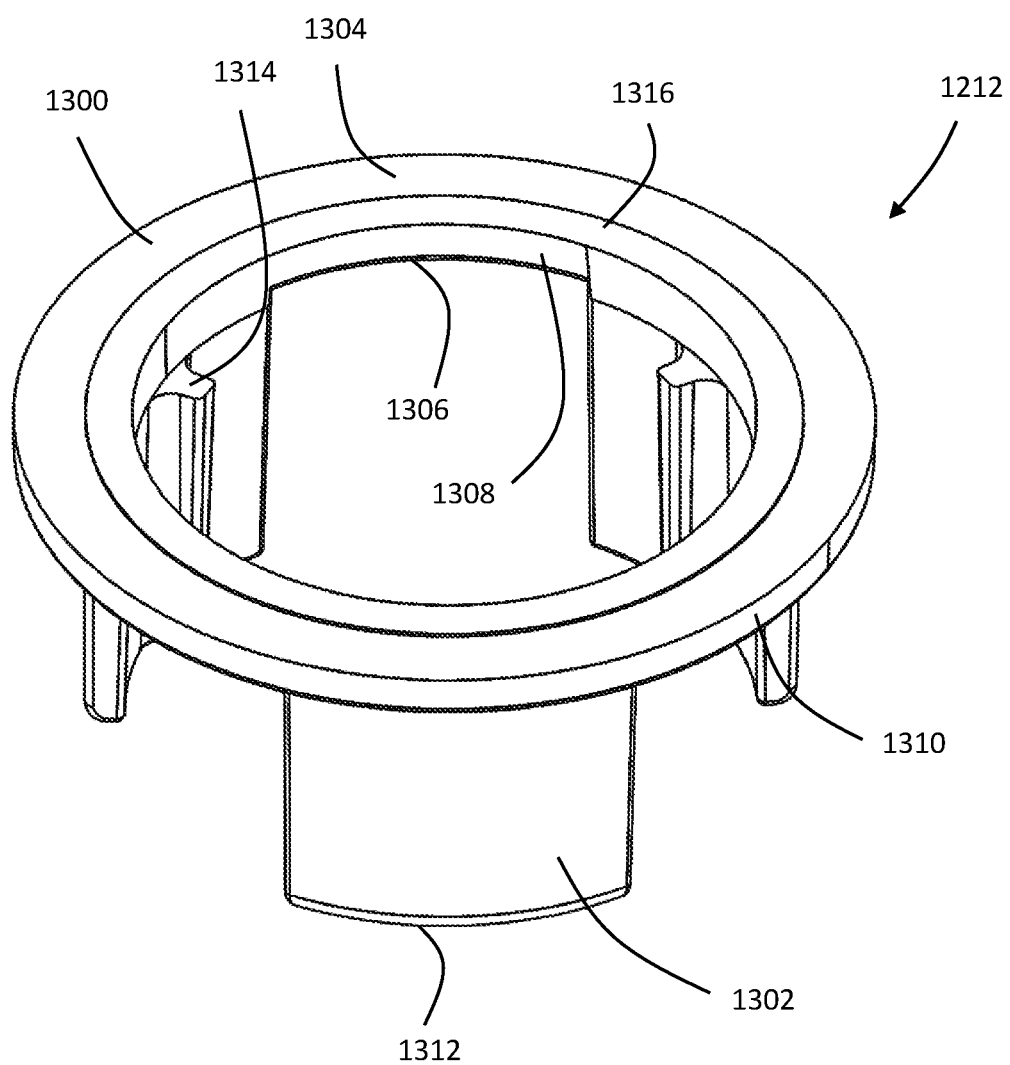
FIG. 26 is a perspective view of a transfer of the priming and reset mechanism of FIG. 19.

Referring to FIG. 26, the transfer 1212 is shown in detail. The transfer 1212 is a unitary, moulded, plastics component comprising an annular body 1300 and three equally spaced, axially extending legs 1302 extending therefrom. The annular body 1300 comprises a first, upper, surface 1304 and a second, lower, surface 1306 as well as an inner rim 1308 and outer rim 1310. The upper surface 1304 defines an annular bearing surface 1316 proximate the inner rim 1308. The annular bearing surface 1316 is slightly upstanding from the surface 1304. Each leg 1302 extends from the second surface 1306 and is circle-segment in section, thus forming a part-cylinder. Each leg 1302 has a free end 1312 and a rib 1314 extending in an axial direction along its length from the annular body 1300 to the free end 1312. Each rib 1314 is disposed along the centreline of the inner surface of each leg 1302. As such, the ribs 1314 face inwardly towards each other.

Figure 27:
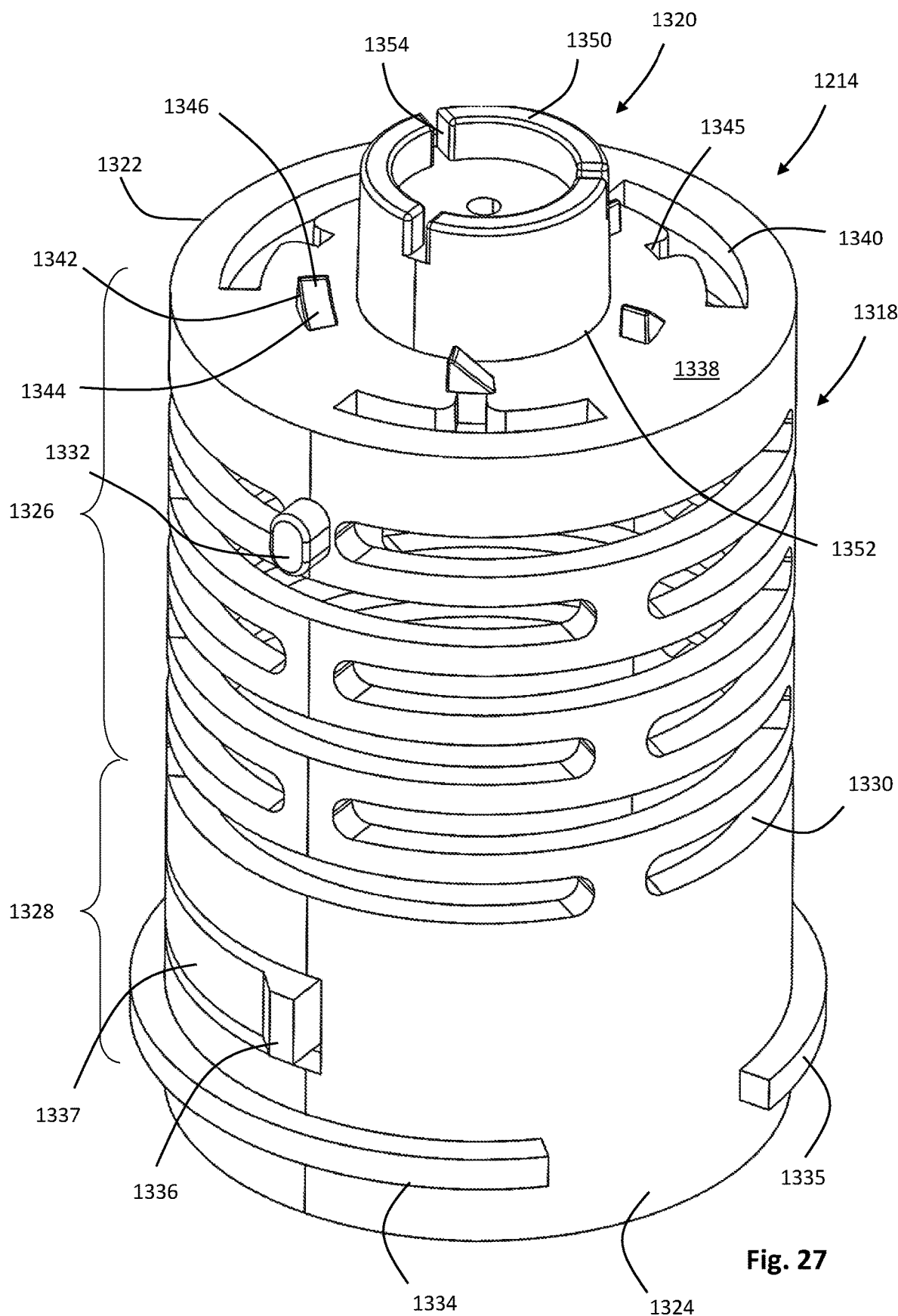
FIG. 27 is a perspective view of a spring of the priming and reset mechanism of FIG. 19.

Referring to FIG. 27 the spring 1214 is shown in detail. The spring 1214 is a unitary, moulded, plastics component. The spring 1214 comprises a cylindrical spring body 1318 and a spring shaft 1320 projecting therefrom.

The spring body 1318 is generally cylindrical having a first, upper, end 1322 and a second, lower, end 1324. The spring body 1318 has a first, upper, region 1326 and a second, lower region 1328.

The first region 1326 is axially extensible and resilient. This is achieved by forming a series of six rows of slot-like openings 1330 through the wall of the body 1318. Each row comprises three openings 1330 which are equally spaced around the circumference of the body 1318. Each row is rotationally offset from the adjacent row or rows. The openings 1330 are formed such that the first region 1326 can be elastically extended, and will resile back to a rest condition as shown in FIG. 27. The first region 1326 further defines an alignment peg 1332 extending radially outwardly therefrom proximate the first, upper end 1322.

The second region 1328 comprises two circle segment radially outwardly projecting ribs 1334, 1335 proximate the second end 1324. Between the ribs 1334, 1335 and the first region 1326 there is provided a radially outwardly projecting tab 1336 which is resiliently biased by an elastically deformable arm 1337 such that upon depression into the body 1326 the tab 1336 resiles outwardly back to the position shown in FIG. 27.

The first end 1322 of the body 1318 terminates in an annular surface 1338 which defines three leg openings 1340 and a series of five spring teeth 1342. Each leg opening 1340 is shaped as a circle-segment. A rib receiving formation 1345 extends in a radially inward direction from the centre of each leg opening Thus each leg opening 1340 is approximately "T" shaped. The spring teeth 1342 are positioned radially inwardly of the leg openings 1340. Each spring tooth 1342 is generally tapered and comprises a tapered surface 1344 which meets a flat axial surface 1346.

The spring shaft 1320 extends from the centre of the annular surface 1338 and is constructed as a hollow cylinder. The spring shaft 1320 has a first, upper end 1350 and a second, lower, end 1352 where it joins the annular surface 1338. The spring shaft 1320 has three equally spaced spring alignment grooves 1354 which extend axially from the first end 1350.

Figure 28A:
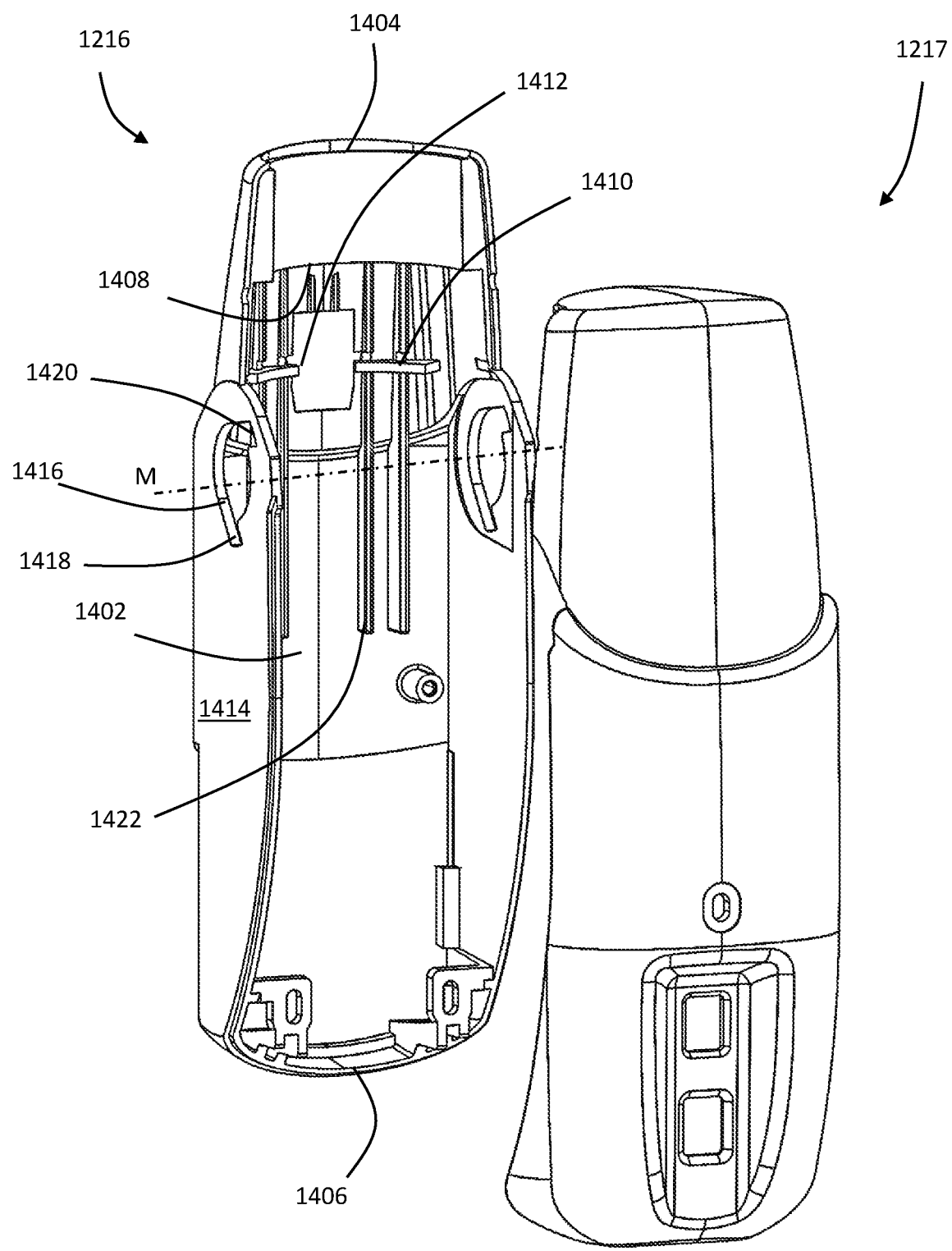
FIGS. 28a and 28b are perspective views of an actuator body of the priming and reset mechanism of FIG. 19.
Figure 28B:
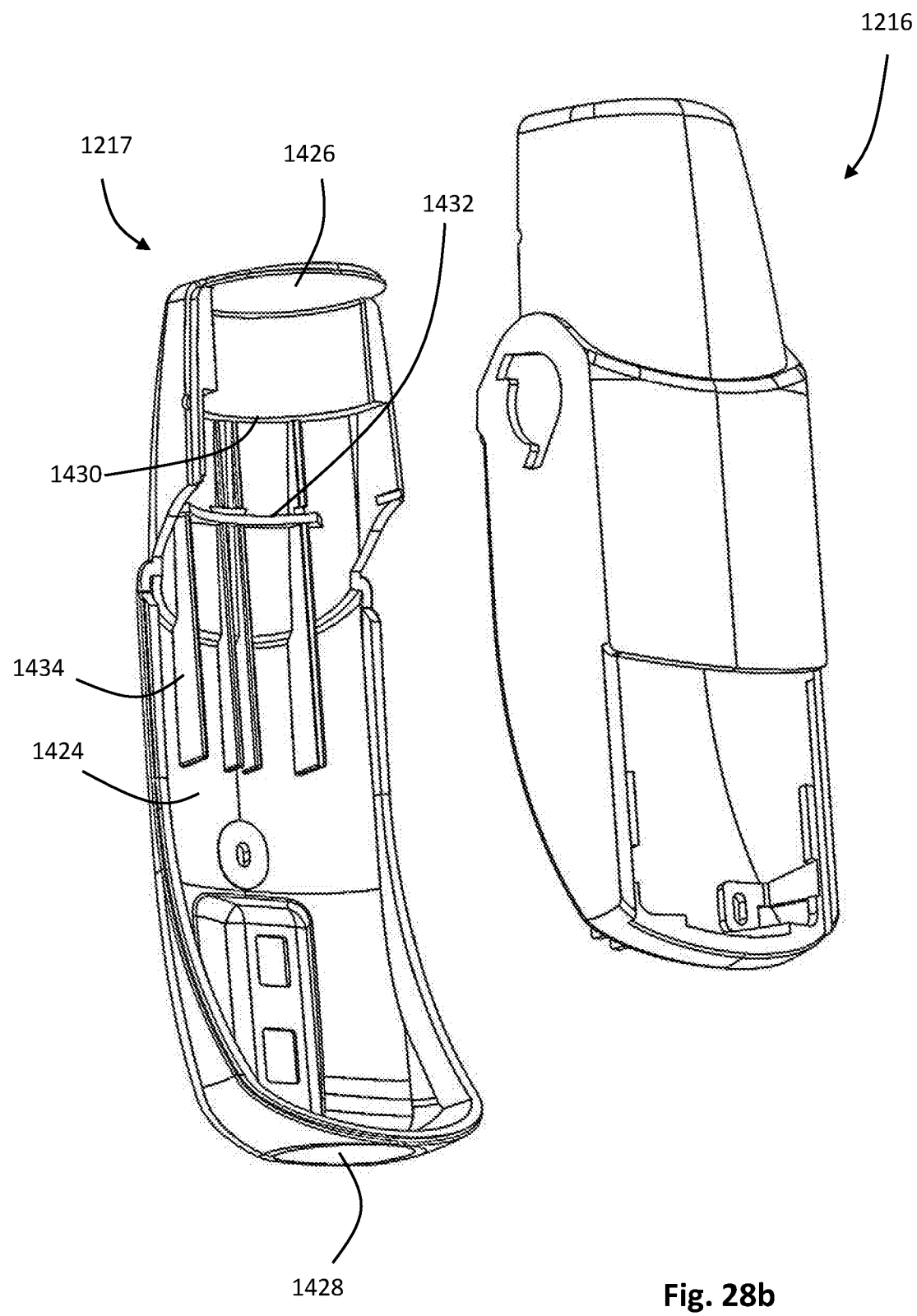

Referring to FIGS. 28*a* and 28*b*, the actuator body parts 1216 and 1217 are shown in detail in exploded form.

The first actuator body part 1216 is a unitary, moulded plastics component which is generally elongate and concave having a curved wall 1402, a first end 1404 and a second end 1406 opposite the first. On the interior side of the concave wall 1402 there is provided a downwardly facing collar abutment 1408 in the form of a shoulder, and an actuator ring abutment 1410, in the form of a circumferentially and radially inwardly extending rib, that has a central gap 1412. The wall 1402 also comprises two parallel side panels 1414 extending from either side thereof. Each side panel 1414 is flat and defines an opening 1416 therein. Each opening 1416 is generally circular having two opposed wings 1418, 1420 extending tangentially therefrom. The wall 1402 also defines four longitudinally extending stiffening ribs 1422. Both openings 1416 lie on a mouthpiece cover axis M.

The second actuator body part 1217 is a unitary, moulded plastics component which is generally elongate and concave having a curved wall 1424, a first endwall 1426 and a second endwall 1428 opposite the first. On the interior side of the concave wall 1424 there is provided a downwardly facing collar abutment 1430 in the form of a shoulder, and an actuator ring abutment 1432 in the form of a circumferentially and radially inwardly extending rib. The wall 1424 also defines four longitudinally extending stiffening ribs 1434.

Figure 29:
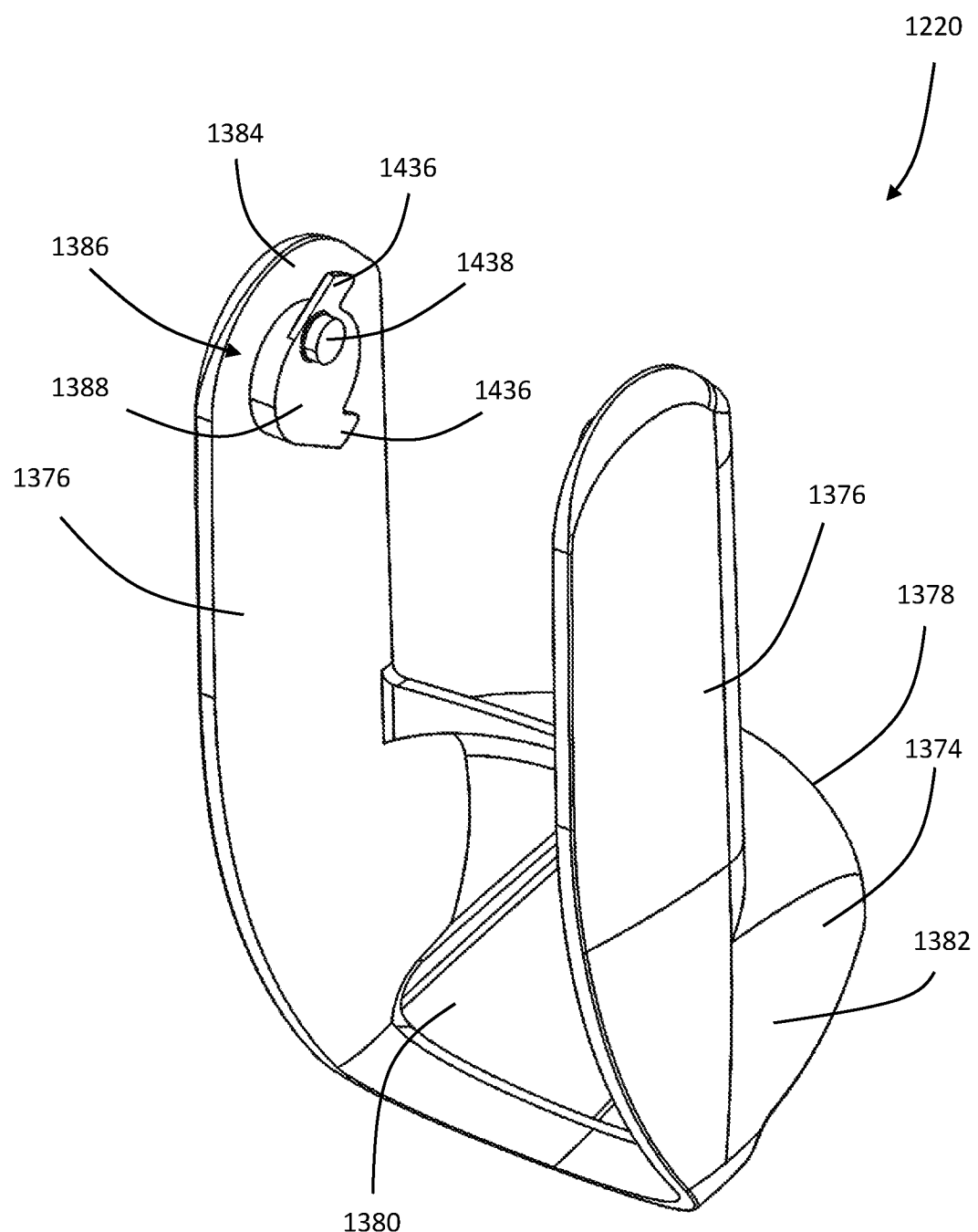
FIG. 29 is a perspective view of a mouthpiece cover of the priming and reset mechanism of FIG. 19.

Referring to FIG. 29, the mouthpiece cover 1220 is shown in more detail. The mouthpiece cover 1220 is a unitary, moulded plastics component. The mouthpiece cover 1220 comprises a cap 1374 and two arms 1376 that are mirror images of each other.

The cap 1374 is an internally concave structure suitable for sealing a mouthpiece of the inhaler patient port 1157. The cap 1374 has a closed end 1378 and an open end 1380. The cap 1374 defines a pair of opposed sidewalls 1382 from which the arms 1376 extend proximate the open end 1380.

Each arm 1376 is an elongate, generally planar structure extending to a free end 1384. At the free end 1384, and on an inwardly facing surface of each arm 1376 there is provided a cam 1386. The cam 1386 comprises a generally cylindrical body 1388 having two tangentially extending, opposed wings 1436. The cam also defines an inwardly projecting cam lug 1438 which is off-centre on the cylindrical body 1388.

Figure 30A:
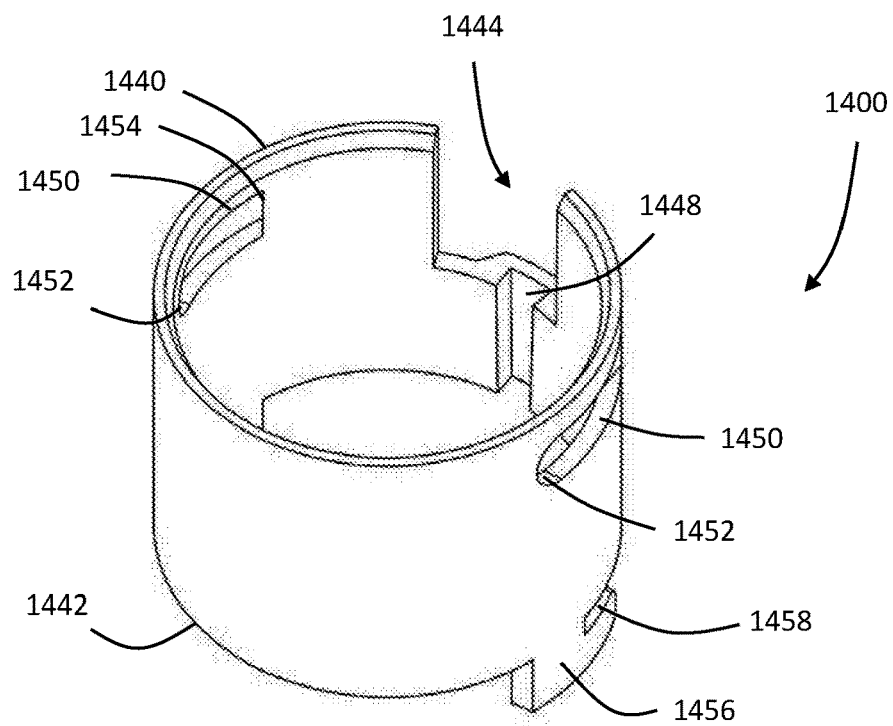
FIGS. 30a and 30b are perspective views of a spring sleeve of the priming and reset mechanism of FIG. 19.
Figure 30B:
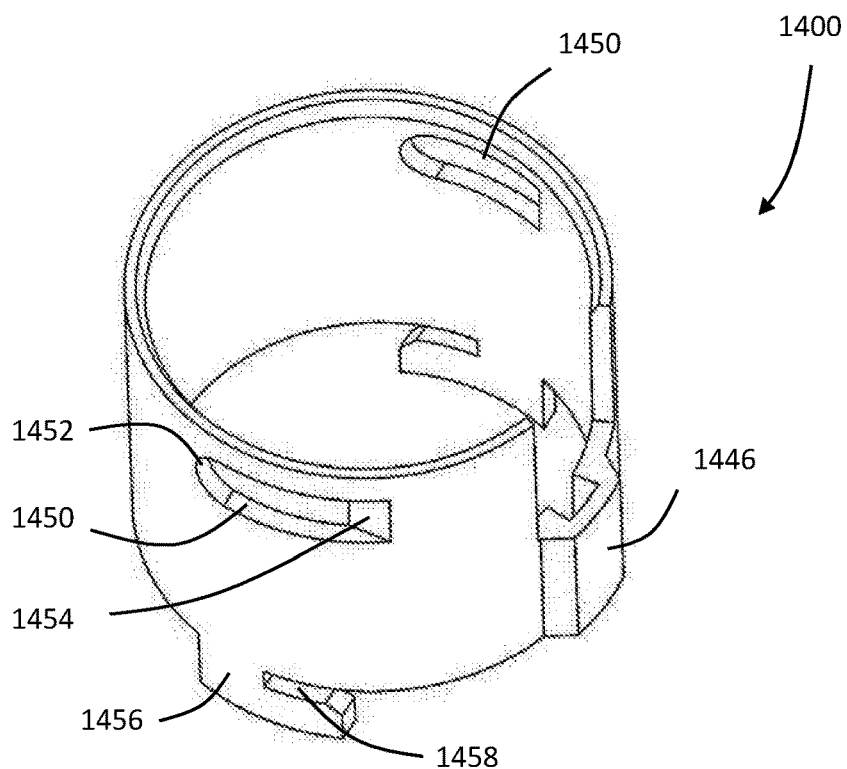

Referring to FIGS. 30*a* and 30*b*, the spring sleeve 1400 is a unitary, moulded plastics component which is generally cylindrical having a first (upper) end 1440 and a second (lower) end 1442. A rectangular, axially extending slot 1444 is provided at one circumferential position on the spring sleeve 1400, the slot 1444 extending from the first end 1440 approximately halfway towards the second end 1442. Extending from the slot 1444 to the second end 1442 there is provided an axially extending ridge 1446, which projects radially outwardly from the spring sleeve 1400. On the interior side of the ridge 1446 there is provided an axially extending recess 1448.

Two elongate openings 1450 are provided in the spring sleeve 1400 proximate and parallel to the first end 1440. Each opening has a curved end 1452 and a ramped end 1454. The openings 1450 are at opposite positions on the spring sleeve 1400 and are mirror images of each other.

At the second end 1442 of the spring sleeve 1400 there are provided two clips 1456, each of which is generally "L" shaped to form a slot 1458 with the second end 1442. The clips 1456 are disposed at opposite circumferential positions on the second end 1442 and face in the same circumferential direction.

Assembly

Figure 31A:
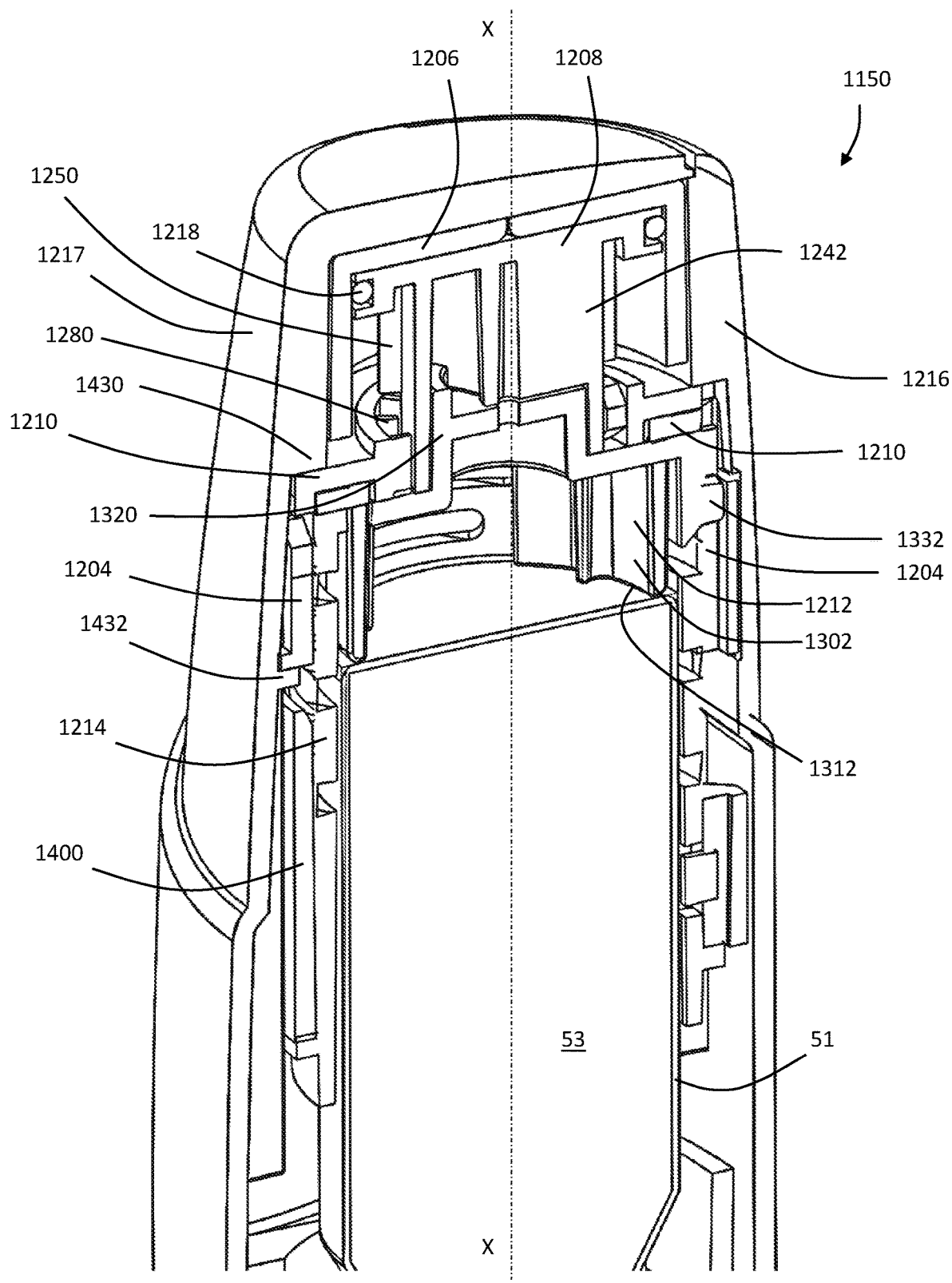
FIGS. 31a to 31d are perspective and section views of various components of the priming and reset mechanism of FIG. 19 in a rest condition.
Figure 31B:
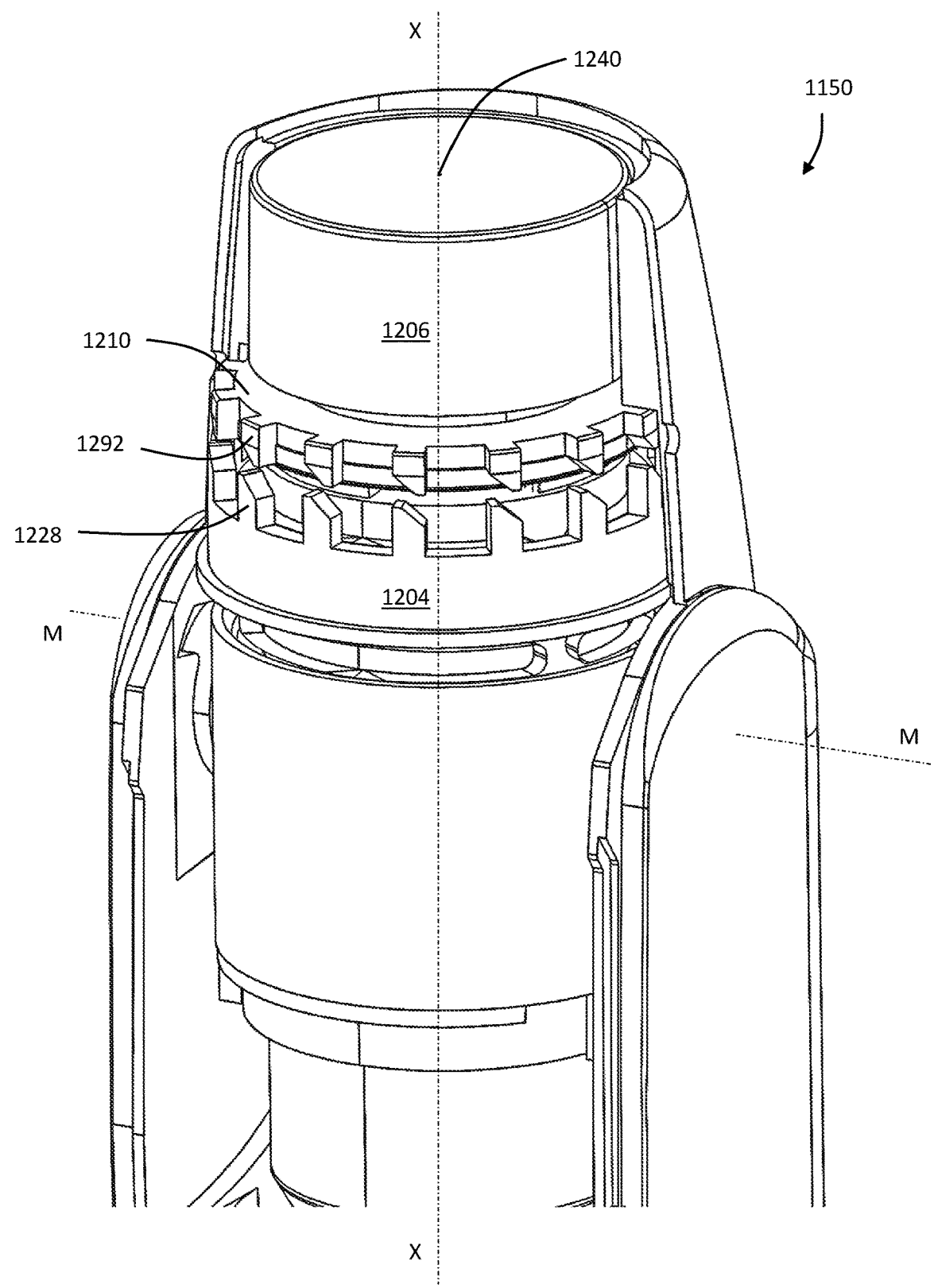

The components described above are aligned on a main axis X. Referring to FIGS. 31a and 31b (as well as the exploded view of FIG. 20), the system is shown in its assembled state, in a rest condition (used for storage and generally when not in operation). The view in FIG. 31a is in section A of FIG. 19. The view in FIG. 31b is in direction B of FIG. 19, but with the first actuator body part 1216 removed.

The o-ring 1218 is assembled into the groove 1260 on the piston 1208, and the piston 1208 is inserted into the open end of the cylinder 1206 to form a seal therewith. The o-ring 1218 seals against the inner sidewall of the cylinder 1206 such that axial movement of the piston results in airflow through the air leak hole 1240. As such, relative motion of the piston 1208 and the cylinder 1206 is damped. Further, because the hole 1240 is tapered, movement of the piston 1208 into the cylinder 1206 is resisted less than movement of the piston 1208 out of the cylinder 1206. In other words, separation of the piston 1208 and cylinder 1206 is damped more than movement of the piston 1208 into the cylinder 1206.

The piston-cylinder assembly is positioned within the actuator body parts 1216, 1217 and can move axially relative thereto.

Next, the collar 1210 is placed into the actuator body parts 1216, 1217 such that the outer collar teeth 1292 face downwardly as shown in FIG. 31b. The upper surface 1286 of the annulus 1272 of the collar 1210 abuts the collar abutments 1408, 1430 of the respective actuator body parts 1216, 1217. The collar surrounds the piston body 1242. The upper surfaces 1282 of the inner collar teeth 1280 face the downwardly facing surfaces 1252 of the piston teeth 1250.

Next, the transfer 1212 is inserted into the actuator body parts 1216, 1217 to engage the underside of the collar 1210. The transfer bearing surface 1316 bears against the lower surface 1288 of the collar annulus 1272 and can rotate relative thereto.

The actuator ring 1204 is secured to the inside of the actuator body parts 1216 and 1217 and rests on the actuator ring abutments 1410, 1432. Rotation of the ring 1204 is inhibited by capture of the retention member 1227 in the central gap 1412 of the actuator ring abutment 1410. Once assembled, the actuator ring 1204 cannot move relative to the actuator body parts 1216, 1217. For example, it may be bonded thereto. As shown in FIG. 31b, the upwardly facing teeth 1228 of the actuator ring 1204 are aligned with the downwardly facing outer teeth 1292 of the collar 1210.

Figure 31C:
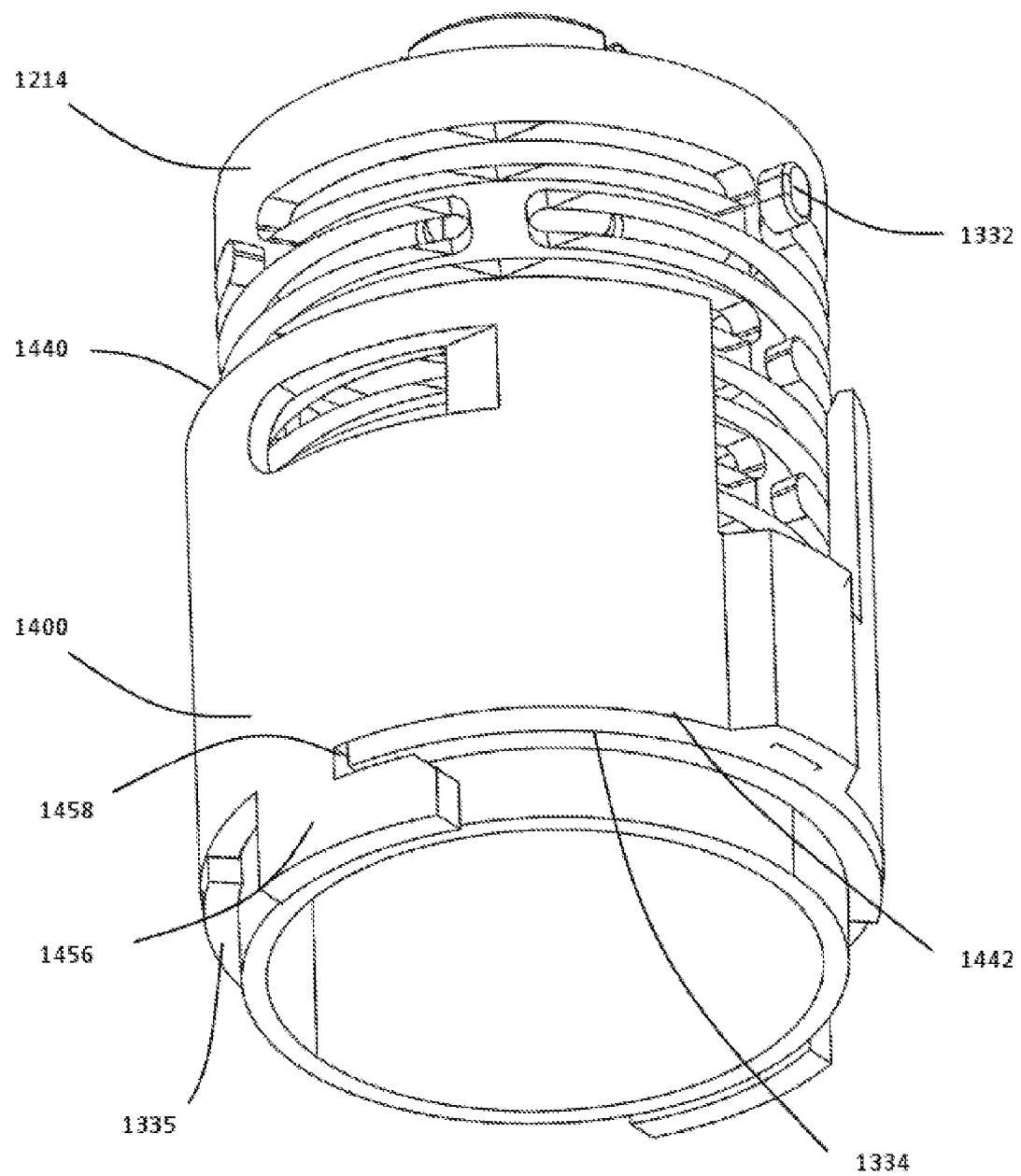

Referring to FIG. 31c, an energy storage arrangement which is a sub-assembly of the spring 1214 and spring sleeve 1400 is shown. The spring 1214 is inserted into the spring sleeve 1400 from the first end 1440 until the clips 1456 pass through the gaps between the ribs 1334, 1335. The second end 1442 of the spring sleeve 1400 abuts the ribs 1334, 1335. At this point, the tab 1336 (not visible in FIG. 31c) is depressed by the interior wall of the spring sleeve 1400. The spring sleeve 1400 is then rotated to the position shown in FIG. 31c such that the ribs 1334, 1335 enter the slots 1458, and the tab 1336 resiles outwardly into the recess 1448. In this way, the spring 1214 and spring sleeve 1400 are attached at their respective first (lower) ends. It will be noted that the spring 1214 can still extend.

The spring 1214 and spring sleeve 1400 are inserted into the actuator body parts 1216, 1217 such that the spring shaft 1320 passes into the piston 1208. The three alignment grooves 1354 are engaged by the ribs 1266 and the spring 1214 and piston 1208 are bonded to prevent relative motion (save for that resulting from deformation of the spring). The legs of the transfer 1212 pass through the leg openings 1340 in the spring body 1318 to allow relative axial movement, but not relative rotational movement between the spring 1214 and transfer 1212. The spring teeth 1342 face the downwardly facing surfaces 1284 of five of the inner teeth 1280 of the collar 1210.

The alignment peg 1332 of the spring engages the slot 1225 of the actuator ring 1204 such that this part of the spring can slide vertically.

The mouthpiece cover 1220 is snap-fitted onto the first actuator body part 1216 in the following manner.

Figure 31D:
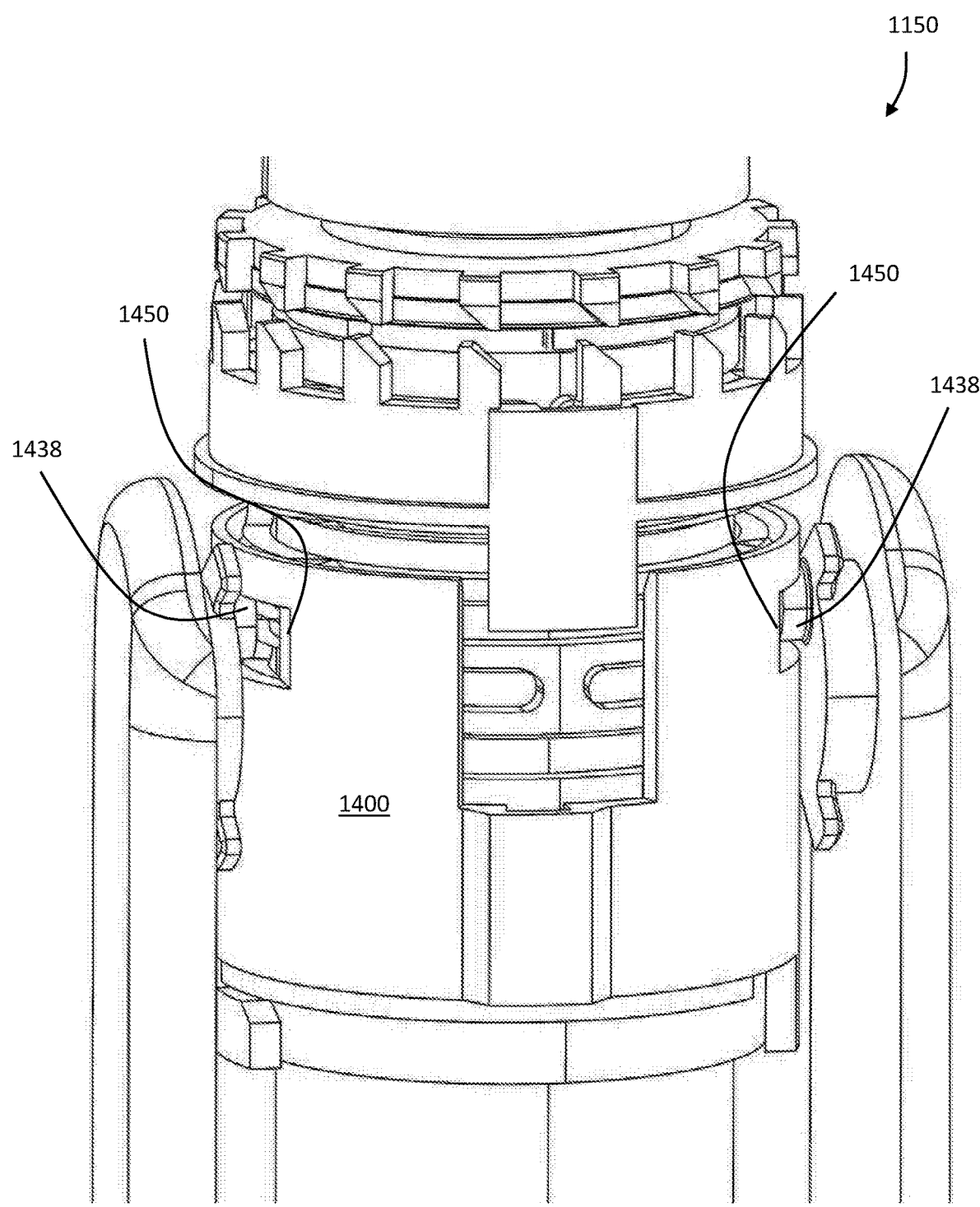
Figure 31E:
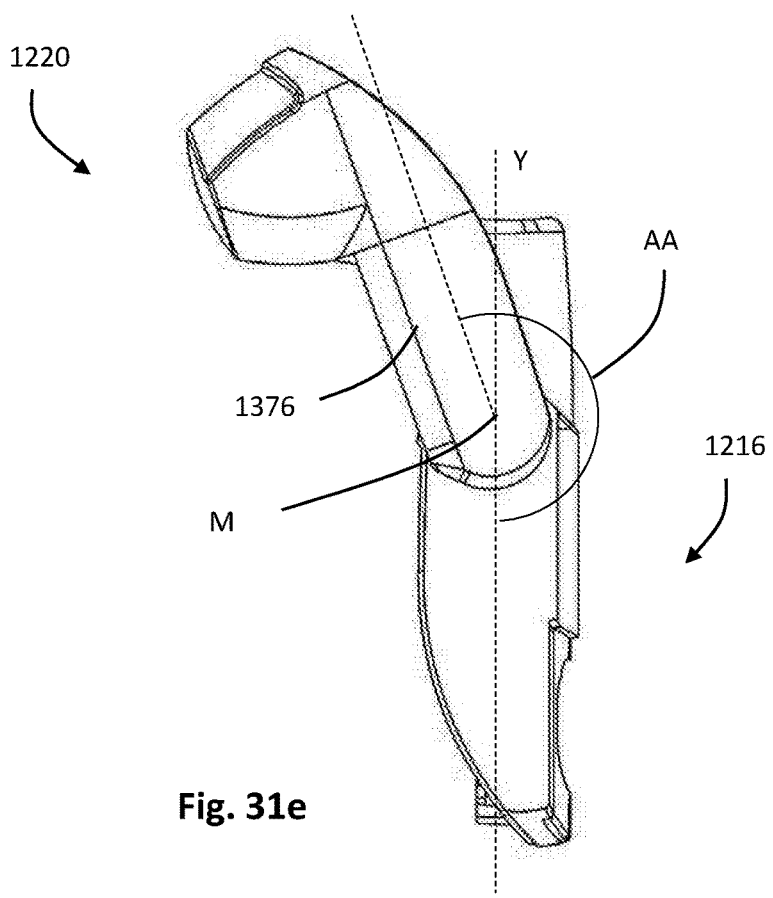
FIGS. 31e to 31g are side and perspective views of stages of assembly of part of the priming and reset mechanism of FIG. 19.
Figure 31F:
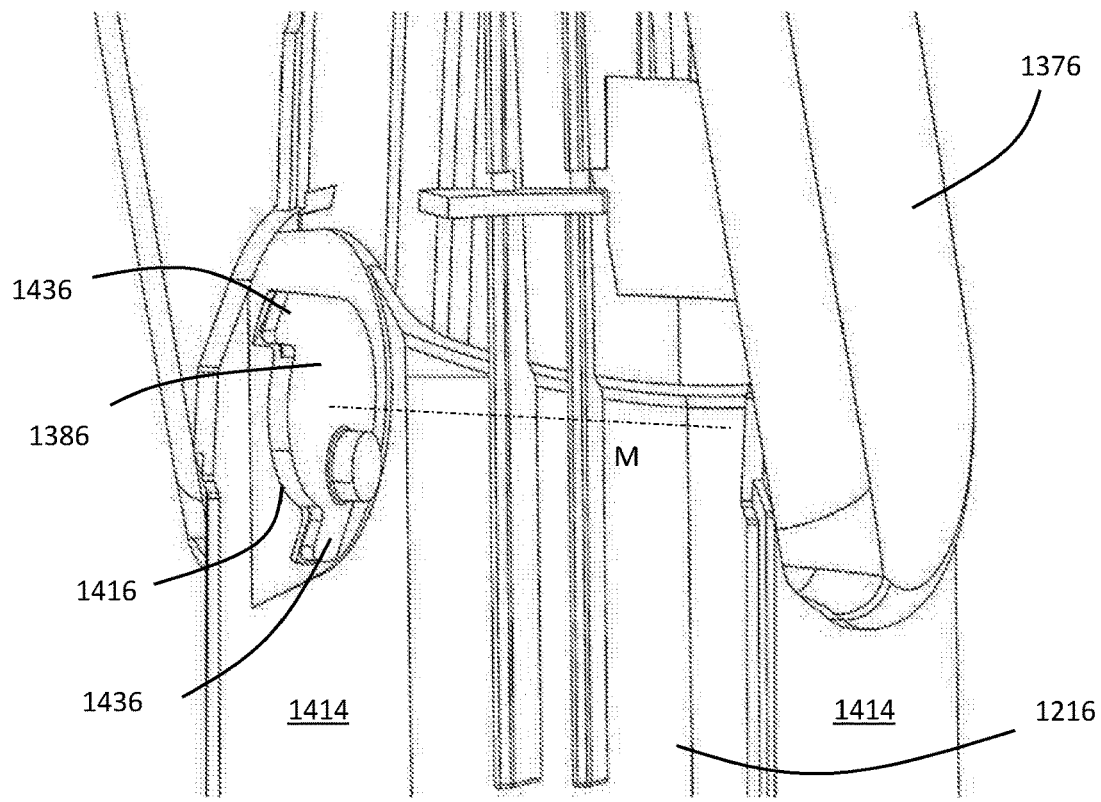
Figure 31G:
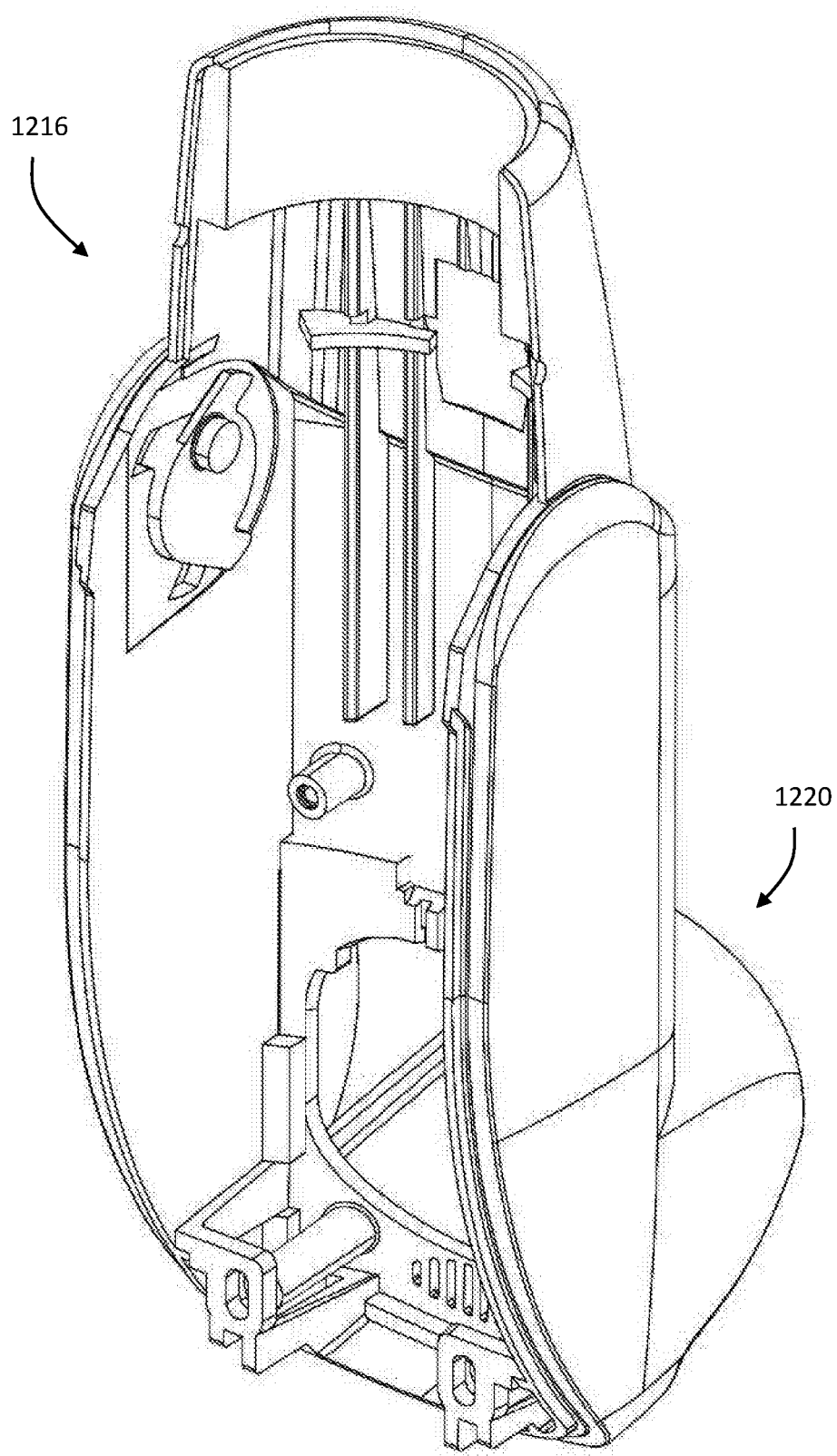

Referring to FIGS. 31e to 31g, the installation of the mouthpiece cover 1220 on the first actuator body part 1216 is shown in detail. The mouthpiece cover 1220 has a rest position defining an axis Y which is parallel to the main axis X of the inhaler. In the rest position, the mouthpiece cover 1220 covers the inhaler mouthpiece (see FIG. 31g).

In FIGS. 31e and 31f, the arms 1376 of the mouthpiece cover 1220 are resiliently separated such that the cams 1386 can be aligned with the openings 1416 in the first actuator body part 1216. The cams 1386 enter the openings 1416 such that the arms 1376 of the mouthpiece cover 1220 are in sliding contact with the walls 1414 of the first actuator body part 1216. It will be noted that in order for full engagement of the cams 1386 with the openings 1416, the wings 1436 of the cam 1386 need to be aligned with the wings 1418, 1420 of the openings 1416. This only occurs at one specific rotational assembly angle AA of the mouthpiece cover 1220, specifically at approximately −200 degrees about the mouthpiece cover axis M from axis Y (FIG. 31e). Referring to FIG. 31f, a detailed view of one of the cams 1386 having entered the opening 1416 is shown.

The mouthpiece cover 1220 is rotated to the in the rest position per FIG. 31g (in which the cap 1374 covers the mouthpiece of the pMDI 1150). In this position, the wings 1436 abut the interior side of the first actuator body part 1416 to hold the mouthpiece in position (but allow rotation about the axis M). It will be noted that upon assembly of the second actuator body part 1217, onto the first actuator body part 1216, the mouthpiece cover is no longer able to rotate further than 180 degrees towards the assembly position of FIGS. 31e and 31f, because the mouthpiece cover 1220 is unable to pass over the top rear edge of the second actuator body part 1217. This ensures that once the inhaler is fully assembled, it is very difficult to remove the mouthpiece cover.

The cam lugs 1438 engage the openings 1450 on the spring sleeve 1400 (FIG. 31d).

Operation

The pMDI 1150 is used as follows. The operation of the pMDI 1150 is best described as passing through a number of operational conditions or stages as will be described below.

1. Rest Condition

The rest condition is shown in FIGS. 31a to 31d. In this condition, a canister 51 having a can 53 and a metering valve 54 with a valve stem 58 is provided within the pMDI. The stem 58 abuts a stem abutment which is static within the pMDI 1150. In the rest condition, downward travel of the canister 51 is inhibited by a trigger abutment which is part of a trigger assembly (not described here, but generally known in the art).

In this position, the canister 51 is positioned partly within the spring 1214 (FIG. 31a), and the free ends 1312 of the legs 1302 of the transfer 1212 abut the bottom of the canister 51 (as it is inverted). The transfer 1212 supports the collar 1210 whose outer collar teeth 1292 are aligned with, and facing, the upwardly projecting teeth 1228 of the actuator ring 1204.

The spring 1214 is also in a rest position, and stores no energy. The spring is fixed to the spring sleeve 1400, which in turn is supported on the lugs 1438 of the mouthpiece cover 1220. Because the spring shaft 1320 is attached to the piston 1208 it also supports the cylinder 1206. The piston 1208 and cylinder 1206 are fully engaged, with the piston abutting the base of the cylinder as shown in FIG. 31a. The piston teeth 1250 are spaced apart along axis X from the inner collar teeth 1280.

The annular surface 1338 of the spring 1214 is abutted by the lower ends of the inner collar teeth 1280, such that they are interdigitated with the spring teeth 1342.

2. Primed Condition

Figure 32A:
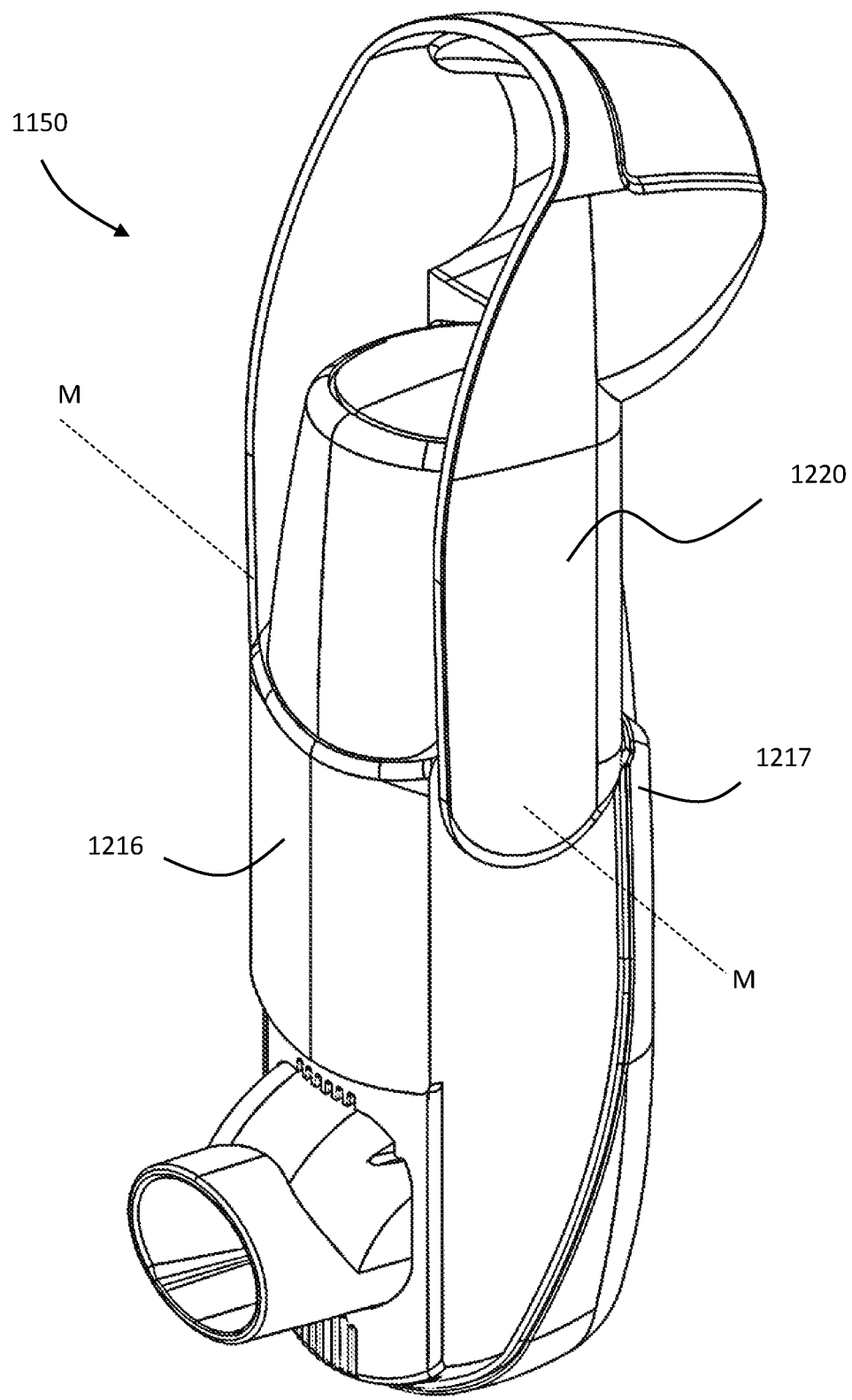
FIGS. 32a to 32d are perspective and section views of various parts of the priming and reset mechanism of FIG. 19 in a primed condition.
Figure 32B:
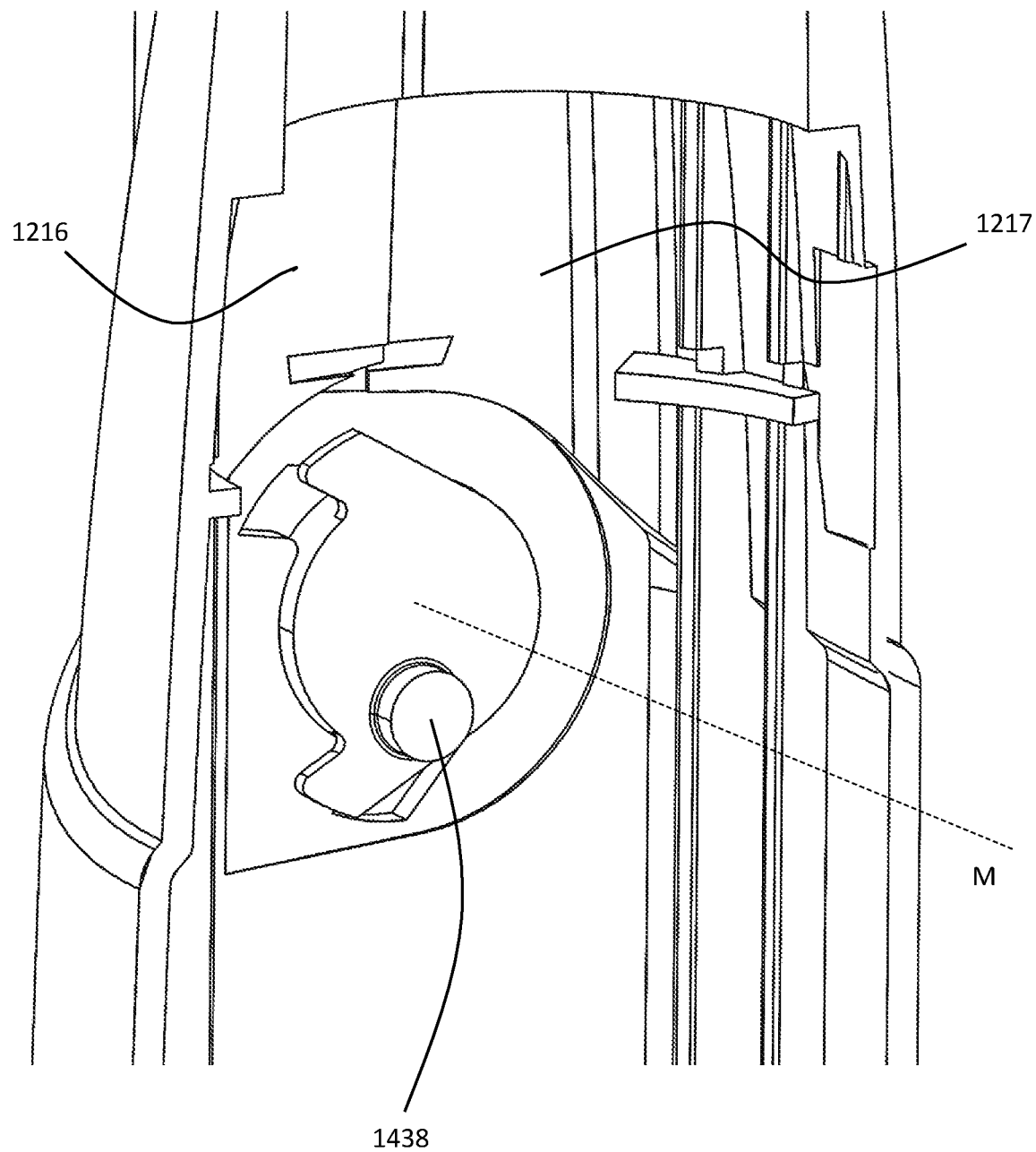
Figure 32C:
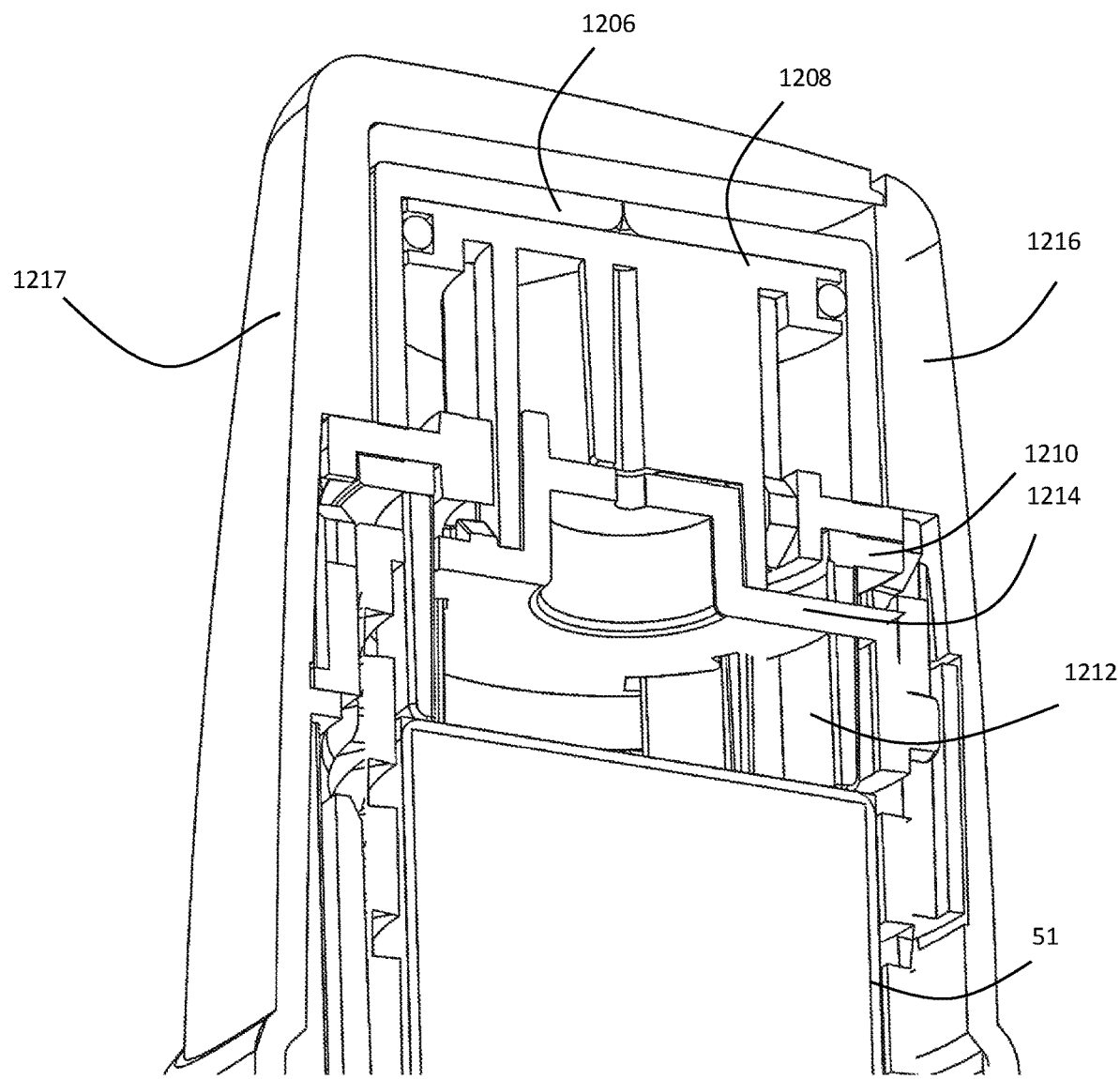

Turning to FIGS. 32a to 32c, the mouthpiece cover 1220 has been rotated about the mouthpiece cover axis M, such that (with reference to FIG. 32b) the lug 1438 has moved downwards in the housing. Because the lugs 1438 are engaged in the openings 1450 in the spring sleeve, rotation of the mouthpiece cover 1220 pushes the spring sleeve 1450 vertically downwards. This action also applies a tensile force to the spring 1214, pulling it downwards.

Referring to FIGS. 32e to 32g, two intermediate steps of rotation of the mouthpiece cover 1220 with respect to the first actuator housing part 1216 from the rest position to the primed position are shown. The second housing part 1217 is omitted for clarity. In FIG. 32e, the mouthpiece cover has been rotated by an angle A of −90 degrees, and the lug 1438 has moved a distance D1 from its rest position (shown in hidden line). In this position, the inhaler is unuseable because the mouthpiece cover would clash with the user's face. In FIG. 32f, the mouthpiece cover 1220 has been rotated by angle an B of approximately −135 degrees. In this position, the lug 1438 has been moved downwards by a total distance D2, and the spring 1214 has been fully tensioned (i.e. with sufficient energy to actuate the mechanism). The final phase of movement from FIGS. 32f to 32g, i.e. to an angle C of 180 degrees, moves the lug 1438 to a total displacement of D3, although it will be noted that due to the curved path of the lug 1438 the distance from D2 to D3 is minimal (and as mentioned, the spring 1214 has already been fully tensioned). Therefore if the user tried to use the inhaler at any point between D2 and D3, it would operate fully.

Referring to FIG. 32c, initially this downward force on the spring 1214 acts to draw the piston 1208 downwards (the piston 1208 and spring 1214 are attached). Because downward movement of the cylinder 1206 is not resisted at this stage, it also moves downwards as shown in FIG. 32c due to gravity and the friction of the o-ring 1218, as well as due to air flow resistance through the air hole. The transfer 1212 remains stationary at this point, as it abuts the canister 51. As the top of the spring 1214 moves downwards along axis X, the spring 1214 and the transfer 1212 start to move apart due to the fact that the transfer legs 1302 can slide in the leg openings 1340.

Figure 32D:
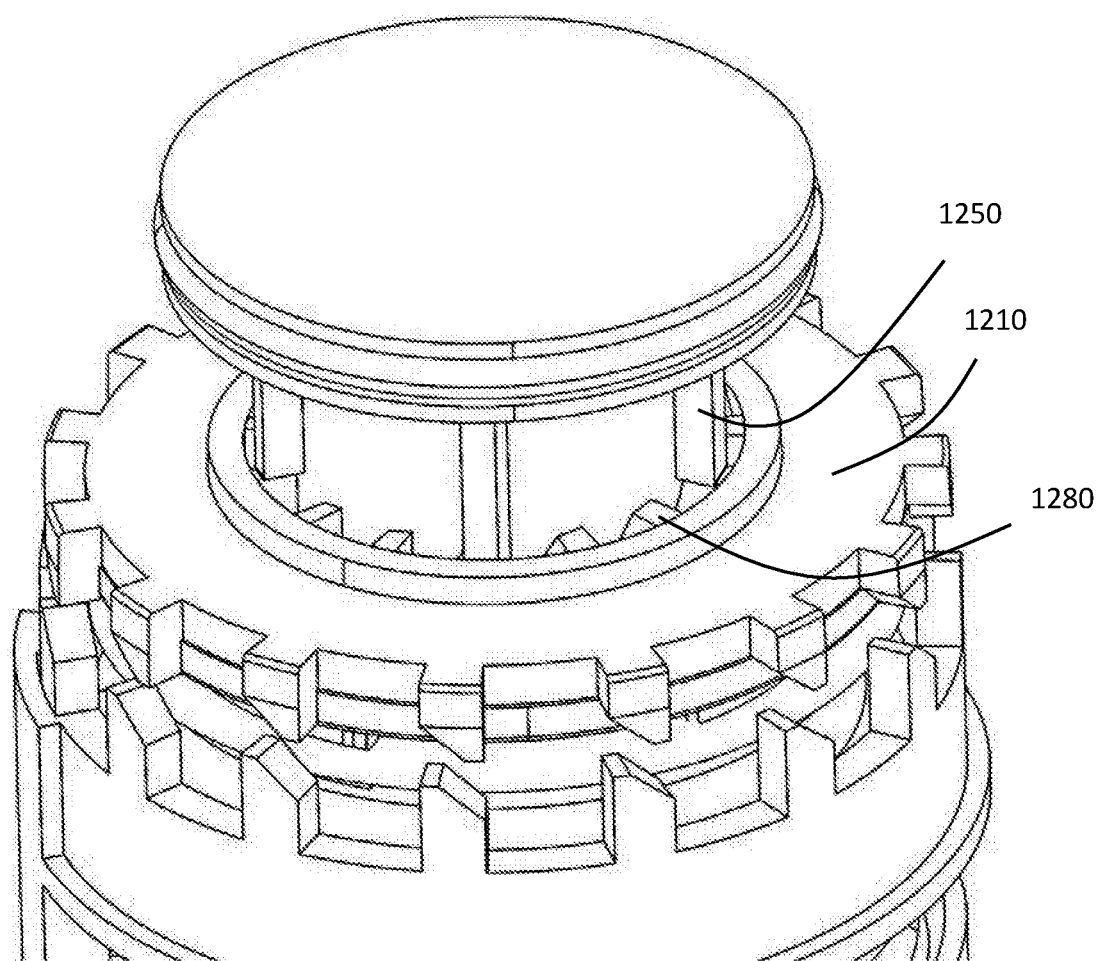

This initial motion occurs until, as shown in FIG. 32d, the tapered surfaces 1252 of the piston teeth 1250 abut the first tapered ends 1282 of the inner collar teeth 1280. As with the earlier embodiment, the piston 1208 and the collar 1210 form a clutch for transfer of the spring force to the canister. At this point, a downward force is exerted on the collar 1210 which cannot move due to the abutment of the transfer 1212 and the canister 51 (held in place by the trigger abutment). The taper angles of the piston teeth 1250 and inner collar teeth 1280 are shallow such that a vertical force is produced without sufficient rotational force about the axis to overcome friction and rotate the collar 1210.

Therefore the spring shaft 1320 can no longer move due to a load path being established through the piston 1208 onto the collar 1210, the transfer 1212 and the canister 51. As the mouthpiece cover 1220 continues to be rotated, the spring 1214 stretches to store potential energy. Once the mouthpiece cover 1220 is in the position shown in FIG. 32a, the spring is "primed".

3. Fired Condition

When the user wishes to dispense the medicament, a trigger mechanism (which is not described here) is fired in which the trigger abutment is moved such that downward motion of the canister 51 is no longer inhibited. Previously, the canister 51 was resisting downward movement of the transfer 1212, which in turn was holding up the piston 1208 and therefore the upper end of the spring 1214 (under tension). Release of the canister 51 releases the transfer 1212, collar 1210 and piston 1208 to move downwards, pulled by the tensile force of the spring 1214 on the piston 1208. The spring force Fs is transferred from the spring 1214, through the piston 1208 into the collar 1210 (i.e. through the clutch formed by the piston 1208 and collar 1210) and to the transfer 1212. As the stored energy in the spring 1214 is released, it serves to push the valve stem 58 onto the valve stem abutment. This also acts against the bias of the valve spring within the valve 54 to open the canister 51 and release a dose of medicament.

Figure 33:
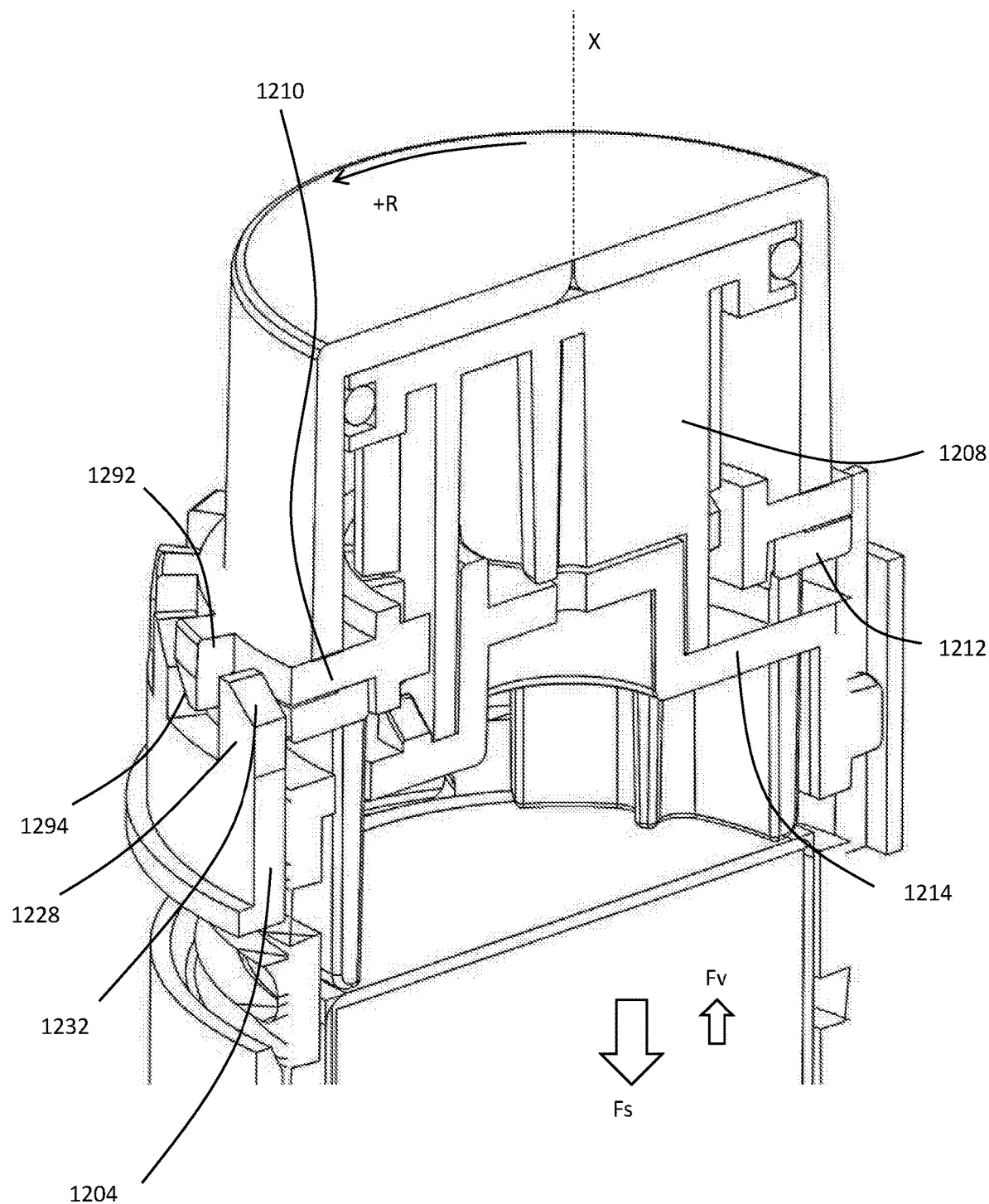
FIG. 33 is a perspective section view of various parts of the priming and reset mechanism of FIG. 19 in a fired condition.

At this point, a spring force Fs is being applied to the canister 51 against the bias of a valve spring force Fv (FIG. 33).

As the collar 1210 moves downwards, the tapered surfaces 1294 of each outer collar tooth 1292 engage the tapered surfaces 1232 of the teeth 1228 of the actuator ring 1204. This acts to rotate the collar 1210 about the axis X in direction +R and begin to move the clutch formed by the piston 1208 and the collar 1210 to a released condition.

4. Auto-Release Condition

At a predetermined angle of rotation of the collar 1210 relative to the piston 1208 (which cannot rotate because it is attached to the spring 1214), the clutch formed by the collar 1210 and piston 1208 becomes detached (or released) in a linear sense. This is because the inner collar teeth 1280 can eventually move through the gaps between the piston teeth 1250 allowing relative linear movement between the piston 1208 and collar 1210 (see FIG. 34). This breaks the load path between the spring 1214 and the canister 51.

5. Can Reset Condition

Figure 34:
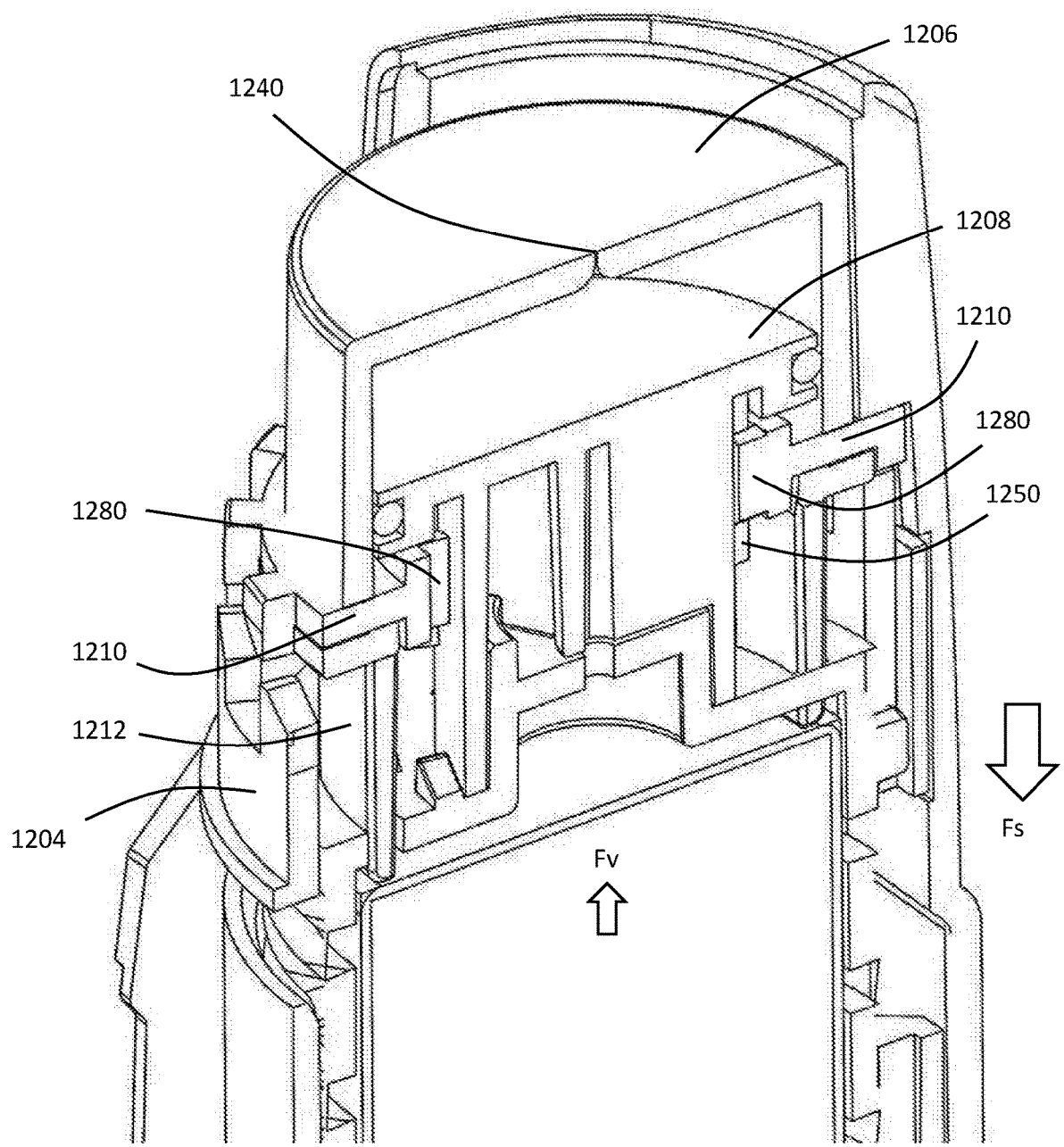
FIG. 34 is a perspective section view of various parts of the priming and reset mechanism of FIG. 19 in an auto-release condition.

The system is now separated into two sub-assemblies which encounter opposing forces Fs and Fv. Reference is made to FIG. 34.

On one hand, the return force of the spring in the canister valve Fv applies an upward force on the transfer (via the canister 51) which in turn lifts the collar 1210 away from the actuator ring 1204. The collar 1210 supports the cylinder 1206 which is also raised upwards.

On the other hand, the tensile force Fs remaining in the spring 1214 acts to draw the piston 1208 downwards. Therefore, as the canister 51 resiles to its rest (unactuated) position, its motion is controlled by the separation of the piston 1208 and cylinder 1206. As mentioned above, relative motion of the piston and cylinder is controlled by ingress of air into the air leak hole 1240. As such, the return of the canister (i.e. the timing of the return of the canister) is controlled, avoiding the aforementioned problems.

6. Return to Rest Condition

The user rotates the mouthpiece cover 1220 back to its original positon, which has the effect of (with reference to FIG. 32e) drawing the lug 1438 upwards and lifting the spring 1214. This motion re-engages the piston 1208 into the cylinder 1206. The shape of the air leak hole 1240 provides a higher coefficient of discharge for air egress, compared to that for air ingress described above.

As the top of the spring 1214 moves towards the collar 1210, the tapered surface 1344 of each spring tooth 1342 engages the tapered second end 1284 of one of five of the inner collar teeth 1280 to further rotate the collar 1210. The rotation is such that the inner collar teeth 1280 are positioned directly below the piston teeth 1250, and the outer collar teeth 1292 are positioned above the actuator ring teeth 1228 ready for the next operation.

The Third Embodiment

Turning to FIGS. 35 to 50, a third pMDI 2150 according to an embodiment of the present invention is shown. The pMDI 2150 comprises a housing or actuator 2155 containing a canister 51 (FIG. 36). The canister 51 contains a medicament formulation. It will be understood that the canister is of the same type as the canister 51 described with reference to FIG. 1 and comprises a can with a metering valve. The canister sits within the housing 2155. The pMDI 2150 has a stem socket and a trigger assembly that allows downward movement of the canister relative to the valve's stem portion, as described earlier in the detailed description, when the patient inhales through the mouthpiece. The stem socket and trigger assembly have been omitted from FIG. 36 for clarity of the drawing.

The pMDI 2150 comprises a portion in the form of a patient port 2157 (e.g., in the form of a mouthpiece) that defines an inspiration orifice (or an air outlet). Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein.

The housing 2155 also comprises an upper section 2202 that comprises a reset mechanism according to an embodiment of the present invention.

Referring to FIG. 36, an exploded view of the reset mechanism is provided. The reset mechanism comprises an actuator ring 2204, a cylinder 2206, a piston 2208, a transfer collar 2210, a spring 2214, a sleeve 2400, a spring abutment 2212, a first actuator body part 2216, a second actuator body part 2217, an o-ring 2218 and a mouthpiece cover 2220.

Figure 37:
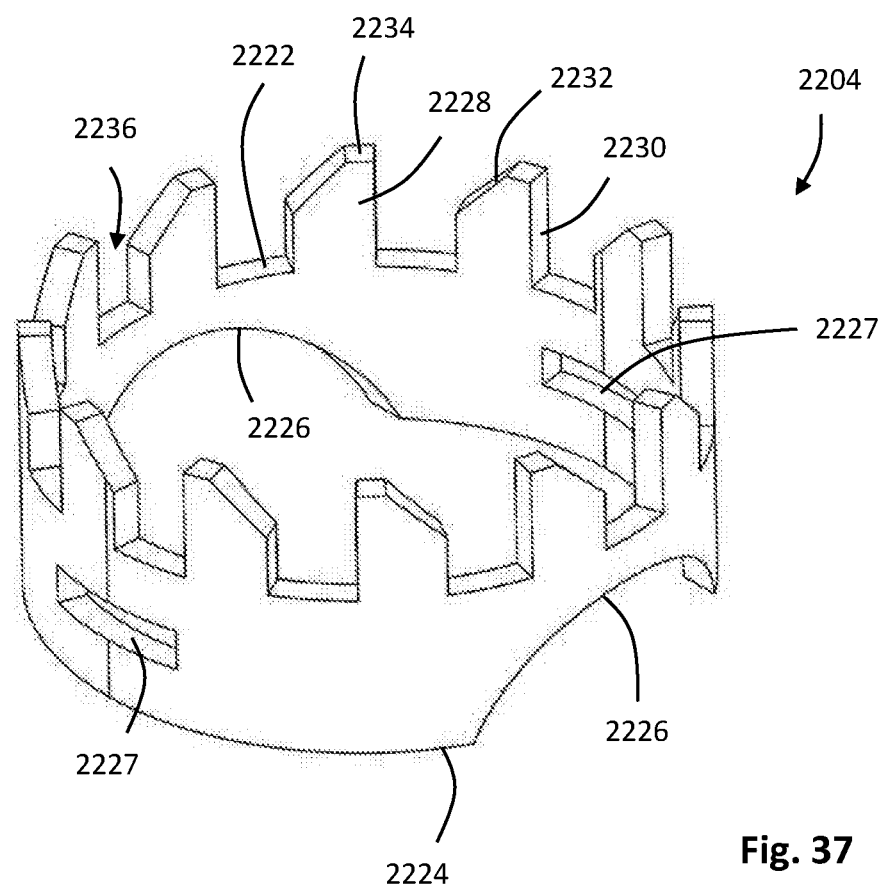
FIG. 37 is a perspective view of an actuator ring of the priming and reset mechanism of FIG. 35.

With reference to FIG. 37, the actuator ring 2204 is a unitary cylindrical body constructed from a moulded plastics material having a first, upper, edge 2222 and a second, lower, edge 2224. The first edge 2222 defines a series of twelve axially extending teeth 2228. Each tooth 2228 comprises a generally triangular formation at its free end, having a straight axial edge 2230 and a tapered surface 2232 (extending both axially and circumferentially) which meet at end flat 2234. Each tooth 2228 is separated at the edge 2222 by an inter-tooth gap 2236. The second edge 2224 defines a pair of opposed curved recesses 2226. Between the recesses 2226 there are provided elongate, circumferentially extending slots 2227 through the wall of the actuator ring 2204.

Figure 38:
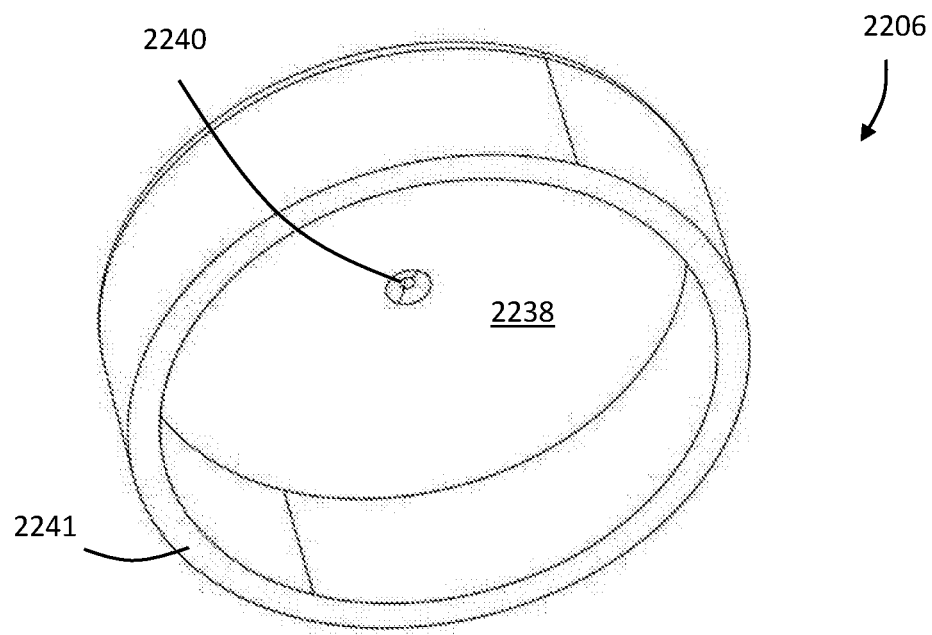
FIG. 38 is a perspective view of a cylinder of the priming and reset mechanism of FIG. 35.

With reference to FIG. 38, the cylinder 2206 is a unitary cylindrical body constructed from a moulded plastics material. The cylinder is closed at a first, upper, end 2238 and open at a second, lower, edge 2241. In the centre of the upper closed end 2238 there is provided a co-axial air leak hole 2240. The air leak hole 2240 is sized to provide the technical effect described below (damping) and as such the exact size required can be determined by the skilled technician. As with the air leak holes 240 and 1240, the air leak hole 2240 is tapered to decrease in area from the interior of the cylinder 2206 to the exterior of the cylinder 2206. This results in a higher coefficient of discharge for fluid exiting the cylinder through the hole 2240 than air entering the cylinder through the hole 2240.

With reference to FIGS. 39a and 39b, the piston 2208 is shown. The piston 2208 is a unitary moulded plastics component. The piston 2208 comprises a generally cylindrical piston body 2242 and a piston head 2244 at one end thereof.

The body 2242 is a hollow cylinder having a first, upper, end 2246 at which the piston head 2244 is located, and a second, lower end 2248 which is open. The body 2242 defines twelve identical, equally spaced, axially extending teeth 2250 on its outer surface. Each tooth 2250 extends from the first end 2246 towards the second end 2248 (although the teeth only extend part-way along the body 2242). The teeth 2250 each terminate at a free end that defines a tapered surface 2252 extending both circumferentially and axially. The body 2241 further defines six inwardly protruding elongate axial ribs 2470.

The piston head 2244 comprises a circular piston end cap 2256 having a radial edge 2258. The end cap 2256 is positioned at the first, upper, end 2246 of the body 2242. The head 2244 comprises an o-ring receiving channel section 2260 extending axially towards the second end 2248 of the body 2242. The o-ring receiving channel section 2260 is formed by the radial edge 2258 of the cap 2256 and a radial edge 2262 of an annular ring section 2264. On the underside of the end cap 2256 (i.e. the surface facing the interior of the body 2242) there is provided a central axially extending shaft 2266 having two wings 2267 defined thereon.

Turning to FIG. 40, the o-ring 2218 is shown. The o-ring 2218 is a standard component and is constructed from an elastomeric material designed to form a fluid seal against plastics material.

Figure 41A:
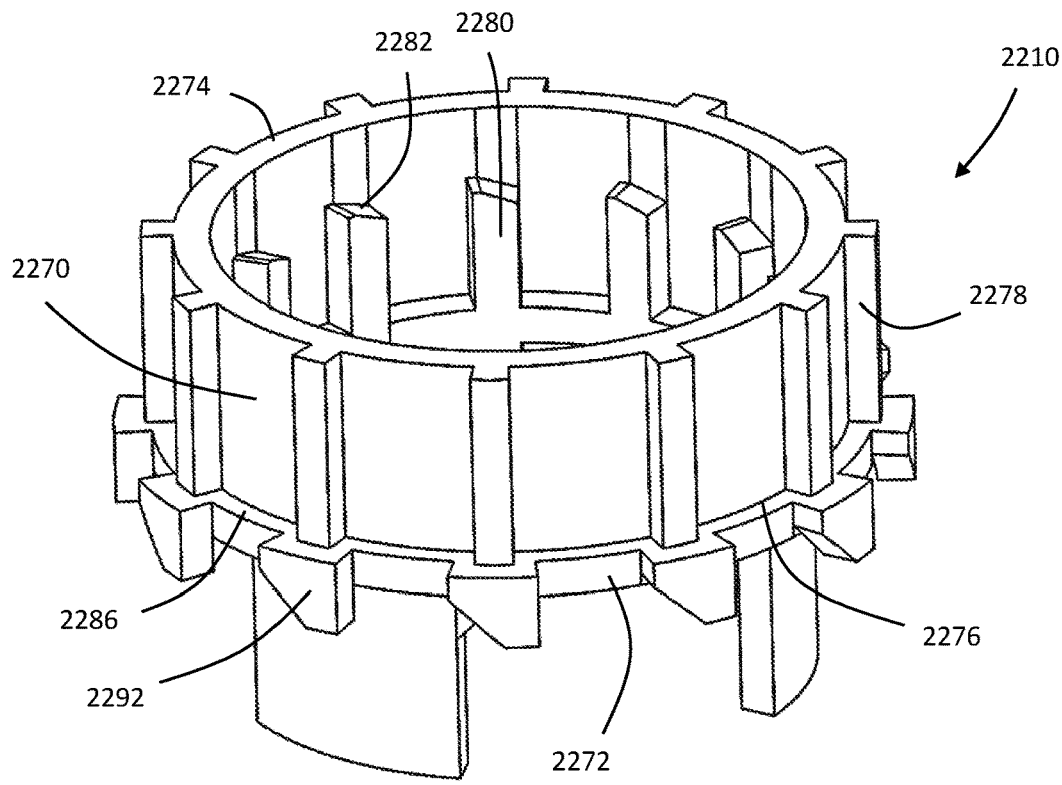
FIGS. 41a and 41b are perspective views of a transfer collar of the priming and reset mechanism of FIG. 35.
Figure 41B:
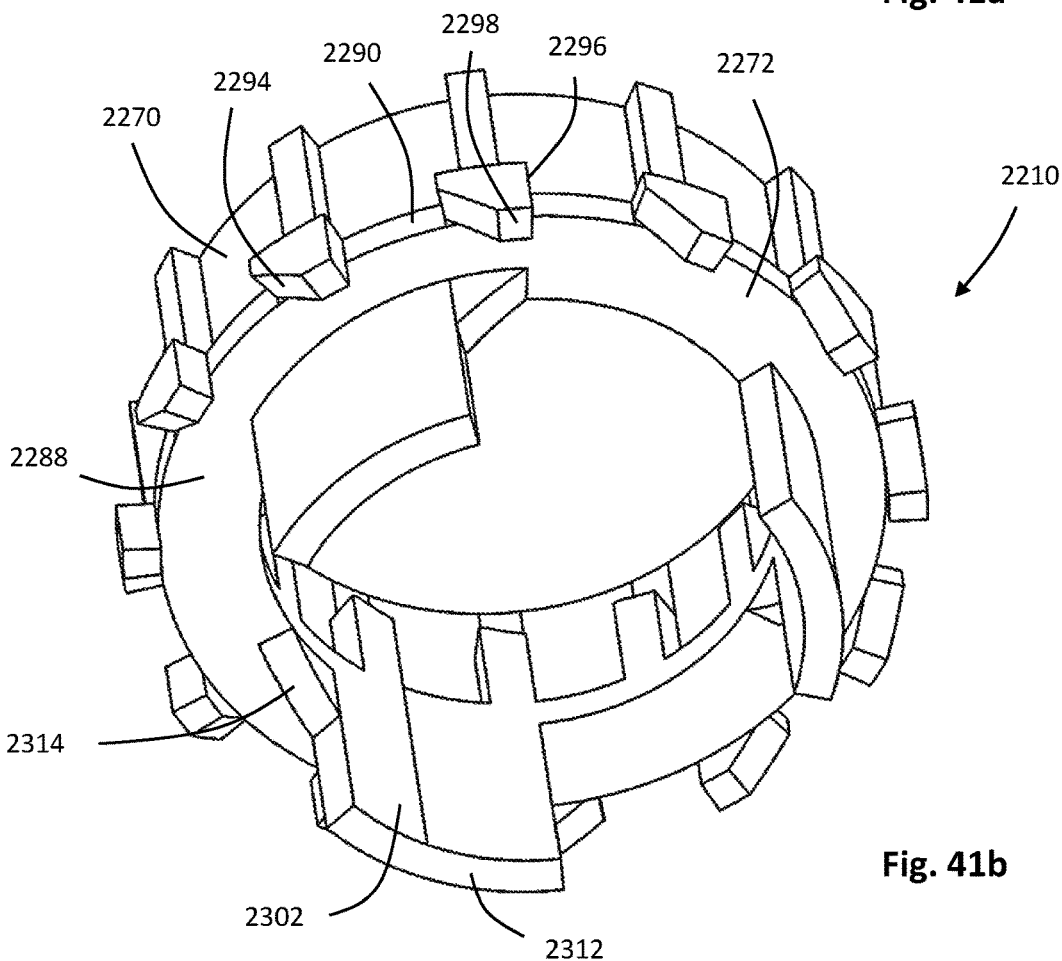

Referring to FIGS. 41a and 41b, the transfer collar 2210 is shown. The transfer collar 2210 combines the functionality of the collars 210, 1210 and the transfers 212, 1212 of the first and second embodiments. Therefore the transfer collar 2210 effectively comprises a transfer and a collar in one unitary component. The transfer collar 2210 is a unitary moulded plastics component.

The transfer collar 2210 comprises a cylindrical shaft 2270, and an annulus 2272.

The shaft 2270 has a first, upper, end 2274 and a second, lower, end 2276. The shaft 2270 defines a series of twelve equally spaced outer shaft teeth 2278 and series of twelve equally spaced inner shaft teeth 2280. The outer shaft teeth 2278 extend from the first end 2274 to the second end 2276.

The inner shaft teeth 2280 each define a tapered first, upper, end 2282 approximately midway along the shaft 2270 and join the annulus 2272 at the lower end.

The annulus 2272 extends both inwardly and outwardly of the second end of the shaft 2270. The annulus 2272 comprises a first, upper surface 2286 and a second, lower surface 2288. The annulus 2272 defines an outer rim 2290. At the outer rim 2290 there are positioned twelve outer collar teeth 2292. Each outer collar tooth 2292 extends radially outwardly and axially downwards away from the second surface 2288. Each outer collar tooth 2292 is tapered becoming narrower as it extends from the second surface 2288. Each tooth 2292 defines a tapered or ramped surface 2294 and a flat, axial surface 2296 which meet at an end flat 2298.

Extending from the annulus 2272 away from the shaft 2270 there are provided three equally spaced, axially extending legs 2302. Each leg 2302 has a free end 2312 and a small ramp 2314 extending between the leg and the annulus 2272, the ramp 2314 being defined by a tapered surface. Each ramp 2314 is positioned on one side of the respective leg 2302.

Figure 42A:
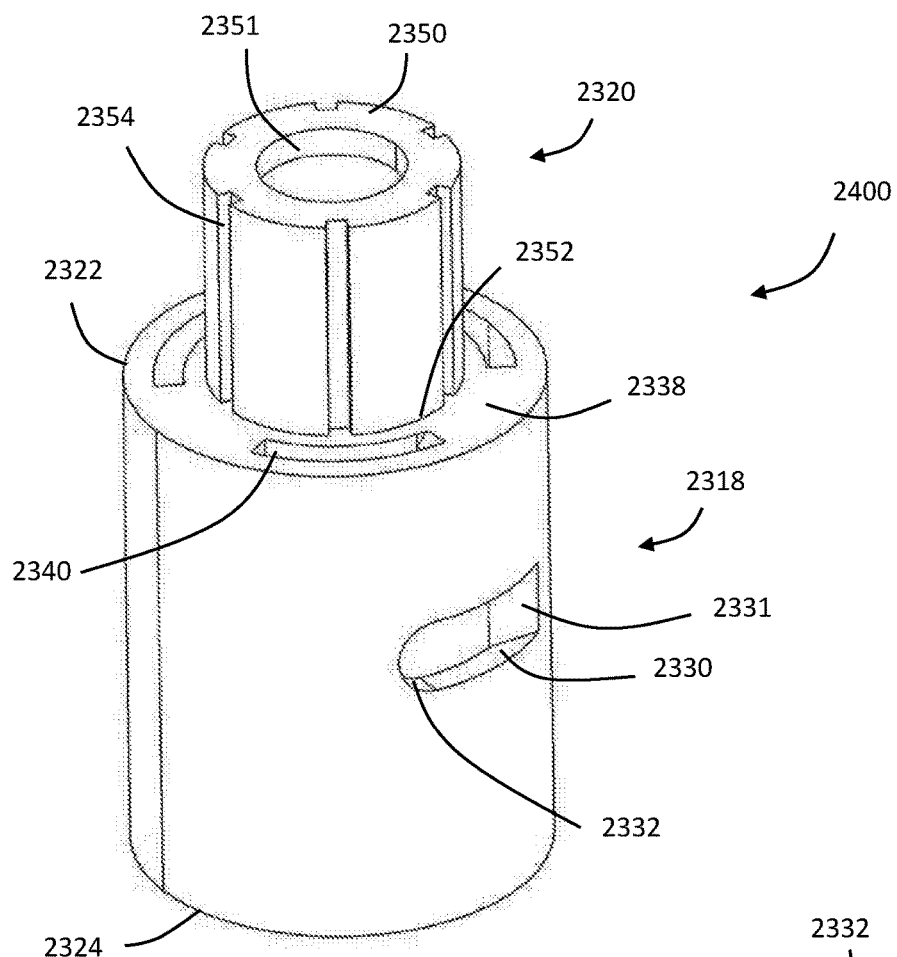
FIGS. 42a and 42b are perspective views of a sleeve of the priming and reset mechanism of FIG. 35.
Figure 42B:
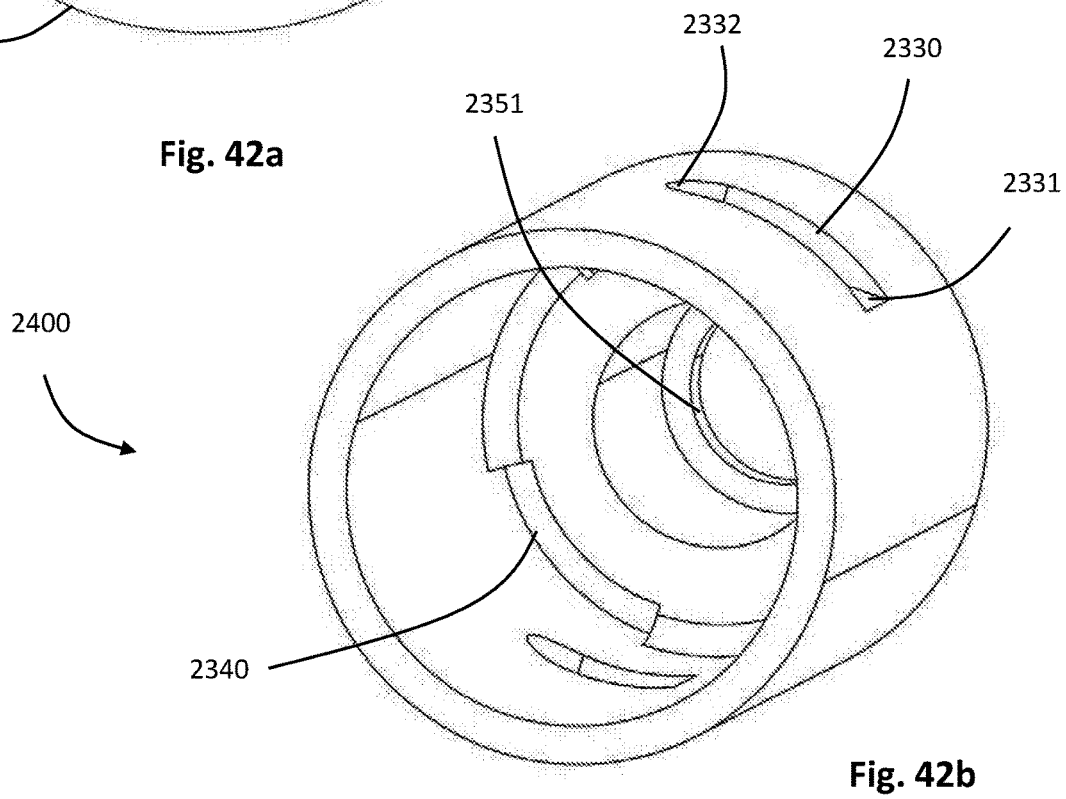

Referring to FIGS. 42a and 42b, the sleeve 2400 is shown in detail. The sleeve 2400 is a unitary, moulded, plastics component. The sleeve 2400 comprises a cylindrical sleeve body 2318 and a sleeve shaft 2320 projecting therefrom.

The sleeve body 2318 is generally cylindrical having a first, upper, end 2322 and a second, lower, end 2324. The sleeve body 2318 defines first and second opposed slots 2330 through the wall of the body 2318. Each slot 2330 has a tapered end 2331 and a curved end 2332. The curved ends 2332 face each other. The tapered ends 2331 result in the slots being shorter at the interior surface of the sleeve body 2318 than at the exterior surface of the sleeve body 2318.

The first end 2322 of the body 2318 terminates in an annular surface 2338 that defines three leg openings 2340. Each leg opening 2340 is shaped as a circle-segment.

The sleeve shaft 2320 extends from the centre of the annular surface 2338 and is constructed as a hollow cylinder. The sleeve shaft 2320 has a first, upper end 2350 having a coaxial opening 2351 and a second, lower, end 2352 where it joins the annular surface 2338. The sleeve shaft 2320 has six axially extending equally spaced grooves 2354 which extend axially from the first end 2350 to the second end 2352.

Figure 43A:
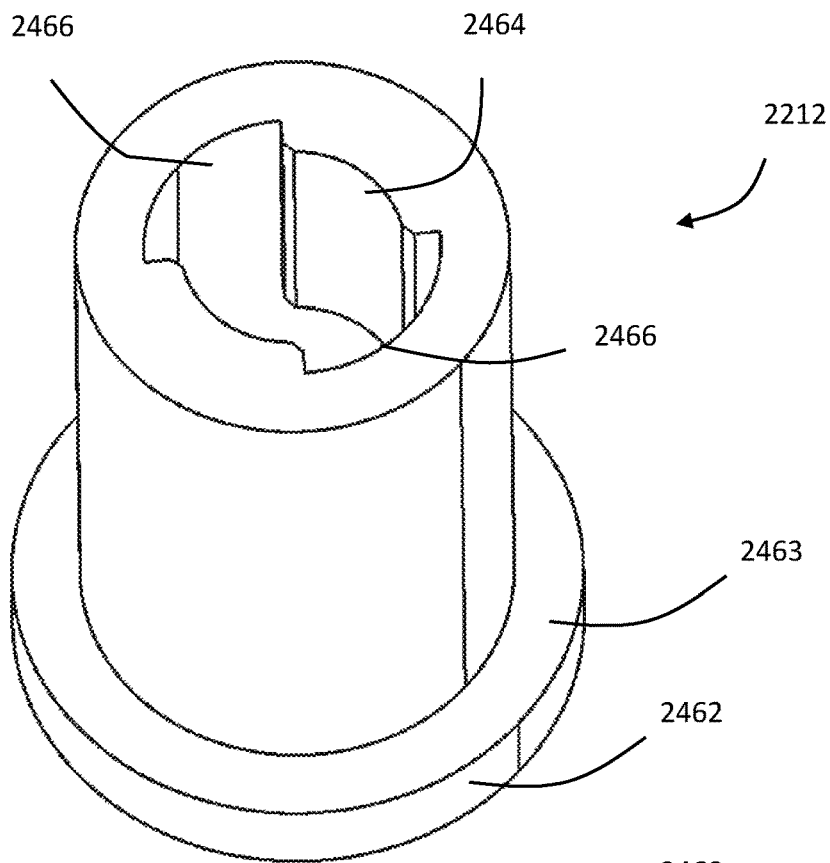
FIGS. 43a and 43b are perspective views of a spring abutment of the priming and reset mechanism of FIG. 35.
Figure 43B:
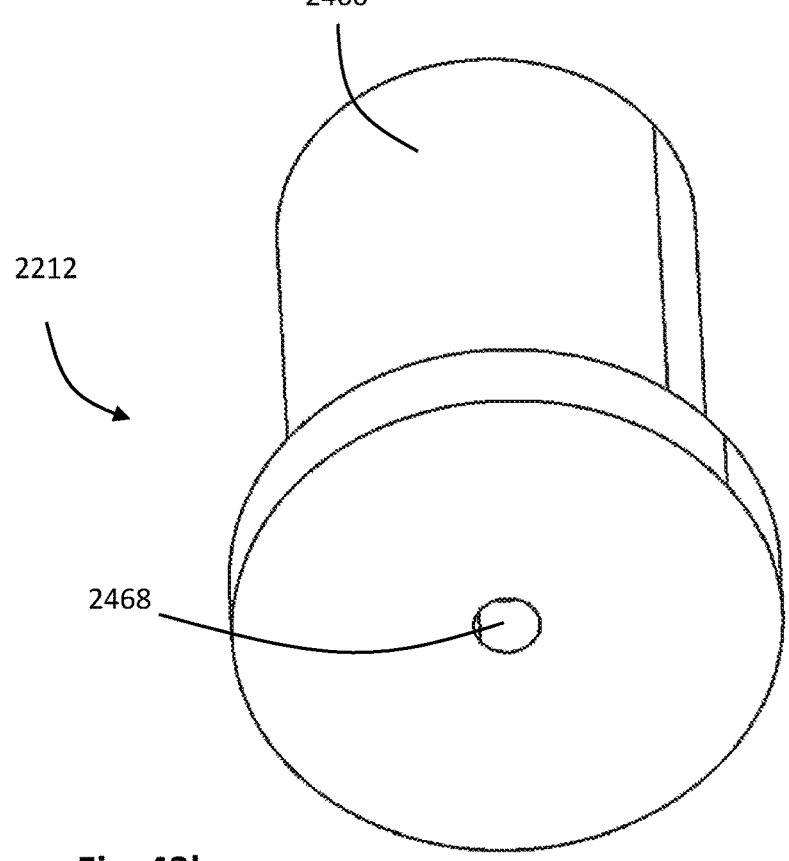

Referring to FIGS. 43a and 43b, the spring abutment 2212 is shown. The spring abutment 2212 comprises a shaft 2460 and an overhanging head 2462 to define a shoulder 2463 therebetween. The shaft 2460 is generally cylindrical and defines an opening 2464 which is generally circular having two opposed wings 2466. The head 2462 defines an opening 2468 at its centre.

Figure 44:
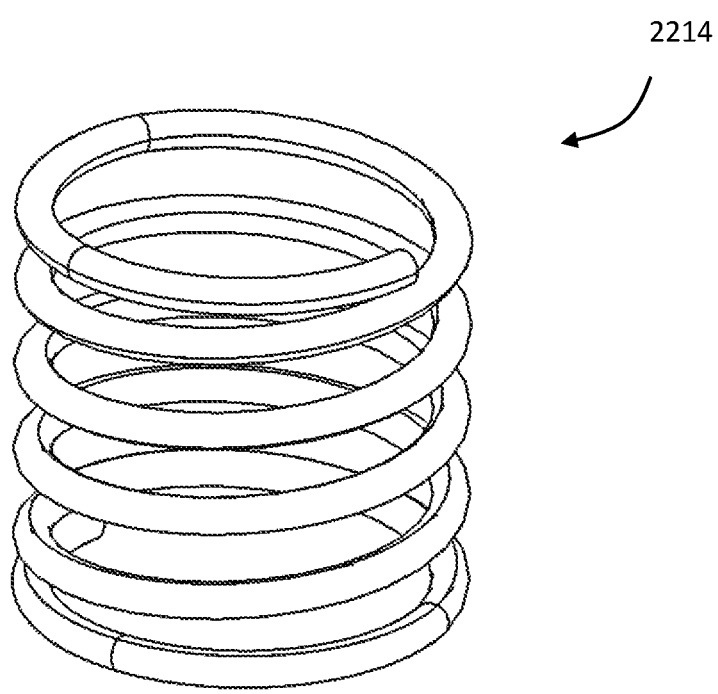
FIG. 44 is a perspective view of a spring of the priming and reset mechanism of FIG. 35.

Referring to FIG. 44, the spring 2214 is shown, which is a metal compression spring (shown in its rest state).

Figure 45A:
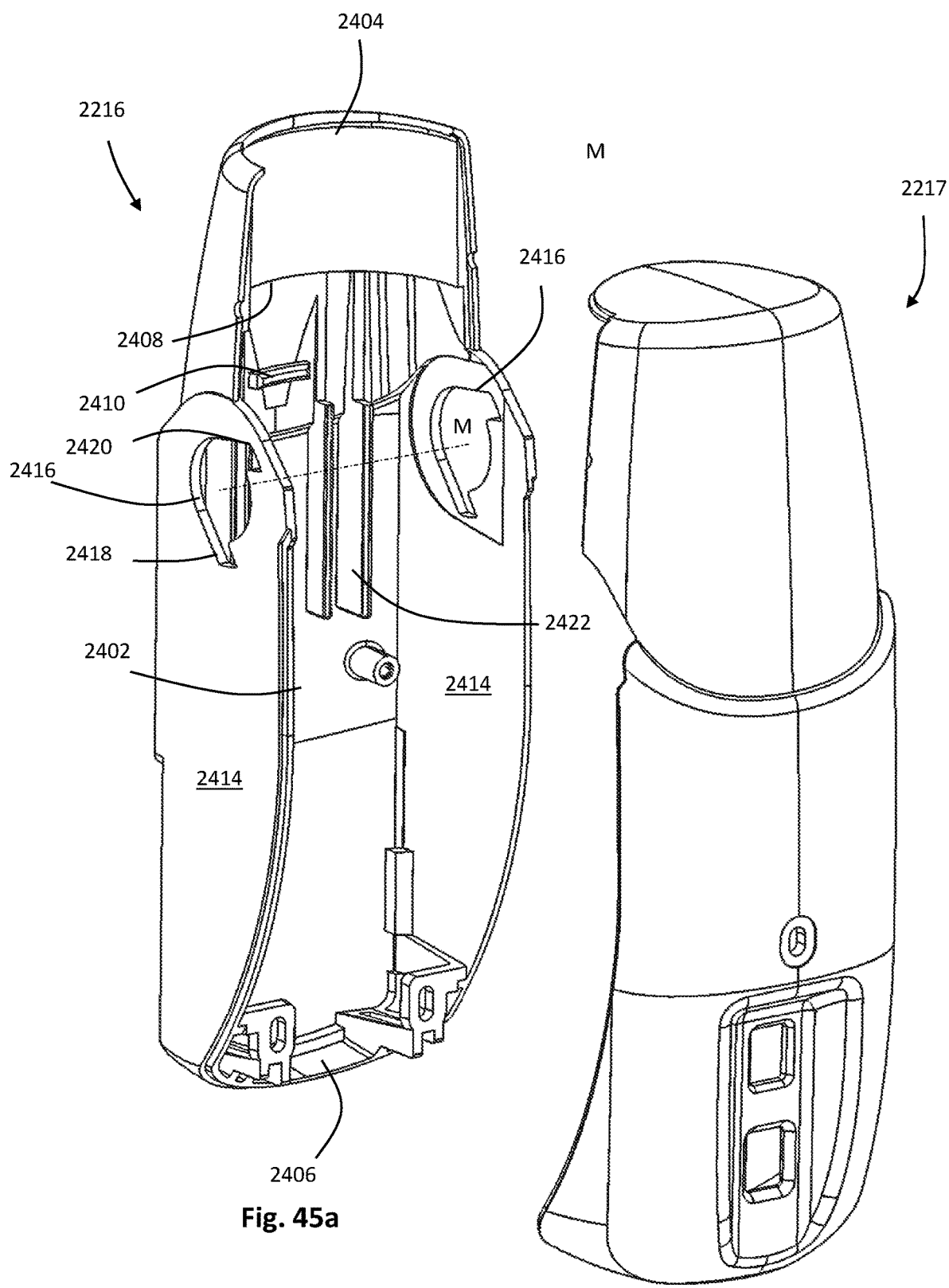
FIGS. 45a and 45b are perspective views of an actuator body of the priming and reset mechanism of FIG. 35.
Figure 45B:
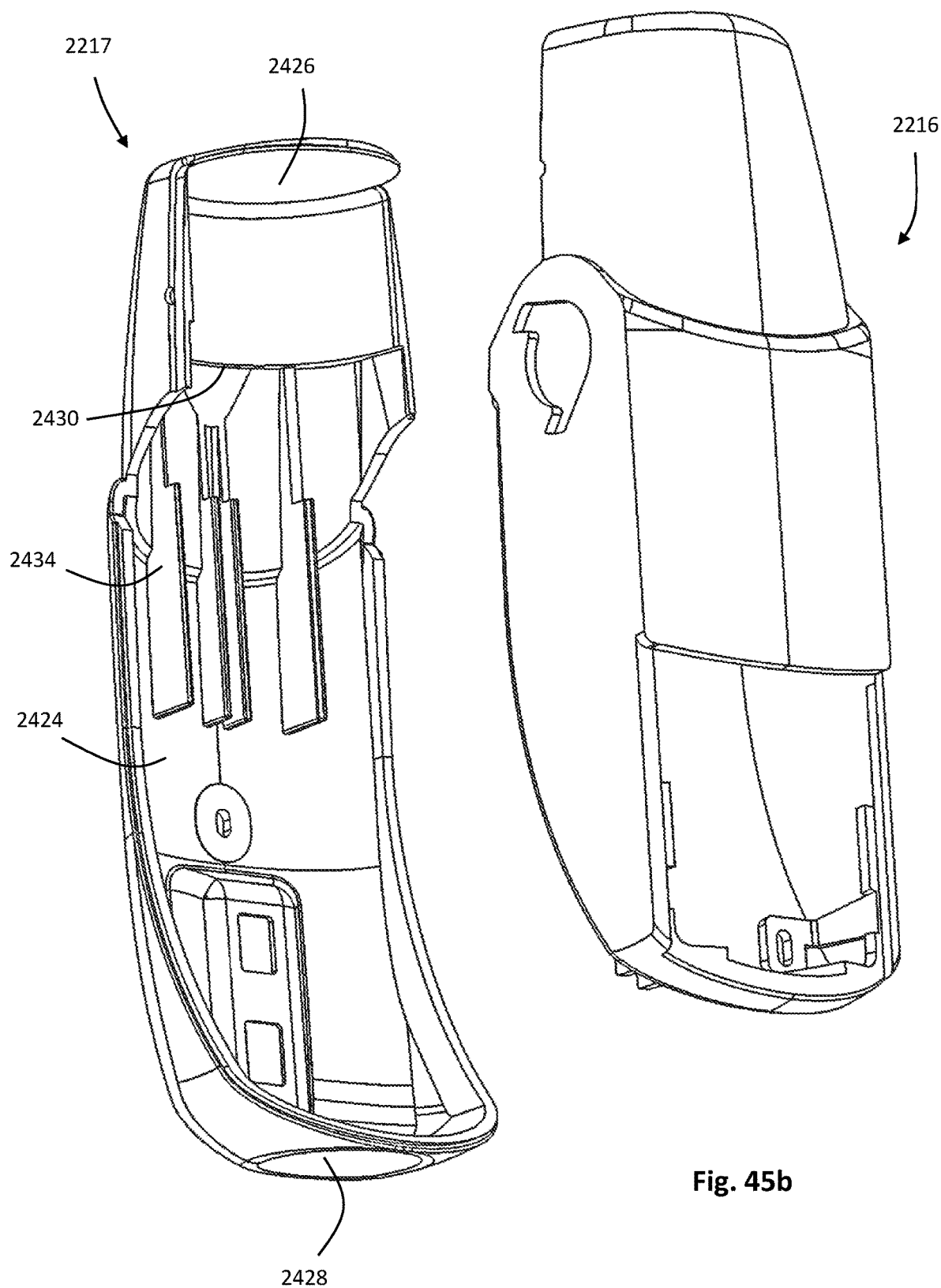

Referring to FIGS. 45a and 45b, the actuator body parts 2216 and 2217 are shown in detail in exploded form.

The first actuator body part 2216 is a unitary, moulded plastics component which is generally elongate and concave having a curved wall 2402, a first end 2404 and a second end 2406 opposite the first. On the interior side of the concave wall 2402 there is provided a downwardly facing transfer collar abutment 2408 in the form of a shoulder, and an actuator ring abutment 2410 in the form of a circumferentially and radially inwardly extending rib. The wall 2402 also comprises two parallel side panels 2414 extending from either side thereof. Each side panel 2414 is flat and defines an opening 2416 therein. Each opening 2416 is generally circular having two opposed wings 2418, 2420 extending tangentially therefrom. The wall 2402 also defines four longitudinally extending stiffening ribs 2422. Both openings 2416 lie on a mouthpiece cover axis M.

The second actuator body part 2217 is a unitary, moulded plastics component which is generally elongate and concave having a curved wall 2424, a first endwall 2426 and a second endwall 2428 opposite the first. On the interior side of the concave wall 2424 there is provided a downwardly facing collar abutment 2430 in the form of a shoulder. The wall 2424 also defines four longitudinally extending stiffening ribs 2434.

Figure 46:
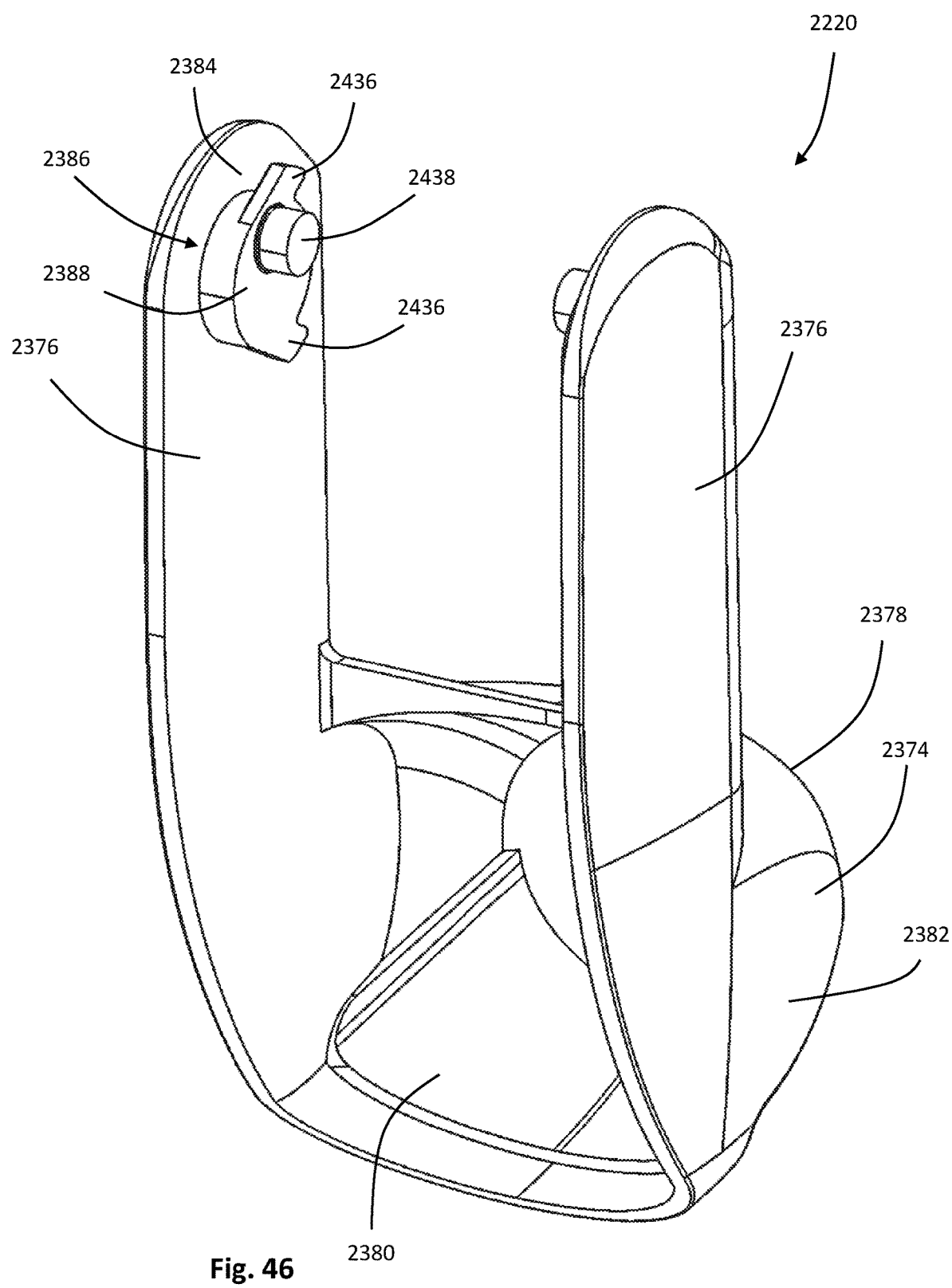
FIG. 46 is a perspective view of a mouthpiece cover of the priming and reset mechanism of FIG. 35.

Referring to FIG. 46, the mouthpiece cover 2220 is shown in more detail. The mouthpiece cover 2220 is a unitary, moulded plastics component. The mouthpiece cover 2220 comprises a cap 2374 and two arms 2376 that are mirror images of each other.

The cap 2374 is an internally concave structure suitable for sealing a mouthpiece of the inhaler patient port 2157. The cap 2374 has a closed end 2378 and an open end 2380. The cap 2374 defines a pair of opposed sidewalls 2382 from which the arms 2376 extend proximate the open end 2380.

Each arm 2376 is an elongate, generally planar structure extending to a free end 2384. At the free end 2384, and on an inwardly facing surface of each arm 2376 there is provided a cam 2386. The cam 2386 comprises a generally cylindrical body 2388 having two tangentially extending, opposed wings 2436. The cam also defines an inwardly projecting cam lug 2438 which is off-centre on the cylindrical body 2388.

Assembly

Figure 47A:
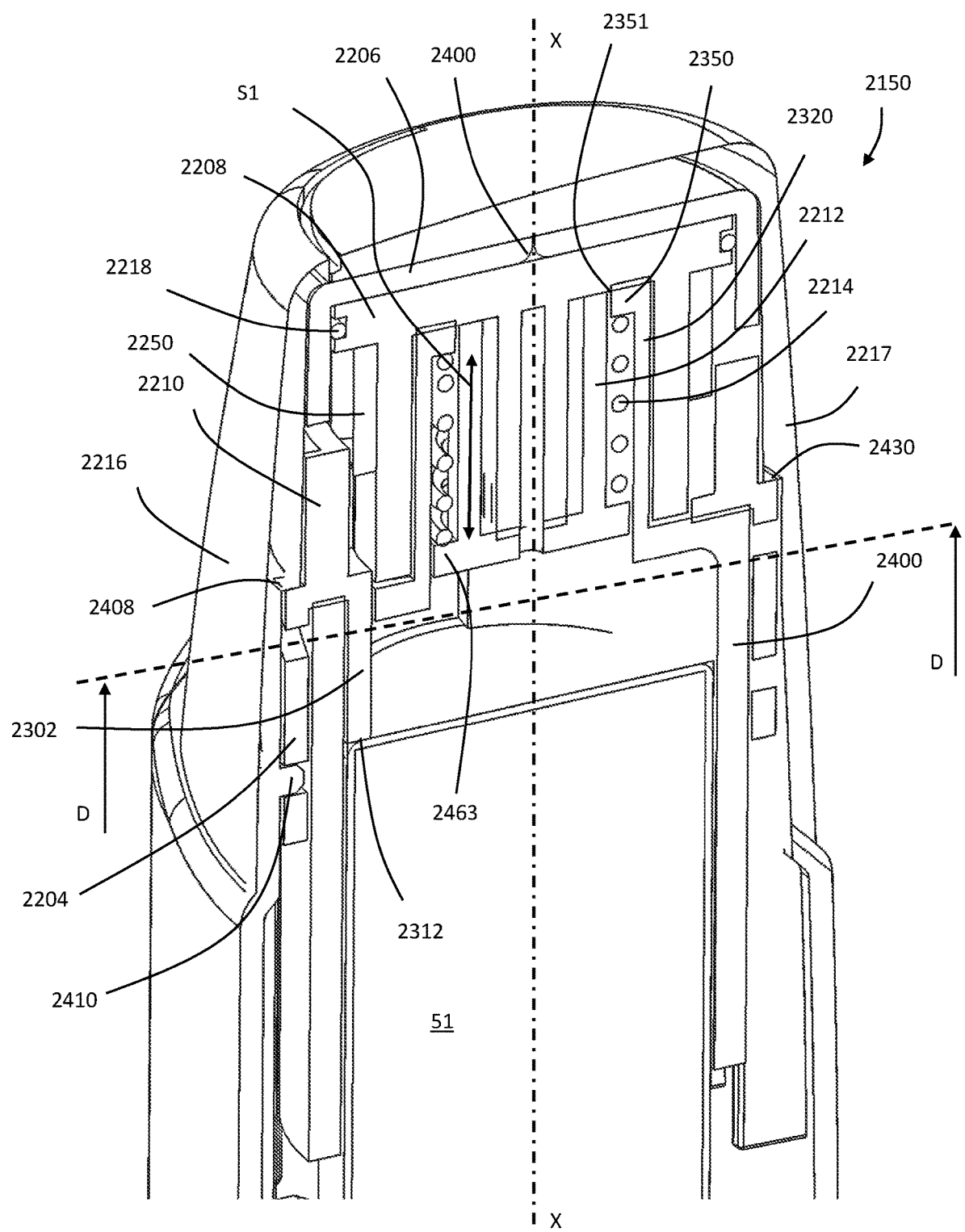
FIG. 47a is a section view of the priming and reset mechanism of FIG. 35 in a rest condition.
Figure 47B:
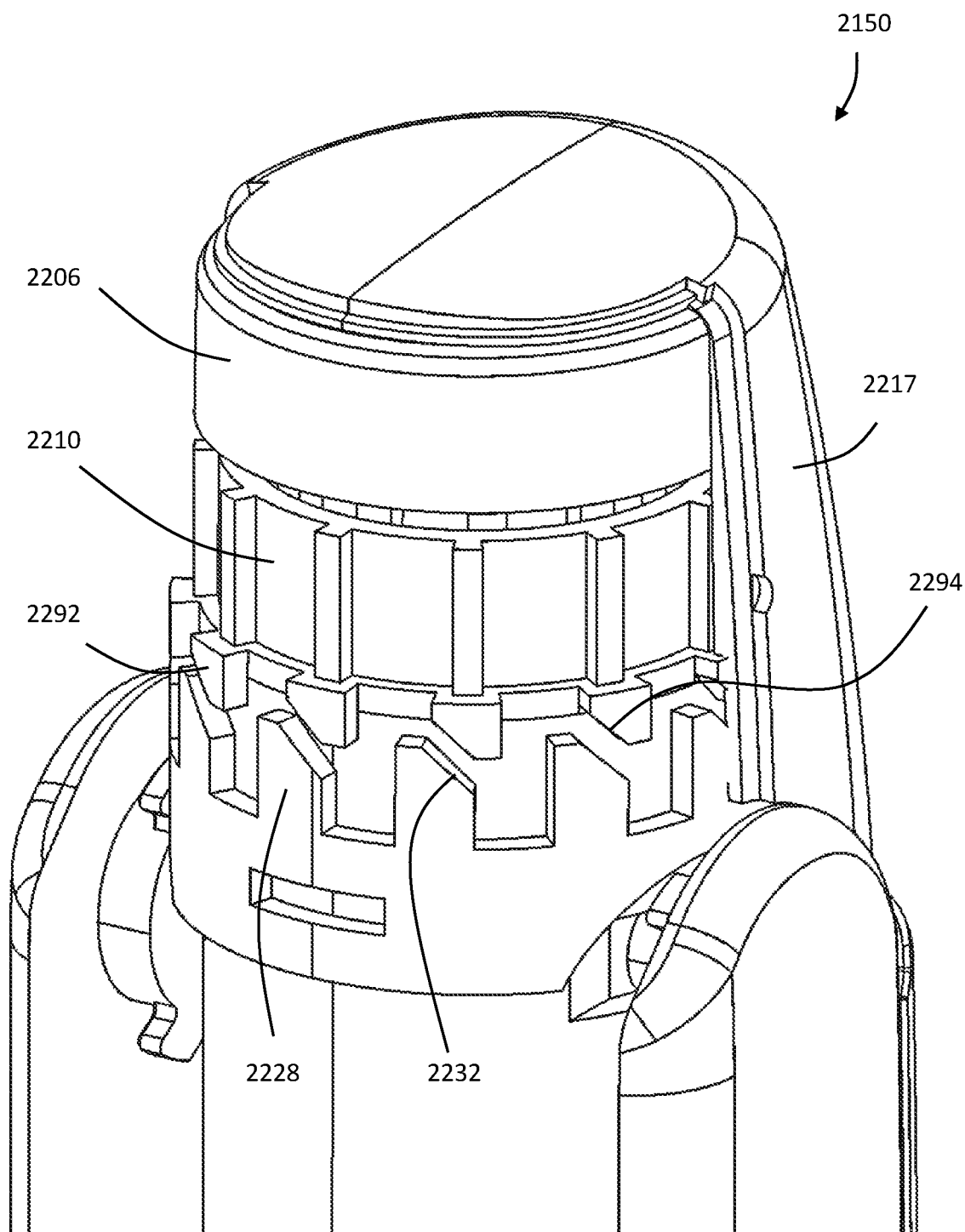
FIGS. 47b to 47d are various perspective views of components of the priming and reset mechanism of FIG. 35 in a rest condition.
Figure 47C:
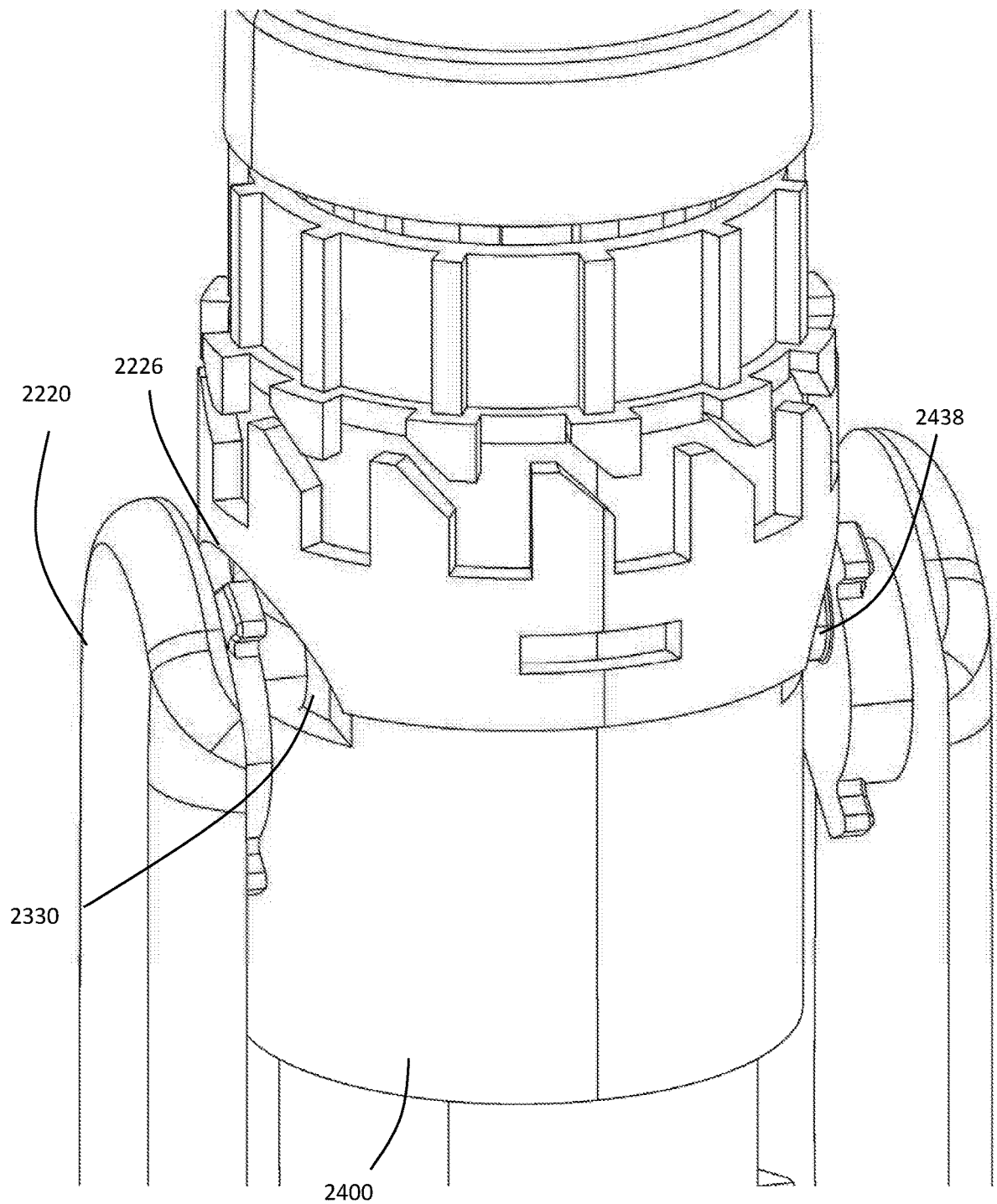
Figure 47D:
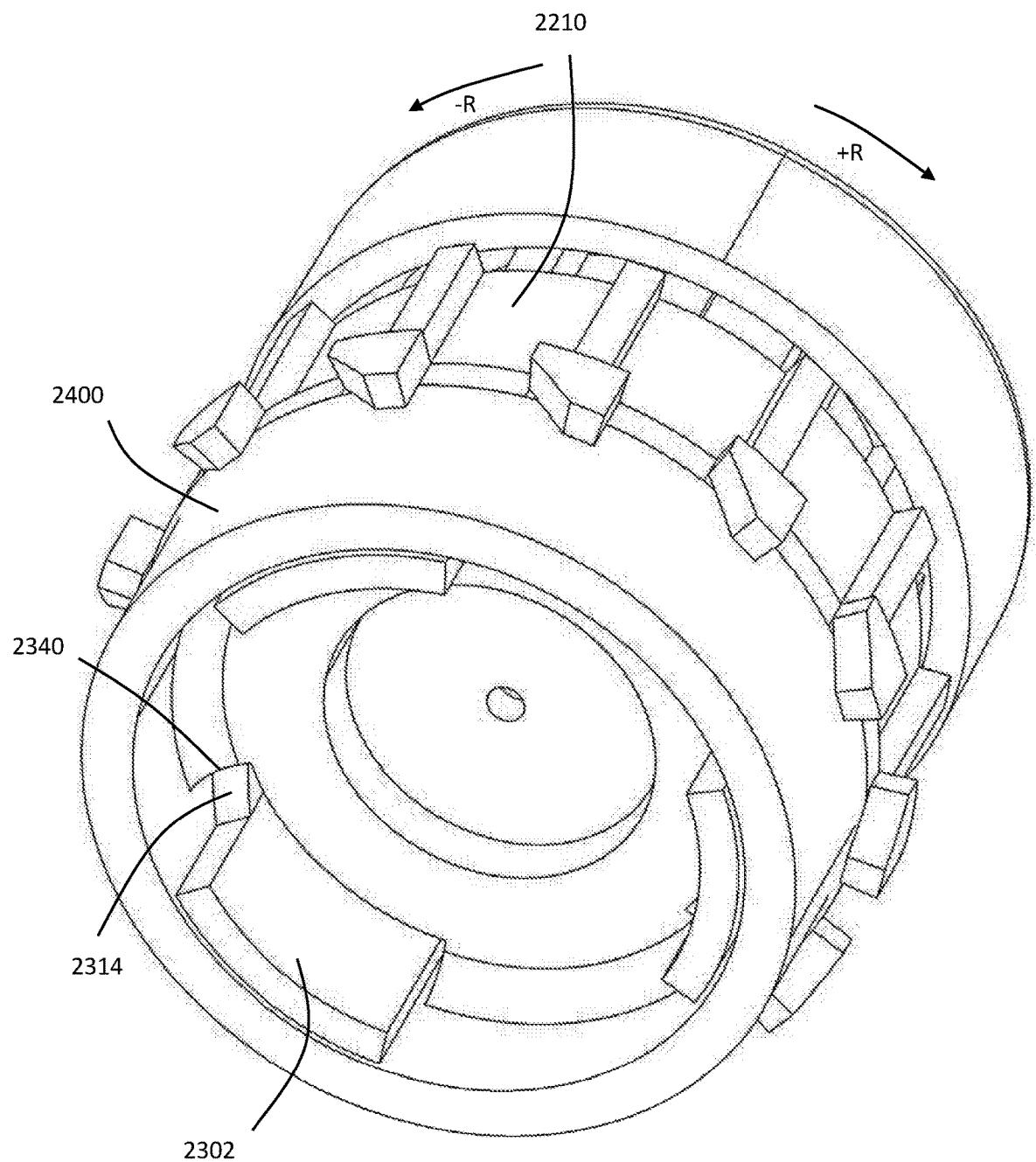

The components described above are aligned on a main axis X. Referring to FIGS. 47a to 47d (as well as the exploded view of FIG. 36), the system is shown in its assembled state, in a rest condition (used for storage and generally when not in operation). The view in FIG. 47a is in section A of FIG. 35. The views in FIGS. 47b and 47c are approximately in direction B of FIG. 35, but with the first actuator body part 2216 removed in the case of FIG. 47b, and with both actuator body parts removed in FIG. 47c. The view of FIG. 47d is a section in the approximate direction of D in FIG. 47a.

The transfer collar 2210 is assembled with the sleeve 2400 by passing the legs 2302 into the openings 2340. Referring to FIG. 47d, the legs 2302 and ramps 2314 are fully engaged in the openings 2340 of the sleeve 2400.

Referring to FIG. 47a, the spring 2214 is inserted into the sleeve shaft 2320 so that it abuts the upper end 2350 thereof. The spring abutment 2212 is then inserted into the spring 2214 such that the end of the shaft 2460 extends into the opening 2351 in the sleeve shaft 2320.

The spring 2214 is thereby trapped by the shoulder 2463 of the spring abutment 2212. The spring abutment can slide relative to the sleeve 2400 along the axis X to compress the spring 2214. The sub-assembly of the sleeve 2240, spring 2214 and spring abutment 2212 form an energy storage arrangement.

The piston 2208 is slid over the sleeve shaft 2320 such that the piston shaft 2266 engages and mates with the opening 2464 on the spring abutment 2212. The end of the piston shaft 2266 abuts the head 2462 of the spring abutment 2212 and is bonded thereto such that the piston 2208 and the spring abutment are fixed.

It will also be noted that the inwardly extending ribs 2470 of the piston 2208 engage the grooves 2354 on the exterior of the sleeve shaft 2320 to facilitate relative sliding of the piston-spring abutment sub-assembly relative to the sleeve 2400.

The o-ring 2218 is assembled into the groove 2260 on the piston 2208, and the piston 2208 is inserted into the open end of the cylinder 2206 to form a seal therewith. The o-ring 2218 seals against the inner sidewall of the cylinder 2206 such that axial movement of the piston results in airflow through the air leak hole 2240. As such, relative motion of the piston 2208 and cylinder 2206 is damped. Further, because the hole 2240 is tapered, movement of the piston 2208 into the cylinder 2206 is resisted less than movement of the piston 2208 out of the cylinder 2206. In other words, separation of the piston 2208 and cylinder 2206 is damped more than movement of the piston 2208 into the cylinder 2206.

The assembly of the transfer collar 2210, sleeve 2400, spring 2214, spring abutment 2212, piston 2208, o-ring 2218 and cylinder 2206 is positioned within the actuator body parts 2216, 2217 and can move axially relative thereto.

The actuator ring 2204 is then positioned within the actuator body parts 2216, 2217 and held stationary relative thereto by engagement of the slot 2227 with the actuator ring abutment 2410.

In this rest position, the outer collar teeth 2292 face downwardly as shown in FIG. 47b to face the tapered edges 2232 of the actuator ring teeth 2228. The teeth 2292, 2228 are offset. The upper surfaces 2282 of the inner collar teeth 2280 face the downwardly facing surfaces 2252 of the piston teeth 2250. The upper surface of the teeth 2292 of the transfer collar 2210 abut the collar abutments 2408, 2430 of the respective actuator body parts 2216, 2217.

The mouthpiece cover 2220 is snap-fitted onto the first actuator body part 2216 in the same manner as with the second embodiment (and as such will not be described in detail here). It will be noted that instead of engaging the spring 2214, the cam lugs 2438 engage the slots 2330 on the sleeve 2400 (FIG. 47c). The provision of the curved recesses 2226 on the actuator ring 2204 facilitate this engagement, resulting in a compact assembly.

Figure 35:
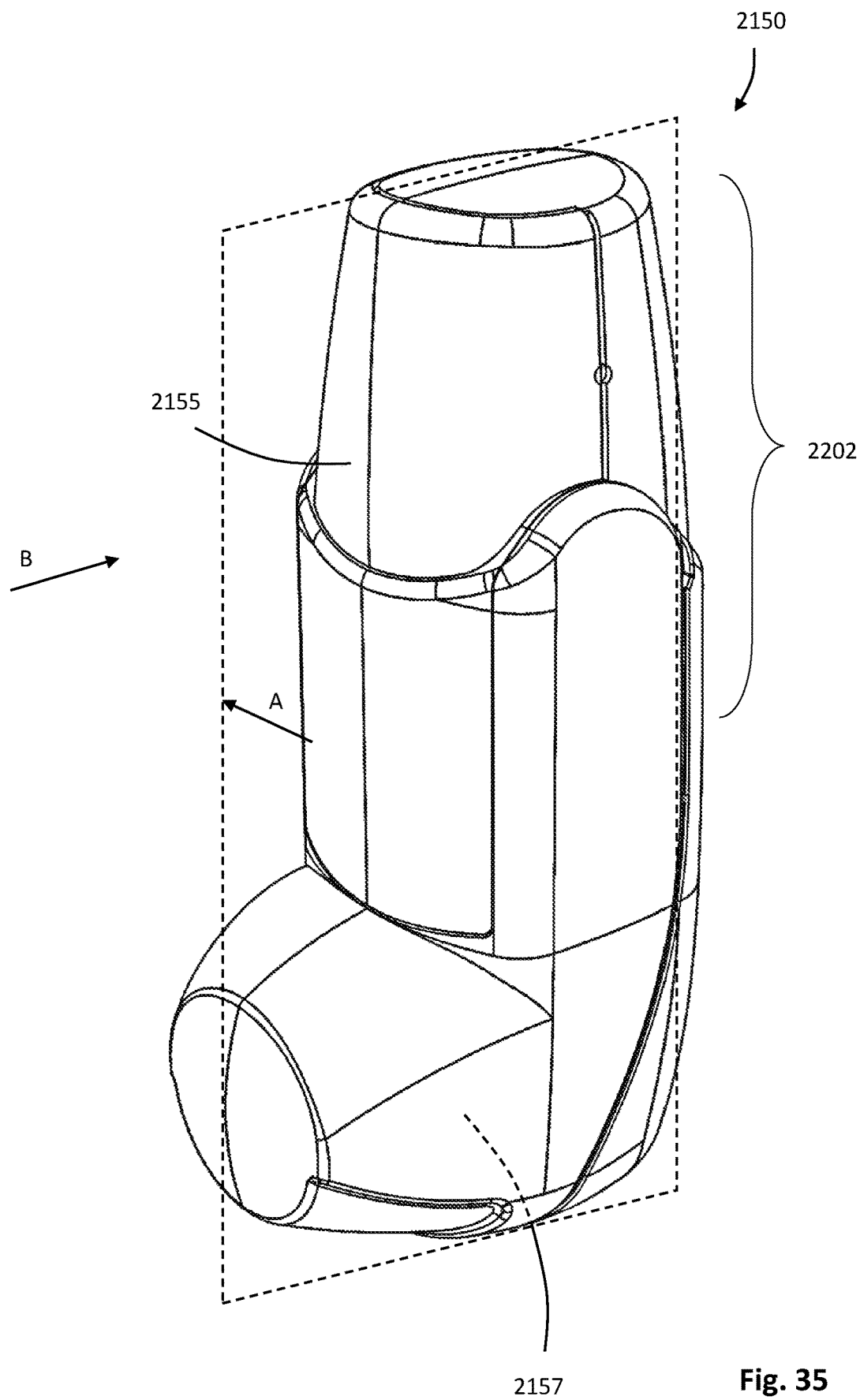
FIG. 35 is a perspective view of a pMDI comprising a third priming and reset mechanism in accordance with an embodiment of the present invention.
Figure 36:
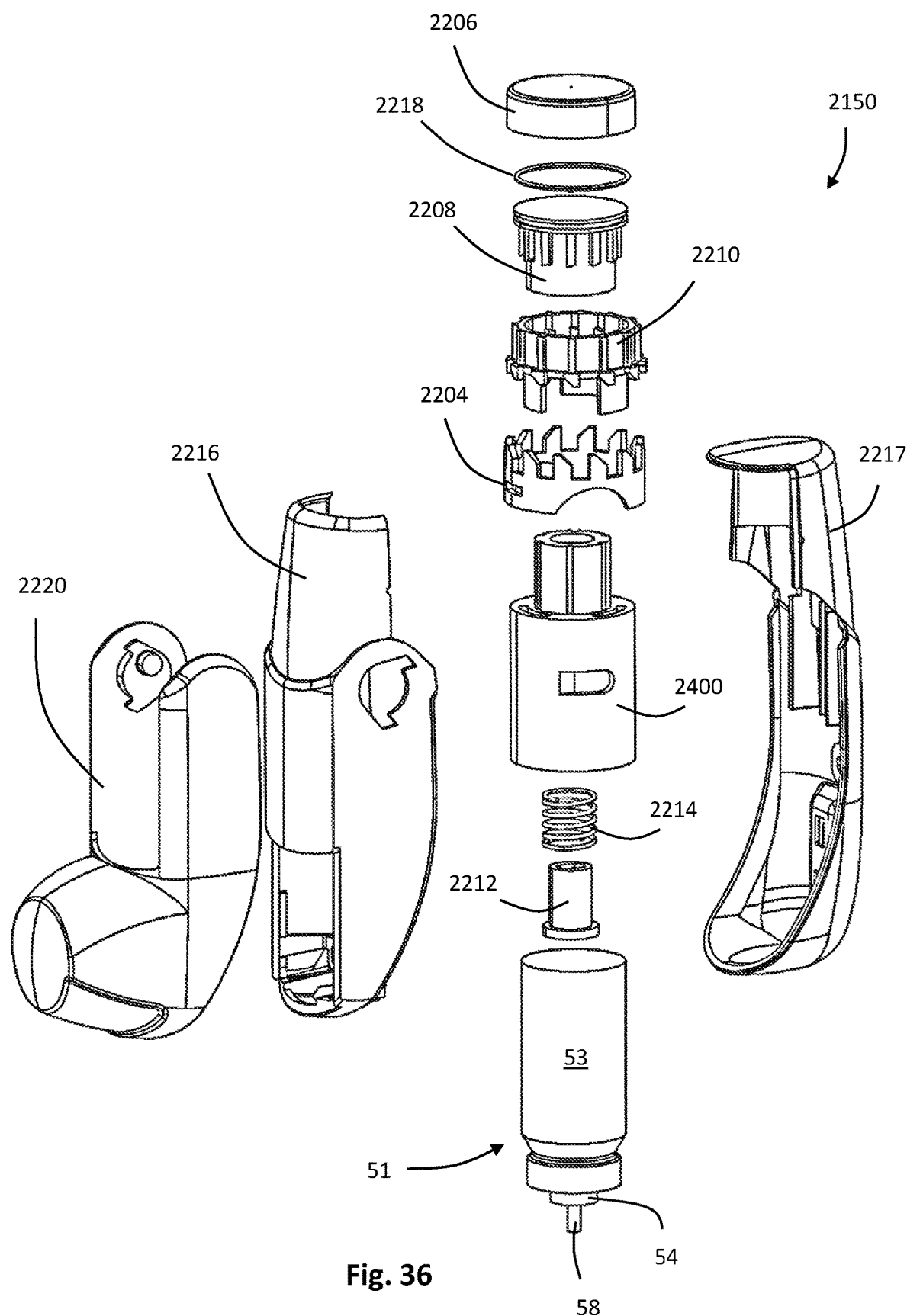
FIG. 36 is an exploded view of the priming and reset mechanism of FIG. 35.

In the rest position, the mouthpiece cover 2220 covers the inhaler mouthpiece (see FIG. 35).

Operation

The pMDI 2150 is used as follows. The operation of the pMDI 2150 is best described as passing through a number of operational conditions or stages as will be described below.

1. Rest Condition

The rest condition is shown in FIGS. 35, 36 and 47a to 47d. In this condition, a canister 51 having a can 53 and a metering valve 54 with a valve stem 58 is provided within the pMDI. The stem 58 abuts a stem abutment which is static within the pMDI 2150. In the rest condition, downward travel of the canister 51 is inhibited by a trigger abutment which is part of a trigger assembly (not described here, but generally known in the art).

In this position, the canister 51 is positioned partly within the sleeve 2400 (FIG. 47a), and the free ends 2312 of the legs 2302 of the transfer collar 2210 abut the bottom of the canister 51 (as it is inverted). The tapered surfaces 2294 of the outer collar teeth 2292 are aligned with, and facing, the tapered surfaces 2232 of the upwardly projecting teeth 2228 of the actuator ring 2204 (FIG. 47b).

The spring 2214 is also in a rest position, and stores no energy. As shown in FIG. 47a, the spring 2214 is at length S1. The piston 2208 and cylinder 2206 are fully engaged, with the sleeve shaft 2320 fully engaged in the piston as shown in FIG. 47a. The piston teeth 2250 are spaced apart along axis X from the inner collar teeth 2280.

2. Primed Condition

Figure 48A:
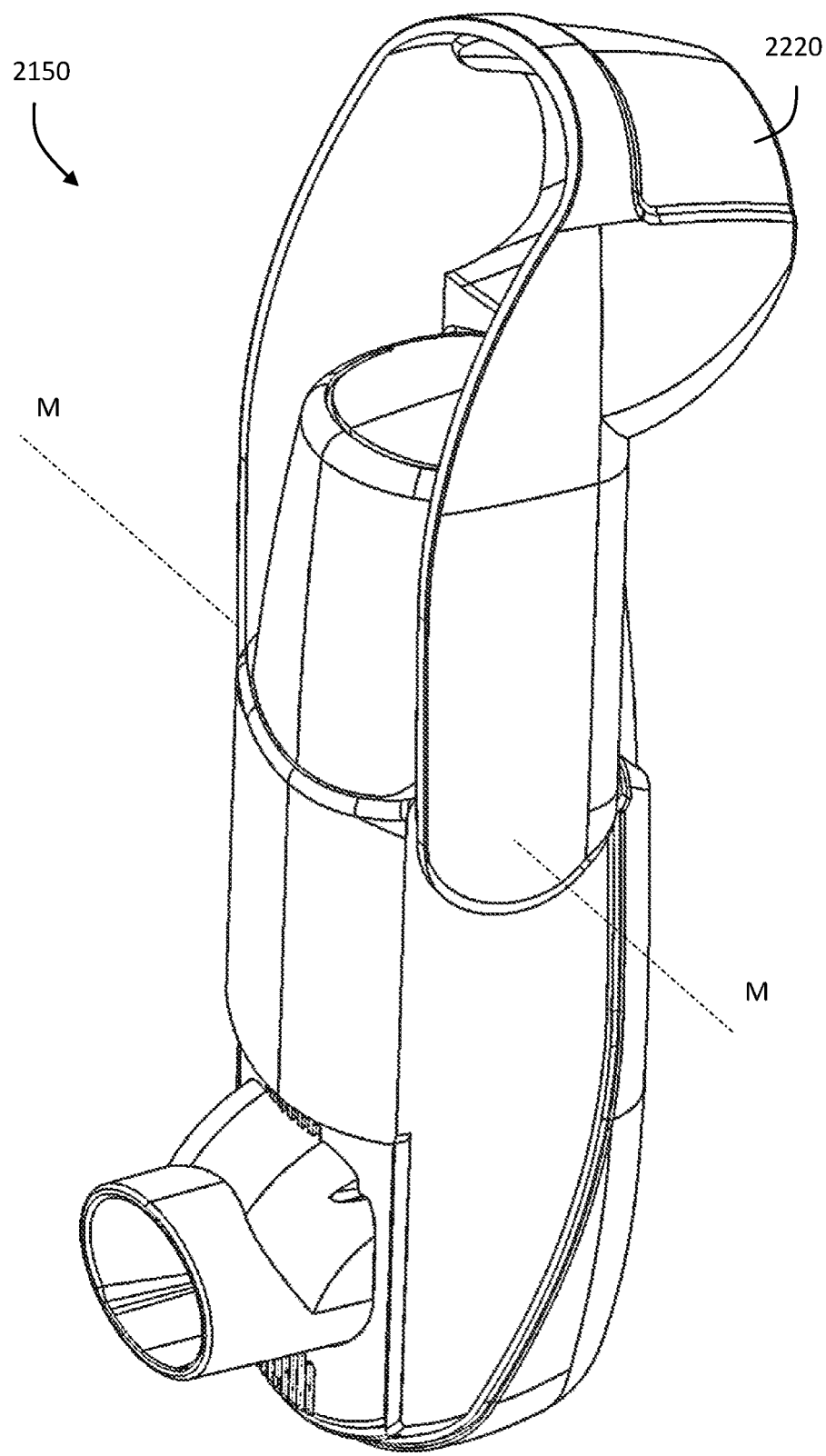
FIG. 48a is a perspective view of the pMDI of FIG. 35 in a primed condition.
Figure 48B:
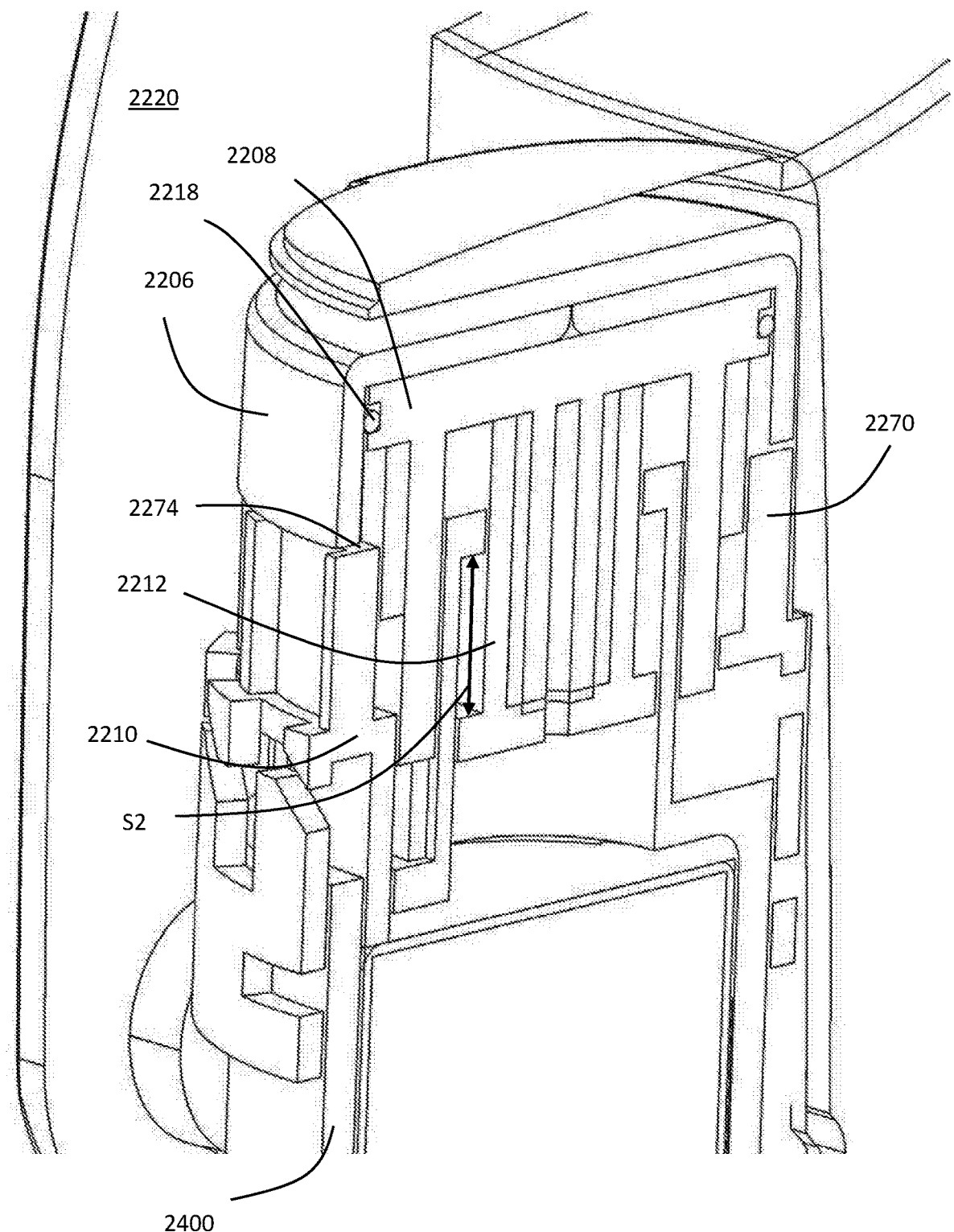
FIGS. 48b and 48c are section views of the priming and reset mechanism of FIG. 35 in a primed condition.

Turning to FIGS. 48a to 48b, the mouthpiece cover 2220 has been rotated about the mouthpiece cover axis M, such that the lugs 2438 have moved downwards in the housing and drawn the sleeve 2400 vertically downwards.

Figure 48C:
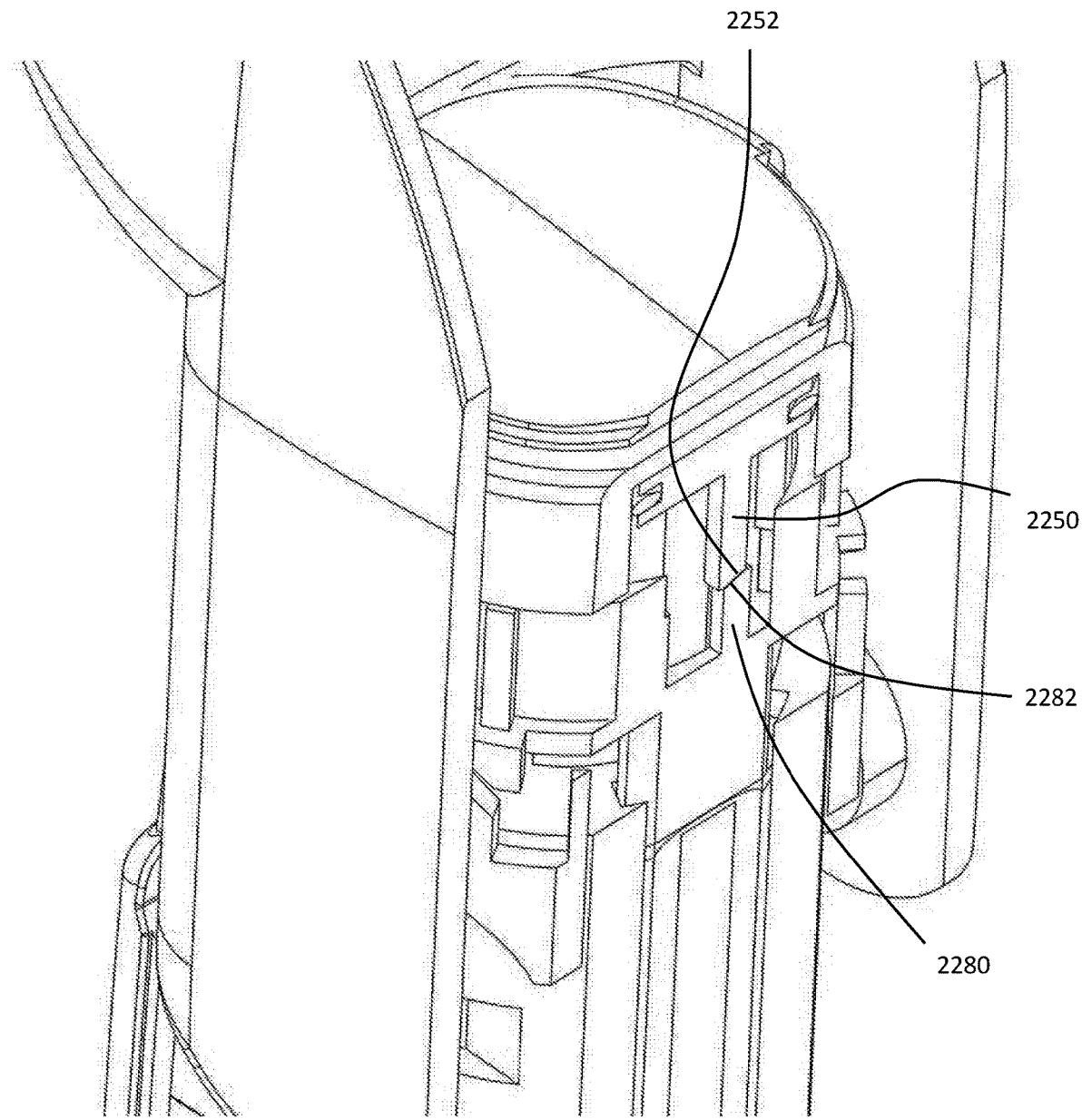

Referring to FIG. 48b, the sleeve 2400 produces a downward force along axis X on the spring 2214 (omitted for clarity from FIG. 48b). This, in turn, draws the spring abutment 2212 downwards which in turn draws the piston 2208 downwards. Because there is a resistance to separation of the piston 2208 and the cylinder 2206 (due to both the size of the opening 2240 and the o-ring 2218), the cylinder 2206 is also drawn downwards until it abuts the first end 2274 of the shaft 2270 of the transfer collar 2210. At the same time, as shown in FIG. 48c, the tapered surfaces 2252 of the piston teeth 2250 abut the ends 2282 of the inner shaft teeth 2280.

It will be noted that the canister 51 is held in position by the trigger mechanism, and as such the transfer collar 2210 cannot move downwards. Neither the cylinder 2206 nor the piston 2208 can move further downwards as they are both supported by the transfer collar 2210.

Further movement of the mouthpiece cover 2220 to draw the sleeve 2400 down compresses the spring to length S2 (FIG. 48b). The spring thereby stores the actuation energy for the canister 51.

As with the FIGS. 32e to 32g, the spring 2214 is fully compressed (i.e. with sufficient energy to actuate the mechanism) at an intermediate position of the mouthpiece.

3. Fired Condition

When the user wishes to dispense the medicament, a trigger mechanism (which is not described here) is fired in which the trigger abutment is moved such that downward motion of the canister 51 is no longer inhibited.

In the primed condition, the canister 51 was resisting downward movement of the transfer collar 2210, which in turn was holding up the piston 2208 and therefore the lower end of the spring 2214 (under compression) via the spring abutment 2212.

Release of the canister 51 releases the transfer collar 2210 in a downward direction. Because the sleeve 2400 is held in position by the mouthpiece cover 2220, the spring 2214 pushes the spring abutment-piston assembly in a downwards direction, which in turn produces a downwards force on the transfer collar 2210 (due to the abutment of the teeth shown in FIG. 48c). The energy of the spring 2214 therefore acts to compress the canister 51 by pushing the valve stem 58 onto the valve stem abutment. This also acts against the bias of the valve spring within the valve 54 to open the canister 51 and release a dose of medicament.

Figure 49:
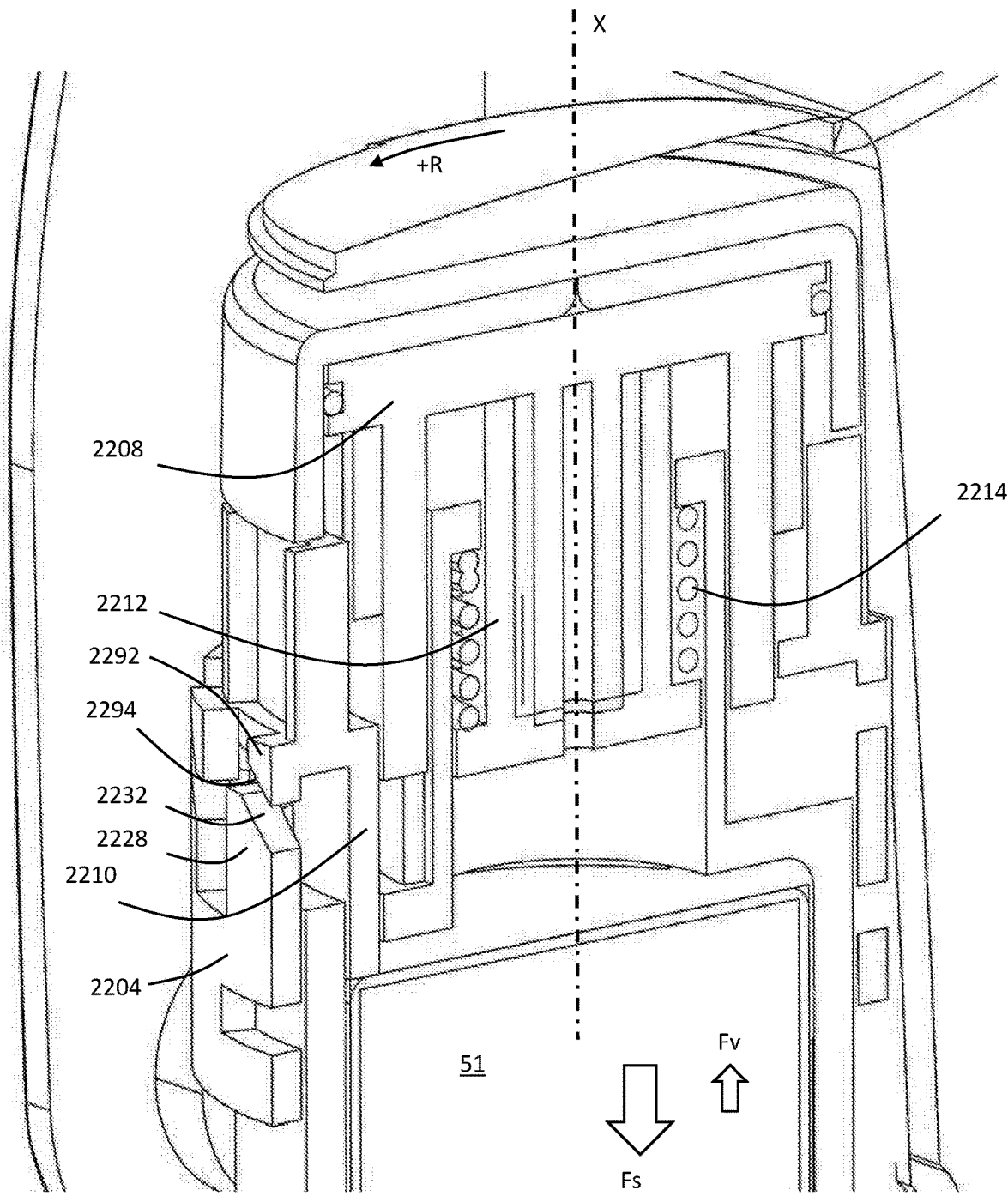
FIG. 49 is a section view of the priming and reset mechanism of FIG. 35 in a fired condition.

At this point, a spring force Fs is being applied to the canister 51 against the bias of a valve spring force Fv (FIG. 49).

Still referring to FIG. 49, as the transfer collar 2210 moves downwards along the axis X, the tapered surfaces 2294 of the outer collar teeth 2292 engage the tapered surfaces 2232 of the teeth 2228 of the actuator ring 2204. This acts to rotate the transfer collar 2210 about the axis X in direction +R and begins to move the clutch formed by the piston 2208 and the transfer collar 2210 to a released condition.

4. Auto-Release Condition

At a predetermined angle of rotation of the transfer collar 2210 relative to the piston 2208 (which cannot rotate) the clutch formed by the transfer collar 2210 and piston 2208 becomes detached (or released) in a linear sense. This is because the inner collar teeth 2280 can eventually move through the gaps between the piston teeth 2250 allowing relative linear movement between the piston 2208 and the transfer collar 2210 (see FIG. 50). This breaks the load path between the spring 2214 and the canister 51.

5. Can Reset Condition

Figure 50:
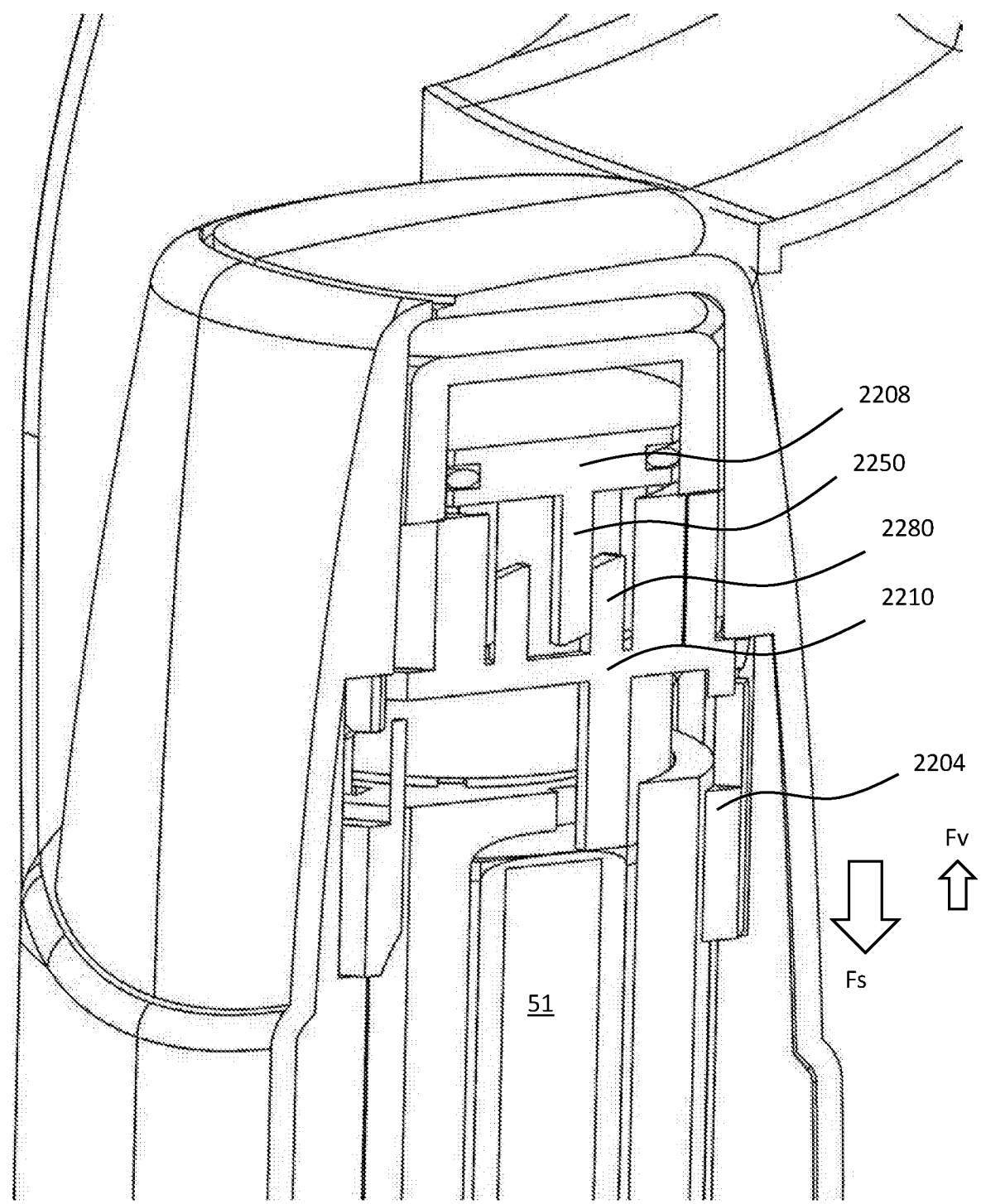
FIG. 50 is a section view of the priming and reset mechanism of FIG. 35 in an auto-release condition.
Figure 51:
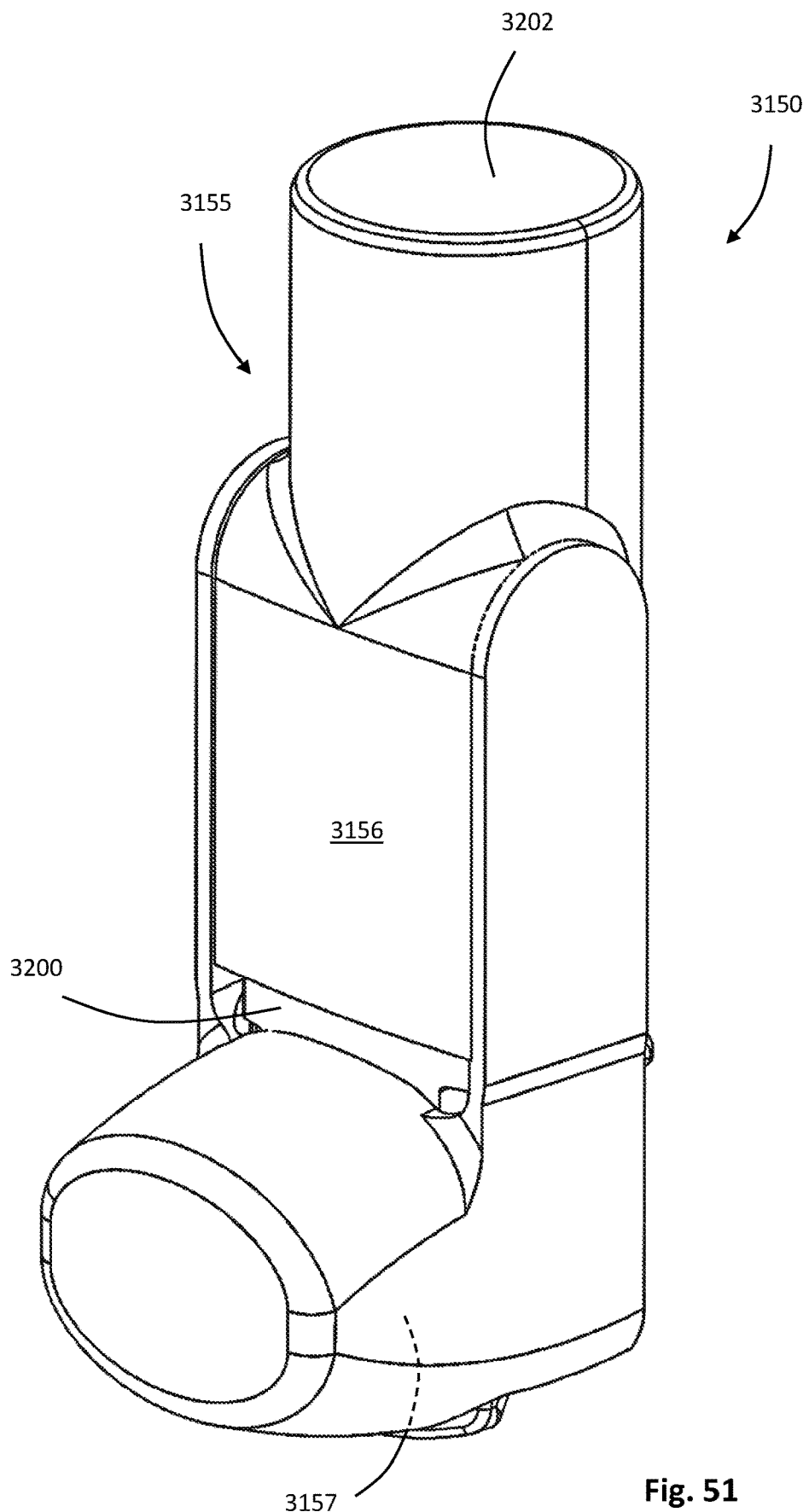
FIG. 51 is a perspective view of a pMDI comprising a fourth priming and reset mechanism in accordance with an embodiment of the present invention.

The system is now separated into two sub-assemblies which encounter opposing forces Fs and Fv. Reference is made to FIG. 50.

On one hand, the return force of the spring in the canister valve Fv applies an upward force on the transfer collar 2210 (via the canister 51) such that it lifts away from the actuator ring 2204. The transfer collar 2210 supports the cylinder 2206 which is also raised upwards.

On the other hand, the compressive force Fs remaining in the spring 2214 acts to drag the piston 2208 downwards. Therefore, as the canister 51 resiles to its rest (unactuated) position, its motion is controlled by the separation of the piston 2208 and cylinder 2206. As mentioned above, relative motion of the piston and cylinder is controlled by ingress of air into the air leak hole 2240. As such, the return of the canister (i.e. the timing of the return of the canister) is controlled, avoiding the aforementioned problems.

6. Return to Rest Condition

The user rotates the mouthpiece cover 2220 back to its original positon, which has the effect of drawing the lugs 2438 upwards and lifting the sleeve 2400. This motion re-engages the piston 2208 into the cylinder 2206. The shape of the air leak hole 2240 provides a higher coefficient of discharge for air egress, compared to that of air ingress described above.

Upward movement of the sleeve 2400 acts to fully engage the legs 2302 within the leg openings 2340 of the sleeve 2400 such that the ramps 2314 cause return/reciprocal rotation of the transfer collar 2210. Referring to FIG. 47*d*, when fired, the clutch release acts in direction +R. Upon return to rest, the transfer collar is rotated back to its original position in direction –R by the ramps 2314. By contrast with the pMDIs 150 and 1150, the transfer collar 2210 (unlike the collars 210, 1210) has a reciprocal rather than a continuously rotating motion. The rotation back to the original position realigns the tapered surfaces 2252 of the piston teeth 2250 and the ends 2282 of the inner shaft teeth 2280. In other words, the clutch is reset to a position in which axial force can be transmitted from the spring to the canister ready for the next operation.

The Fourth Embodiment

Figure 52:
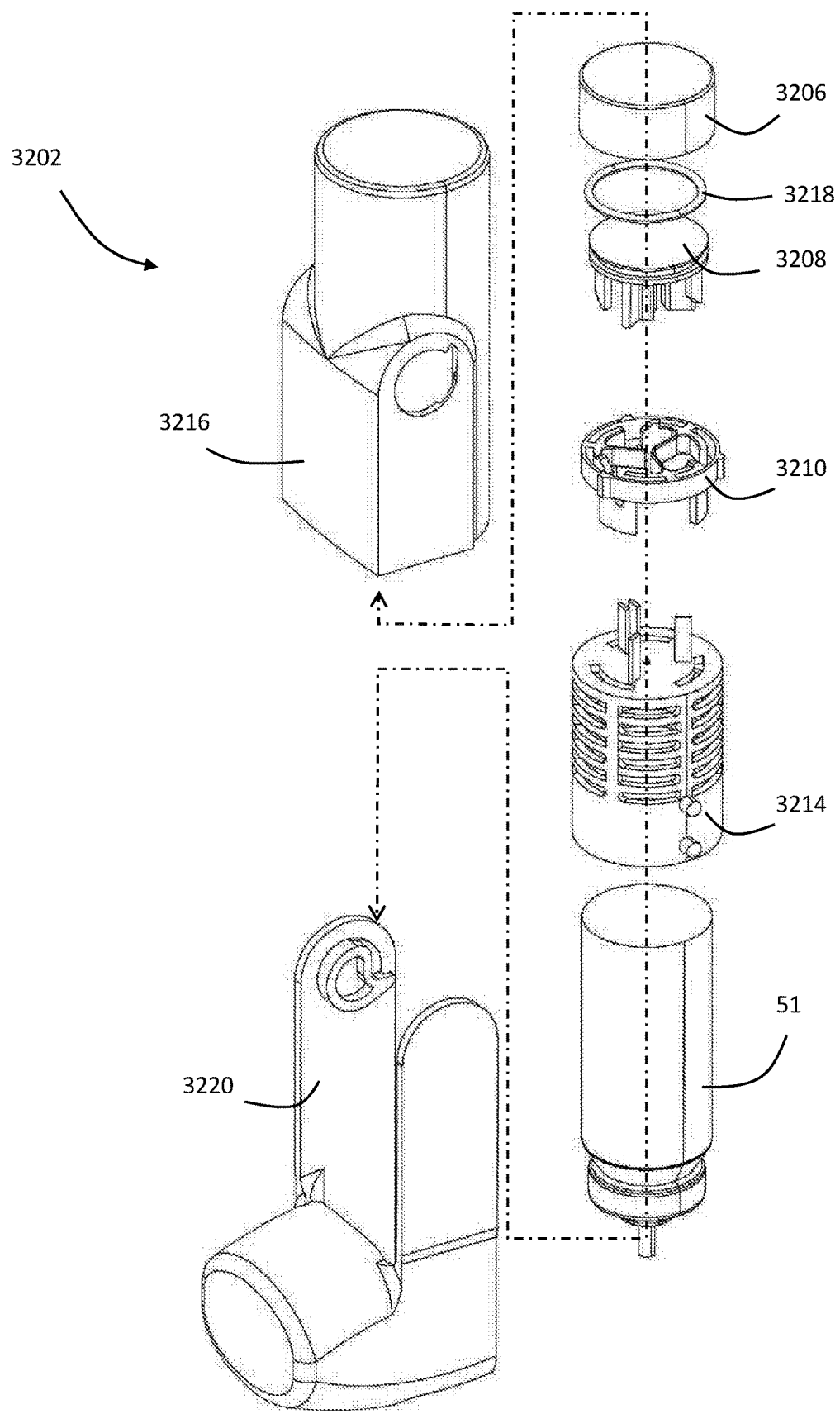
FIG. 52 is an exploded view of the priming and reset mechanism of FIG. 51.

Turning to FIGS. 51 to 64, part of a fourth pMDI 3150 according to an embodiment of the present invention is shown. The pMDI 3150 comprises a housing or actuator 3155 containing a canister 51 (FIG. 52). The canister contains a medicament formulation. It will be understood that the canister is of the same type as the canister 51 described with reference to FIG. 1 and comprises a can with a metering valve. The canister sits within the housing 3155.

The housing 3155 comprises a lower section 3200 having a tubular sleeve portion 3156 dimensioned to receive the canister, and a portion in the form of a patient port 3157 (e.g., in the form of a mouthpiece) that defines an inspiration orifice (or an air outlet).

The housing 3155 also comprises an upper section 3202 which comprises the reset mechanism according to an embodiment of the present invention.

Referring to FIG. 52, an exploded view of the upper section 3202 is provided. The upper section comprises a cylinder 3206, a piston 3208, a transfer collar 3210, a spring 3214, an actuator body 3216, an o-ring 3218 and a mouthpiece cover 3220.

Figure 53:
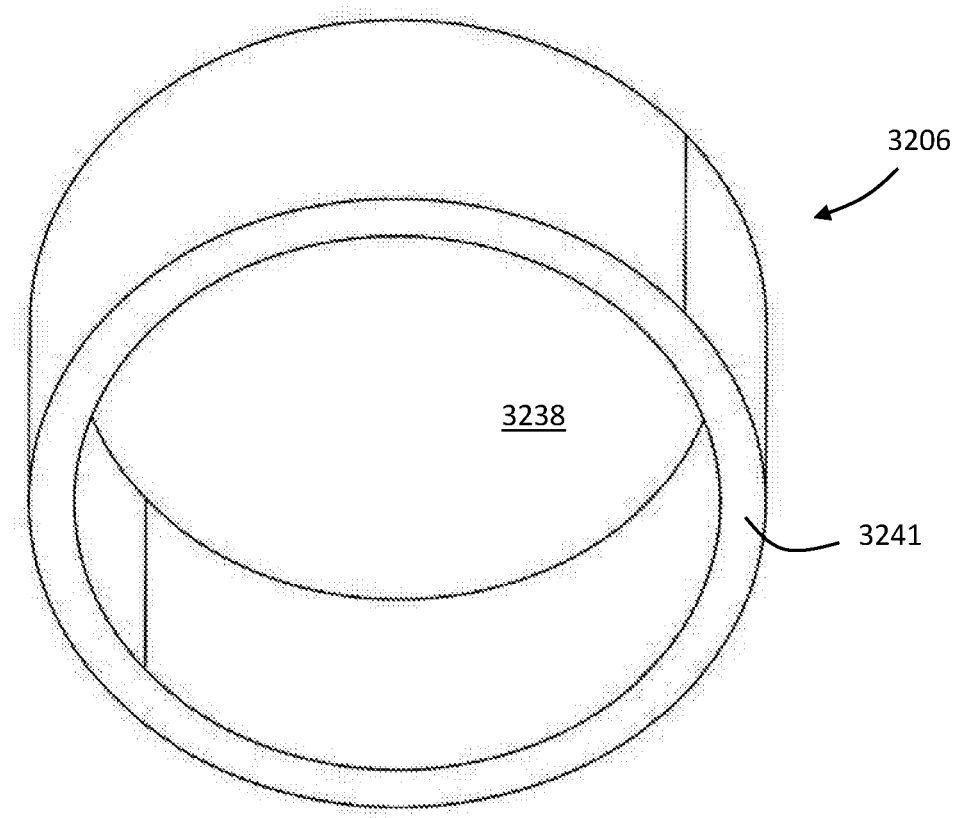
FIG. 53 is a perspective view of a cylinder of the priming and reset mechanism of FIG. 51.

With reference to FIG. 53, the cylinder 3206 is a unitary cylindrical body constructed from a moulded plastics material. The cylinder is closed at a first, upper, end 3238 and open at a second, lower, edge 3241. The cylinder, unlike the embodiments above, has no leak hole.

Figure 54:
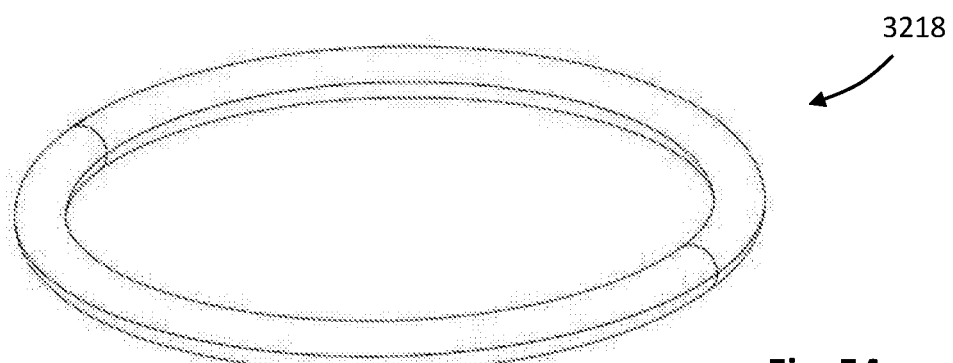
FIG. 54 is a perspective view of an o-ring of the priming and reset mechanism of FIG. 51.

Turning to FIG. 54, the o-ring 3218 is shown. The o-ring 3218 is a standard component and is constructed from an elastomeric material designed to form a fluid seal against plastics material.

Figure 55A:
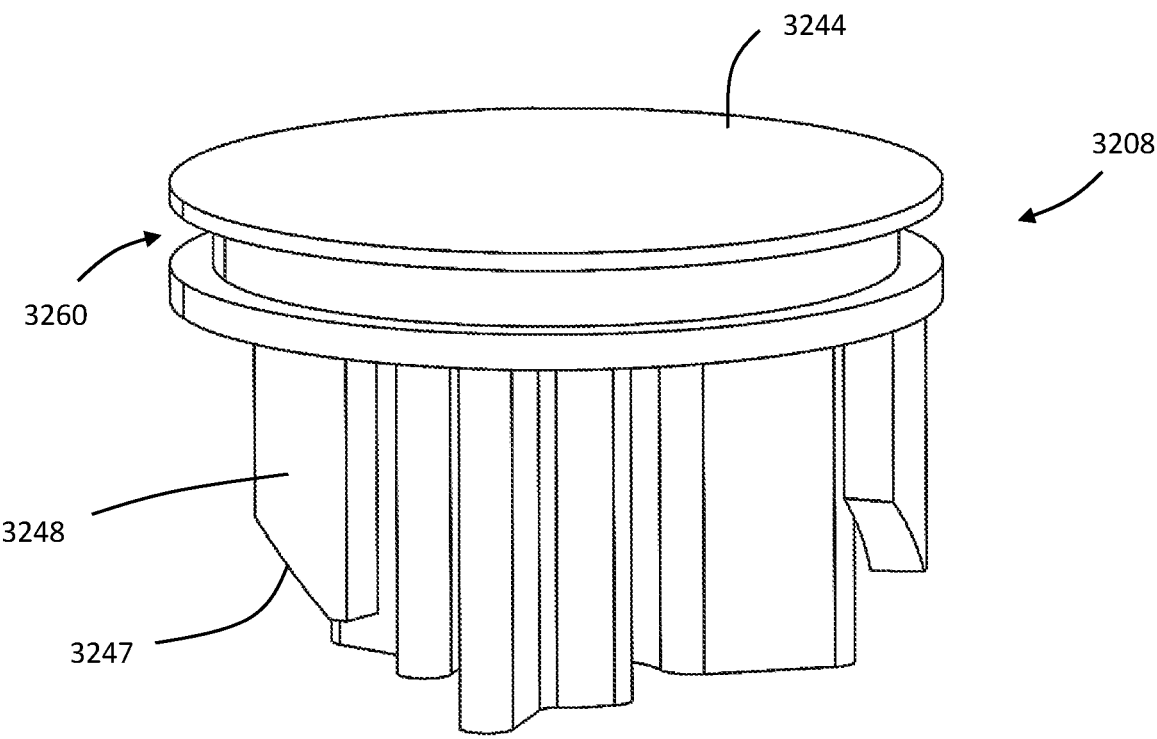
FIGS. 55a and 55b are perspective views of a piston of the priming and reset mechanism of FIG. 51.
Figure 55B:
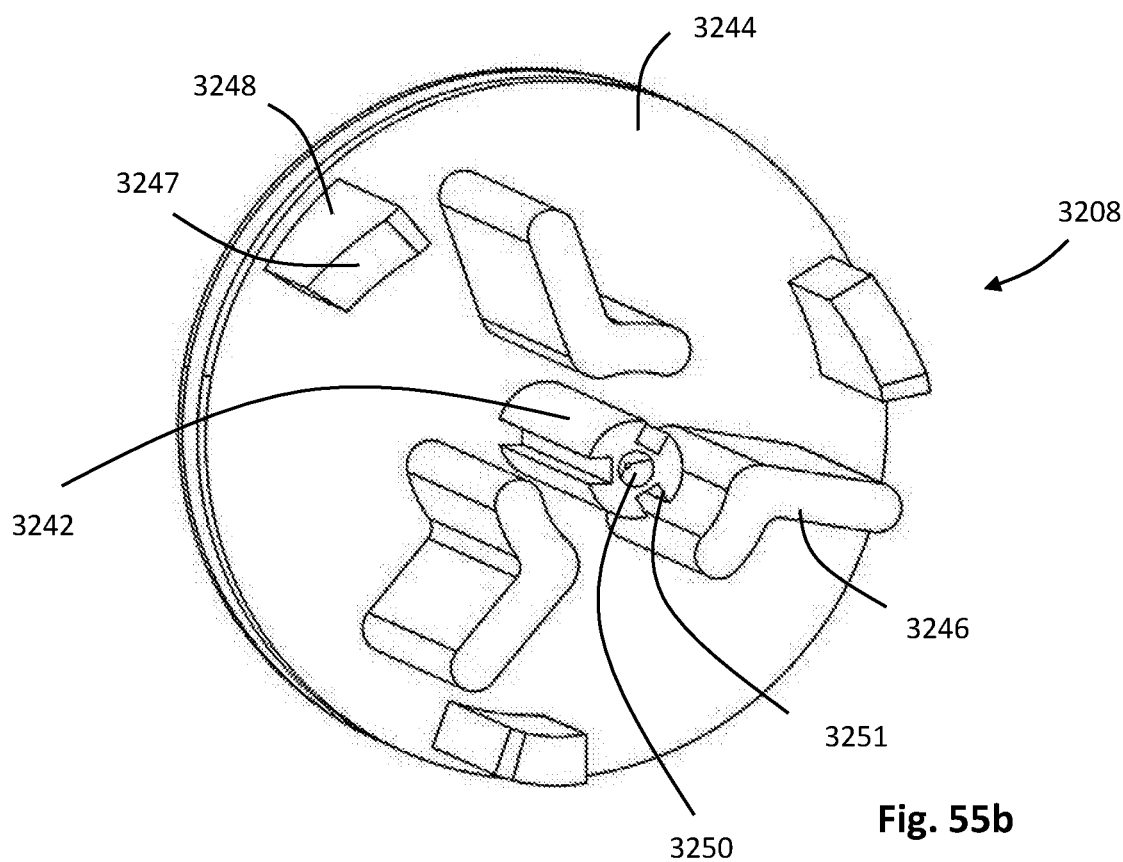

With reference to FIGS. 55*a* and 55*b*, the piston 3208 is shown. The piston 3208 is a unitary moulded plastics component. The piston 3208 comprises a disc-like piston head 3244, a central shaft 3242, three legs 3246 and three teeth 3248 extending axially therefrom.

The piston head 3244 comprises an o-ring receiving channel section 3260.

The central shaft 3242 extends axially from the head 3244, has a central axial bore 3250 as well as three axially extending slots 3251.

The legs 3246 are equally spaced around the shaft 3242 and are each generally "L" shaped in cross section extending in an axial direction.

The teeth 3248 are equally spaced proximate the periphery of the head 3244, and each defines a tapered surface 3247 at a free end thereof.

Figure 56A:
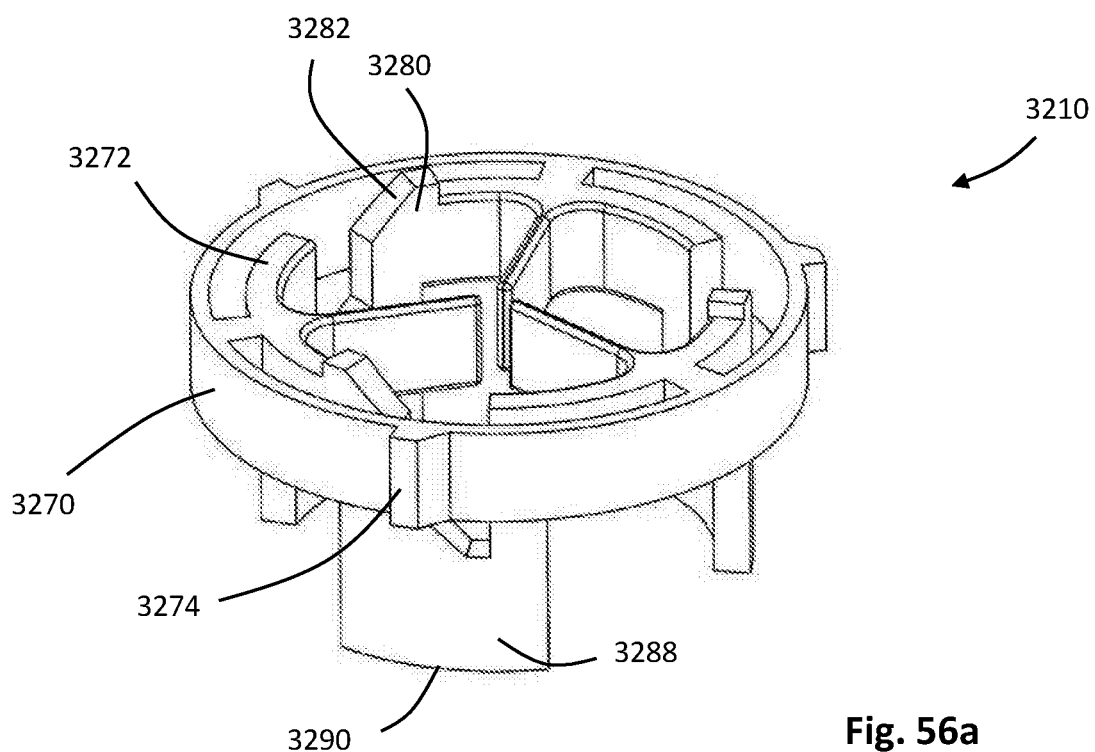
FIGS. 56a to 56c are perspective views of a transfer collar of the priming and reset mechanism of FIG. 51.
Figure 56B:
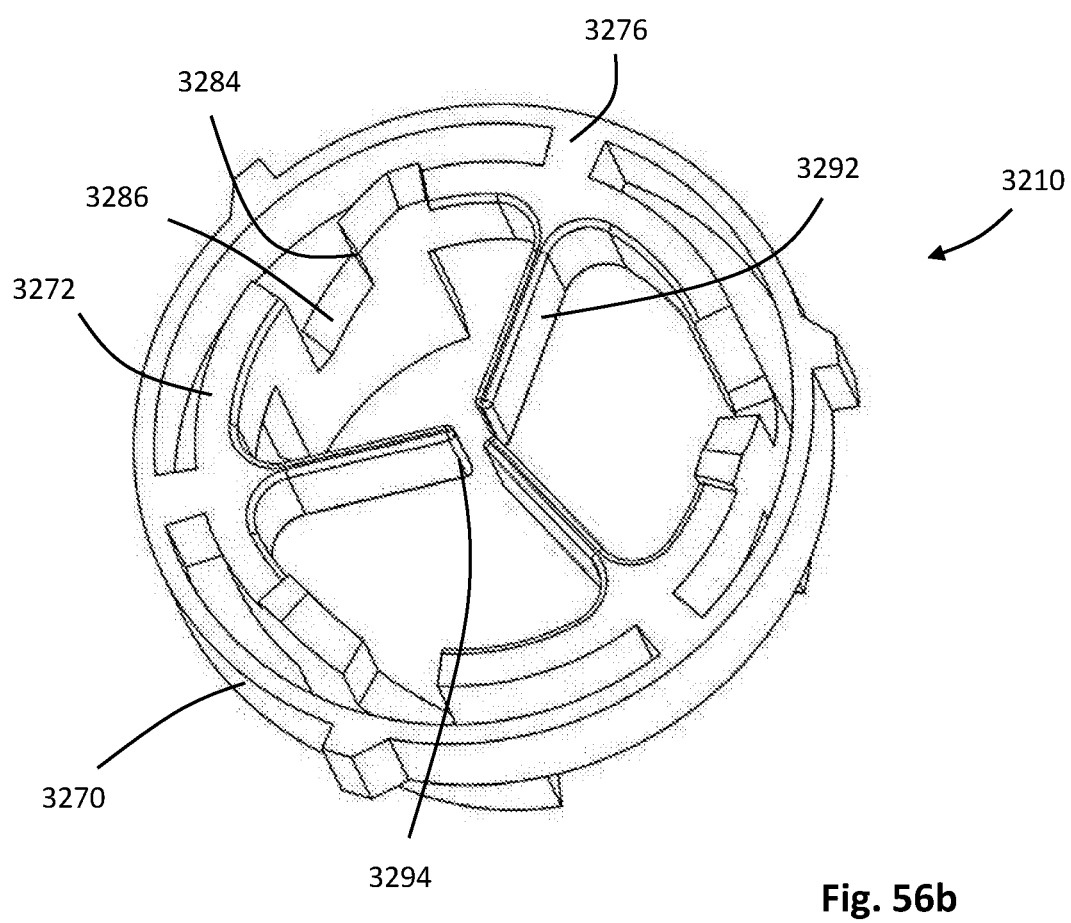
Figure 56C:
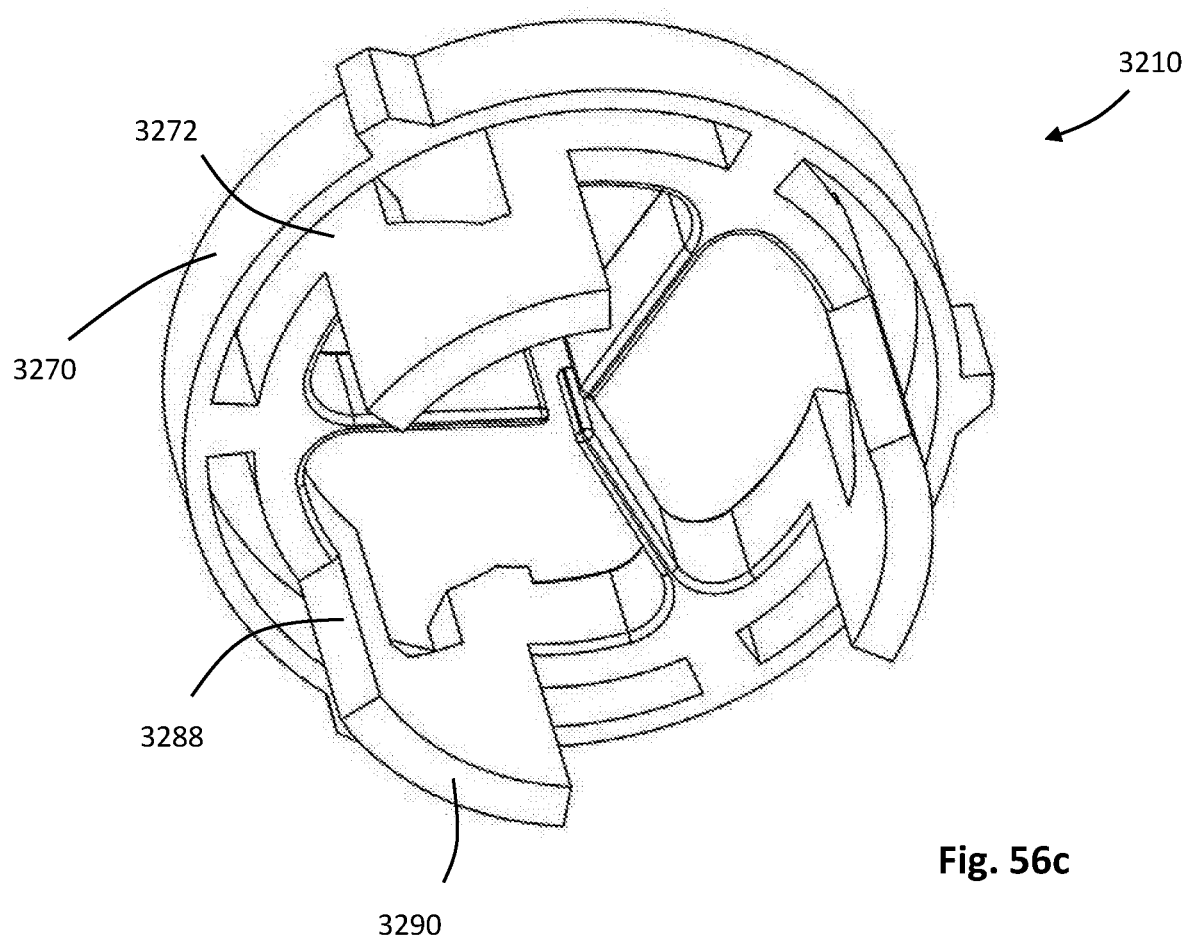

Referring to FIGS. 56*a* to 56*c*, the transfer collar 3210 is shown. The transfer collar 3210 is a unitary moulded plastics component. The transfer collar 3218 comprises an outer ring 3270 and an inner ring 3272.

The outer ring 3270 is generally cylindrical and defines three equally spaced external tabs 3274.

The inner ring 3272 is also generally cylindrical and is connected to the outer ring 3270 by three equally spaced ribs 3276. The inner ring 3272 defines three axially extending teeth 3280 each of which has a tapered surface 3282. Adjacent each tooth the ring defines an axially extending recess 3284 each of which defines a tapered surface 3286. Protruding opposite to the teeth 3280 and the recesses 3284 there are provided three transfer legs 3288 having free ends 3290. The recesses 3284 extend partway into the transfer legs 3288.

Protruding radially inwardly from the inner ring 3272 there are provided three arms 3292 having free ends 3294 which almost meet at the centre of the inner ring 3272. The arms 3292 are at the same circumferential positions as the ribs 3276.

Figure 57:
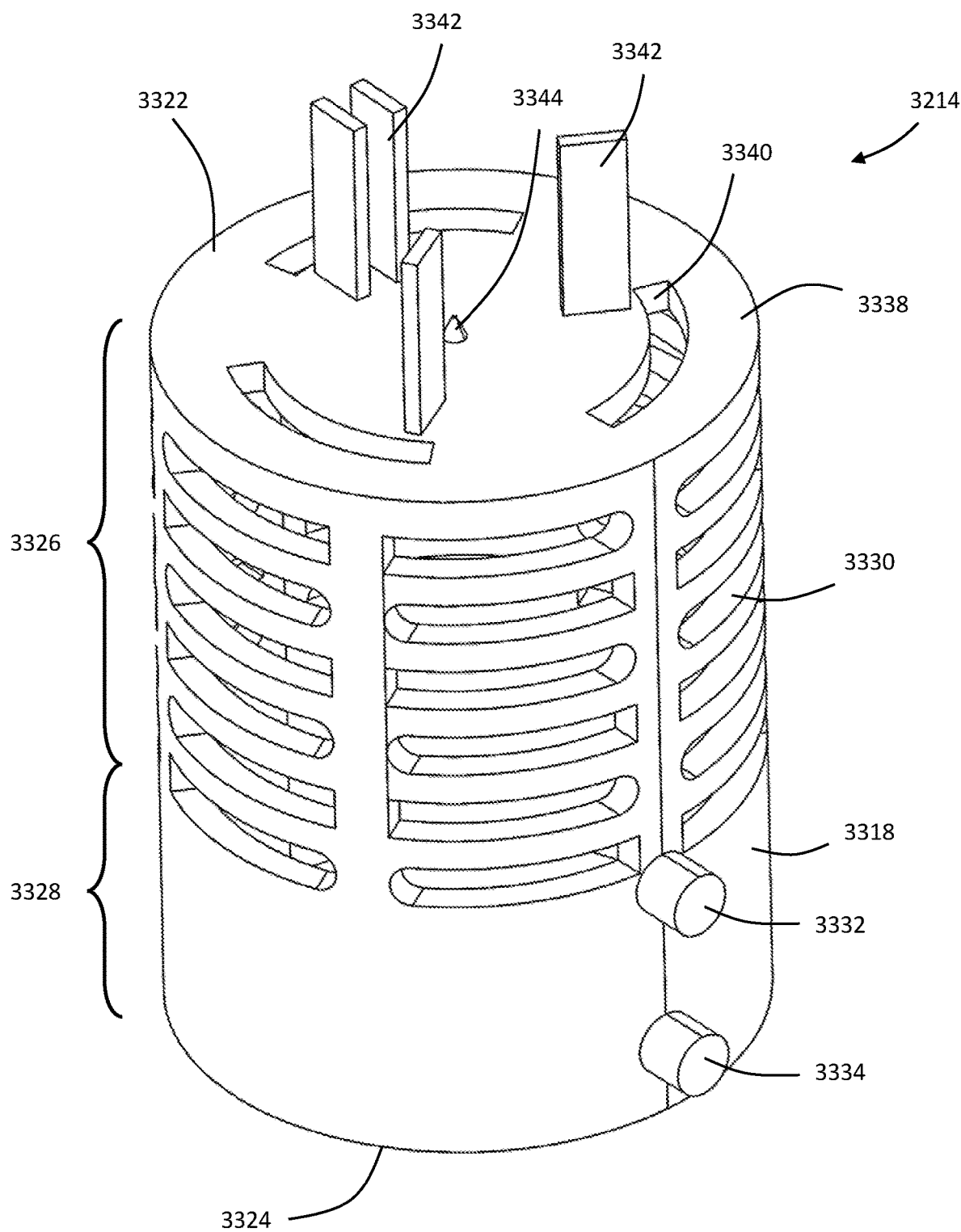
FIG. 57 is a perspective view of a spring of the priming and reset mechanism of FIG. 51.

Referring to FIG. 57, the spring 3214 is shown in detail. The spring 3214 is a unitary, moulded, plastics component which acts as a unitary energy storage arrangement, in contrast to the pMDIs 1150 and 2150 which utilise multiple component energy storage arrangements.

The spring 3214 comprises a tubular spring body 3318 that is generally cylindrical, having a first, upper, end 3322 and a second, lower, end 3324. The spring body 3318 has a first, upper, region 3326 and a second, lower, region 3328.

The first region 3326 is axially extensible and resilient. This is achieved by forming a series of six rows of slot-like openings 3330 through the wall of the body 3318. Each row comprises six openings 3330 which are equally spaced around the circumference of the body 3318. The openings 3330 are formed such that the first region 3326 can be elastically extended, and will resile back to a rest condition as shown in FIG. 57. The second region 3328 comprises a first and second pair of outwardly extending, diametrically opposed pegs 3332, 3334 respectively. The pegs 3332, 3334 are cylindrical. The first pair of pegs 3334 is positioned adjacent the first region 3326, and the second pegs are positioned proximate the second end 3324.

The first end 3322 of the body 3318 terminates in a flat surface 3338 that defines three leg openings 3340. Four axially extending flat spring members 3342 are provided projecting from the surface 3338. Two of the spring members 3342 are provided as a pair, and as such, the spring members are positioned in three groups (two individual members and one pair) equidistantly spaced. The members 3342 are generally rectangular. In the centre of the surface 3338 there is provided a locating pin 3344.

Figure 58A:
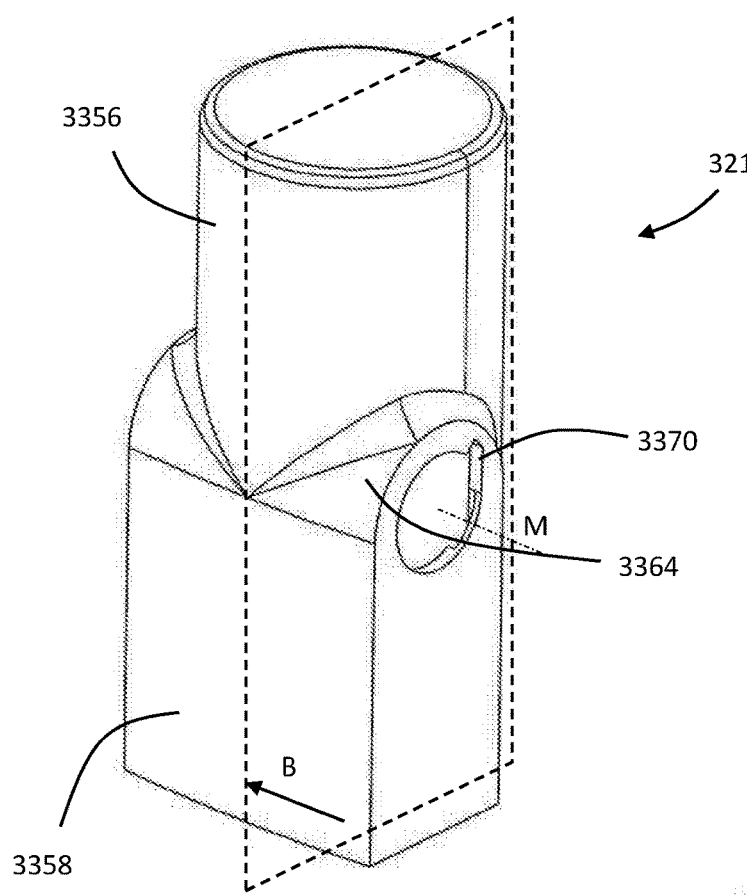
FIGS. 58a and 58b are perspective views of an actuator body of the priming and reset mechanism of FIG. 51.
Figure 58B:
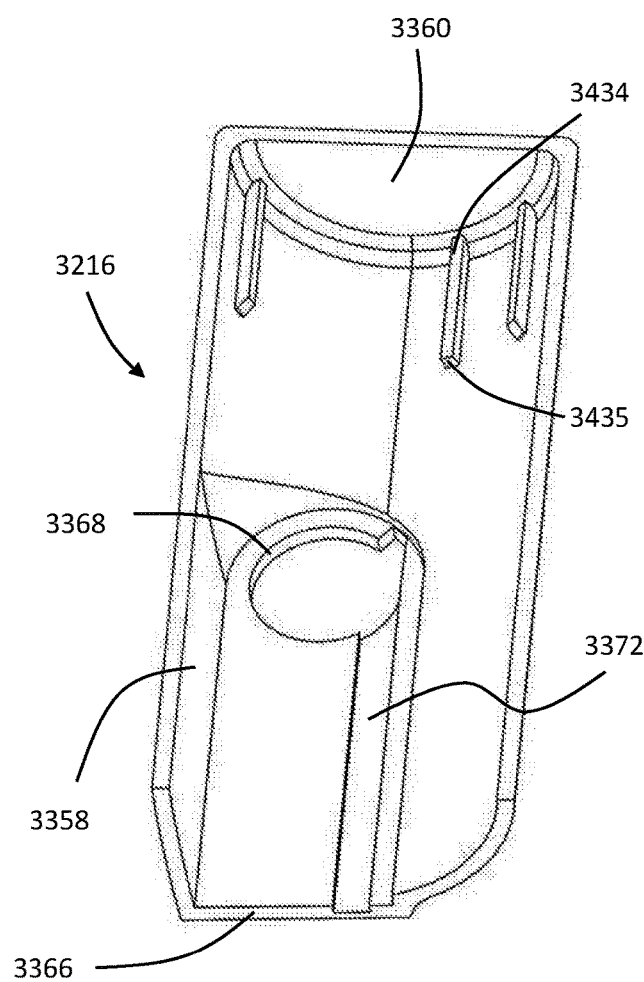

Referring to FIGS. 58a and 58b, the actuator body 3216 is shown in detail. FIG. 58b is in cross-section through plane B in FIG. 58a. The actuator body 3216 comprises a first, upper, section 3356 and a second, lower, section 3358. The sections 3356, 3358 define a generally elongate housing enclosing a cavity which is open at the lower end.

The first section 3356 is generally cylindrical having a first, upper end which is closed by an endwall 3360. Transfer collar abutments 3434 are defined on the inner surface thereof, being axially extending ribs having ends 3435.

The second section 3358 is generally rectangular in cross-section and joins the first section 3356 via a pair of shoulders 3364. The second section 3358 has an open end 3366. A pair of opposed circular apertures 3368 are disposed in opposing walls of the second section proximate the shoulders 3364. Each aperture 3368 defines a tangential notch 3370 projecting outwardly. Both apertures lie on a mouthpiece cover axis M. Extending from each aperture 3368 along the respective interior sidewall of the second section 3358 there is provided a spring peg groove 3372. The spring peg grooves 3372 start from a position substantially opposite the notch 3370 and extend axially within the second section 3358 to the open end 3366.

Figure 59:
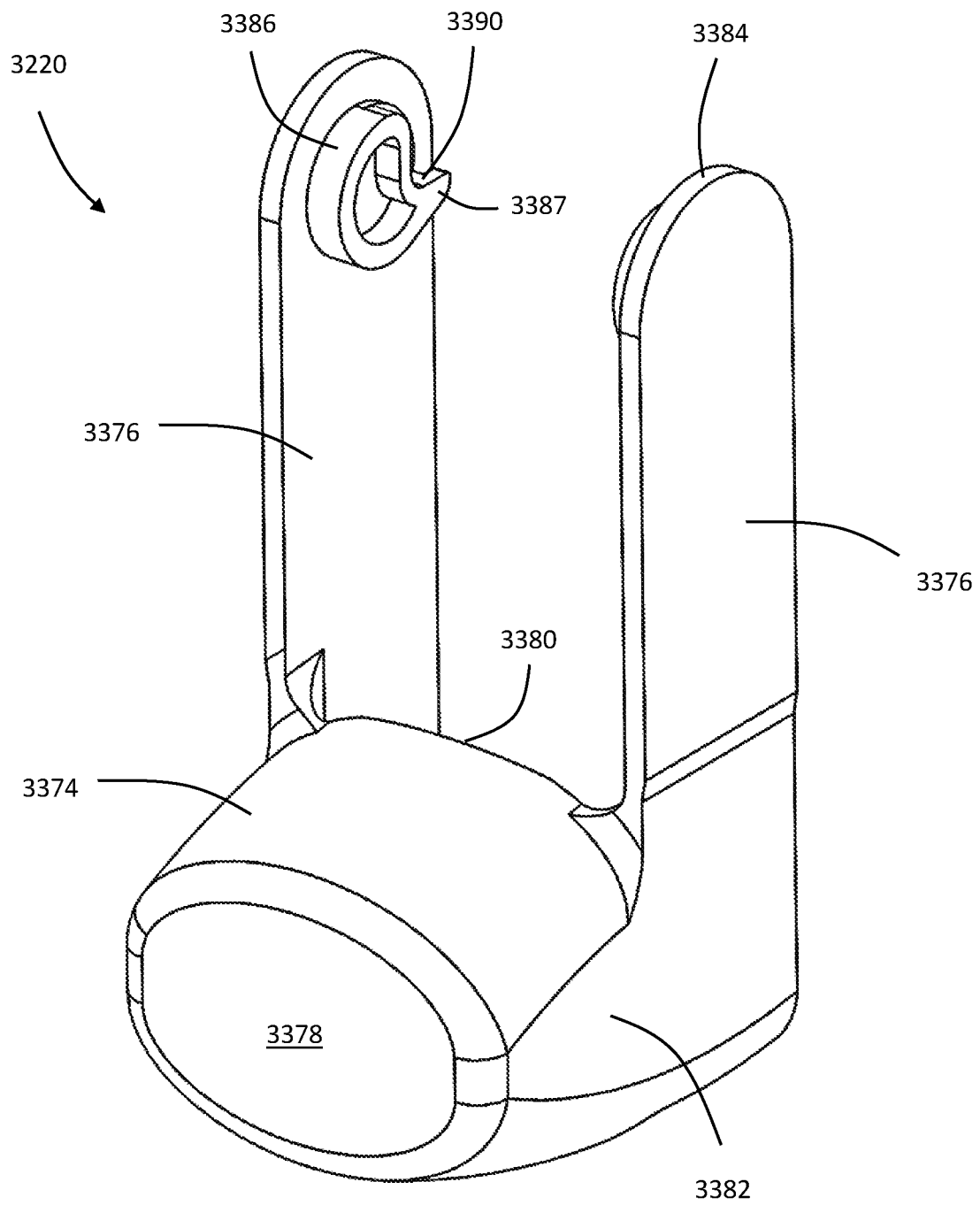
FIG. 59 is a perspective view of a mouthpiece cover of the priming and reset mechanism of FIG. 51.

Referring to FIG. 59, the mouthpiece cover 3220 is shown in more detail. The mouthpiece cover 3220 is a unitary, moulded plastics component. The mouthpiece cover 3220 comprises a cap 3374 and two arms 3376 that are mirror images of each other.

The cap 3374 is an internally concave structure suitable for sealing a mouthpiece of the inhaler patient port 3157. The cap 3374 has a closed end 3378 and an open end 3380. The cap 3374 defines a pair of opposed sidewalls 3382 from which the arms 3376 extend proximate the open end 3380.

Each arm 3376 is an elongate, generally planar structure extending to a free end 3384. At the free end, and on an inwardly facing surface of each arm 3376 there is provided a cam 3386. The cam comprises a lobe 3387 which has an undercut portion.

The cam 3386, is similar in shape to the cam 386 and has an outer radius and a peg-receiving notch 3390 which extends radially inwardly.

Assembly

Figure 60A:
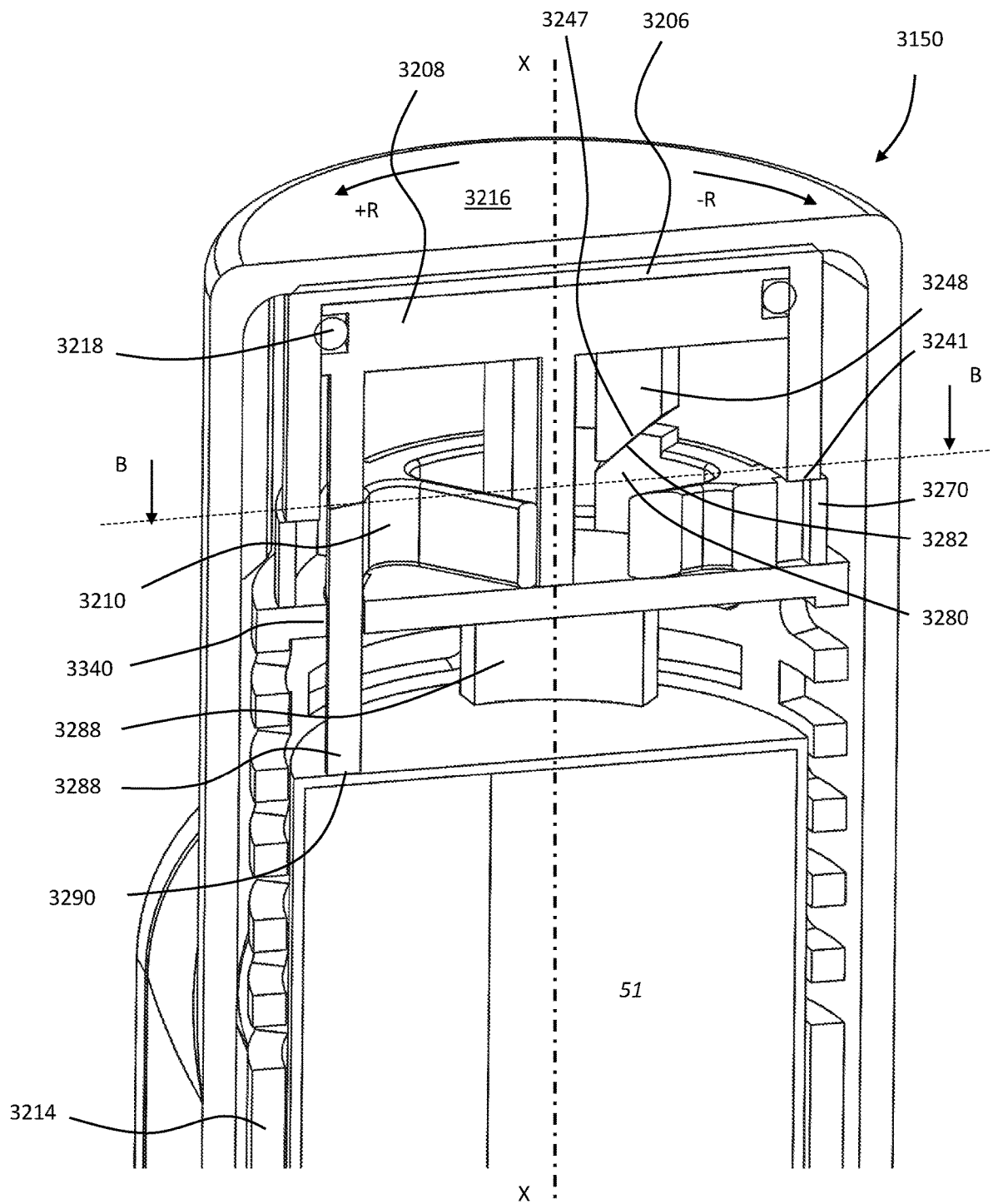
FIG. 60a is a section view of the priming and reset mechanism of FIG. 51 in a rest condition.
Figure 60B:
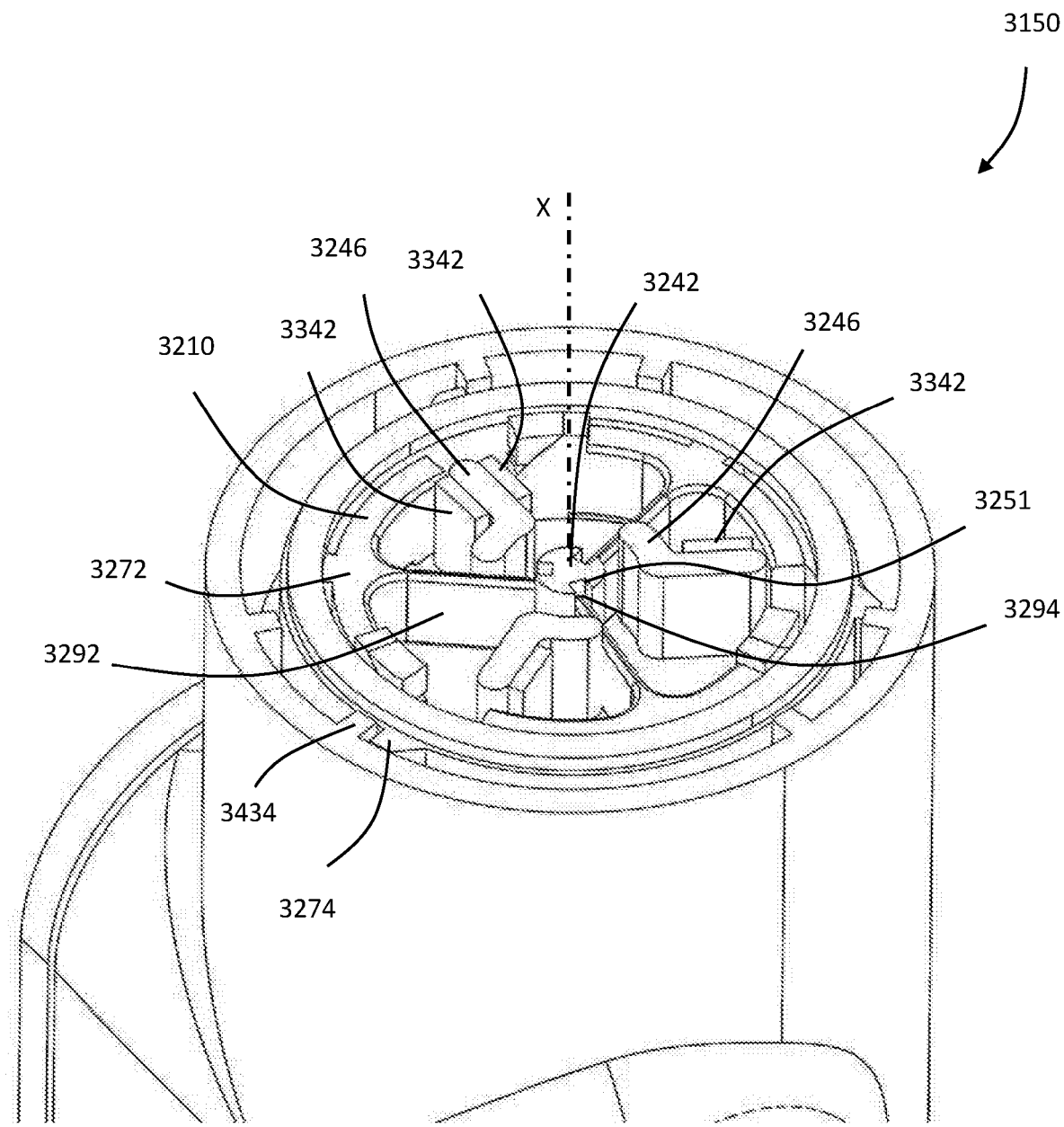
FIG. 60b is a section view through line B of FIG. 60a in a rest condition.
Figure 60C:
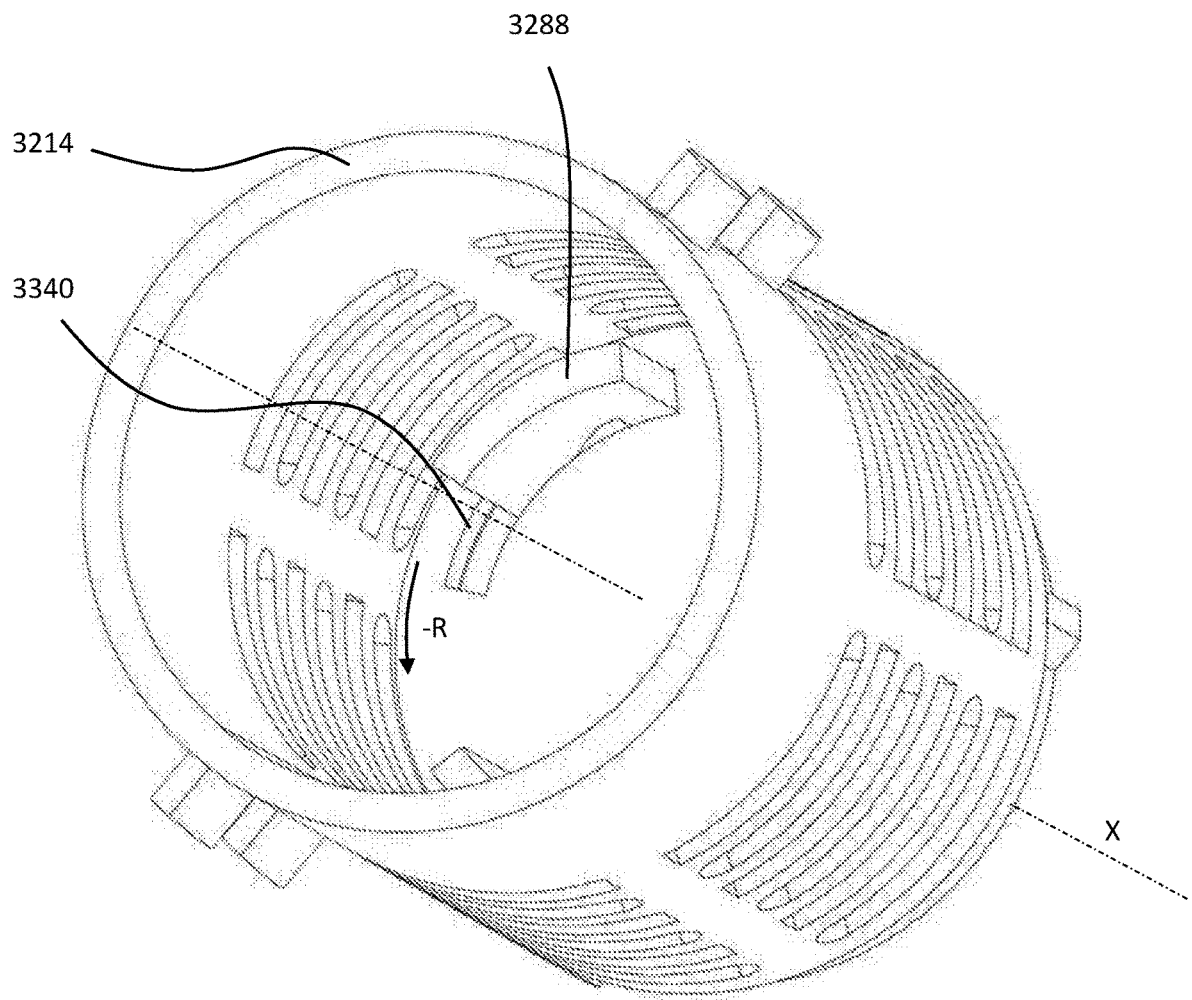
FIG. 60c is a perspective view of a subassembly of the priming and reset mechanism of FIG. 51 in a rest condition.

All of the components described above are aligned on a main axis X. Referring to FIGS. 60a to 60c (as well as the exploded view of FIG. 52), the pMDI 3150 is shown in its assembled state, in a rest condition (used for storage and generally when not in operation).

The transfer collar 3210 and the spring 3214 are assembled by passing the transfer legs 3288 into the leg openings 3340. Referring to FIG. 60c the openings 3340 are longer than the legs 3288 and as such allow a predetermined degree of rotation (approximately 10 degrees) of the transfer collar 3210 about the axis X relative to the spring 3214. The spring members 3342 project through the inner ring 3272.

Referring to FIG. 60b, the piston 3208 is assembled with the transfer collar 3210 and spring 3214 by inserting the central shaft 3242 between the free ends 3294 of the arms 3292 which enter the slots 3251. The arms 3292 also abut the ends of the legs 3246 of the piston 3208. The axial bore 3250 mates with the locating pin 3344. The piston 3208 and spring 3214 are then bonded together.

The piston legs 3246 each abut a spring member 3342, with one leg 3246 being trapped between two spring members 3342 as visible with respect to the top left leg in FIG. 60b. Referring to FIG. 60a, the tapered surfaces 3247 of the teeth 3248 of the piston 3208 abut the tapered surfaces 3282 of the teeth 3280 of the transfer collar 3210.

Referring to FIG. 60a, the o-ring 3218 is positioned within the groove 3260 on the piston 3208, and the cylinder 3206 is assembled over the piston 3208. The lower edge 3241 of the cylinder 3206 abuts the top of the outer ring 3270 of the transfer collar 3210.

The assembly is positioned within the actuator body 3216 with the external tabs 3274 of the transfer collar 3210 abutting the transfer collar abutments 3434 (FIG. 60b). Pegs 3332, 3334 of the spring 3214 are slidably engaged in the spring peg grooves 3372. The mouthpiece cover 3220 is assembled onto the actuator body 3216 and rotated into position. It will be noted that as with the earlier embodiments, the mouthpiece cover 3220 can only be assembled in one rotational position such that the cams 3386 can engage the apertures 3368. Like the mouthpiece 220, assembly can only be achieved before the lower part of the housing and patient portion is provided (reference is made to FIGS. 13d to 13e and the accompanying description). The pMDI 150 achieves this with a retaining flange 370 whereas the pMDI 3150 utilises a shaped cam 3390 which can only enter the aperture 3368 in one rotational position thereof due to the presence of the lobe 3387. Once engaged, because the lobe 3387 is undercut, the mouthpiece cover 3220 can rotate about the mouthpiece cover axis M.

In the rest position, like the mouthpiece cover 220, the notch 3390 traps the upper peg 3332 of the spring 3214.

Operation

The pMDI 3150 is used as follows. The operation of the pMDI 3150 is best described as passing through a number of operational conditions or stages as will be described below.

1. Rest Condition

The rest condition is shown in FIGS. 60a to 60c. In this condition, a canister 51 is provided within the pMDI. As with previous embodiments, a stem of the canister 51 abuts a stem abutment that is static within the pMDI 3150. In the rest condition, downward travel of the canister 51 is inhibited by a trigger abutment that is part of a trigger assembly (not described here, but generally known in the art).

In this position, the canister 51 is positioned partly within the spring 3214 (FIG. 60a), and the free ends 3290 of the legs 3288 of the transfer collar 3210 abut the bottom of the canister 51 (as it is inverted). The transfer collar 3210 supports the piston 3208 which in turn supports the cylinder 3206. The spring 3214 is held up by the engagement of the peg 3332 with the notch 3390 on the mouthpiece cover 3220. The spring 3214 is in a rest position, and stores no energy.

2. Primed Condition

In this condition, the mouthpiece cover 3220 has been rotated about the mouthpiece cover axis M, such that the first pegs 3332 have been drawn into the spring peg grooves 3372. This action tends to apply a tensile force to the first region of the spring 3326, drawing it downwards.

The movement of the mouthpiece cover 3220 to extend and thereby actuate the spring is the same as with the first embodiment, i.e., a 90 degree rotation of the mouthpiece cover 3220 urges the peg 3332 almost fully into the groove 3372. At this position, the inhaler is unusable because the mouthpiece cover 3220 would clash with the user's face if they tried to place their mouth over the mouthpiece.

Rotation to approximately 135 degrees rotates the cam 3386 to an extent that the peg 3332 is almost fully within the groove 3372. At this point, because the notch 3390 has cleared the peg 3332, further rotation of the mouthpiece cover 3220 has no effect on the linear position of the peg 3332. At this position it is still not possible to use the inhaler because the mouthpiece cover is in a position where it would clash with the user's face.

The final, primed position of the mouthpiece cover is at an angle of 180 degrees which only serves to move the mouthpiece 3220 out of the way (the spring is not extended any further). As with the first embodiment, this lost motion ensures that should a user attempt to use the inhaler when the mouthpiece cover 3220 is not fully rotated, the inhaler will operate as normal because the spring 3214 is fully energised.

Initially this downward force on the spring 3214 acts to draw the piston 3208 downwards (the piston 3208 and spring 3214 are attached). Downward motion of the piston is resisted by the abutment of the piston teeth 3248 with the transfer collar teeth 3280, and the transfer collar 3210 is held in position by the canister 51 which is held up by the trigger mechanism. Although the teeth abut at tapered surfaces (producing a torque on the transfer collar 3210 in direction −R), rotation of the transfer collar 3210 is resisted by abutment of the external tabs 3274 of the transfer collar 3210 with the transfer collar abutments 3434 of the actuator body 3216.

Downward movement of the cylinder 3206 is resisted by the piston and by the abutment of the cylinder 3206 with the transfer collar 3210.

The only movement between the rest and primed conditions is therefore extension of the spring 3214.

3. Fired Condition

When the user wishes to dispense the medicament, a trigger mechanism (which is not described here) is fired in which the trigger abutment is moved such that downward motion of the canister 51 is no longer inhibited.

Figure 61:
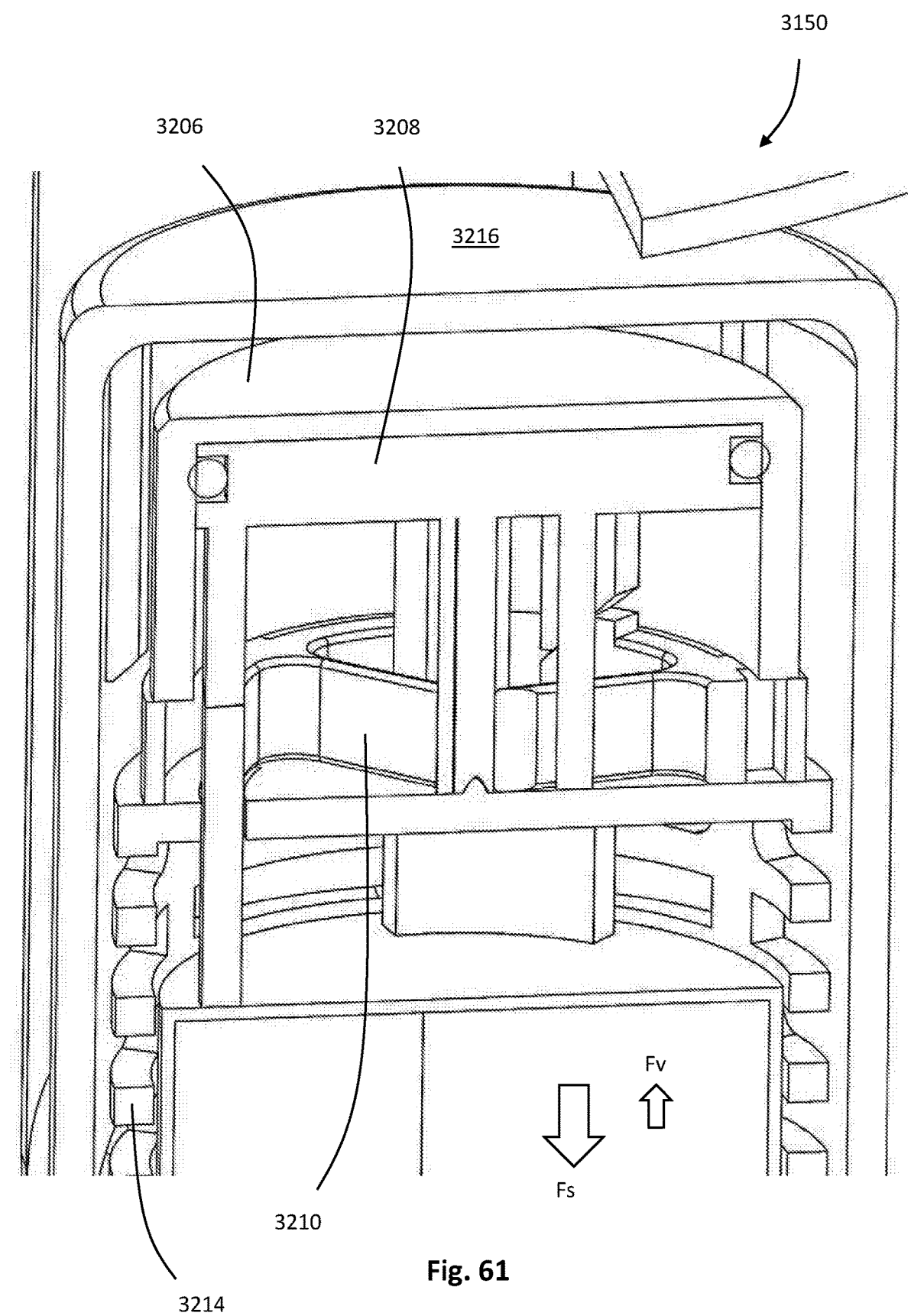
FIG. 61 is a section view of the priming and reset mechanism of FIG. 51 in a primed condition.

Release of the canister 51 releases the transfer collar 3210 and piston 3208 to move downwards, pulled by the tensile force of the spring 3214 on the attached piston 3208. The cylinder 3206 has also moved downwards as shown in FIG. 61a. As the stored energy in the spring 3214 is released, it serves to push the valve stem onto the valve stem abutment. This also acts against the bias of the valve spring within the valve to open the canister 51 and release a dose of medicament. Because the force from the spring 3214, Fs, exceeds that from the valve, Fv, at this juncture, dose release is ensured (FIG. 61).

4. Auto-Release Condition

Figure 62A:
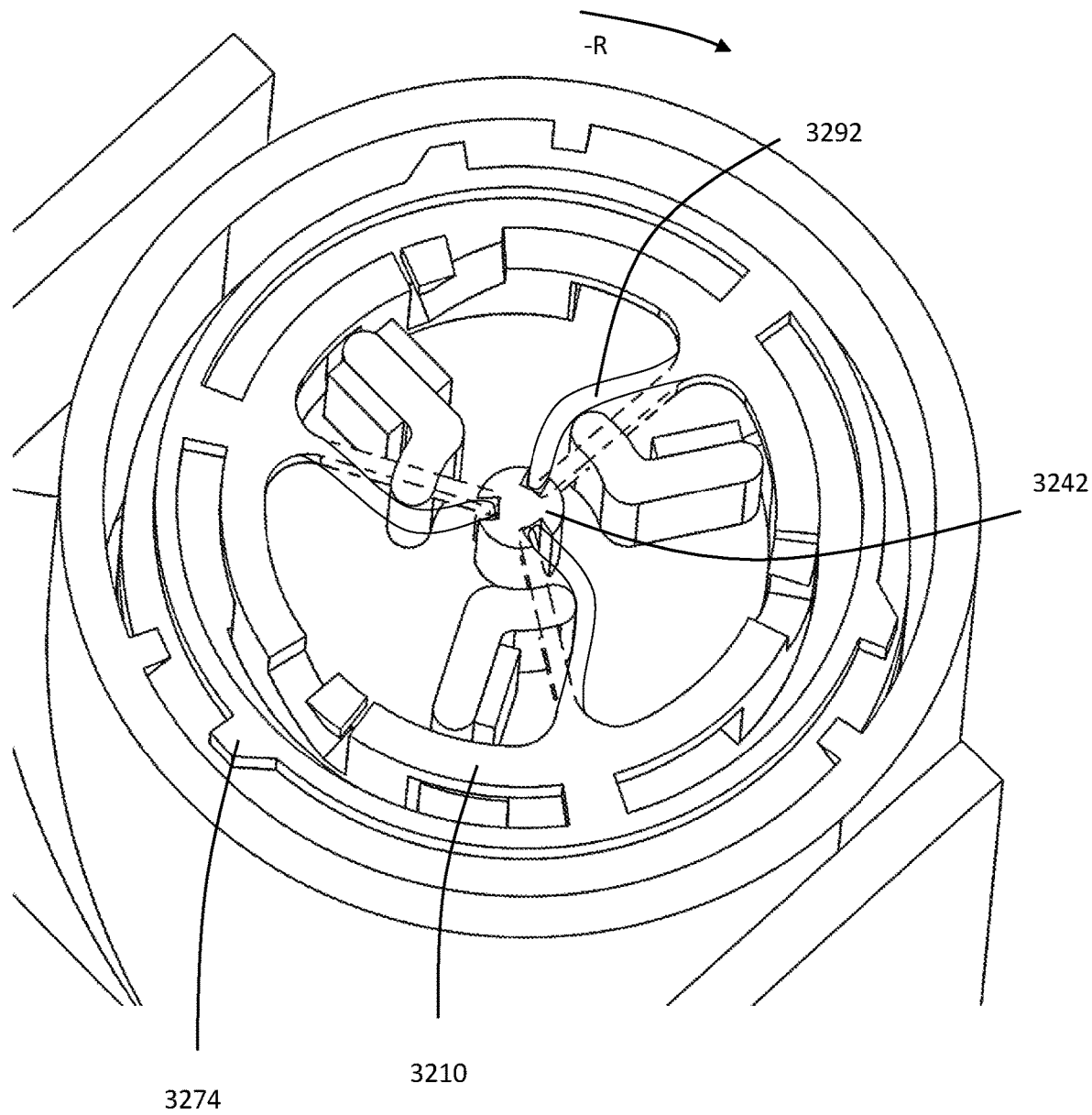
FIG. 62a is a section view the priming and reset mechanism of FIG. 51 in an auto-release condition.

The external tabs 3274 of the transfer collar 3210 eventually clear the free ends 3435 of the transfer collar abutments 3434. This allows the transfer collar 3210 to rotate about the axis X in direction −R (FIG. 62a). This rotation occurs due to the torque created by the abutment of the tapered surfaces 3247 of the piston teeth 3248 abutting the tapered surfaces 3282 of the transfer collar teeth 3280 (FIG. 60a).

As shown in FIG. 62a, the arms 3292 are still engaged with the shaft 3242 and abut the legs 3246 and as such need to elastically and resiliently deform as the transfer collar 3210 rotates (the hidden lines show their undeformed state).

Figure 62B:
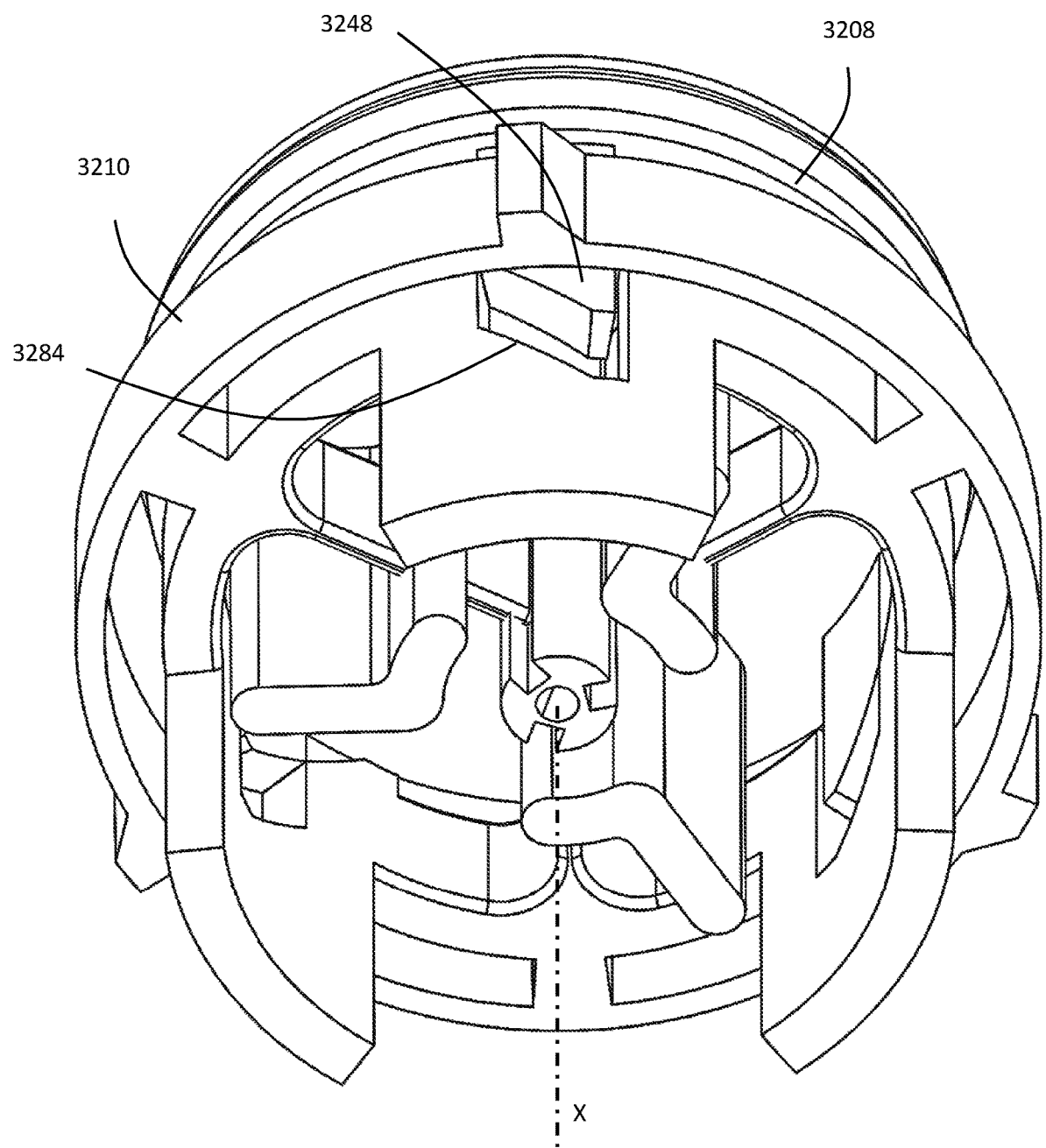
FIG. 62b is a perspective view of a subassembly of the priming and reset mechanism of FIG. 51 in an auto-release condition.

At a predetermined angle of rotation of the transfer collar 3210 relative to the piston 3208 (which cannot rotate, because it is bonded to the spring 3214, which itself cannot rotate) the transfer collar 3210 and piston 3208 become detached (or released) in a linear sense. In other words, as the collar 3210 rotates, the clutch formed by the collar 3210 and piston 3208 is released. This is because the piston teeth 3248 can eventually move into the recesses 3284 in the transfer collar 3210 as shown in FIG. 62b.

5. Can Reset Condition

Figure 63:
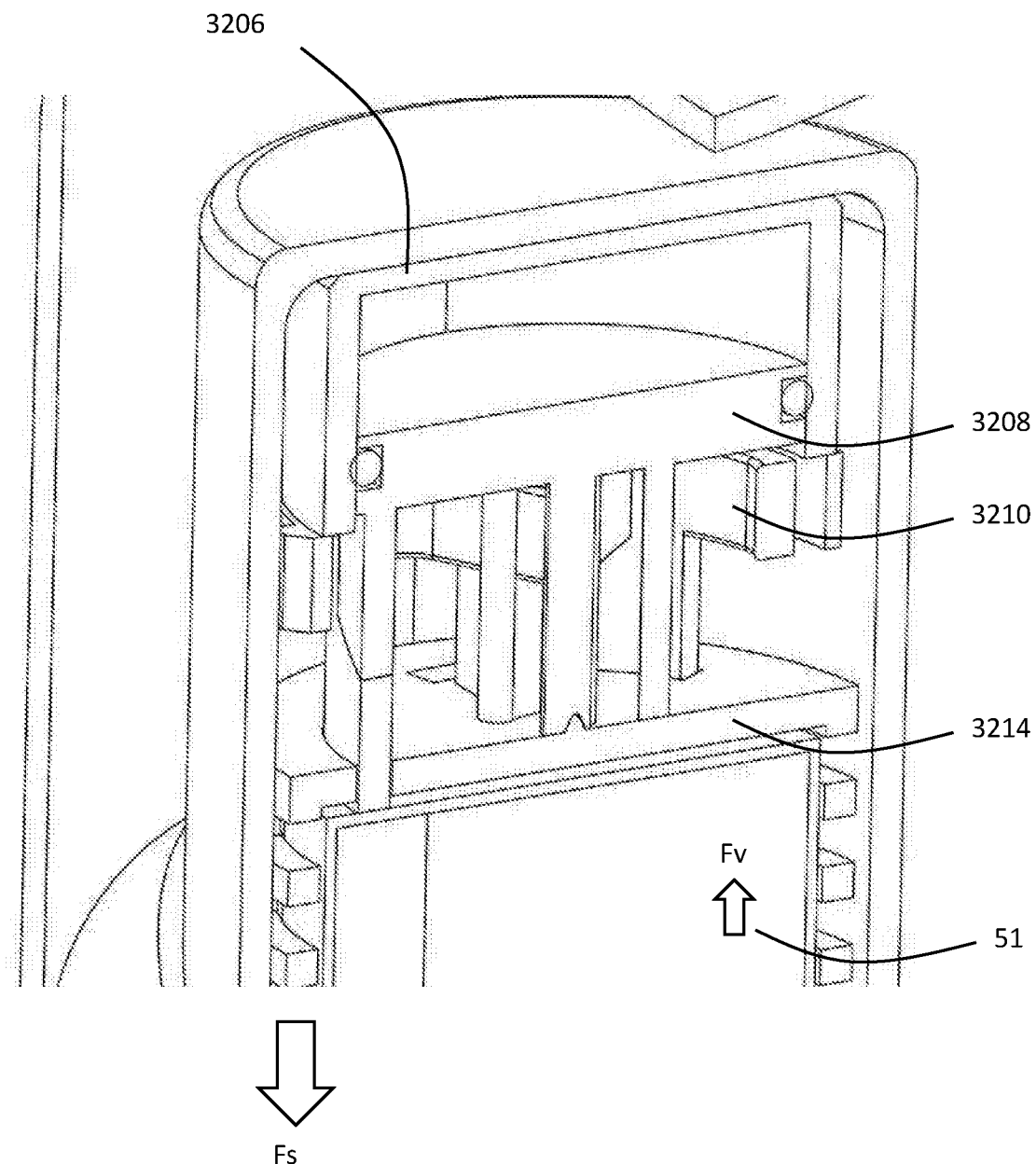
FIG. 63 is a section view of the priming and reset mechanism of FIG. 51 in a can reset condition; and, FIG. 64 is a section view of the priming and reset mechanism of FIG. 51 in a return to reset condition.

The release of the clutch now separates the system into two sub-assemblies which encounter opposing forces. Reference is made to FIG. 63.

On one hand, the return force of the spring in the canister valve Fv applies an upward force on the transfer collar 3210 (via the canister 51), which in turn lifts the transfer collar 3210 and also the cylinder 3206.

On the other hand, the tensile force Fs remaining in the spring 3214 acts to draw the piston 3208 downwards. Therefore, as the canister 51 resiles to its rest (unactuated) position, its motion is controlled by the separation of the piston 3208 and cylinder 3206. The vacuum (or at least low air pressure) created within the cylinder damps the return, controlling the speed at which the canister returns to its rest state.

The piston 3208 and transfer collar 3210 become fully engaged. The transfer collar ends up in the rest position in a vertical (axial) sense, although cannot rotate back under the resilience of the arms 3292 as it is held, unable to rotate, by the piston 3208.

6. Return to Rest Condition

Figure 64:
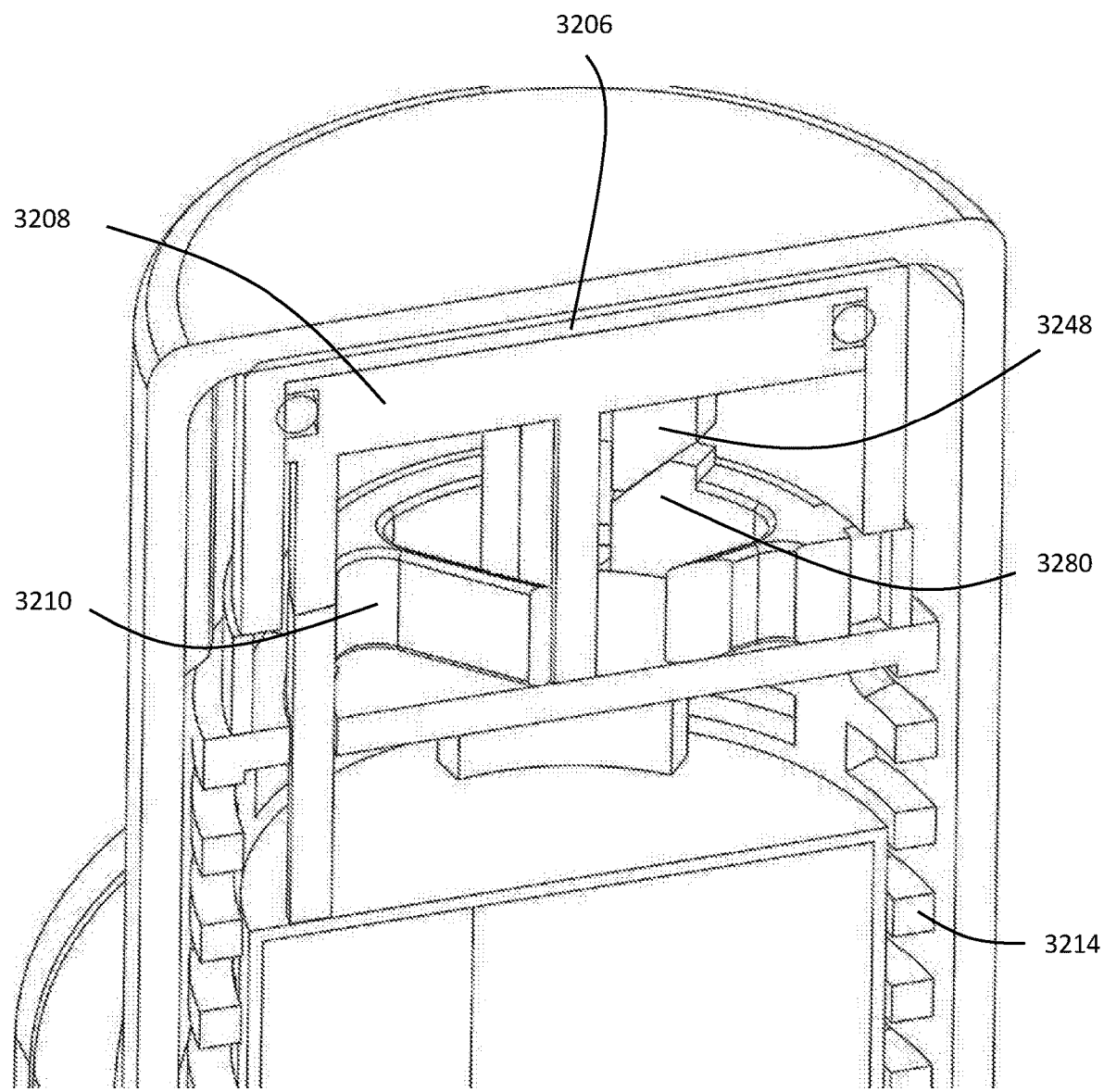

The user rotates the mouthpiece cover 3220 back to its original positon, which has the effect of drawing the first peg 3332 of the spring 3214 upwards towards its starting (rest) position. This motion allows the re-engagement of the piston 3208 into the cylinder 3206, which is partly urged by the vacuum/low pressure in the cylinder. The separation of the piston 3208 and the transfer collar 3210 allows the transfer collar 3210 to rotate under the bias of the arms 3292 to its original rotational position whereby the piston teeth 3248 and the transfer collar teeth 3280 are in vertical abutment as shown in FIG. 64.

It will be understood that variations in the above embodiments fall within the scope of the claims. For example, the inhaler does not have to be a pMDI, and may be a DPI or other type of inhaler.

The invention claimed is:

1. A mechanical return assembly for a valved-container inhaler comprising:
   a resilient structure;
   a transfer configured to transfer stored potential energy from the resilient structure to a resilient, valved container in the form of a force to thereby release a medicament therefrom;
   a clutch in a load path of the force between the resilient structure and the transfer, the clutch having a first part and a second part, in which rotation of the second part relative to the first part moves the clutch between:
   a first condition in which load is transferred from the resilient structure to the transfer, and
   a second condition in which the resilient structure and the transfer can move relative to one another to interrupt the load path and disconnect the valved canister from the force and thereby allow the valved container to resile after actuation.

2. The mechanical return assembly for a valved-container inhaler according to claim 1, in which the rotation of the second part relative to the first part is effected by a linear force applied to a ramped surface.

3. The mechanical return assembly for a valved-container inhaler according to claim 2, in which the ramped surface is defined on at least the second part to effect the rotation thereof.

4. The mechanical return assembly for a valved-container inhaler according to claim 3, comprising:
- a housing; and,
- a static actuator formation fixed with respect to the housing, wherein the static actuator formation is configured to engage the ramped surface of the second part;
- in which the linear force is applied from the first part to the second part to rotate the second part by engagement of the ramped surface of the second part with the static actuator formation.

5. The mechanical return assembly for a valved-container inhaler according to claim 4, in which the clutch is configured to move linearly from:
- a first position in which the clutch is in the first condition to a second position in which the clutch is in the first condition to transfer the stored potential energy from the resilient structure to the transfer; and,
- the second position to a third position upon engagement of the ramped surface of the second part with the static actuator formation to move the clutch to the second condition.

6. The mechanical return assembly for a valved-container inhaler according to claim 4, in which the resilient structure comprises a compression spring.

7. The mechanical return assembly for a valved-container inhaler according to claim 3, in which the second part is capable of linear movement relative to the first part, and the linear force is applied from the first part to the ramped surface on the second part to effect rotation of the second part.

8. The mechanical return assembly for a valved-container inhaler according to claim 7, in which the first part is rotationally fixed, and rotation of the second part is inhibited for part of the linear movement of the second part.

9. The mechanical return assembly for a valved-container inhaler according to claim 8, in which the clutch is configured to move linearly through:
- a first stage linear movement in which the clutch is in the first condition to transfer the stored potential energy from the resilient structure to the transfer, during which rotation of the second part is inhibited; and,
- a second stage linear movement during which rotation of the second part is permitted to thereby move the clutch to the second condition.

10. The mechanical return assembly for a valved-container inhaler according to claim 9, in which the first part of the clutch and the resilient structure are positioned on opposite sides of the second part of the clutch, in which the first part of the clutch moves into the second part of the clutch when moving from the first to the second condition.

11. The mechanical return assembly for a valved-container inhaler according to claim 10, in which the first and second parts of the clutch are in sliding engagement.

12. The mechanical return assembly for a valved-container inhaler according to claim 10, in which the first part of the clutch comprises a first abutment and the second part of the clutch comprises a second abutment, in which in the first condition the first and second abutments are aligned and in contact, and in the second condition the first and second abutments are misaligned.

13. The mechanical return assembly for a valved-container inhaler according to claim 12, in which the first and/or second abutments comprise a plurality of spaced-apart teeth.

14. The mechanical return assembly for a valved-container inhaler according to claim 13, in which a damper is provided to damp relative movement between the transfer and the resilient structure upon movement of the clutch to the second condition.

15. The mechanical return assembly for a valved-container inhaler according to claim 14, in which the resilient structure comprises a tension spring.

16. The mechanical return assembly for a valved-container inhaler according to claim 1, in which the resilient structure defines a body having an interior space in which to receive the valved container.

17. A valved-container inhaler comprising a mechanical return assembly according to claim 16, comprising a priming mechanism configured to transfer energy to the resilient structure.

18. The valved-container inhaler according to claim 17, in which the priming mechanism is user-actuated.

19. The valved-container inhaler according to claim 17, in which the priming mechanism comprises a linearly displaceable element engaged with part of the resilient structure to apply a linear force thereto.

20. The valved-container inhaler according to claim 19, comprising a firing mechanism, in which the return assembly has:
- a rest condition;
- a stable primed condition in which the resilient structure stores potential energy; and
- a fired condition in which the resilient structure has been released to transfer force to the transfer, and the clutch is in the second condition;
- in which the firing mechanism is configured to release the resilient structure.

* * * * *